US007754201B2

(12) United States Patent
Wang et al.

(10) Patent No.: US 7,754,201 B2
(45) Date of Patent: Jul. 13, 2010

(54) METHOD OF VACCINATION THROUGH SEROTYPE ROTATION

(75) Inventors: Danher Wang, Mt. Pleasant, SC (US); Jianyun Dong, Mt. Pleasant, SC (US)

(73) Assignee: GenPhar, Inc, Mt. Pleasant, SC (US)

( * ) Notice: Subject to any disclaimer, the term of this patent is extended or adjusted under 35 U.S.C. 154(b) by 471 days.

(21) Appl. No.: 10/286,332

(22) Filed: Nov. 1, 2002

(65) Prior Publication Data

US 2004/0185064 A9 Sep. 23, 2004

Related U.S. Application Data

(63) Continuation-in-part of application No. 10/003,035, filed on Nov. 1, 2001, now abandoned, which is a continuation-in-part of application No. PCT/US01/18238, filed on Jun. 4, 2001, which is a continuation-in-part of application No. 09/585,599, filed on Jun. 2, 2000, now Pat. No. 6,544,780.

(51) Int. Cl.
*A61K 67/00* (2006.01)
*C12N 15/00* (2006.01)

(52) U.S. Cl. ................ 424/93.1; 424/228.1; 424/225.1; 424/85.1; 435/320.1

(58) Field of Classification Search .............. 435/320.1, 435/91.4; 432/320.1
See application file for complete search history.

(56) References Cited

U.S. PATENT DOCUMENTS

| | | | | |
|---|---|---|---|---|
| 5,866,131 | A | 2/1999 | Ramshaw et al. | |
| 5,866,136 | A | 2/1999 | Ramshaw et al. | |
| 5,962,311 | A * | 10/1999 | Wickham et al. | 435/320.1 |
| 6,730,507 | B1 * | 5/2004 | Graham et al. | 435/235.1 |
| 6,733,993 | B2 * | 5/2004 | Emini et al. | 435/69.1 |
| 6,787,351 | B2 * | 9/2004 | Chen et al. | 435/320.1 |
| 6,913,922 | B1 * | 7/2005 | Bout et al. | 435/320.1 |
| 7,270,811 | B2 * | 9/2007 | Bout et al. | 424/93.2 |

FOREIGN PATENT DOCUMENTS

| | | |
|---|---|---|
| WO | WO 88/00971 | 2/1988 |
| WO | WO 96/11279 | 4/1996 |
| WO | WO 98/17799 | 4/1998 |
| WO | WO 99/32147 | 7/1999 |
| WO | WO99/43839 | 9/1999 |
| WO | WO 0003029 A2 * | 1/2000 |
| WO | WO 0060106 A1 * | 10/2000 |

OTHER PUBLICATIONS

Moore et al (J. Virol. 2001, vol. 75, No. 13, pp. 5721-5729.*
Bruce et al. J. Gene. Virol. 1999, vol. 80, pp. 2621-2628.*
Mack et al. HumanGene. Ther. 1997, vol. 8, pp. 99-109.*
Mastrangeli et al. Human gene ther. 1996, vol. 7, pp. 79-87.*
Torres et al. Virol. 1995, vol. 213, pp. 503-516.*
Castrlden et al. Human Gene Therapy 1997, vol. 8, pp. 2087-2102.*
Imler J-L: "Adenovirus Vectors As Recombinant Viral Vaccines" Vaccine, Butterworth Scientific, 1995, vol. 13, No. 13, pp. 1143-1151 Guildford, GB.
Cohen Adem D et al: "Modulating the Immune Response to Genetic Immunization" FASEB Journal, Fed. of American Soc. For Experimental Biology, Bethesda, MD., US, Dec. 1998, pp. 1611-1626, vol. 12, No. 15.
Robinson H I: "New Hope For An Aids Vaccine" Nature Reviews, Immunology,Apr. 2002, vol. 2, No. 4, pp. 239-250.
Imler, J.L., "Adenvirus vectors as recombinant viral vaccines." Vaccine, Butterworth Scientific, vol. 13, No. 13, pp. 1143-1151 (1995).
Randrianarison-Jewtoukoff Voahagy et al., "Recombinant advenovirus as vaccines." Bilogicals, vol. 23, No. 2, pp. 146-157 (1995).
Romano Gaetano et al., "Latest developments in gene transfer technology: Achievements, perspectives, and controversies over therapeutic applications." Stem Cells (Miamisburg), vol. 18, No. 1, pp. 19-39 (Jan. 2001).
Ruff, A. et al., "Improved DNA vaccines against Ebola virus." American Journal of Tropical Medicine and Hygiene, vol. 61, No. 3, pp. 330-331 (1999).
Vanderzanden, L. et al., "DNA vaccines expressing either the GP or NP genes of Ebola virus protect mice from lethal challenge." Virology, Academic Press, Orlando, US, vol. 246, No. 1, pp. 134-144 (Jun. 20, 2000).
Xu, L. et al, "Immuniatioan for Ebola virus infection." Nature Medicine, vol. 4, No. 1, pp. 37-42 (Jan. 1998).

* cited by examiner

*Primary Examiner*—Robert Mondesi
*Assistant Examiner*—Bao Qun Li
(74) *Attorney, Agent, or Firm*—Benjamin Aaron Adler

(57) ABSTRACT

The present invention discloses recombinant adenovirus and methods of administration of the virus to a host inorder to elicit an immune response against various pathogens in the host. Specifically, a vaccination method to enhance immunity of the host to the pathogen is disclosed herein. Such a method comprises recombinant adenoviruses expressing viral antigens, where the recombinant adenoviruses are derived from different serotypes or subtypes. Alternatively, the adenoviruses in such a method can also be constructed by modifying the backbone of one of the adenoviruses (e.g. the knob, shaft or fiber regions) so that it is of a serotype that is different from the corresponding region(s) in the backbone of the other recombinant adenovirus.

18 Claims, 97 Drawing Sheets

| | |
|---|---|
| DNA | RNA editing signal<br>——————— TTT TTT T ———————<br>[SEQ ID NO: 1] |
| Unedited RNA | ——————— UUU UUU U ——— UAA ———<br>stop codon<br>[SEQ ID NO: 2] |
| Edited RNA | ——————— UUU UUU ———————<br>-1 frame<br>[SEQ ID NO: 6] |
| Modified DNA | Editing signal deleted<br>——————— TTC TTC ———————<br>[SEQ ID NO: 8] |
| mRNA | ——————— UUC UUC ———————<br>no stop codon until the end of GP<br>[SEQ ID NO: 7] |

FIGURE 12
A.
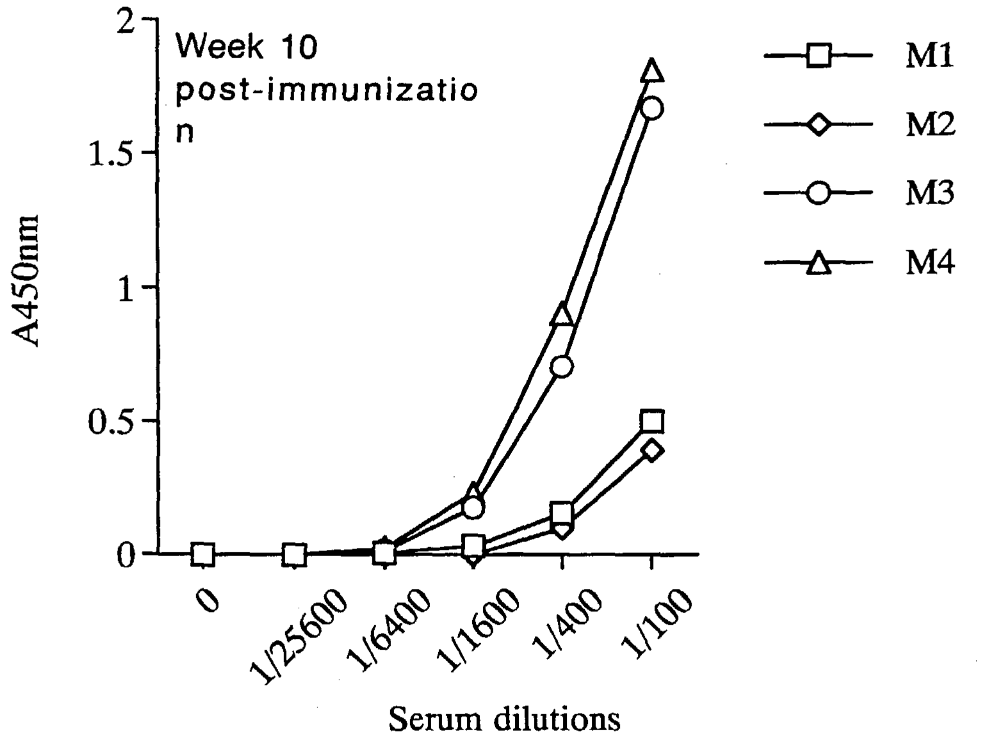
B.
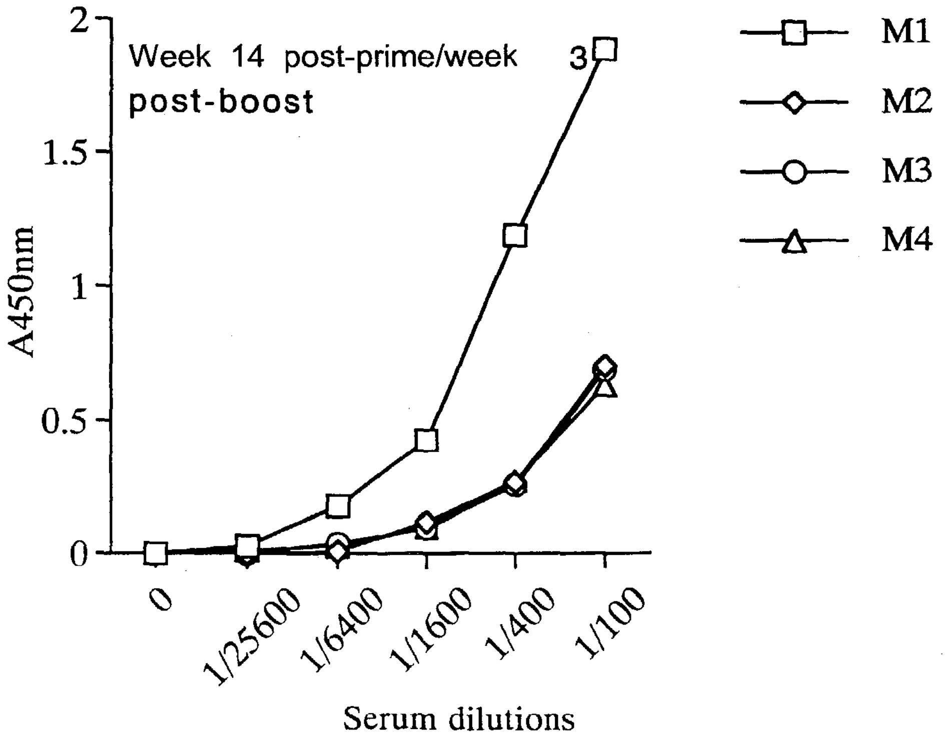

FIGURE 14
Gag-specific IFNγ secreting splenic cells after immunization of mice with Ad(3C, Gag, Env)
A.
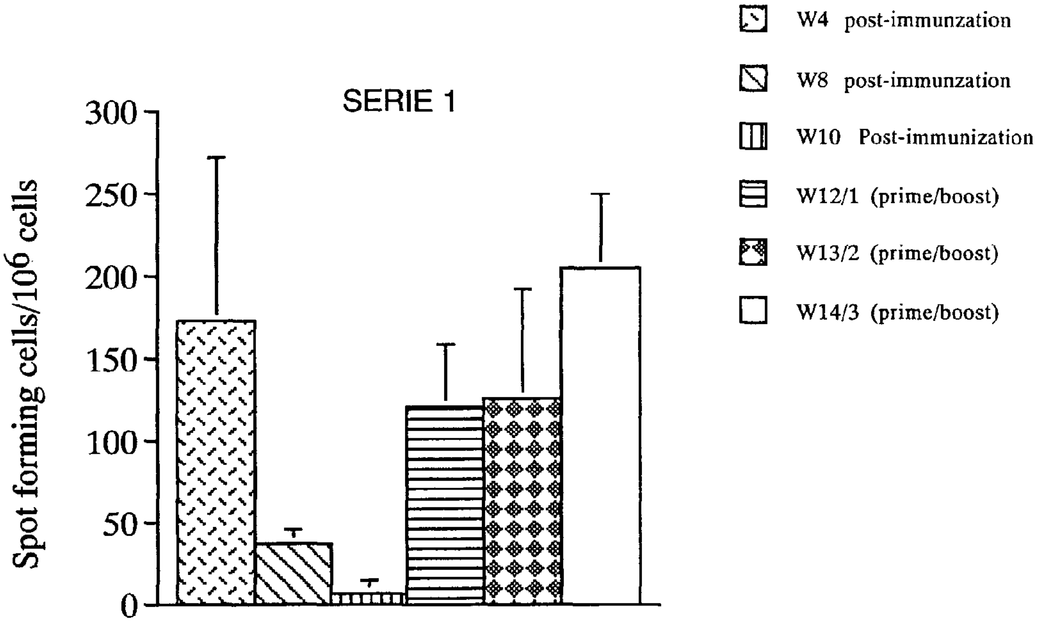
B.
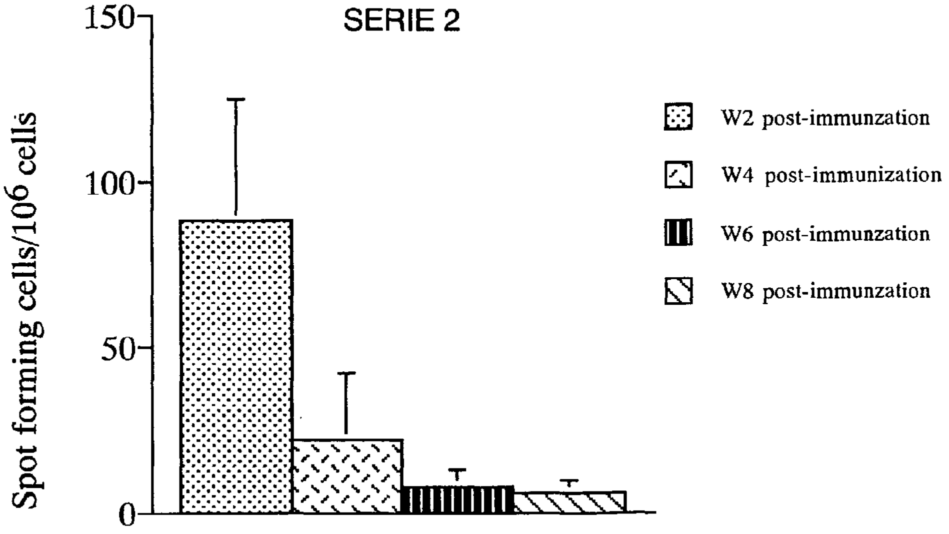

FIGURE 15 L23: ELISPOT for IFNγ secretion: Serie1 spleen cells from mice at week W13/2 (post-prime/boost)
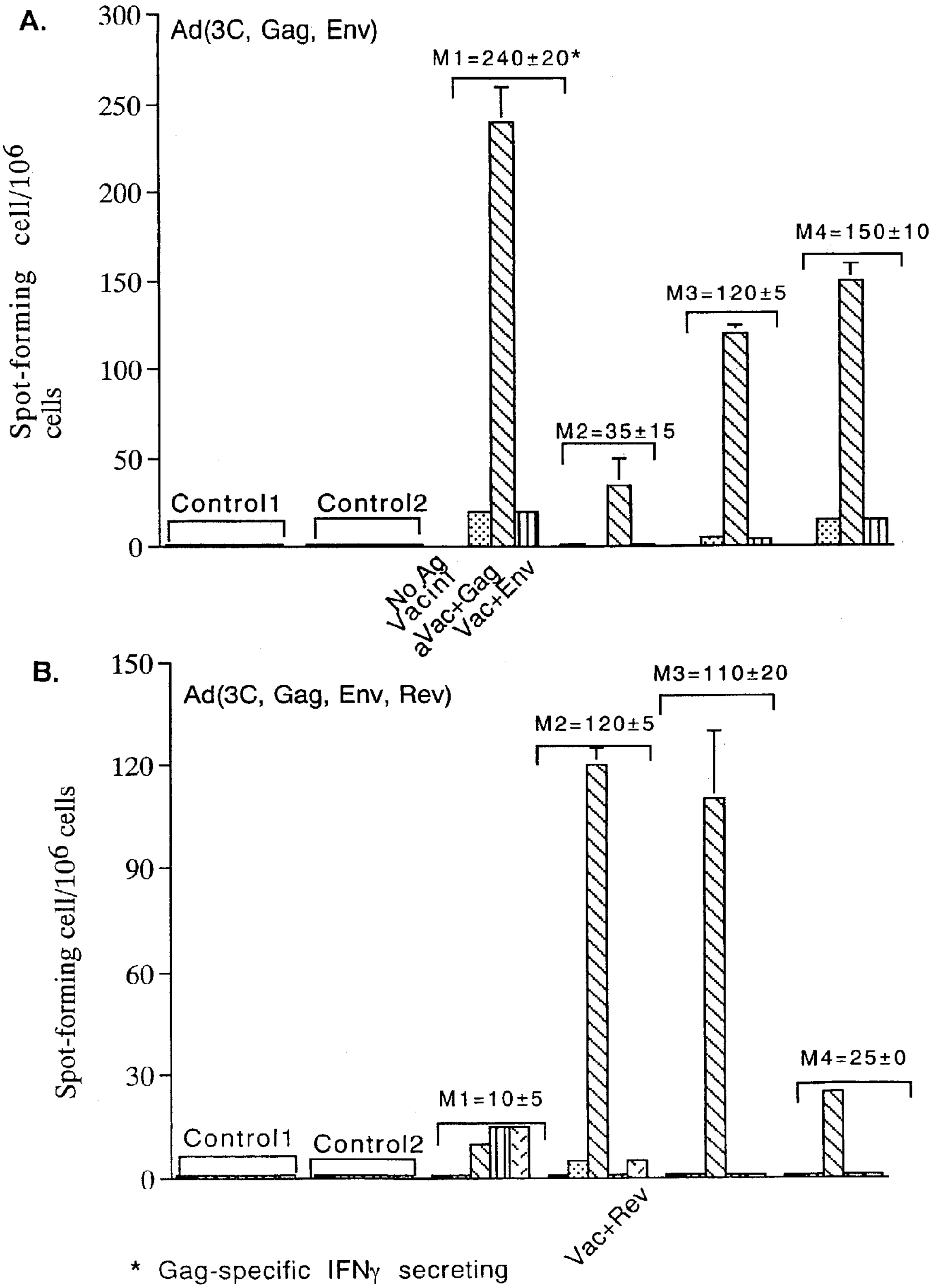
* Gag-specific IFNγ secreting pLAd-E.T.R pRAd.ORF6-IL2 pRAd.ORF6-$E^{m}\Delta C\Delta T^{300}$-G pLAd-3C pRAd.ORF6-$E^m\Delta C\Delta T^{99}$.T.R-G pLAd-$E^m\Delta V_{1,2}\Delta C\Delta T$.T.R-IL2 pRAd.ORF6-G.IL2 pLAd-E$^{III}$ΔC.N pLAd-E$^{m}$ΔCΔT$^{300}$.T pLAd-$E^m$ΔC pRAd.ORF6-$E^m\Delta C$ FIGURE 24
Step 1. Amplification of each individual clade A-G
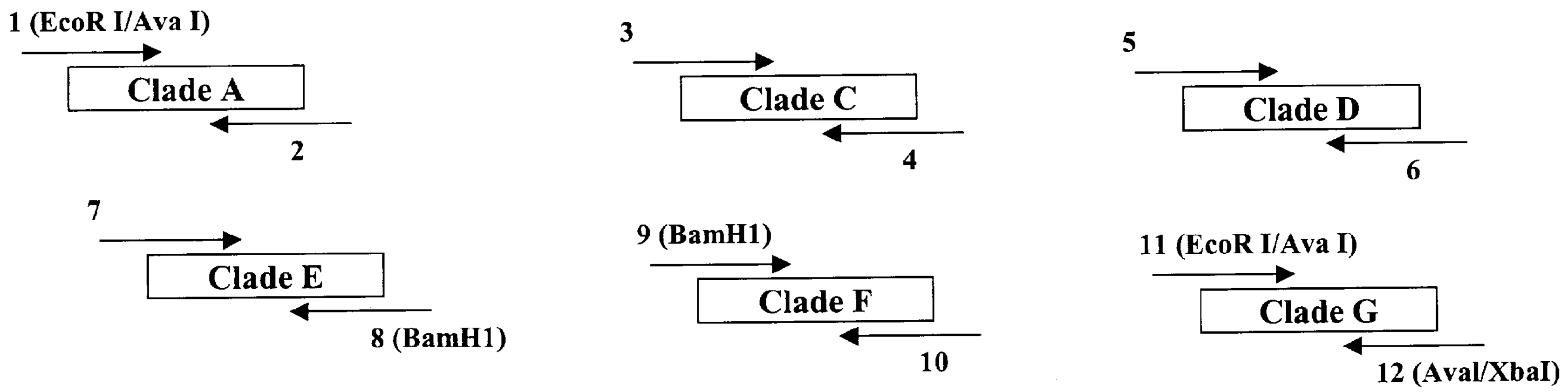
Step 2. Amplification of every two clades AC, DE, FG
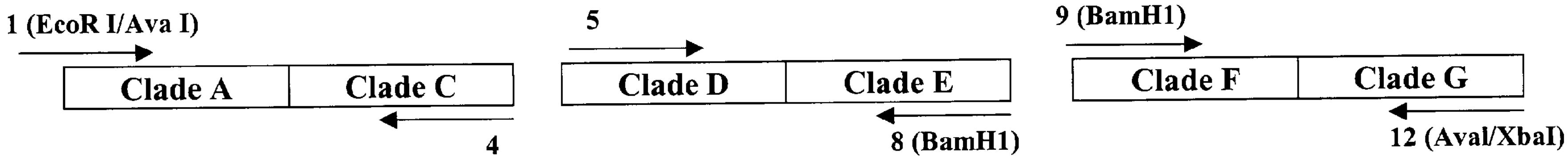

FIGURE 24-cont.
Step 3. Amplification of clades ACDE
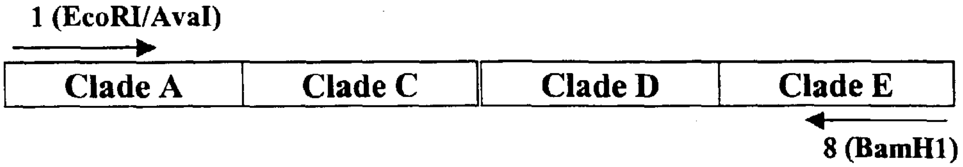
Step 4. Cloning the multi-clades into pSP73 vector
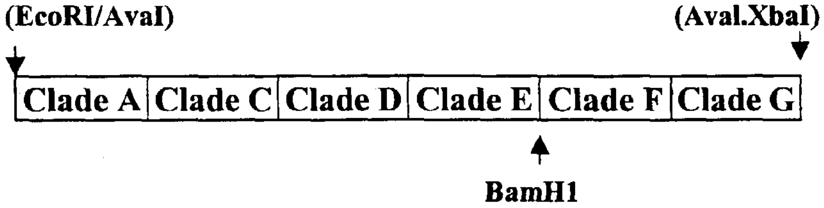
Step 5. Generation of duplicated multi-clades
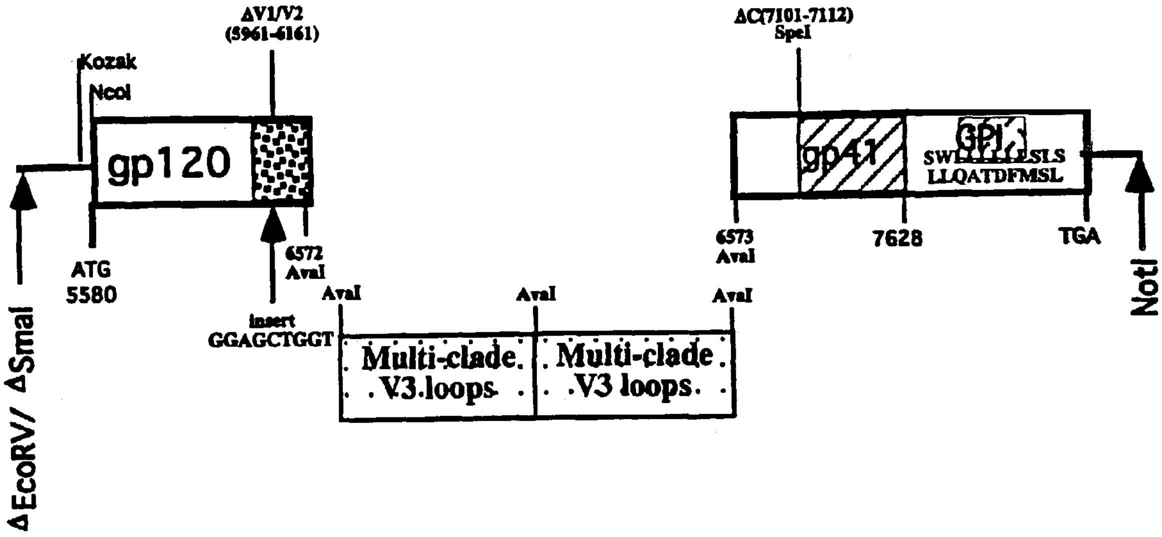

pLAd-$E^{m}$.V3 pRAd.ORF6-p17/p24 pRAd.ORF6-p17/24sec pRAd.ORF6-p17/24MB pRAd.ORF6-p17 pRAd.ORF6-p17sec pRAd.ORF6-p17MB pRAd.ORF6-p24 pRAd.ORF6-p24sec pRAd.ORF6-p24MB

FIGURE 30B-continued
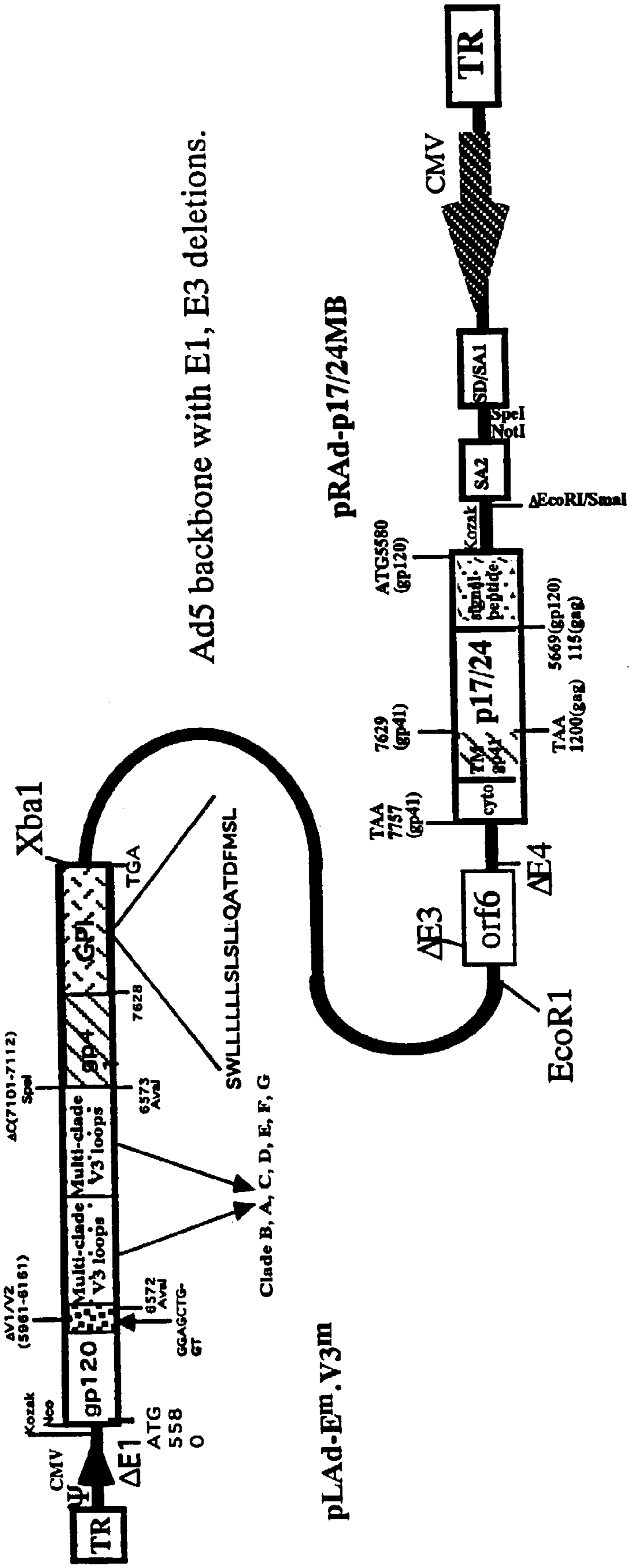

FIGURE 31B-continued
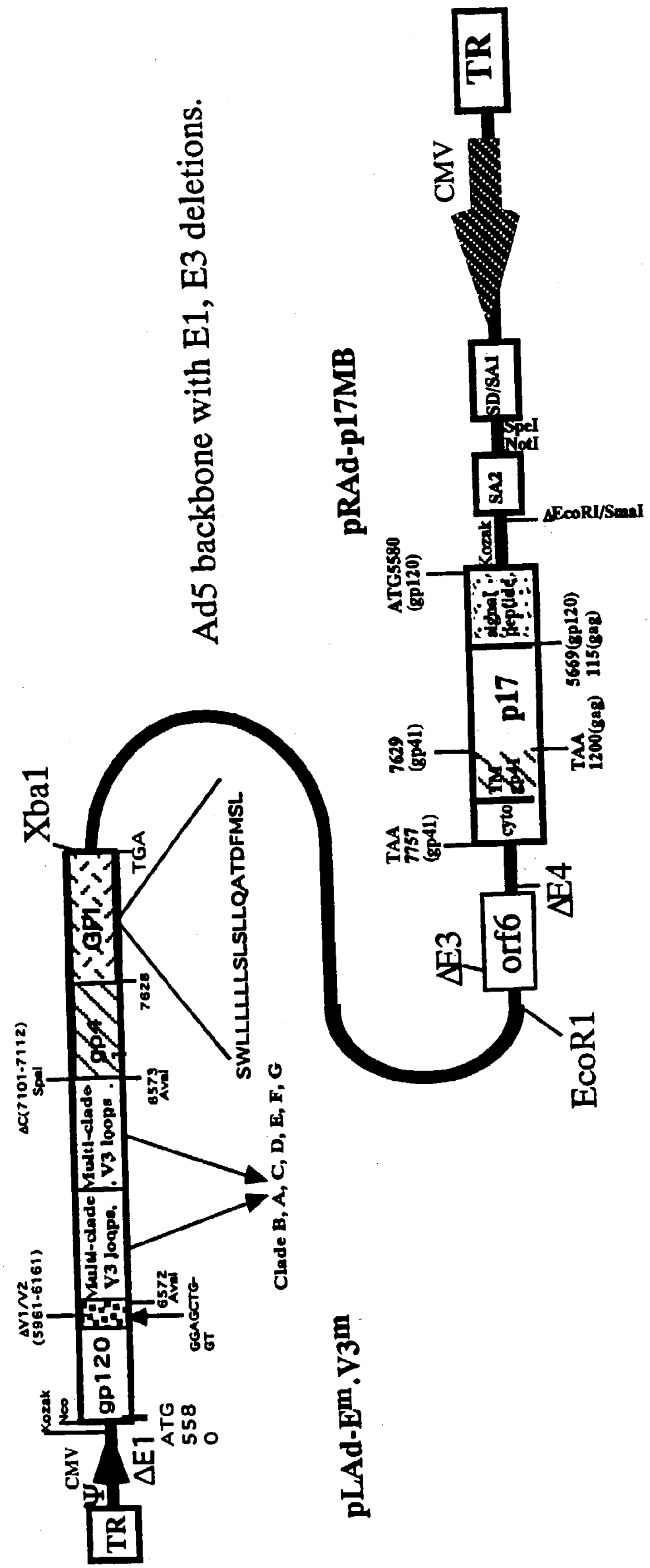

FIGURE 32B-continued
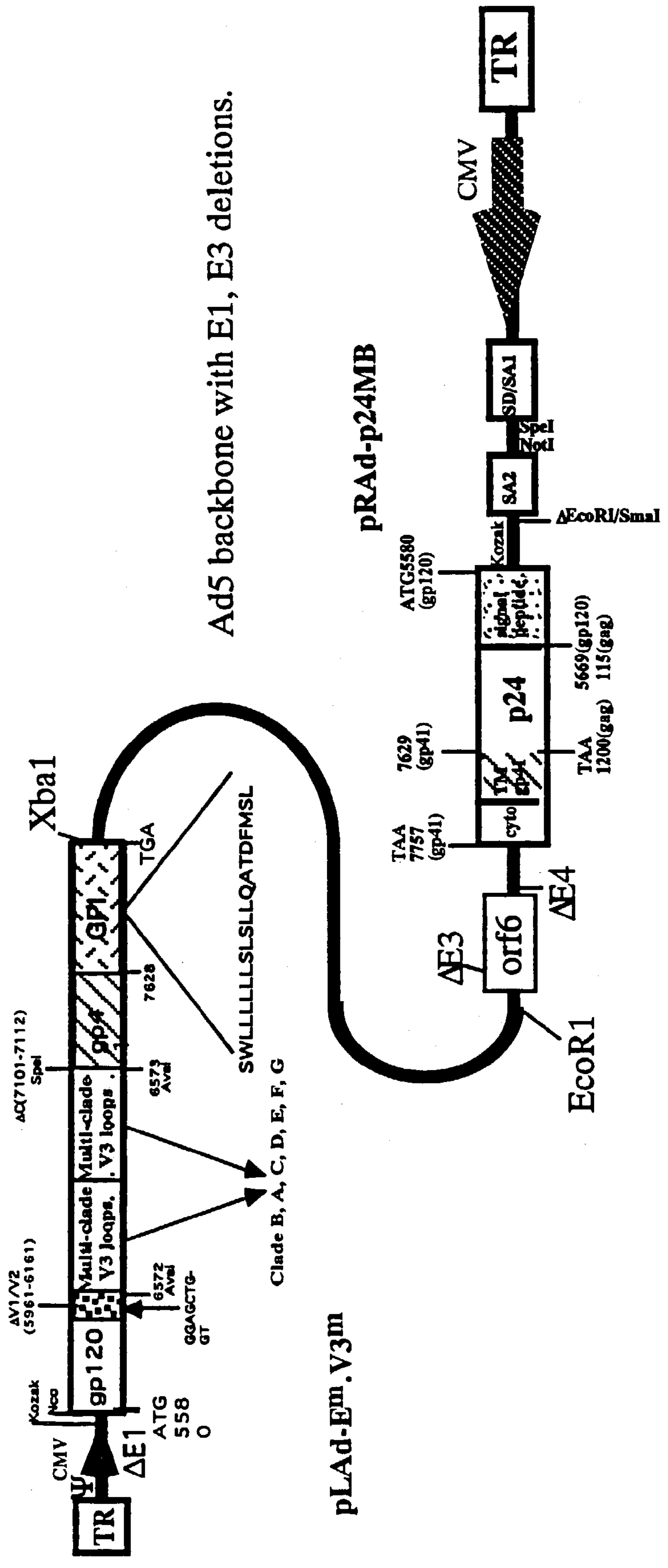

pRAd.ORF6-G.PI pRAd.ORF6-G-PI

SD/SA1.2.3 vector

FIGURE 38

DNA Sequence of Env/Tat/Rev from BH10 clone [SEQ ID NO: 14]:

Gaattctgcaacaactgctgtttatccattttcagaattgggtgtcgacat
EcoRI
agcagaataggcgttactcgacagaggagagcaagaaatggagccagtagatcctagactagagccctgga
agcatccaggaagtcagcctaaaactgcttgtaccaattgctattgtaaaaagtgttgctttcattgccaa
gtttgtttcataacaaaagccttaggcatctcctatggcaggaagaagcggagacagcgacgaagacctcc
tcaaggcagtcagactcatcaagtttctctatcaaagcagtaagtagtacatgtaatgcaacctatacaaa
tagcaatagtagcattagtagtagcaataataatagcaatagttgtgtggtccatagtaatcatagaatat
aggaaaatattaagacaaagaaaaatagacaggttaattgatagactaatagaaagagcagaagacagtgg
caatgagagtgaaggagaaatatcagcacttgtggagatgggggtggagatggggcaccatgctccttggg
atgttgatgatctgtagtgctacagaaaaattgtgggtcacagtctattatggggtacctgtgtggaagga
agcaaccaccactctattttgtgcatcagatgctaaagcatatgatacagaggtacataatgtttgggcca
cacatgcctgtgtacccacagaccccaacccacaagaagtagtattggtaaatgtgacagaaaattttaac
atgtggaaaaatgacatggtagaacagatgcatgaggatataatcagtttatgggatcaaagcctaaagcc
atgtgtaaaattaaccccactctgtgttagtttaaagtgcactgatttgaagaatgatactaataccaata
gtagtagcgggagaatgataatggagaaaggagagataaaaaactgctctttcaatatcagcacaagcata
agaggtaaggtgcagaaagaatatgcatttttttataaacttgatataataccaatagataatgatactac
cagctatacgttgacaagttgtaacacctcagtcattacacaggcctgtccaaaggtatcctttgagccaa
ttcccatacattattgtgccccggctggttttgcgattctaaaatgtaataataagacgttcaatggaaca
ggaccatgtacaaatgtcagcacagtacaatgtacacatggaattaggccagtagtatcaactcaactgct
gttaaatggcagtctggcagaagaagaggtagtaattagatctgccaatttcacagacaatgctaaaacca
taatagtacagctgaaccaatctgtagaaattaattgtacaagacccaacaacaatacaagaaaaagtatc
cgtatccagagaggaccagggagagcatttgttacaataggaaaaataggaaatatgagacaagcacattg
taacattagtagagcaaaatggaataacactttaaaacagatagatagcaaattaagagaacaatttggaa
ataataaaacaataatctttaagcagtcctcaggaggggacccagaaattgtaacgcacagttttaattgt
ggaggggaatttttctactgtaattcaacacaactgtttaatagtacttggtttaatagtacttggagta
ctaaagggtcaaataacactgaaggaagtgacacaatcaccctcccatgcagaataaaacaaattataaac
atgtggcaggaagtaggaaaagcaatgtatgcccctcccatcagtggacaaattagatgttcatcaaatat
tacagggctgctattaacaagagatggtggtaatagcaacaatgagtccgagatcttcagacctggaggag
gagatatgagggacaattggagaagtgaattatataaatataaagtagtaaaaattgaaccattaggagta
gcacccaccaaggcaaagagaagagtggtgcagagagaaaaaagagcagtgggaataggagctttgttcct
tgggttcttgggagcagcaggaagcactatgggcgcagcgtcaatgacgctgacggtacaggccagacaat
tattgtctggtatagtgcagcagcagaacaatttgctgagggctattgaggcgcaacagcatctgttgcaa
ctcacagtctggggcatcaagcagctccaggcaagaatcctggctgtggaaagatacctaaaggatcaaca
gctcctggggatttggggttgctctggaaaactcatttgcaccactgctgtgccttggaatgctagttgga
gtaataaatctctggaacagatttggaataacatgacctggatggagtgggacagagaaattaacaattac
acaagcttaatacactccttaattgaagaatcgcaaaaccagcaagaaaagaatgaacaagaattattgga
attagataaatgggcaagtttgtggaattggtttaacataacaaattggctgtggtatataaaattattca
taatgatagtaggaggcttggtaggtttaagaatagtttttgctgtactttctgtagtgaatagagttagg
cagggatattcaccattatcgtttcagacccacctcccaatcccgaggggacccgacaggcccgaaggaat
agaagaagaaggtggagagagagacagagacagatccattcgattagtgaacggatccttagcacttatct
gggacgatctgcggagcctgtgcctcttcagctaccaccgcttgagagacttactcttgattgtaacgagg
attgtggaacttctgggacgcagggggtgggaagccctcaaatattggtggaatctcctacagtattggag
tcaggagctaaagaatagtgctgttagcttgctcaatgccacagctatagcagtagctgaggggacagata
gggttatagaagtagtacaaggagcttatagagctattcgccacatacctagaagaataagacagggcttg
gaaaggattttgctataagatgggtggcaagtggtcaaaaagtagtgtggttggatggcctgctgtaaggg
aaagaatgagacgagctgagccagcagcagatggggtgggagcagcatctcgag
XhoI

FIGURE 39

DNA Sequence of IL-2ΔX [SEQ ID NO: 15]:

```
Tcactctctttaatcactactcacagtaacctcaactcctgccacaatgta
caggatgcaactcctgtcttgcattgcactaagtcttgcacttgtcacaaa
cagtgcacctacttcaagttctacaaagaaaacacagctacaactggagca
tttactgctggatttacagatgattttgaatggaattaataattacaagaa
tcccaaactcaccaggatgctcacatttaagttttacatgcccaagaaggc
cacagaactgaaacatcttcagtgtcttgaagaagaactcaaacctctgga
                     ΔXbaI (cta → ctt)
ggaagtgctaaatttagctcaaagcaaaaactttcacttaagacccaggga
cttaatcagcaatatcaacgtaatagttctggaactaaagggatctgaaac
aacattcatgtgtgaatatgctgatgagacagcaaccattgtagaatttct
gaacagatggattaccttttgtcaaagcatcatctcaacactaacttga
```

FIGURE 40

DNA Sequence of Env$^{m}$ΔCΔT$^{300}$ (HIV strain BH10) [SEQ ID NO: 16]:

Gaattcgccaccatgggagtgaaggagaaatatcagcacttgtggagatg
EcoRI Kozak NcoI
ggggtggagatggggcaccatgctccttgggatgttgatgatctgtagtgctacagaaaaa
ttgtgggtcacagtctattatggggtacctgtgtggaaggaagcaaccaccactctatttt
gtgcatcagatgctaaagcatatgatacagaggtacataatgtttgggccacacatgcctg
tgtacccacagaccccaacccacaagaagtagtattggtaaatgtgacagaaaattttaac
atgtggaaaaatgacatggtagaacagatgcatgaggatataatcagtttatgggatcaaa
gcctaaagccatgtgtaaaattaaccccactctgtgttagtttaaagtgcactgatttgaa
gaatgatactaataccaatagtagtagcgggagaatgataatggagaaaggagagataaaa
aactgctctttcaatatcagcacaagcataagaggtaaggtgcagaaagaatatgcatttt
tttataaacttgatataataccaatagataatgatactaccagctatacgttgacaagttg
taacacctcagtcattacacaggcctgtccaaaggtatcctttgagccaattcccatacat
tattgtgccccggctggttttgcgattctaaaatgtaataataagacgttcaatggaacag
gaccatgtacaaatgtcagcacagtacaatgtacacatggaattaggccagtagtatcaac
tcaactgctgttaaatggcagtctggcagaagaagaggtagtaattagatctgccaatttc
acagacaatgctaaaaccataatagtacagctgaaccaatctgtagaaattaattgtacaa
gacccaacaacaatacaagaaaaagtatccgtatccagagaggaccagggagagcatttgt
tacaataggaaaaataggaaatatgagacaagcacattgtaacattagtagagcaaaatgg
aataacactttaaaacagatagatagcaaattaagagaacaatttggaaataataaaacaa
taatctttaagcagtcctcaggaggggacccagaaattgtaacgcacagttttaattgtgg
aggggaatttttctactgtaattcaacacaactgtttaatagtacttggtttaatagtact
tggagtactaaagggtcaaataacactgaaggaagtgacacaatcaccctcccatgcagaa
taaaacaaattataaacatgtggcaggaagtaggaaaagcaatgtatgcccctcccatcag
tggacaaattagatgttcatcaaatattacagggctgctattaacaagagatggtggtaat
agcaacaatgagtccgagatcttcagacctggaggaggagatatgagggacaattggagaa
gtgaattatataaatataaagtagtaaaaattgaaccattaggagtagcacccaccaaggc
aaagagaagagtggtgcagACTAGTgcagtgggaataggagctt
ΔCleavage site(agagaaaaaaga)→SpeI
tgttccttgggttcttgggagcagcaggaagcactatgggcgcagcgtcaatgacgctgac
ggtacaggccagacaattattgtctggtatagtgcagcagcagaacaatttgctgagggct
attgaggcgcaacagcatctgttgcaactcacagtctggggcatcaagcagctccaggcaa
gaatcctggctgtggaaagatacctaaaggatcaacagctcctggggatttggggttgctc
tggaaaactcatttgcaccactgctgtgccttggaatgctagttggagtaataaatctctg
gaacagatttggaataacatgacctggatggagtgggacagagaaattaacaattacacaa
gcttaatacactccttaattgaagaatcgcaaaaccagcaagaaaagaatgaacaagaatt
attggaattagataaatgggcaagtttgtggaattggtttaacataacaaattggctgtgg
tatataaaattattcataatgatagtaggaggcttggtaggtttaagaatagtttttgctg
tactttctgtagtgaatagagttaggcagggatattcaccattatcgtttcagacccacct
cccaatcccgaggggacccgacaggcccgaaggaatagaagaagaaggtggagagagagac
agagacagatccattcgattagtgaacggatccttagcacttatctggtaa

FIGURE 41A

DNA Sequence of Full length HIV-1 Gag [SEQ ID NO: 17]:

ggctagaaggagagaggatgggtgcgagagcgtcagtattaagcgggggag
aattagatcgatgggaaaaaattcggttaaggccagggggaaagaaaaaat
ataaattaaaacatatagtatgggcaagcagggagctagaacgactacaac
catcccttcagacaggatcagaagaacttagatcattatataatacagtag
caaccctctattgtgtgcatcaaaggatagagataaaagacaccaaggaag
ctttagacaagatagaggaagagcaaaacaaaagtaagaaaaaagcacagc
aagcagcagctgacacaggacacagcagtcaggtcagccaaaattaccta
tagtgcagaacatccaggggcaaatggtacatcaggccatatcacctagaa
ctttaaatgcatgggtaaaagtagtagaagagaaggctttcagcccagaag
taatacccatgttttcagcattatcagaaggagccaccccacaagatttaa
acaccatgctaaacacagtggggggacatcaagcagccatgcaaatgttaa
aagagaccatcaatgaggaagctgcagaatgggatagagtacatccagtgc
atgcagggcctattgcaccaggccagatgagagaaccaaggggaagtgaca
tagcaggaactactagtacccttcaggaacaaataggatggatgacaaata
atccacctatcccagtaggagaaatttataaaagatggataatcctgggat
taaataaaatagtaagaatgtatagccctaccagcattctggacataagac
aaggaccaaaagaaccttttagagactatgtagaccggttctataaaactc
taagagccgagcaagcttcacaggaggtaaaaaattggatgacagaaacct
tgttggtccaaaatgcgaacccagattgtaagactattttaaaagcattgg
gaccagcggctacactagaagaaatgatgacagcatgtcagggagtaggag
gacccggccataaggcaagagttttggctgaagcaatgagccaagtaacaa
atacagctaccataatgatgcagagaggcaattttaggaaccaaagaaaga
tggttaagtgtttcaattgtggcaaagaagggcacacagccagaaattgca
gggcccctaggaaaaagggctgttggaaatgtggaaaggaaggacaccaaa
tgaaagattgtactgagagacaggctaattttttagggaagatctggcctt
cctacaagggaaggccagggaatttcttcagagcagaccagagccaacag
ccccaccatttcttcagagcagaccagagccaacagccccaccagaagaga
gcttcaggtctggggtagagacaacaactcccccctcagaagcaggagccga
tagacaaggaactgtatcctttaacttccctcagatcactctttggcaacg
acccctcgtcacaataa

FIGURE 41B

Amino Acid Sequence of HIV-1 (Strain BH10) Gag [SEQ ID NO: 18]:

| | | | | | | | | | | | | | | | | | |
|---|---|---|---|---|---|---|---|---|---|---|---|---|---|---|---|---|---|
| M | G | A | R | A | S | V | L | S | G | G | E | L | D | R | W | E | K |
| I | R | L | R | P | G | G | K | K | K | Y | K | L | K | H | I | V | W |
| A | S | R | E | L | E | R | L | Q | P | S | L | Q | T | G | S | E | E |
| L | R | S | L | Y | N | T | V | A | T | L | Y | C | V | H | Q | R | I |
| E | I | K | D | T | K | E | A | L | D | K | I | E | E | E | Q | N | K |
| S | K | K | K | A | Q | Q | A | A | A | D | T | G | H | S | S | Q | V |
| S | Q | N | Y | P | I | V | Q | N | I | Q | G | Q | M | V | H | Q | A |
| I | S | P | R | T | L | N | A | W | V | K | V | V | E | E | K | A | F |
| S | P | E | V | I | P | M | F | S | A | L | S | E | G | A | T | P | Q |
| D | L | N | T | M | L | N | T | V | G | G | H | Q | A | A | M | Q | M |
| L | K | E | T | I | N | E | E | A | A | E | W | D | R | V | H | P | V |
| H | A | G | P | I | A | P | G | Q | M | R | E | P | R | G | S | D | I |
| A | G | T | T | S | T | L | Q | E | Q | I | G | W | M | T | N | N | P |
| P | I | P | V | G | E | I | Y | K | R | W | I | I | L | G | L | N | K |
| I | V | R | M | Y | S | P | T | S | I | L | D | I | R | Q | G | P | K |
| E | P | F | R | D | Y | V | D | R | F | Y | K | T | L | R | A | E | Q |
| A | S | Q | E | V | K | N | W | M | T | E | T | L | L | V | Q | N | A |
| N | P | D | C | K | T | I | L | K | A | L | G | P | A | A | T | L | E |
| E | M | M | T | A | C | Q | G | V | G | G | P | G | H | K | A | R | V |
| L | A | E | A | M | S | Q | V | T | N | T | A | T | I | M | M | Q | R |
| G | N | F | R | N | Q | R | K | M | V | K | C | F | N | C | G | K | E |
| G | H | T | A | R | N | C | R | A | P | R | K | K | G | C | W | K | C |
| G | K | E | G | H | Q | M | K | D | C | T | E | R | Q | A | N | F | L |
| G | K | I | W | P | S | Y | K | G | R | P | G | N | F | L | Q | S | R |
| P | E | P | T | A | P | P | F | L | Q | S | R | P | E | P | T | A | P |
| P | E | E | S | F | R | S | G | V | E | T | T | T | P | P | Q | K | Q |
| E | P | I | D | K | E | L | Y | P | L | T | S | L | R | S | L | F | G |
| N | D | P | S | S | Q | * | | | | | | | | | | | |

FIGURE 42

DNA Sequence of $E^{m}\Delta C\Delta T^{99}$.T.R (HIV strain pNL4-3) [SEQ ID NO: 19]:

Gaattctgcaacaactgctgtttatccatttcagaattgggtgtcgacatag
EcoRI
cagaataggcgttactcgacagaggagagcaagaaatggagccagtagatcctagactagagccctggaagca
tccaggaagtcagcctaaaactgcttgtaccaattgctattgtaaaaagtgttgctttcattgccaagtttgt
ttcatgacaaaagccttaggcatctcctatggcaggaagaagcggagacagcgacgaagagctcatcagaaca
gtcagactcatcaagcttctctatcaaagcagtaagtagtacatgtaatgcaacctataatagtagcaatagt
agcattagtagtagcaataataatagcaatagttgtgtggtccatagtaatcatagaatataggaaaatatta
agacaaagaaaaatagacaggttaattgatagactaatagaaagagcagaagacagtggcaatgagagtgaag
gagaagtatcagcacttgtggagatggggtggaaatggggcaccatgctccttgggatattgatgatctgta
gtgctacagaaaaattgtgggtcacagtctattatggggtacctgtgtggaaggaagcaaccaccactctatt
ttgtgcatcagatgctaaagcatatgatacagaggtacataatgtttgggccacacatgcctgtgtacccaca
gaccccaacccacaagaagtagtattggtaaatgtgacagaaaattttaacatgtggaaaaatgacatggtag
aacagatgcatgaggatataatcagtttatgggatcaaagcctaaagccatgtgtaaaattaaccccactctg
tgttagtttaaagtgcactgatttgaagaatgatactaataccaatagtagtagcgggagaatgataatggag
aaaggagagataaaaaactgctctttcaatatcagcacaagcataagagataaggtgcagaaagaatatgcat
tcttttataaacttgatatagtaccaatagataatacca
gctataggttgataagttgtaacacctcagtcattacacaggcctgtccaaaggtatcctttgagccaattcc
catacattattgtgccccggctggttttgcgattctaaaatgtaataataagacgttcaatggaacaggacca
tgtacaaatgtcagcacagtacaatgtacacatggaatcaggccagtagtatcaactcaactgctgttaaatg
gcagtctagcagaagaagatgtagtaattagatctgccaatttcacagacaatgctaaaaccataatagtaca
gctgaacacatctgtagaaattaattgtacaagacccaacaacaatacaagaaaaagtatccgtatccagagg
ggaccagggagagcatttgttacaataggaaaaataggaaatatgagacaagcacattgtaacattagtagag
caaaatggaatgccactttaaaacagatagctagcaaattaagagaacaatttggaaataataaaacaataat
ctttaagcaatcctcaggaggggacccagaaattgtaacgcacagttttaattgtggaggggaatttttctac
tgtaattcaacacaactgtttaatagtacttggtttaatagtacttggagtactgaagggtcaataacactg
aaggaagtgacacaatcacactcccatgcagaataaaacaatttataaacatgtggcaggaagtaggaaaagc
aatgtatgcccctcccatcagtggacaaattagatgttcatcaaatattactgggctgctattaacaagagat
ggtggtaataacaacaatgggtccgagatcttcagacctggaggaggcgatatgagggacaattggagaagtg
aattatataaatataaagtagtaaaaattgaaccattaggagtagcacccaccaaggcaaagagaagagtggt
gcagACTAGTgcagtgggaataggagctttgttccttg
ΔCleavage site(agagaaaaaaga)→SpeI
ggttcttgggagcagcaggaagcactatgggctgcacgtcaatgacgctgacggtacaggccagacaattatt
gtctgatatagtgcagcagcagaacaatttgctgagggctattgaggcgcaacagcatctgttgcaactcaca
gtctggggcatcaaacagctccaggcaagaatcctggctgtggaaagatacctaaaggatcaacagctcctgg
ggatttggggttgctctggaaaactcatttgcaccactgctgtgccttggaatgctagttggagtaataaatc
tctggaacagatttggaataacatgacctggatggagtgggacagagaaattaacaattacacaagcttaata
cactccttaattgaagaatcgcaaaaccagcaagaaaagaatgaacaagaattattggaattagataaatggg
caagtttgtggaattggtttaacataacaaattggctgtggtatataaaattattcataatgatagtaggagg
cttggtaggtttaagaatagtttttgctgtactttctatagtgaatagagttaggcagggatattcaccatta
tcgtttcagacccacctcccaatcccgaggggacccgacaggcccgaaggaatagaagaagaaggtggagaga
gagacagagacagatccattcgattagtgaacggatccttagcacttatctgggacgatctgcggagcctgtg
cctcttcagctaccaccgcttgagagacttactcttgattgtaacgaggattgtggaacttctgggacgcagg
gggtgggaagccctcaaatattggtggaatctcctacagtattggagtcaggaactaaagaatagtgctgtta
acttgctcaatgccacagccatagcagtagctgagtaa

FIGURE 43

DNA Sequence of $E^{m}\Delta V_{12}\Delta C\Delta T^{99}$.T.R (Strain pNL4-3) [SEQ ID NO: 20]:

Gaattctgcaacaactgctgtttatccatttcagaattgggtgtcgacatag
EcoRI
Cagaataggcgttactcgacagaggagagcaagaaatggagccagtagatcctagactagagccctggaagca
tccaggaagtcagcctaaaactgcttgtaccaattgctattgtaaaaagtgttgctttcattgccaagtttgt
ttcatgacaaaagccttaggcatctcctatggcaggaagaagcggagacagcgacgaagagctcatcagaaca
gtcagactcatcaagcttctctatcaaagcagtaagtagtacatgtaatgcaacctataatagtagcaatagt
agcattagtagtagcaataataatagcaatagttgtgtggtccatagtaatcatagaatataggaaaatatta
agacaaagaaaaatagacaggttaattgatagactaatagaaagagcagaagacagtggcaatgagagtgaag
gagaagtatcagcacttgtggagatggggtggaaatggggcaccatgctccttgggatattgatgatctgta
gtgctacagaaaaattgtgggtcacagtctattatggggtacctgtgtggaaggaagcaaccaccactctatt
ttgtgcatcagatgctaaagcatatgatacagaggtacataatgtttgggccacacatgcctgtgtacccaca
gacccaacccacaagaagtagtattggtaaatgtgacagaaaattttaacatgtggaaaaatgacatggtag
aacagatgcatgaggatataatcagtttatgggatcaaagcctaaagccatgtgtaaaattaaccccactctg
tgtt ΔV1 and V2 loops
Agttgtaacacctcagtcattacacaggcctgtccaaaggtatcctttgagccaattcccatacattattgtg
ccccggctggttttgcgattctaaaatgtaataataagacgttcaatggaacaggaccatgtacaaatgtcag
cacagtacaatgtacacatggaatcaggccagtagtatcaactcaactgctgttaaatggcagtctagcagaa
gaagatgtagtaattagatctgccaatttcacagacaatgctaaaaccataatagtacagctgaacacatctg
tagaaattaattgtacaagacccaacaacaatacaagaaaaagtatccgtatccagaggggaccagggagagc
atttgttacaataggaaaaataggaaatatgagacaagcacattgtaacattagtagagcaaaatggaatgcc
actttaaaacagatagctagcaaattaagagaacaatttggaaataataaaacaataatctttaagcaatcct
caggaggggacccagaaattgtaacgcacagttttaattgtggaggggaatttttctactgtaattcaacaca
actgtttaatagtacttggtttaatagtacttggagtactgaagggtcaaataacactgaaggaagtgacaca
atcacactcccatgcagaataaaacaatttataaacatgtggcaggaagtaggaaaagcaatgtatgcccctc
ccatcagtggacaaattagatgttcatcaaatattactgggctgctattaacaagagatggtggtaataacaa
caatgggtccgagatcttcagacctggaggaggcgatatgagggacaattggagaagtgaattatataaatat
aaagtagtaaaaattgaaccattaggagtagcacccaccaaggcaaagagaagagtggtgcagACTAGTgcag
tgggaataggagctttgttccttgggttcttgggagca
ΔCleavage site(agagaaaaaaga)→SpeI
gcaggaagcactatgggctgcacgtcaatgacgctgacggtacaggccagacaattattgtctgatatagtgc
agcagcagaacaatttgctgagggctattgaggcgcaacagcatctgttgcaactcacagtctggggcatcaa
acagctccaggcaagaatcctggctgtggaaagatacctaaaggatcaacagctcctggggatttggggttgc
tctggaaaactcatttgcaccactgctgtgccttggaatgctagttggagtaataaatctctggaacagattt
ggaataacatgacctggatggagtgggacagagaaattaacaattacacaagcttaatacactccttaattga
agaatcgcaaaaccagcaagaaaagaatgaacaagaattattggaattagataaatgggcaagtttgtggaat
tggtttaacataacaaattggctgtggtatataaaattattcataatgatagtaggaggcttggtaggtttaa
gaatagtttttgctgtactttctatagtgaatagagttaggcagggatattcaccattatcgtttcagaccca
cctcccaatcccgaggggacccgacaggcccgaaggaatagaagaagaaggtggagagagagacagagacaga
tccattcgattagtgaacggatccttagcacttatctgggacgatctgcggagcctgtgcctcttcagctacc
accgcttgagagacttactcttgattgtaacgaggattgtggaacttctgggacgcagggggtgggaagccct
caaatattggtggaatctcctacagtattggagtcaggaactaaagaatagtgctgttaacttgctcaatgcc
acagccatagcagtagctgagtaa

FIGURE 44

DNA Sequence of Env$^{m}$ΔC.T.R.N (Strain BH10) [SEQ ID NO: 21]:

Gaattctgcaacaactgctgtttatccattttcagaattgggtgtcgacat
EcoRI
agcagaataggcgttactcgacagaggagagcaagaaatggagccagtagatcctagactagagccctgga
agcatccaggaagtcagcctaaaactgcttgtaccaattgctattgtaaaaagtgttgctttcattgccaa
gtttgtttcataacaaaagccttaggcatctcctatggcaggaagaagcggagacagcgacgaagacctcc
tcaaggcagtcagactcatcaagtttctctatcaaagcagtaagtagtacatgtaatgcaacctatacaaa
tagcaatagtagcattagtagtagcaataataatagcaatagttgtgtggtccatagtaatcatagaatat
aggaaaatattaagacaaagaaaaatagacaggttaattgatagactaatagaaagagcagaagacagtgg
caatgagagtgaaggagaaatatcagcacttgtggagatggggtggagatggggcaccatgctccttggg
atgttgatgatctgtagtgctacagaaaaattgtgggtcacagtctattatggggtacctgtgtggaagga
agcaaccaccactctattttgtgcatcagatgctaaagcatatgatacagaggtacataatgtttgggcca
cacatgcctgtgtacccacagaccccaacccacaagaagtagtattggtaaatgtgacagaaaattttaac
atgtggaaaaatgacatggtagaacagatgcatgaggatataatcagtttatgggatcaaagcctaaagcc
atgtgtaaaattaaccccactctgtgttagtttaaagtgcactgatttgaagaatgatactaataccaata
gtagtagcgggagaatgataatggagaaaggagagataaaaaactgctctttcaatatcagcacaagcata
agaggtaaggtgcagaaagaatatgcatttttttataaacttgatataataccaatagataatgatactac
cagctatacgttgacaagttgtaacacctcagtcattacacaggcctgtccaaaggtatcctttgagccaa
ttcccatacattattgtgccccggctggttttgcgattctaaaatgtaataataagacgttcaatggaaca
ggaccatgtacaaatgtcagcacagtacaatgtacacatggaattaggccagtagtatcaactcaactgct
gttaaatggcagtctggcagaagaagaggtagtaattagatctgccaatttcacagacaatgctaaaacca
taatagtacagctgaaccaatctgtagaaattaattgtacaagacccaacaacaatacaagaaaaagtatc
cgtatccagagaggaccagggagagcatttgttacaataggaaaaataggaaatatgagacaagcacattg
taacattagtagagcaaaatggaataacactttaaaacagatagatagcaaattaagagaacaatttggaa
ataataaaacaataatctttaagcagtcctcaggaggggacccagaaattgtaacgcacagttttaattgt
ggaggggaatttttctactgtaattcaacacaactgtttaatagtacttggtttaatagtacttggagtac
taaagggtcaaataacactgaaggaagtgacacaatcaccctcccatgcagaataaaacaaattataaaca
tgtggcaggaagtaggaaaagcaatgtatgcccctcccatcagtggacaaattagatgttcatcaaatatt
acagggctgctattaacaagagatggtggtaatagcaacaatgagtccgagatcttcagacctggaggagg
agatatgagggacaattggagaagtgaattatataaatataaagtagtaaaaattgaaccattaggagtag
cacccaccaaggcaaagagaagagtggtgcagACTAGTgcagtgggaataggagctttgttccttgggttc
t
ΔCleavage site (agagaaaaaga)→SpeI
tgggagcagcaggaagcactatgggcgcagcgtcaatgacgctgacggtacaggccagacaattattgtct
ggtatagtgcagcagcagaacaatttgctgagggctattgaggcgcaacagcatctgttgcaactcacagt
ctggggcatcaagcagctccaggcaagaatcctggctgtggaaagatacctaaaggatcaacagctcctgg
ggatttggggttgctctggaaaactcatttgcaccactgctgtgccttggaatgctagttggagtaataaa
tctctggaacagatttggaataacatgacctggatggagtgggacagagaaattaacaattacacaagctt
aatacactccttaattgaagaatcgcaaaaccagcaagaaaagaatgaacaagaattattggaattagata
aatgggcaagtttgtggaattggtttaacataacaaattggctgtggtatataaaattattcataatgata
gtaggaggcttggtaggtttaagaatagtttttgctgtactttctgtagtgaatagagttaggcagggata
ttcaccattatcgtttcagacccacctcccaatcccgaggggacccgacaggcccgaaggaatagaagaag
aaggtggagagagagacagagacagatccattcgattagtgaacggatccttagcacttatctgggacgat
ctgcggagcctgtgcctcttcagctaccaccgcttgagagacttactcttgattgtaacgaggattgtgga
acttctgggacgcagggggtgggaagccctcaaatattggtggaatctcctacagtattggagtcaggagc
taaagaatagtgctgttagcttgctcaatgccacagctatagcagtagctgaggggacagatagggttata
gaagtagtacaaggagcttatagagctattcgccacatacctagaagaataagacagggcttggaaaggat
tttgctataagatgggtggcaagtggtcaaaaagtagtgtggttggatggcctgctgtaagggaaagaatg
agacgagctgagccagcagcagatggggtgggagcagcatctcgagacctagaaaaacatggagcaatcac
aagtagcaacacagcagctaacaatgctgattgtgcctggctagaagcacaagaggaggaggaggtgggtt
ttccagtcacacctcaggtacctttaagaccaatgacttacaaggcagctgtagatcttagccactttta
aaagaaaaggggggactggaagggctaattcactcccaacgaagacaagatatccttgatctgtggatcta
ccacacacaaggctacttccctgattag

FIGURE 45

DNA Sequence of $E^m\Delta$C.N (Strain BH10) [SEQ ID NO: 22]:

```
Gaattcgccaccatgggagtgaaggagaaatatcagcacttgtggagatgg
EcoRI   Kozak  NcoI
gggtggagatggggcaccatgctccttgggatgttgatgatctgtagtgctacagaaaaattgtgggtcac
agtctattatggggtacctgtgtggaaggaagcaaccaccactctattttgtgcatcagatgctaaagcat
atgatacagaggtacataatgtttgggccacacatgcctgtgtacccacagaccccaacccacaagaagta
gtattggtaaatgtgacagaaaattttaacatgtggaaaaatgacatggtagaacagatgcatgaggatat
aatcagtttatgggatcaaagcctaaagccatgtgtaaaattaaccccactctgtgttagtttaaagtgca
ctgatttgaagaatgatactaataccaatagtagtagcgggagaatgataatggagaaaggagagataaaa
aactgctctttcaatatcagcacaagcataagaggtaaggtgcagaaagaatatgcatttttttataaact
tgatataataccaatagataatgatactaccagctatacgttgacaagttgtaacacctcagtcattacac
aggcctgtccaaaggtatcctttgagccaattcccatacattattgtgccccggctggttttgcgattcta
aaatgtaataataagacgttcaatggaacaggaccatgtacaaatgtcagcacagtacaatgtacacatgg
aattaggccagtagtatcaactcaactgctgttaaatggcagtctggcagaagaagaggtagtaattagat
ctgccaatttcacagacaatgctaaaaccataatagtacagctgaaccaatctgtagaaattaattgtaca
agacccaacaacaatacaagaaaaagtatccgtatccagagaggaccagggagagcatttgttacaatagg
aaaaataggaaatatgagacaagcacattgtaacattagtagagcaaaatggaataacactttaaaacaga
tagatagcaaattaagagaacaatttggaaataataaaacaataatctttaagcagtcctcaggaggggac
ccagaaattgtaacgcacagttttaattgtggaggggaatttttctactgtaattcaacacaactgtttaa
tagtacttggtttaatagtacttggagtactaaagggtcaaataacactgaaggaagtgacacaatcaccc
tcccatgcagaataaaacaaattataaacatgtggcaggaagtaggaaaagcaatgtatgcccctcccatc
agtggacaaattagatgttcatcaaatattacagggctgctattaacaagagatggtggtaatagcaacaa
tgagtccgagatcttcagacctggaggaggagatatgagggacaattggagaagtgaattatataaatata
aagtagtaaaaattgaaccattaggagtagcacccaccaaggcaaagagaagagtggtgcagACTAGTgca
gtgggaataggagctttgttccttgggttcttgggagc
```

ΔCleavage site(agagaaaaaaga)→SpeI

```
agcaggaagcactatgggcgcagcgtcaatgacgctgacggtacaggccagacaattattgtctggtatag
tgcagcagcagaacaatttgctgagggctattgaggcgcaacagcatctgttgcaactcacagtctggggc
atcaagcagctccaggcaagaatcctggctgtggaaagatacctaaaggatcaacagctcctggggatttg
gggttgctctggaaaactcatttgcaccactgctgtgccttggaatgctagttggagtaataaatctctgg
aacagatttggaataacatgacctggatggagtgggacagagaaattaacaattacacaagcttaatacac
tccttaattgaagaatcgcaaaaccagcaagaaaagaatgaacaagaattattggaattagataaatgggc
aagtttgtggaattggtttaacataacaaattggctgtggtatataaaattattcataatgatagtaggag
gcttggtaggtttaagaatagtttttgctgtactttctgtagtgaatagagttaggcagggatattcacca
ttatcgtttcagacccacctcccaatcccgaggggacccgacaggcccgaaggaatagaagaagaaggtgg
agagagagacagagacagatccattcgattagtgaacggatccttagcacttatctgggacgatctgcgga
gcctgtgcctcttcagctaccaccgcttgagagacttactcttgattgtaacgaggattgtggaacttctg
ggacgcagggggtgggaagccctcaaatattggtggaatctcctacagtattggagtcaggagctaaagaa
tagtgctgttagcttgctcaatgccacagctatagcagtagctgaggggacagatagggttatagaagtag
tacaaggagcttatagagctattcgccacatacctagaagaataagacagggcttggaaaggattttgcta
taagatgggtggcaagtggtcaaaaagtagtgtggttggatggcctgctgtaagggaaagaatgagacgag
ctgagccagcagcagatggggtgggagcagcatctcgagacctagaaaaacatggagcaatcacaagtagc
aacacagcagctaacaatgctgattgtgcctggctagaagcacaagaggaggaggaggtgggttttccagt
cacacctcaggtacctttaagaccaatgacttacaaggcagctgtagatcttagccacttttaaaagaaa
aggggggactggaagggctaattcactcccaacgaagacaagatatccttgatctgtggatctaccacaca
caaggctacttccctgattag
```

FIGURE 46

DNA Sequence of $E^{m}\Delta C\Delta T^{300}$.T (BH10) [SEQ ID NO: 23]:

Gaattctgcaacaactgctgtttatccattttcagaattgggtgtcgacat
EcoRI
Agcagaataggcgttactcgacagaggagagcaagaaatggagccagtaga
Tat 1
tcctagactagagccctggaagcatccaggaagtcagcctaaaactgcttgtaccaattgctattgtaaaa
agtgttgctttcattgccaagtttgtttcataacaaaagccttaggcatctcctatggcaggaagaagcgg
agacagcgacgaagacctcctcaaggcagtcagactcatcaagtttctctatcaaagcagtaagtagtaca
tgtaatgcaacctatacaaatagcaatagtagcattagtagtagcaataataatagcaatagttgtgtggt
ccatagtaatcatagaatataggaaaatattaagacaaagaaaaatagacaggttaattgatagactaata
gaaagagcagaagacagtggcaatgagagtgaaggagaaatatcagcacttgtggagatggggggtggagat
ggggcaccatgctccttgggatgttgatgatctgtagtgctacagaaaaattgtgggtcacagtctattat
ggggtacctgtgtggaaggaagcaaccaccactctattttgtgcatcagatgctaaagcatatgatacaga
ggtacataatgtttgggccacacatgcctgtgtacccacagaccccaacccacaagaagtagtattggtaa
atgtgacagaaaattttaacatgtggaaaaatgacatggtagaacagatgcatgaggatataatcagttta
tgggatcaaagcctaaagccatgtgtaaaattaaccccactctgtgttagtttaaagtgcactgatttgaa
gaatgatactaataccaatagtagtagcgggagaatgataatggagaaaggagagataaaaaactgctctt
tcaatatcagcacaagcataagaggtaaggtgcagaaagaatatgcatttttttataaacttgatataata
ccaatagataatgatactaccagctatacgttgacaagttgtaacacctcagtcattacacaggcctgtcc
aaaggtatcctttgagccaattcccatacattattgtgccccggctggttttgcgattctaaaatgtaata
ataagacgttcaatggaacaggaccatgtacaaatgtcagcacagtacaatgtacacatggaattaggcca
gtagtatcaactcaactgctgttaaatggcagtctggcagaagaagaggtagtaattagatctgccaattt
cacagacaatgctaaaaccataatagtacagctgaaccaatctgtagaaattaattgtacaagacccaaca
acaatacaagaaaaagtatccgtatccagagaggaccagggagagcatttgttacaataggaaaaatagga
aatatgagacaagcacattgtaacattagtagagcaaaatggaataacactttaaaacagatagatagcaa
attaagagaacaatttggaaataataaaacaataatctttaagcagtcctcaggaggggacccagaaattg
taacgcacagttttaattgtggaggggaatttttctactgtaattcaacacaactgtttaatagtacttgg
tttaatagtacttggagtactaaagggtcaaataacactgaaggaagtgacacaatcaccctcccatgcag
aataaaacaaattataaacatgtggcaggaagtaggaaaagcaatgtatgcccctcccatcagtggacaaa
ttagatgttcatcaaatattacagggctgctattaacaagagatggtggtaatagcaacaatgagtccgag
atcttcagacctggaggaggagatatgagggacaattggagaagtgaattatataaatataaagtagtaaa
aattgaaccattaggagtagcacccaccaaggcaaagagaagagtggtgcagACTAGTgcagtgggaatag
gagctttgttccttgggttc
ΔCleavage site(agagaaaaaaga)→SpeI
ttgggagcagcaggaagcactatgggcgcagcgtcaatgacgctgacggtacaggccagacaattattgtc
tggtatagtgcagcagcagaacaatttgctgagggctattgaggcgcaacagcatctgttgcaactcacag
tctggggcatcaagcagctccaggcaagaatcctggctgtggaaagatacctaaaggatcaacagctcctg
gggatttggggttgctctggaaaactcatttgcaccactgctgtgccttggaatgctagttggagtaataa
atctctggaacagatttggaataacatgacctggatggagtgggacagagaaattaacaattacacaagct
taatacactccttaattgaagaatcgcaaaaccagcaagaaaagaatgaacaagaattattggaattagat
aaatgggcaagtttgtggaattggtttaacataacaaattggctgtggtatataaaattattcataatgat
agtaggaggcttggtaggtttaagaatagtttttgctgtactttctgtagtgaatagagttaggcagggat
attcaccattatcgtttcagacccacctcccaatcccgaggggacccgacaggcccgaaggaatagaagaa
gaaggtggagagagagacagagacagatccattcgattagtgaacggatccttagcacttatctggtaa

Figure 47

DNA Sequence of $E^m/E^m$ (BH10) [SEQ ID NO: 24]:

```
Gaattcgccaccatgggagtgaaggagaaatatcagcacttgtggagatgg
EcoRI  Kozak  NcoI
gggtggagatggggcaccatgctccttgggatgttgatgatctgtagtgctacagaaaaattgtgggtcac
agtctattatggggtacctgtgtggaaggaagcaaccaccactctattttgtgcatcagatgctaaagcat
atgatacagaggtacataatgtttgggccacacatgcctgtgtacccacagaccccaacccacaagaagta
gtattggtaaatgtgacagaaaattttaacatgtggaaaaatgacatggtagaacagatgcatgaggatat
aatcagtttatgggatcaaagcctaaagccatgtgtaaaattaaccccactctgtgttagtttaaagtgca
ctgatttgaagaatgatactaataccaatagtagtagcgggagaatgataatggagaaaggagagataaaa
aactgctctttcaatatcagcacaagcataagaggtaaggtgcagaaagaatatgcatttttttataaact
tgatataataccaatagataatgatactaccagctatacgttgacaagttgtaacacctcagtcattacac
aggcctgtccaaaggtatcctttgagccaattcccatacattattgtgccccggctggttttgcgattcta
aaatgtaataataagacgttcaatggaacaggaccatgtacaaatgtcagcacagtacaatgtacacatgg
aattaggccagtagtatcaactcaactgctgttaaatggcagtctggcagaagaagaggtagtaattagat
ctgccaatttcacagacaatgctaaaaccataatagtacagctgaaccaatctgtagaaattaattgtaca
agacccaacaacaatacaagaaaaagtatccgtatccagagaggaccagggagagcatttgttacaatagg
aaaaataggaaatatgagacaagcacattgtaacattagtagagcaaaatggaataacactttaaaacaga
tagatagcaaattaagagaacaatttggaaataataaaacaataatctttaagcagtcctcaggaggggac
ccagaaattgtaacgcacagttttaattgtggaggggaatttttctactgtaattcaacacaactgtttaa
tagtacttggtttaatagtacttggagtactaaagggtcaaataacactgaaggaagtgacacaatcaccc
tcccatgcagaataaaacaaattataaacatgtggcaggaagtaggaaaagcaatgtatgcccctcccatc
agtggacaaattagatgttcatcaaatattacagggctgctattaacaagagatggtggtaatagcaacaa
tgagtccgagatcttcagacctggaggaggagatatgagggacaattggagaagtgaattatataaatata
aagtagtaaaaattgaaccattaggagtagcacccaccaaggcaaagagaagagtggtgcagagagaaaaa
agagcagtgggaataggagctttgttccttgggttcttgggagcagcaggaagcactatgggcgcagcgtc
aatgacgctgacggtacaggccagacaattattgtctggtatagtgcagcagcagaacaatttgctgaggg
ctattgaggcgcaacagcatctgttgcaactcacagtctggggcatcaagcagctccaggcaagaatcctg
gctgtggaaagatacctaaaggatcaacagctcctggggatttggggttgctctggaaaactcatttgcac
cactgctgtgccttggaatgctagttggagtaataaatctctggaacagatttggaataacatgacctgga
tggagtgggacagagaaattaacaattacacaagcttaatacactccttaattgaagaatcgcaaaaccag
caagaaaagaatgaacaagaattattggaattagataaatgggcaagtttgtggaattggtttaacataac
aaattggctgtggtatataaaattattcataatgatagtaggaggcttggtaggtttaagaatagtttttg
ctgtactttctgtagtgaatagagttaggcagggatattcaccattatcgtttcagacccacctcccaatc
ccgaggggacccgacaggcccgaaggaatagaagaagaaggtggagagagagacagagacagatccattcg
attagtgaacggatccttagcacttatctgggacgatctgcggagcctgtgcctcttcagctaccaccgct
tgagagacttactcttgattgtaacgaggattgtggaacttctgggacgcagggggtgggaagccctcaaa
tattggtggaatctcctacagtattggagtcaggagctaaagaatagtgctgttagcttgctcaatgccac
agctatagcagtagctgaggggacagatagggttatagaagtagtacaaggagcttatagagctattcgcc
acatacctagaagaataagacagggcttggaaaggattttgctataa
```

FIGURE 48

Sequences of V3 loop Multi-clade HIV-1 Clones:

| Clade | ACC# | HIV-1 Strain | From(nt) | To(nt) |
|---|---|---|---|---|
| B | M15654 | BH10 | 885 | 992 |
| A | U09127 | 192UG037WHO.01083hED | 888 | 992 |
| C | U09126 | 192BR025WHO.01093hED | 876 | 980 |
| D | U43386 | 192UG024.2 | 888 | 989 |
| E | U08458 | 193TH976.17 | 894 | 998 |
| F | U27401 | 193BR020.17 | 888 | 992 |
| G | U30312 | 192RU131.9 | 885 | 989 |

Tgtacaagacccaacaacaatacaagaaaaagtatccgtatccagagagga
ccagggagagcatttgttacaataggaaaaataggaaatatgagacaagca
cattgt Clade B [SEQ ID NO: 25]

Tgtaccagacctaacaacaatacaagaaaaagtgtacgtataggaccagga
caaacattctatgcaacaggtgatataataggggatataagacaagcacat
tgt Clade A [SEQ ID NO: 26]

Tgtacgagacccaacaataatacaagaaaaagtataaggataggaccagga
caagcattctatgcaacaggagaaataataggagatataagacaagcacat
tgt Clade C [SEQ ID NO: 27]

Tgcacaaggccctacaacaatataagacaaaggacccccataggactaggg
caagcactctatacaacaagaagaatagaagatataagaagagcacattgt
Clade D [SEQ ID NO: 28]

Tgtaccagaccctccaccaatacaagaacaagtatacgtataggaccagga
caagtattctatagaacaggagacataacaggagatataagaaaagcatat
tgt Clade E [SEQ ID NO: 29]

Tgtacaagacccaacaacaatacaagaaaaagaatatctttaggaccagga
cgagtattttatacagcaggagaaataataggagacatcagaaaggcacat
tgt Clade F [SEQ ID NO: 30]

Tgtaccagacctaataacaatacaagaaaaagtataactttgcaccagga
caagcgctctatgcaacaggtgaaataataggagatataagacaagcacat
tgt Clade G [SEQ ID NO: 31]

FIGURE 49A

DNA sequence of modified Env including multi-clade V3 loops [SEQ ID NO: 32]:

Atgagagtgaaggagaaatatcagcacttgtggagatgggggtggagatggggcaccatgctccttgggat
gttgatgatctgtagtgctacagaaaaattgtgggtcacagtctattatggggtacctgtgtggaaggaag
caaccaccactctattttgtgcatcagatgctaaagcatatgatacagaggtacataatgtttgggccaca
catgcctgtgtacccacagaccccaacccacaagaagtagtattggtaaatgtgacagaaaattttaacat
gtggaaaaatgacatggtagaacagatgcatgaggatataatcagtttatgggatcaaagcctaaagccat
gtgtaaaattaaccccactctgtgttggagctggtagttgtaacacctcagt
V1, V2 deletion, GAG insertion
Cattacacaggcctgtccaaaggtatcctttgagccaattcccatacattattgtgccccggctggttttg
cgattctaaaatgtaataataagacgttcaatggaacaggaccatgtacaaatgtcagcacagtacaatgt
acacatggaattaggccagtagtatcaactcaactgctgttaaatggcagtctggcagaagaagaggtagt
aattagatctgccaatttcacagacaatgctaaaaccataatagtacagctgaaccaatctgtagaaatta
attgtacaagacccaacaacaa
Start of Clade B
Tacaagaaaaagtatccgtatccagagaggaccagggagagcatttgttacaataggaaaaataggaaata
tgagacaagcacattgtctcgggtgtaccag
Insert a AvaI site Clade A
Acctaacaacaatacaagaaaaagtgtacgtataggaccaggacaaacattctatgcaacaggtgatataa
taggggatataagacaagcacattgttgtac
Clade C
Gagacccaacaataatacaagaaaaagtataaggataggaccaggacaagcattctatgcaacaggagaaa
taataggagatataagacaagcacattgttg
Clade D
Cacaaggccctacaacaatataagacaaaggacccccataggactagggcaagcactctatacaacaagaa
gaatagaagatataagaagagcacattgttg
Clade E
Taccagaccctccaccaatacaagaacaagtatacgtataggaccaggacaagtattctatagaacaggag
acataacaggagatataagaaaagcatattgtggatcctgtacaagacccaacaacaatacaagaaaaaga
atatctttagg
BamHI clade F
Accaggacgagtattttatacagcaggagaaataataggagacatcagaaaggcacattgttgtaccagac
ctaataacaatacaagaaaaagtataacttt
Clade G
Tgcaccaggacaagcgctctatgcaacaggtgaaataataggagatataagacaagcacattgtctcggga
acattagtagagcaaaatggaataacacttt
Insert a AvaI
Aaaacagatagatagcaaattaagagaacaatttggaaataataaaacaataatctttaagcagtcctcag
gaggggacccagaaattgtaacgcacagttttaattgtggaggggaatttttctactgtaattcaacacaa
ctgtttaatagtacttggtttaatagtacttggagtactaaagggtcaaataacactgaaggaagtgacac
aatcaccctcccatgcagaataaaacaaattataaacatgtggcaggaagtaggaaaagcaatgtatgccc
ctcccatcagtggacaaattagatgttcatcaaatattacagggctgctattaacaagagatggtggtaat
agcaacaatgagtccgagatcttcagacctggaggaggagatatgagggacaattggagaagtgaattata
taaatataaagtagtaaaaattgaaccattaggagtagcacccaccaaggcaaagagaagagtggtgcaga
ctagtgcagtggg
Cleavage site mutation (SpeI)
Aataggagctttgttccttgggttcttgggagcagcaggaagcactatgggcgcagcgtcaatgacgctga
cggtacaggccagacaattattgtctggtatagtgcagcagcagaacaatttgctgagggctattgaggcg
caacagcatctgttgcaactcacagtctggggcatcaagcagctccaggcaagaatcctggctgtggaaag
atacctaaaggatcaacagctcctggggatttggggttgctctggaaaactcatttgcaccactgctgtgc
cttggaatgctagttggagtaataaatctctggaacagatttggaataacatgacctggatggagtgggac
agagaaattaacaattacacaagcttaatacactccttaattgaagaatcgcaaaaccagcaagaaaagaa
tgaacaagaattattggaattagataaatgggcaagtttgtggaattggtttaacataacaaattggctgt
ggtatataaaatcgtggctgctgctgctcctgctctccctctccctcctccaggccacggatttcatgtcc
ctgtga GPI anchor

FIGURE 49B

Amino acid sequence of modified Env including multi-clade V3 loops [SEQ ID NO: 33]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | T | E | K | L | W | V |
| T | V | Y | Y | G | V | P | V | W | K | E | A | T | T | T | L | F | C |
| A | S | D | A | K | A | Y | D | T | E | V | H | N | V | W | A | T | H |
| A | C | V | P | T | D | P | N | P | Q | E | V | V | L | V | N | V | T |
| E | N | F | N | M | W | K | N | D | M | V | E | Q | M | H | E | D | I |
| I | S | L | W | D | Q | S | L | K | P | C | V | K | L | T | P | L | C |
| V | G | A | G | S | C | N | T | S | V | I | T | Q | A | C | P | K | V |
| S | F | E | P | I | P | I | H | Y | C | A | P | A | G | F | A | I | L |
| K | C | N | N | K | T | F | N | G | T | G | P | C | T | N | V | S | T |
| V | Q | C | T | H | G | I | R | P | V | V | S | T | Q | L | L | L | N |
| G | S | L | A | E | E | E | V | V | I | R | S | A | N | F | T | D | N |
| A | K | T | I | I | V | Q | L | N | Q | S | V | E | I | N | C | T | R |
| P | N | N | N | T | R | K | S | I | R | I | Q | R | G | P | G | R | A |
| F | V | T | I | G | K | I | G | N | M | R | Q | A | H | C | L | G | C |
| T | R | P | N | N | N | T | R | K | S | V | R | I | G | P | G | Q | T |
| F | Y | A | T | G | D | I | I | G | D | I | R | Q | A | H | C | C | T |
| R | P | N | N | N | T | R | K | S | I | R | I | G | P | G | Q | A | F |
| Y | A | T | G | E | I | I | G | D | I | R | Q | A | H | C | C | T | R |
| P | Y | N | N | I | R | Q | R | T | P | I | G | L | G | Q | A | L | Y |
| T | T | R | R | I | E | D | I | R | R | A | H | C | C | T | R | P | S |
| T | N | T | R | T | S | I | R | I | G | P | G | Q | V | F | Y | R | T |
| G | D | I | T | G | D | I | R | K | A | Y | C | G | S | C | T | R | P |
| N | N | N | T | R | K | R | I | S | L | G | P | G | R | V | F | Y | T |
| A | G | E | I | I | G | D | I | R | K | A | H | C | C | T | R | P | N |
| N | N | T | R | K | S | I | T | F | A | P | G | Q | A | L | Y | A | T |
| G | E | I | I | G | D | I | R | Q | A | H | C | L | G | N | I | S | R |
| A | K | W | N | N | T | L | K | Q | I | D | S | K | L | R | E | Q | F |
| G | N | N | K | T | I | I | F | K | Q | S | S | G | G | D | P | E | I |
| V | T | H | S | F | N | C | G | G | E | F | F | Y | C | N | S | T | Q |
| L | F | N | S | T | W | F | N | S | T | W | S | T | K | G | S | N | N |
| T | E | G | S | D | T | I | T | L | P | C | R | I | K | Q | I | I | N |
| M | W | Q | E | V | G | K | A | M | Y | A | P | P | I | S | G | Q | I |
| R | C | S | S | N | I | T | G | L | L | L | T | R | D | G | G | N | S |
| N | N | E | S | E | I | F | R | P | G | G | G | D | M | R | D | N | W |
| R | S | E | L | Y | K | Y | K | V | V | K | I | E | P | L | G | V | A |
| P | T | K | A | K | R | R | V | V | Q | T | S | A | V | G | I | G | A |
| L | F | L | G | F | L | G | A | A | G | S | T | M | G | A | A | S | M |
| T | L | T | V | Q | A | R | Q | L | L | S | G | I | V | Q | Q | Q | N |
| N | L | L | R | A | I | E | A | Q | Q | H | L | L | Q | L | T | V | W |
| G | I | K | Q | L | Q | A | R | I | L | A | V | E | R | Y | L | K | D |
| Q | Q | L | L | G | I | W | G | C | S | G | K | L | I | C | T | T | A |
| V | P | W | N | A | S | W | S | N | K | S | L | E | Q | I | W | N | N |
| M | T | W | M | E | W | D | R | E | I | N | N | Y | T | S | L | I | H |
| S | L | I | E | E | S | Q | N | Q | Q | E | K | N | E | Q | E | L | L |
| E | L | D | K | W | A | S | L | W | N | W | F | N | I | T | N | W | L |
| W | Y | I | K | S | W | L | L | L | L | L | L | S | L | S | L | L | Q |
| A | T | D | F | M | S | L | * | | | | | | | | | | |

FIGURE 50A

1. DNA sequence of p17/24 in natural form [SEQ ID NO: 34]:

atgggtgcgagagcgtcagtattaagcgggggagaattagatcgatgggaaaaaattcggttaaggccagg
gggaaagaaaaaatataaattaaaacatatagtatgggcaagcagggagctagaacgattcgcagttaatc
ctggcctgttagaaacatcagaaggctgtagacaaatactgggacagctacaaccatcccttcagacagga
tcagaagaacttagatcattatataatacagtagcaaccctctattgtgtgcatcaaaggatagagataaa
agacaccaaggaagctttagacaagatagaggaagagcaaaacaaaagtaagaaaaaagcacagcaagcag
cagctgacacaggacacagcagtcaggtcagccaaaattaccctatagtgcagaacatccaggggcaaatg
gtacatcaggccatatcacctagaactttaaatgcatgggtaaaagtagtagaagagaaggctttcagccc
agaagtaatacccatgttttcagcattatcagaaggagccaccccacaagatttaaacaccatgctaaaca
cagtgggggacatcaagcagccatgcaaatgttaaaagagaccatcaatgaggaagctgcagaatgggat
agagtacatccagtgcatgcagggcctattgcaccaggccagatgagagaaccaaggggaagtgacatagc
aggaactactagtacccttcaggaacaaataggatggatgacaaataatccacctatcccagtaggagaaa
tttataaaagatggataatcctgggattaaataaaatagtaagaatgtatagccctaccagcattctggac
ataagacaaggaccaaaagaacctttagagactatgtagaccggttctataaaactctaagagccgagca
agcttcacaggaggtaaaaaattggatgacagaaaccttgttggtccaaaatgcgaacccagattgtaaga
ctattttaaaagcattgggaccagcggctacactagaagaaatgatgacagcatgtcagggagtaggagga
cccggccataaggcaagagttttgtaa

2. DNA sequence of p17/24 in secreted form [SEQ ID NO: 35]:

atgagagtgaaggagaaatatcagcacttgtggagatggggtggagatgg
gp120 signal peptide
ggcaccatgctccttgggatgttgatgatctgtagtgctggtgcgagagcg
p17/p24
tcagtattaagcgggggagaattagatcgatgggaaaaaattcggttaaggccagggggaaagaaaaaata
taaattaaaacatatagtatgggcaagcagggagctagaacgattcgcagttaatcctggcctgttagaaa
catcagaaggctgtagacaaatactgggacagctacaaccatcccttcagacaggatcagaagaacttaga
tcattatataatacagtagcaaccctctattgtgtgcatcaaaggatagagataaaagacaccaaggaagc
tttagacaagatagaggaagagcaaaacaaaagtaagaaaaaagcacagcaagcagcagctgacacaggac
acagcagtcaggtcagccaaaattaccctatagtgcagaacatccaggggcaaatggtacatcaggccata
tcacctagaactttaaatgcatgggtaaaagtagtagaagagaaggctttcagcccagaagtaatacccat
gttttcagcattatcagaaggagccaccccacaagatttaaacaccatgctaaacacagtgggggacatc
aagcagccatgcaaatgttaaaagagaccatcaatgaggaagctgcagaatgggatagagtacatccagtg
catgcagggcctattgcaccaggccagatgagagaaccaaggggaagtgacatagcaggaactactagtac
ccttcaggaacaaataggatggatgacaaataatccacctatcccagtaggagaaatttataaaagatgga
taatcctgggattaaataaaatagtaagaatgtatagccctaccagcattctggacataagacaaggacca
aaagaacctttagagactatgtagaccggttctataaaactctaagagccgagcaagcttcacaggaggt
aaaaaattggatgacagaaaccttgttggtccaaaatgcgaacccagattgtaagactattttaaaagcat
tgggaccagcggctacactagaagaaatgatgacagcatgtcagggagtaggaggacccggccataaggca
agagttttgtaa

FIGURE 50A -continued

1. DNA sequence of p17/24 in membrane form [SEQ ID NO: 36]:

<u>atgagagtgaaggagaaatatcagcacttgtggagatgggggtggagatgg</u>
gp120 signal peptide
<u>Ggcaccatgctccttgggatgttgatgatctgtagtgctggtgcgagagcg</u>
                                            P17/p24
tcagtattaagcgggggagaattagatcgatgggaaaaaattcggttaaggccagggggaaagaaaaaata
taaattaaaacatatagtatgggcaagcagggagctagaacgattcgcagttaatcctggcctgttagaaa
catcagaaggctgtagacaaatactgggacagctacaaccatcccttcagacaggatcagaagaacttaga
tcattatataatacagtagcaaccctctattgtgtgcatcaaaggatagagataaaagacaccaaggaagc
tttagacaagatagaggaagagcaaaacaaaagtaagaaaaaagcacagcaagcagcagctgacacaggac
acagcagtcaggtcagccaaaattaccctatagtgcagaacatccaggggcaaatggtacatcaggccata
tcacctagaactttaaatgcatgggtaaaagtagtagaagagaaggctttcagcccagaagtaatacccat
gttttcagcattatcagaaggagccaccccacaagatttaaacaccatgctaaacacagtggggggacatc
aagcagccatgcaaatgttaaaagagaccatcaatgaggaagctgcagaatgggatagagtacatccagtg
catgcagggcctattgcaccaggccagatgagagaaccaaggggaagtgacatagcaggaactactagtac
ccttcaggaacaaataggatggatgacaaataatccacctatcccagtaggagaaatttataaaagatgga
taatcctgggattaaataaaatagtaagaatgtatagccctaccagcattctggacataagacaaggacca
aaagaaccttttagagactatgtagaccggttctataaaactctaagagccgagcaagcttcacaggaggt
aaaaaattggatgacagaaaccttgttggtccaaaatgcgaacccagattgtaagactattttaaaagcat
tgggaccagcggctacactagaagaaatgatgacagcatgtcagggagtaggaggacccggccataaggca
agagttttg
<u>ttattcataatgatagtaggaggcttggtaggtttaagaatagttttttgctgtactttctgtagtgaatag
agttaggcagggatattcaccattatcgtttcagacccacctcccaatcccgaggggataa</u>
gp41 transmembrane domain

FIGURE 50B

1. Amino acid sequence of p17/24 in natural form [SEQ ID NO: 37]:

M G A R A S V L S G G E L D R W E K
I R L R P G G K K K Y K L K H I V W
A S R E L E R F A V N P G L L E T S
E G C R Q I L G Q L Q P S L Q T G S
E E L R S L Y N T V A T L Y C V H Q
R I E I K D T K E A L D K I E E E Q
N K S K K K A Q Q A A A D T G H S S
Q V S Q N Y P I V Q N I Q G Q M V H
Q A I S P R T L N A W V K V V E E K
A F S P E V I P M F S A L S E G A T
P Q D L N T M L N T V G G H Q A A M
Q M L K E T I N E E A A E W D R V H
P V H A G P I A P G Q M R E P R G S
D I A G T T S T L Q E Q I G W M T N
N P P I P V G E I Y K R W I I L G L
N K I V R M Y S P T S I L D I R Q G
P K E P F R D Y V D R F Y K T L R A
E Q A S Q E V K N W M T E T L L V Q
N A N P D C K T I L K A L G P A A T
L E E M M T A C Q G V G G P G H K A
R V L *

2. Amino acid sequence of p17/24 in secreted form [SEQ ID NO: 38]:

1. Amino acid sequence of p17/24 in membrane bound form [SEQ ID NO: 39]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | G | A | R | A | S | V |
| L | S | G | G | E | L | D | R | W | E | K | I | R | L | R | P | G | G |
| L | S | G | G | E | L | D | R | W | E | K | I | R | L | R | P | G | G |
| K | K | K | Y | K | L | K | H | I | V | W | A | S | R | E | L | E | R |
| F | A | V | N | P | G | L | L | E | T | S | E | G | C | R | Q | I | L |
| G | Q | L | Q | P | S | L | Q | T | G | S | E | E | L | R | S | L | Y |
| N | T | V | A | T | L | Y | C | V | H | Q | R | I | E | I | K | D | T |
| K | E | A | L | D | K | I | E | E | E | Q | N | K | S | K | K | K | A |
| Q | Q | A | A | A | D | T | G | H | S | S | Q | V | S | Q | N | Y | P |
| I | V | Q | N | I | Q | G | Q | M | V | H | Q | A | I | S | P | R | T |
| L | N | A | W | V | K | V | V | E | E | K | A | F | S | P | E | V | I |
| P | M | F | S | A | L | S | E | G | A | T | P | Q | D | L | N | T | M |
| L | N | T | V | G | G | H | Q | A | A | M | Q | M | L | K | E | T | I |
| N | E | E | A | A | E | W | D | R | V | H | P | V | H | A | G | P | I |
| A | P | G | Q | M | R | E | P | R | G | S | D | I | A | G | T | T | S |
| T | L | Q | E | Q | I | G | W | M | T | N | N | P | P | I | P | V | G |
| E | I | Y | K | R | W | I | I | L | G | L | N | K | I | V | R | M | Y |
| S | P | T | S | I | L | D | I | R | Q | G | P | K | E | P | F | R | D |
| Y | V | D | R | F | Y | K | T | L | R | A | E | Q | A | S | Q | E | V |
| K | N | W | M | T | E | T | L | L | V | Q | N | A | N | P | D | C | K |
| T | I | L | K | A | L | G | P | A | A | T | L | E | E | M | M | T | A |
| C | Q | G | V | G | G | P | G | H | K | A | R | V | L | L | F | I | M |
| I | V | G | G | L | V | G | L | R | I | V | F | A | V | L | S | V | V |
| N | R | V | R | Q | G | Y | S | P | L | S | F | Q | T | H | L | P | I |
| P | R | G | * | | | | | | | | | | | | | | |

FIGURE 51A

1. DNA sequence of p17 in natural form [SEQ ID NO: 40]:

atgggtgcgagagcgtcagtattaagcgggggagaattagatcgatgggaaaaaattcg
gttaaggccagggggaaagaaaaaatataaattaaaacatatagtatgggcaagcaggg
agctagaacgattcgcagttaatcctggcctgttagaaacatcagaaggctgtagacaa
atactgggacagctacaaccatcccttcagacaggatcagaagaacttagatcattata
taatacagtagcaaccctctattgtgtgcatcaaaggatagagataaaagacaccaagg
aagctttagacaagatagaggaagagcaaaacaaaagtaagaaaaaagcacagcaagca
gcagctgacacaggacacagcagtcaggtcagccaaaattactaa

2. DNA sequence of p17 in secreted form [SEQ ID NO: 41]:

atgagagtgaaggagaaatatcagcacttgtggagatgggggtggagatgg
gp120 signal peptide
ggcaccatgctccttgggatgttgatgatctgtagtgctggtgcgagagcg
p17
tcagtattaagcgggggagaattagatcgatgggaaaaaattcggttaaggccaggggg
aaagaaaaaatataaattaaaacatatagtatgggcaagcagggagctagaacgattcg
cagttaatcctggcctgttagaaacatcagaaggctgtagacaaatactgggacagcta
caaccatcccttcagacaggatcagaagaacttagatcattatataatacagtagcaac
cctctattgtgtgcatcaaaggatagagataaaagacaccaaggaagctttagacaaga
tagaggaagagcaaaacaaaagtaagaaaaaagcacagcaagcagcagctgacacagga
cacagcagtcaggtcagccaaaattactaa

3. DNA sequence of p17 in membrane bound form [SEQ ID NO: 42]:

atgagagtgaaggagaaatatcagcacttgtggagatgggggtggagatgg
gp120 signal peptide
ggcaccatgctccttgggatgttgatgatctgtagtgctggtgcgagagcg
p17
tcagtattaagcgggggagaattagatcgatgggaaaaaattcggttaaggccaggggg
aaagaaaaaatataaattaaaacatatagtatgggcaagcagggagctagaacgattcg
cagttaatcctggcctgttagaaacatcagaaggctgtagacaaatactgggacagcta
caaccatcccttcagacaggatcagaagaacttagatcattatataatacagtagcaac
cctctattgtgtgcatcaaaggatagagataaaagacaccaaggaagctttagacaaga
tagaggaagagcaaaacaaaagtaagaaaaaagcacagcaagcagcagctgacacagga
cacagcagtcaggtcagccaaaattac
ttattcataatgatagtaggaggcttggtaggtttaagaatagttttgctgtactttc
tgtagtgaatagagttaggcagggatattcaccattatcgtttcagacccacctcccaa
tccccgaggggataa
gp41 transmembrane domain

FIGURE 51B

1. Amino acid sequence of p17 in natural form [SEQ ID NO: 43]:

| | | | | | | | | | | | | | | | | | |
|---|---|---|---|---|---|---|---|---|---|---|---|---|---|---|---|---|---|
| M | G | A | R | A | S | V | L | S | G | G | E | L | D | R | W | E | K |
| I | R | L | R | P | G | G | K | K | K | Y | K | L | K | H | I | V | W |
| A | S | R | E | L | E | R | F | A | V | N | P | G | L | L | E | T | S |
| E | G | C | R | Q | I | L | G | Q | L | Q | P | S | L | Q | T | G | S |
| E | E | L | R | S | L | Y | N | T | V | A | T | L | Y | C | V | H | Q |
| R | I | E | I | K | D | T | K | E | A | L | D | K | I | E | E | E | Q |
| N | K | S | K | K | K | A | Q | Q | A | A | A | D | T | G | H | S | S |
| Q | V | S | Q | N | Y | * | | | | | | | | | | | |

2. Amino acid sequence of p17 in secreted form [SEQ ID NO: 44]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | G | A | R | A | S | V |
| L | S | G | G | E | L | D | R | W | E | K | I | R | L | R | P | G | G |
| K | K | K | Y | K | L | K | H | I | V | W | A | S | R | E | L | E | R |
| F | A | V | N | P | G | L | L | E | T | S | E | G | C | R | Q | I | L |
| G | Q | L | Q | P | S | L | Q | T | G | S | E | E | L | R | S | L | Y |
| G | Q | L | Q | P | S | L | Q | T | G | S | E | E | L | R | S | L | Y |
| N | T | V | A | T | L | Y | C | V | H | Q | R | I | E | I | K | D | T |
| K | E | A | L | D | K | I | E | E | E | Q | N | K | S | K | K | K | A |
| Q | Q | A | A | A | D | T | G | H | S | S | Q | V | S | Q | N | Y | * |

3. Amino acid sequence of p17 in membrane bound form [SEQ ID NO: 45]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | G | A | R | A | S | V |
| L | S | G | G | E | L | D | R | W | E | K | I | R | L | R | P | G | G |
| K | K | K | Y | K | L | K | H | I | V | W | A | S | R | E | L | E | R |
| G | Q | L | Q | P | S | L | Q | T | G | S | E | E | L | R | S | L | Y |
| N | T | V | A | T | L | Y | C | V | H | Q | R | I | E | I | K | D | T |
| K | E | A | L | D | K | I | E | E | E | Q | N | K | S | K | K | K | A |
| Q | Q | A | A | A | D | T | G | H | S | S | Q | V | S | Q | N | Y | L |
| F | I | M | I | V | G | G | L | V | G | L | R | I | V | F | A | V | L |
| S | V | V | N | R | V | R | Q | G | Y | S | P | L | S | F | Q | T | H |
| L | P | I | P | R | G | * | | | | | | | | | | | |

FIGURE 52A

1. DNA sequence of p24 in natural form [SEQ ID NO: 46]:

atgcctatagtgcagaacatccaggggcaaatggtacatcaggccatatcacctagaactttaaatgcatgg
gtaaaagtagtagaagagaaggctttcagcccagaagtaatacccatgttttcagcattatcagaaggagcc
accccacaagatttaaacaccatgctaaacacagtggggggacatcaagcagccatgcaaatgttaaaagag
accatcaatgaggaagctgcagaatgggatagagtacatccagtgcatgcagggcctattgcaccaggccag
atgagagaaccaaggggaagtgacatagcaggaactactagtacccttcaggaacaaataggatggatgaca
aataatccacctatcccagtaggagaaatttataaaagatggataatc
ctgggattaaataaaatagtaagaatgtatagccctaccagcattctggacataagacaaggaccaaaagaa
ccctttagagactatgtagaccggttctataaaactctaagagccgagcaagcttcacaggaggtaaaaaat
tggatgacagaaaccttgttggtccaaaatgcgaacccagattgtaagactattttaaaagcattgggacca
gcggctacactagaagaaatgatgacagcatgtcagggagtaggaggacccggccataaggcaagagttttg
taa

2. DNA sequence of p24 in secreted form [SEQ ID NO: 47]:

atgagagtgaaggagaaatatcagcacttgtggagatggggggtggagatgg
gp120 signal peptide ggcaccatgctccttgggatgttgatgatctgtagtgctcctatagtgcag
p24
aacatccaggggcaaatggtacatcaggccatatcacctagaactttaaatgcatgggtaaaagtagtagaa
gagaaggctttcagcccagaagtaatacccatgttttcagcattatcagaaggagccaccccacaagattta
aacaccatgctaaacacagtggggggacatcaagcagccatgcaaatgttaaaagagaccatcaatgaggaa
gctgcagaatgggatagagtacatccagtgcatgcagggcctattgcaccaggccagatgagagaaccaagg
ggaagtgacatagcaggaactactagtacccttcaggaacaaataggatggatgacaaataatccacctatc
ccagtaggagaaatttataaaagatggataatcctgggattaaataaaatagtaagaatgtatagccctacc
agcattctggacataagacaaggaccaaaagaaccctttagagactatgtagaccggttctataaaactcta
agagccgagcaagcttcacaggaggtaaaaaattggatgacagaaaccttgttggtccaaaatgcgaaccca
gattgtaagactattttaaaagcattgggaccagcggctacactagaagaaatgatgacagcatgtcaggga
gtaggaggacccggccataaggcaagagttttgtaa

3. DNA sequence of p24 in membrane bound form [SEQ ID NO: 48]:

atgagagtgaaggagaaatatcagcacttgtggagatggggggtggagatgg
gp120 signal peptide ggcaccatgctccttgggatgttgatgatctgtagtgctcctatagtgcag
p24
aacatccaggggcaaatggtacatcaggccatatcacctagaactttaaatgcatgggtaaaagtagtagaa
gagaaggctttcagcccagaagtaatacccatgttttcagcattatcagaaggagccaccccacaagattta
aacaccatgctaaacacagtggggggacatcaagcagccatgcaaatgttaaaagagaccatcaatgaggaa
gctgcagaatgggatagagtacatccagtgcatgcagggcctattgcaccaggccagatgagagaaccaagg
ggaagtgacatagcaggaactactagtacccttcaggaacaaataggatggatgacaaataatccacctatc
ccagtaggagaaatttataaaagatggataatcctgggattaaataaaatagtaagaatgtatagccctacc
agcattctggacataagacaaggaccaaaagaaccctttagagactatgtagaccggttctataaaactcta
agagccgagcaagcttcacaggaggtaaaaaattggatgacagaaaccttgttggtccaaaatgcgaaccca
gattgtaagactattttaaaagcattgggaccagcggctacactagaagaaatgatgacagcatgtcaggga
gtaggaggacccggccataaggcaagagttttg
ttattcataatgatagtaggaggcttggtaggtttaagaatagtttttgctgtactttctgtagtgaataga
gttaggcagggatattcaccattatcgtttcagacccacctcccaatcccgaggggataa
gp41 transmembrane domain

FIGURE 52B

1. Amino acid sequence of p24 in natural form [SEQ ID NO: 49]:

| | | | | | | | | | | | | | | | | | |
|---|---|---|---|---|---|---|---|---|---|---|---|---|---|---|---|---|---|
| M | P | I | V | Q | N | I | Q | G | Q | M | V | H | Q | A | I | S | P |
| R | T | L | N | A | W | V | K | V | V | E | E | K | A | F | S | P | E |
| V | I | P | M | F | S | A | L | S | E | G | A | T | P | Q | D | L | N |
| T | M | L | N | T | V | G | G | H | Q | A | A | M | Q | M | L | K | E |
| T | I | N | E | E | A | A | E | W | D | R | V | H | P | V | H | A | G |
| P | I | A | P | G | Q | M | R | E | P | R | G | S | D | I | A | G | T |
| T | S | T | L | Q | E | Q | I | G | W | M | T | N | N | P | P | I | P |
| V | G | E | I | Y | K | R | W | I | I | L | G | L | N | K | I | V | R |
| M | Y | S | P | T | S | I | L | D | I | R | Q | G | P | K | E | P | F |
| R | D | Y | V | D | R | F | Y | K | T | L | R | A | E | Q | A | S | Q |
| E | V | K | N | W | M | T | E | T | L | L | V | Q | N | A | N | P | D |
| C | K | T | I | L | K | A | L | G | P | A | A | T | L | E | E | M | M |
| T | A | C | Q | G | V | G | G | P | G | H | K | A | R | V | L | * | |

2. Amino acid sequence of p24 in secreted form [SEQ ID NO: 50]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | P | I | V | Q | N | I |
| Q | G | Q | M | V | H | Q | A | I | S | P | R | T | L | N | A | W | V |
| K | V | V | E | E | K | A | F | S | P | E | V | I | P | M | F | S | A |
| L | S | E | G | A | T | P | Q | D | L | N | T | M | L | N | T | V | G |
| G | H | Q | A | A | M | Q | M | L | K | E | T | I | N | E | E | A | A |
| E | W | D | R | V | H | P | V | H | A | G | P | I | A | P | G | Q | M |
| R | E | P | R | G | S | D | I | A | G | T | T | S | T | L | Q | E | Q |
| I | G | W | M | T | N | N | P | P | I | P | V | G | E | I | Y | K | R |
| W | I | I | L | G | L | N | K | I | V | R | M | Y | S | P | T | S | I |
| L | D | I | R | Q | G | P | K | E | P | F | R | D | Y | V | D | R | F |
| Y | K | T | L | R | A | E | Q | A | S | Q | E | V | K | N | W | M | T |
| E | T | L | L | V | Q | N | A | N | P | D | C | K | T | I | L | K | A |
| L | G | P | A | A | T | L | E | E | M | M | T | A | C | Q | G | V | G |
| G | P | G | H | K | A | R | V | L | * | | | | | | | | |

3. Amino acid sequence of p24 in secreted form [SEQ ID NO: 51]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | P | I | V | Q | N | I |
| Q | G | Q | M | V | H | Q | A | I | S | P | R | T | L | N | A | W | V |
| K | V | V | E | E | K | A | F | S | P | E | V | I | P | M | F | S | A |
| L | S | E | G | A | T | P | Q | D | L | N | T | M | L | N | T | V | G |
| G | H | Q | A | A | M | Q | M | L | K | E | T | I | N | E | E | A | A |
| R | E | P | R | G | S | D | I | A | G | T | T | S | T | L | Q | E | Q |
| I | G | W | M | T | N | N | P | P | I | P | V | G | E | I | Y | K | R |
| W | I | I | L | G | L | N | K | I | V | R | M | Y | S | P | T | S | I |
| L | D | I | R | Q | G | P | K | E | P | F | R | D | Y | V | D | R | F |
| Y | K | T | L | R | A | E | Q | A | S | Q | E | V | K | N | W | M | T |
| E | T | L | L | V | Q | N | A | N | P | D | C | K | T | I | L | K | A |
| L | G | P | A | A | T | L | E | E | M | M | T | A | C | Q | G | V | G |
| G | P | G | H | K | A | R | V | L | L | F | I | M | I | V | G | G | L |
| V | G | L | R | I | V | F | A | V | L | S | V | V | N | R | V | R | Q |
| G | Y | S | P | L | S | F | Q | T | H | L | P | I | P | R | G | * | |

FIGURE 53A

DNA sequence of modified Env including multi-clade V3 loops and Tat [SEQ ID NO: 52]:

Gaattctgcaacaactgctgtttatccattttcagaattgggtgtcgacatagcagaataggcgt
tactcgacagaggagagcaagaaatggagccagtagatcctagactagagccc Tat1

Tggaagcatccaggaagtcagcctaaaactgcttgtaccaattgctattgtaaaaagtgttgctt
tcattgccaagtttgtttcataacaaaagccttaggcatctcctatggcaggaagaagcggagac
agcgacgaagacctcctcaaggcagtcagactcatcaagtttctctatcaaagcagtaagtagta
catgtaatgcaacctatacaaatagcaatagtagcattagtagtagcaataataatagcaatagt
tgtgtggtccatagtaatcatagaatataggaaaatattaagacaaagaaaaatagacaggttaa
ttgatagactaatagaaagagcagaagacagtggcaatgagagtgaaggagaaatatcagcactt
gtggagatgggggtggagatggg Envelope Gcaccatgctccttgggatgttgatgatctgtagtgctacagaaaaattgtgggtcacagtctat
tatggggtacctgtgtggaaggaagcaaccaccactctattttgtgcatcagatgctaaagcata
tgatacagaggtacataatgtttgggccacacatgcctgtgtacccacagaccccaacccacaag
aagtagtattggtaaatgtgacagaaaattttaacatgtggaaaaatgacatggtagaacagatg
catgaggatataatcagtttatgggatcaaagcctaaagccatgtgtaaaattaaccccactctg
tgttggagctggtagttgtaacacctca Delete V1V2, insert Gly,Ala,Gly gtcattacacaggcctgtccaaaggtatcctttgagccaattcccatacattattgtgccccggc
tggttttgcgattctaaaatgtaataataagacgttcaatggaacaggaccatgtacaaatgtca
gcacagtacaatgtacacatggaattaggccagtagtatcaactcaactgctgttaaatggcagt
ctggcagaagaagaggtagtaattagatctgccaatttcacagacaatgctaaaaccataatagt
acagctgaaccaatctgtagaaattaattgtacaag First multi-clade repeat Acccaacaacaatacaagaaaaagtatccgtatccagagaggaccagggagagcatttgttacaa
taggaaaaataggaaatatgagacaagcacattgtctcgggtgtaccagacctaacaacaataca
agaaaaagtgtacgtataggaccaggacaaacattctatgcaacaggtgatataataggggatat
aagacaagcacattgttgtacgagacccaacaataatacaagaaaaagtataaggataggaccag
gacaagcattctatgcaacaggagaaataataggagatataagacaagcacattgttgcacaagg
ccctacaacaatataagacaaaggacccccataggactagggcaagcactctatacaacaagaag
aatagaagatataagaagagcacattgttgtaccagaccctccaccaatacaagaacaagtatac
gtataggaccaggacaagtattctatagaacaggagacataacaggagatataagaaaagcatat
tgtggatcctgtacaagacccaacaacaatacaagaaaaagaatatctttaggaccaggacgagt
attttatacagcaggagaaataataggagacatcagaaaggcacattgttgtaccagacctaata
acaatacaagaaaaagtataacttttgcaccaggacaagcgctctatgcaacaggtgaaataata
ggagatataagacaagcacattgtctcgggtgtaccagacctaacaacaata Second multi-clade repeat Caagaaaaagtgtacgtataggaccaggacaaacattctatgcaacaggtgatataataggggat
ataagacaagcacattgttgtacgagacccaacaataatacaagaaaaagtataaggataggacc
aggacaagcattctatgcaacaggagaaataataggagatataagacaagcacattgttgcacaa
ggccctacaacaatataagacaaaggacccccataggactagggcaagcactctatacaacaaga
agaatagaagatataagaagagcacattgttgtaccagaccctccaccaatacaagaacaagtat
acgtataggaccaggacaagtattctatagaacaggagacataacaggagatataagaaaagcat
attgtggatcctgtacaagacccaacaacaatacaagaaaaagaatatctttaggaccaggacga
gtattttatacagcaggagaaataataggagacatcagaaaggcacattgttgtaccagacctaa
taacaatacaagaaaaagtataacttttgcaccaggacaagcgctctatgcaacaggtgaaataa

FIGURE 53A-continued taggagatataagacaagcacattgtctcgggaacattagtagagcaaaatggaataacacttt
AvaI site, end of two multi-clade repeat
Aaaacagatagatagcaaattaagagaacaatttggaaataataaaacaataatctttaagcagt
cctcaggaggggacccagaaattgtaacgcacagttttaattgtggaggggaatttttctactgt
aattcaacacaactgtttaatagtacttggtttaatagtacttggagtactaaagggtcaaataa
cactgaaggaagtgacacaatcaccctcccatgcagaataaaacaaattataaacatgtggcagg
aagtaggaaaagcaatgtatgcccctcccatcagtggacaaattagatgttcatcaaatattaca
gggctgctattaacaagagatggtggtaatagcaacaatgagtccgagatcttcagacctggagg
aggagatatgagggacaattggagaagtgaattatataaatataaagtagtaaaaattgaaccat
taggagtagcacccaccaaggcaaagagaagagtggtgcagactagtgcagtgggaataggagct
ttgttccttgg
Delete the cleavage site, insert SpeI site
gttcttgggagcagcaggaagcactatgggcgcagcgtcaatgacgctgacggtacaggccagac
aattattgtctggtatagtgcagcagcagaacaatttgctgagggctattgaggcgcaacagcat
ctgttgcaactcacagtctggggcatcaagcagctccaggcaagaatcctggctgtggaaagata
cctaaaggatcaacagctcctggggatttggggttgctctggaaaactcatttgcaccactgctg
tgccttggaatgctagttggagtaataaatctctggaacagatttggaataacatgacctggatg
gagtgggacagagaaattaacaattacacaagcttaatacactccttaattgaagaatcgcaaaa
ccagcaagaaaagaatgaacaagaattattggaattagataaatgggcaagtttgtggaattggt
ttaacataacaaattggctgtggtatataaaattattcataatgatagtaggaggcttggtaggt
ttaagaatagtttttgctgtactttctgtagtgaatagagttaggcagggatattcaccattatc
gtttcagacccacctcccaatcccgaggggacccgacaggcccgaaggaatagaagaagaaggtg
gagagagagacagagacagatccattcgattagtgaacggatccttagcacttatctggtaa gp41, delete the 300 bp at C-terminal

FIGURE 53B

Amino acid sequence of modified Env including multi-clade V3 loops and Tat [SEQ ID NO: 53]:

| | | | | | | | | | | | | | | | | | |
|---|---|---|---|---|---|---|---|---|---|---|---|---|---|---|---|---|---|
| M | R | V | K | E | K | Y | Q | H | L | W | R | W | G | W | R | W | G |
| T | M | L | L | G | M | L | M | I | C | S | A | T | E | K | L | W | V |
| T | V | Y | Y | G | V | P | V | W | K | E | A | T | T | T | L | F | C |
| A | S | D | A | K | A | Y | D | T | E | V | H | N | V | W | A | T | H |
| A | C | V | P | T | D | P | N | P | Q | E | V | V | L | V | N | V | T |
| E | N | F | N | M | W | K | N | D | M | V | E | Q | M | H | E | D | I |
| I | S | L | W | D | Q | S | L | K | P | C | V | K | L | T | P | L | C |
| V | G | A | G | S | C | N | T | S | V | I | T | Q | A | C | P | K | V |
| S | F | E | P | I | P | I | H | Y | C | A | P | A | G | F | A | I | L |
| K | C | N | N | K | T | F | N | G | T | G | P | C | T | N | V | S | T |
| V | Q | C | T | H | G | I | R | P | V | V | S | T | Q | L | L | L | N |
| G | S | L | A | E | E | E | V | V | I | R | S | A | N | F | T | D | N |
| A | K | T | I | I | V | Q | L | N | Q | S | V | E | I | N | C | T | R |
| P | N | N | N | T | R | K | S | I | R | I | Q | R | G | P | G | R | A |
| F | V | T | I | G | K | I | G | N | M | R | Q | A | H | C | L | G | C |
| T | R | P | N | N | N | T | R | K | S | V | R | I | G | P | G | Q | T |
| F | Y | A | T | G | D | I | I | G | D | I | R | Q | A | H | C | C | T |
| R | P | N | N | N | T | R | K | S | I | R | I | G | P | G | Q | A | F |
| Y | A | T | G | E | I | I | G | D | I | R | Q | A | H | C | C | T | R |
| P | Y | N | N | I | R | Q | R | T | P | I | G | L | G | Q | A | L | Y |
| T | T | R | R | I | E | D | I | R | R | A | H | C | C | T | R | P | S |
| T | N | T | R | T | S | I | R | I | G | P | G | Q | V | F | Y | R | T |
| G | D | I | T | G | D | I | R | K | A | Y | C | G | S | C | T | R | P |
| N | N | N | T | R | K | R | I | S | L | G | P | G | R | V | F | Y | T |
| A | G | E | I | I | G | D | I | R | K | A | H | C | C | T | R | P | N |
| N | N | T | R | K | S | I | T | F | A | P | G | Q | A | L | Y | A | T |
| G | E | I | I | G | D | I | R | Q | A | H | C | L | G | C | T | R | P |
| N | N | N | T | R | K | S | V | R | I | G | P | G | Q | T | F | Y | A |
| T | G | D | I | I | G | D | I | R | Q | A | H | C | C | T | R | P | N |
| N | N | T | R | K | S | I | R | I | G | P | G | Q | A | F | Y | A | T |
| G | E | I | I | G | D | I | R | Q | A | H | C | C | T | R | P | Y | N |
| N | I | R | Q | R | T | P | I | G | L | G | Q | A | L | Y | T | T | R |
| R | I | E | D | I | R | R | A | H | C | C | T | R | P | S | T | N | T |
| R | T | S | I | R | I | G | P | G | Q | V | F | Y | R | T | G | D | I |
| T | G | D | I | R | K | A | Y | C | G | S | C | T | R | P | N | N | N |
| T | R | K | R | I | S | L | G | P | G | R | V | F | Y | T | A | G | E |
| I | I | G | D | I | R | K | A | H | C | C | T | R | P | N | N | N | T |
| R | K | S | I | T | F | A | P | G | Q | A | L | Y | A | T | G | E | I |
| I | G | D | I | R | Q | A | H | C | L | G | N | I | S | R | A | K | W |
| N | N | T | L | K | Q | I | D | S | K | L | R | E | Q | F | G | N | N |
| K | T | I | I | F | K | Q | S | S | G | G | D | P | E | I | V | T | H |
| S | F | N | C | G | G | E | F | F | Y | C | N | S | T | Q | L | F | N |
| S | T | W | F | N | S | T | W | S | T | K | G | S | N | N | T | E | G |
| S | D | T | I | T | L | P | C | R | I | K | Q | I | I | N | M | W | Q |
| E | V | G | K | A | M | Y | A | P | P | I | S | G | Q | I | R | C | S |
| S | N | I | T | G | L | L | L | T | R | D | G | G | N | S | N | N | E |
| S | E | I | F | R | P | G | G | G | D | M | R | D | N | W | R | S | E |
| L | Y | K | Y | K | V | V | K | I | E | P | L | G | V | A | P | T | K |
| A | K | R | R | V | V | Q | T | S | A | V | G | I | G | A | L | F | L |
| G | F | L | G | A | A | G | S | T | M | G | A | A | S | M | T | L | T |
| V | Q | A | R | Q | L | L | S | G | I | V | Q | Q | Q | N | N | L | L |
| R | A | I | E | A | Q | Q | H | L | L | Q | L | T | V | W | G | I | K |
| Q | L | Q | A | R | I | L | A | V | E | R | Y | L | K | D | Q | Q | L |
| L | G | I | W | G | C | S | G | K | L | I | C | T | T | A | V | P | W |
| N | A | S | W | S | N | K | S | L | E | Q | I | W | N | N | M | T | W |
| M | E | W | D | R | E | I | N | N | Y | T | S | L | I | H | S | L | I |
| E | E | S | Q | N | Q | Q | E | K | N | E | Q | E | L | L | E | L | D |
| K | W | A | S | L | W | N | W | F | N | I | T | N | W | L | W | Y | I |
| K | L | F | I | M | I | V | G | G | L | V | G | L | R | I | V | F | A |
| T | H | L | P | I | P | R | G | P | D | R | P | E | G | I | E | E | E |
| G | G | E | R | D | R | D | R | S | I | R | L | V | N | G | S | L | A |
| L | I | W | * | | | | | | | | | | | | | | |

FIGURE 54A

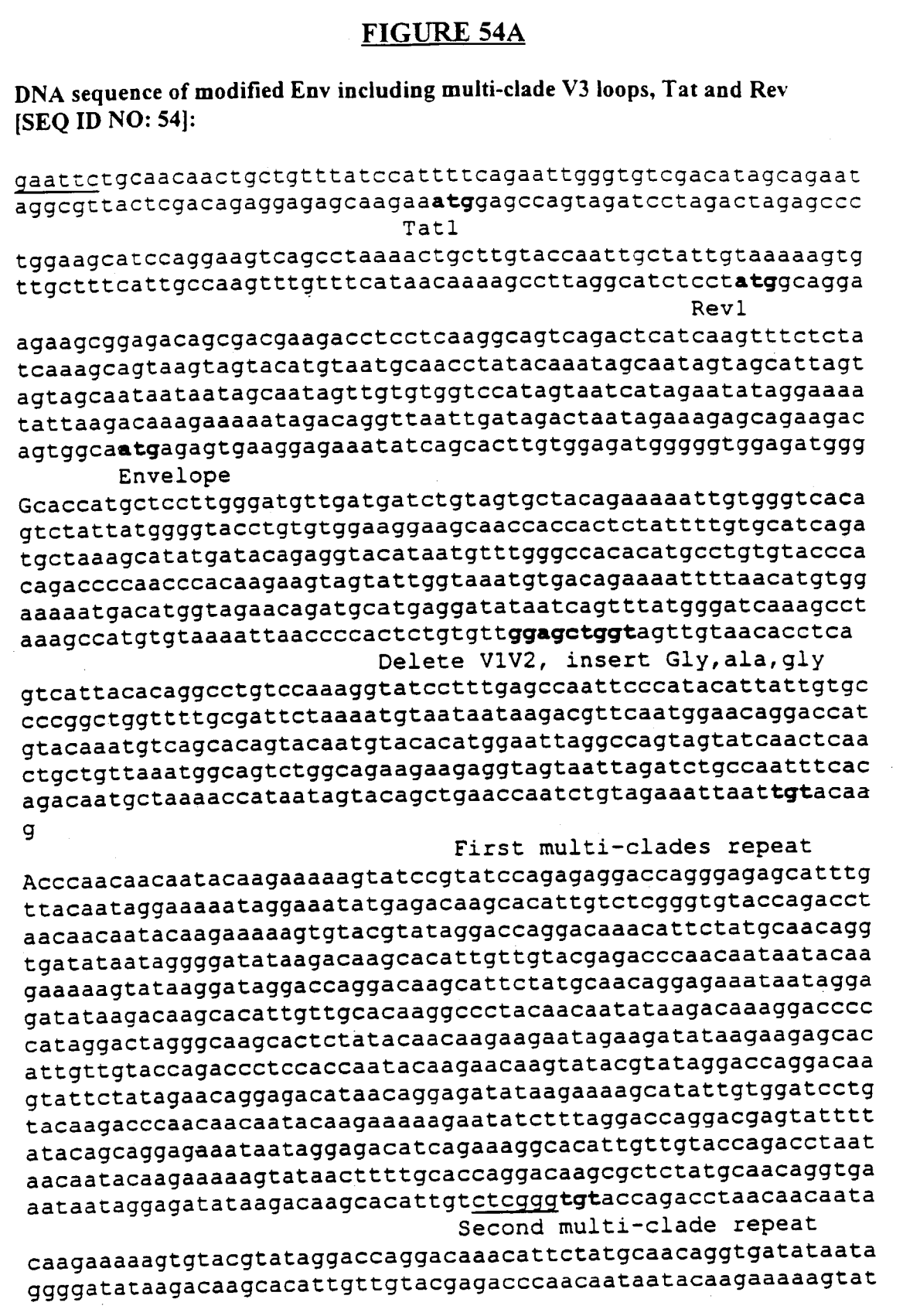

DNA sequence of modified Env including multi-clade V3 loops, Tat and Rev [SEQ ID NO: 54]:

gaattctgcaacaactgctgtttatccattttcagaattgggtgtcgacatagcagaat
aggcgttactcgacagaggagagcaagaaatggagccagtagatcctagactagagccc
Tat1
tggaagcatccaggaagtcagcctaaaactgcttgtaccaattgctattgtaaaaagtg
ttgctttcattgccaagtttgtttcataacaaaagccttaggcatctcctatggcagga
Rev1
agaagcggagacagcgacgaagacctcctcaaggcagtcagactcatcaagtttctcta
tcaaagcagtaagtagtacatgtaatgcaacctatacaaatagcaatagtagcattagt
agtagcaataataatagcaatagttgtgtggtccatagtaatcatagaatataggaaaa
tattaagacaaagaaaaatagacaggttaattgatagactaatagaaagagcagaagac
agtggcaatgagagtgaaggagaaatatcagcacttgtggagatgggggtggagatggg
Envelope
Gcaccatgctccttgggatgttgatgatctgtagtgctacagaaaaattgtgggtcaca
gtctattatggggtacctgtgtggaaggaagcaaccaccactctattttgtgcatcaga
tgctaaagcatatgatacagaggtacataatgtttgggccacacatgcctgtgtaccca
cagaccccaacccacaagaagtagtattggtaaatgtgacagaaaattttaacatgtgg
aaaaatgacatggtagaacagatgcatgaggatataatcagtttatgggatcaaagcct
aaagccatgtgtaaaattaaccccactctgtgttggagctggtagttgtaacacctca
Delete V1V2, insert Gly,ala,gly
gtcattacacaggcctgtccaaaggtatcctttgagccaattcccatacattattgtgc
cccggctggttttgcgattctaaaatgtaataataagacgttcaatggaacaggaccat
gtacaaatgtcagcacagtacaatgtacacatggaattaggccagtagtatcaactcaa
ctgctgttaaatggcagtctggcagaagaagaggtagtaattagatctgccaatttcac
agacaatgctaaaaccataatagtacagctgaaccaatctgtagaaattaattgtacaa
g
First multi-clades repeat
Acccaacaacaatacaagaaaaagtatccgtatccagagaggaccagggagagcatttg
ttacaataggaaaaataggaaatatgagacaagcacattgtctcgggtgtaccagacct
aacaacaatacaagaaaaagtgtacgtataggaccaggacaaacattctatgcaacagg
tgatataatagggatataagacaagcacattgttgtacgagacccaacaataatacaa
gaaaaagtataaggataggaccaggacaagcattctatgcaacaggagaaataatagga
gatataagacaagcacattgttgcacaaggccctacaacaatataagacaaaggacccc
cataggactagggcaagcactctatacaacaagaagaatagaagatataagaagagcac
attgttgtaccagaccctccaccaatacaagaacaagtatacgtataggaccaggacaa
gtattctatagaacaggagacataacaggagatataagaaaagcatattgtggatcctg
tacaagacccaacaacaatacaagaaaaagaatatctttaggaccaggacgagtatttt
atacagcaggagaaataataggagacatcagaaaggcacattgttgtaccagacctaat
aacaatacaagaaaaagtataacttttgcaccaggacaagcgctctatgcaacaggtga
aataataggagatataagacaagcacattgtctcgggtgtaccagacctaacaacaata
Second multi-clade repeat
caagaaaaagtgtacgtataggaccaggacaaacattctatgcaacaggtgatataata
ggggatataagacaagcacattgttgtacgagacccaacaataatacaagaaaaagtat FIGURE 54A-continued aaggataggaccaggacaagcattctatgcaacaggagaaataataggagatataagac
aagcacattgttgcacaaggccctacaacaatataagacaaaggacccccataggacta
gggcaagcactctatacaacaagaagaatagaagatataagaagagcacattgttgtac
cagaccctccaccaatacaagaacaagtatacgtataggaccaggacaagtattctata
gaacaggagacataacaggagatataagaaaagcatattgtggatcctgtacaagaccc
aacaacaatacaagaaaaagaatatctttaggaccaggacgagtattttatacagcagg
agaaataataggagacatcagaaaggcacattgttgtaccagacctaataacaatacaa
gaaaaagtataacttttgcaccaggacaagcgctctatgcaacaggtgaaataatagga
gatataagacaagcacattgtctcgggaacattagtagagcaaaatggaataacacttt
AvaI site, end of two multi-clade repeat
Aaaacagatagatagcaaattaagagaacaatttggaaataataaaacaataatcttta
agcagtcctcaggaggggacccagaaattgtaacgcacagttttaattgtggaggggaa
tttttctactgtaattcaacacaactgtttaatagtacttggtttaatagtacttggag
tactaaagggtcaaataacactgaaggaagtgacacaatcaccctcccatgcagaataa
aacaaattataaacatgtggcaggaagtaggaaaagcaatgtatgcccctcccatcagt
ggacaaattagatgttcatcaaatattacagggctgctattaacaagagatggtggtaa
tagcaacaatgagtccgagatcttcagacctggaggaggagatatgagggacaattgga
gaagtgaattatataaatataaagtagtaaaaattgaaccattaggagtagcacccacc
aaggcaaagagaagagtggtgcagactagtgcagtgggaataggagctttgttccttgg
Delete the cleavage site, insert SpeI
gttcttgggagcagcaggaagcactatgggctgcacgtcaatgacgctgacggtacagg
ccagacaattattgtctgatatagtgcagcagcagaacaatttgctgagggctattgag
gcgcaacagcatctgttgcaactcacagtctggggcatcaaacagctccaggcaagaat
cctggctgtggaaagatacctaaaggatcaacagctcctggggatttggggttgctctg
gaaaactcatttgcaccactgctgtgccttggaatgctagttggagtaataaatctctg
gaacagatttggaataacatgacctggatggagtgggacagagaaattaacaattacac
aagcttaatacactccttaattgaagaatcgcaaaaccagcaagaaaagaatgaacaag
aattattggaattagataaatgggcaagtttgtggaattggtttaacataacaaattgg
ctgtggtatataaaattattcataatgatagtaggaggcttggtaggtttaagaatagt
ttttgctgtactttctatagtgaatagagttaggcagggatattcaccattatcgtttc
agacccacctcccaatcccgaggggacccgacaggcccgaaggaatagaagaagaaggt
ggagagagagacagagacagatccattcgattagtgaacggatccttagcacttatctg
ggacgatctgcggagcctgtgcctcttcagctaccaccgcttgagagacttactcttga
ttgtaacgaggattgtggaacttctgggacgcagggggtgggaagccctcaaatattgg
tggaatctcctacagtattggagtcaggaactaaagaatagtgctgttaacttgctcaa
tgccacagccatagcagtagctgagtaa gp41, but 99 bp truncation at C-terminal

FIGURE 54B

Amino acid sequence of modified Env including multi-clade V3 loops, Tat and Rev [SEQ ID NO: 55]:

DNA sequence of HIV-1 (strain BH10) Protease (PI, nt 1407-1907) [SEQ ID NO: 56]:

atgttctttagggaagatctggccttcctacaagggaaggccagggaattttcttcagagcagaccagagcca
acagccccaccatttcttcagagcagaccagagccaacagccccaccagaagagagcttcaggtctggggt
agagacaacaactccccctcagaagcaggagccgatagacaaggaactgtatcctttaacttccctcagatc
actctttggcaacgacccctcgtcacaataaagataggggggcaactaaaggaagctctattagatacagga
gcagatgatacagtattagaagaaatgagtttgccaggaagatggaaaccaaaaatgatagggggaattgg
aggttttatcaaagtaagacagtatgatcagatactcatagaaatctgtggacataaagctataggtacagtatt
agtaggacctacacctgtcaacataattggaagaaatctgttgactcagattggttgcactttaaatttttaa

FIGURE 55B

Amino acid sequence of HIV-1 (strain BH10) Protease (PI) [SEQ ID NO: 57]:

DNA sequence of HIV-1 (strain BH10) Gag-PI [SEQ ID NO: 58]:

Atgggtgcgagagcgtcagtattaagcgggggagaattagatcgatgggaaaaaattcg
gttaaggccagggggaaagaaaaaatataaattaaaacatatagtatgggcaagcaggg
agctagaacgattcgcagttaatcctggcctgttagaaacatcagaaggctgtagacaa
atactgggacagctacaaccatcccttcagacaggatcagaagaacttagatcattata
taatacagtagcaaccctctattgtgtgcatcaaaggatagagataaaagacaccaagg
aagctttagacaagatagaggaagagcaaaacaaaagtaagaaaaaagcacagcaagca
gcagctgacacaggacacagcagtcaggtcagccaaaattaccctatagtgcagaacat
ccaggggcaaatggtacatcaggccatatcacctagaactttaaatgcatgggtaaaag
tagtagaagagaaggctttcagcccagaagtaatacccatgttttcagcattatcagaa
ggagccaccccacaagatttaaacaccatgctaaacacagtggggggacatcaagcagc
catgcaaatgttaaaagagaccatcaatgaggaagctgcagaatgggatagagtacatc
cagtgcatgcagggcctattgcaccaggccagatgagagaaccaaggggaagtgacata
gcaggaactactagtacccttcaggaacaaataggatggatgacaaataatccacctat
cccagtaggagaaatttataaaagatggataatcctgggattaaataaaatagtaagaa
tgtatagccctaccagcattctggacataagacaaggaccaaaagaaccttttagagac
tatgtagaccggttctataaaactctaagagccgagcaagcttcacaggaggtaaaaaa
ttggatgacagaaaccttgttggtccaaaatgcgaacccagattgtaagactattttaa
aagcattgggaccagcggctacactagaagaaatgatgacagcatgtcagggagtagga
ggacccggccataaggcaagagttttggctgaagcaatgagccaagtaacaaatacagc
taccataatgatgcagagaggcaattttaggaaccaaagaaagatggttaagtgtttca
attgtggcaaagaagggcacacagccagaaattgcagggcccctaggaaaaagggctgt
tggaaatgtggaaaggaaggacaccaaatgaaagattgtactgagagacaggctaattt
tttagggaagatctggccttcctacaagggaaggccagggaattttcttcagagcaga
ccagagccaacagccccaccatttcttcagagcagaccagagccaacagccccaccaga
agagagcttcaggtctggggtagagacaacaactccccctcagaagcaggagccgatag
acaaggaactgtatcctttaacttccctcagatcactctttggcaacgacccctcgtca
caataaagataggggggcaactaaaggaagctctattagatacaggagcagatgataca
gtattagaagaaatgagtttgccaggaagatggaaaccaaaaatgatagggggaattgg
aggttttatcaaagtaagacagtatgatcagatactcatagaaatctgtggacataaag
ctataggtacagtattagtaggacctacacctgtcaacataattggaagaaatctgttg
actcagattggttgcactttaaattttaa

FIGURE 56B

Amino acid sequence of HIV-1 (strain BH10) Gag-PI [SEQ ID NO: 59]:

| | | | | | | | | | | | | | | | | | |
|---|---|---|---|---|---|---|---|---|---|---|---|---|---|---|---|---|---|
| M | G | A | R | A | S | V | L | S | G | G | E | L | D | R | W | E | K |
| I | R | L | R | P | G | G | K | K | K | Y | K | L | K | H | I | V | W |
| A | S | R | E | L | E | R | F | A | V | N | P | G | L | L | E | T | S |
| E | G | C | R | Q | I | L | G | Q | L | Q | P | S | L | Q | T | G | S |
| E | E | L | R | S | L | Y | N | T | V | A | T | L | Y | C | V | H | Q |
| R | I | E | I | K | D | T | K | E | A | L | D | K | I | E | E | E | Q |
| N | K | S | K | K | K | A | Q | Q | A | A | A | D | T | G | H | S | S |
| Q | V | S | Q | N | Y | P | I | V | Q | N | I | Q | G | Q | M | V | H |
| Q | A | I | S | P | R | T | L | N | A | W | V | K | V | V | E | E | K |
| A | F | S | P | E | V | I | P | M | F | S | A | L | S | E | G | A | T |
| P | Q | D | L | N | T | M | L | N | T | V | G | G | H | Q | A | A | M |
| Q | M | L | K | E | T | I | N | E | E | A | A | E | W | D | R | V | H |
| P | V | H | A | G | P | I | A | P | G | Q | M | R | E | P | R | G | S |
| D | I | A | G | T | T | S | T | L | Q | E | Q | I | G | W | M | T | N |
| N | P | P | I | P | V | G | E | I | Y | K | R | W | I | I | L | G | L |
| N | K | I | V | R | M | Y | S | P | T | S | I | L | D | I | R | Q | G |
| P | K | E | P | F | R | D | Y | V | D | R | F | Y | K | T | L | R | A |
| E | Q | A | S | Q | E | V | K | N | W | M | T | E | T | L | L | V | Q |
| N | A | N | P | D | C | K | T | I | L | K | A | L | G | P | A | A | T |
| L | E | E | M | M | T | A | C | Q | G | V | G | G | P | G | H | K | A |
| R | V | L | A | E | A | M | S | Q | V | T | N | T | A | T | I | M | M |
| Q | R | G | N | F | R | N | Q | R | K | M | V | K | C | F | N | C | G |
| K | E | G | H | T | A | R | N | C | R | A | P | R | K | K | G | C | W |
| K | C | G | K | E | G | H | Q | M | K | D | C | T | E | R | Q | A | N |
| F | F | R | E | D | L | A | F | L | Q | G | K | A | R | E | F | S | S |
| E | Q | T | R | A | N | S | P | T | I | S | S | E | Q | T | R | A | N |
| S | P | T | R | R | E | L | Q | V | W | G | R | D | N | N | S | P | S |
| E | A | G | A | D | R | Q | G | T | V | S | F | N | F | P | Q | I | T |
| L | W | Q | R | P | L | V | T | I | K | I | G | G | Q | L | K | E | A |
| L | L | D | T | G | A | D | D | T | V | L | E | E | M | S | L | P | G |
| R | W | K | P | K | M | I | G | G | I | G | G | F | I | K | V | R | Q |
| Y | D | Q | I | L | I | E | I | C | G | H | K | A | I | G | T | V | L |
| V | G | P | T | P | V | N | I | I | G | R | N | L | L | T | Q | I | G |
| C | T | L | N | F | * | | | | | | | | | | | | |

FIGURE 57

Primers for multi-clade V3 loops:

Clade A: (1). forward primer A888F5 [SEQ ID NO: 60]:

5'-aaa tca acc gga att gaa ttc cct cgg gtg tac cag acc taa caa caa tac-3'

EcoRI AvaI (2). reverse primer A-CR3 [SEQ ID NO: 61]:

5'-att gtt ggg tct cgt aca aca atg tgc ttg tct tat atc ccc-3'

Clade C: (3). forward primer A-CF5 [SEQ ID NO: 62]:

5'-ggg gat ata aga caa gca cat tgt acg aga ccc aac aat ac-3'

(4). reverse primer C980R3 [SEQ ID NO: 63]:

5'-gtt gta ggg cct tgt gca aca atg tgc ttg tct tat atc –3'

Clade D: (5). forward primer D888F5 [SEQ ID NO: 64]:

5'-gat ata aga caa gca cat tgt tgc aca agg ccc tac aac-3'

(6). reverse primer D-ER3 [SEQ ID NO: 65]:

5'-ggt gga ggg tct ggt aca aca atg tgc tct tct tat –3'

Clade E: (7). forward primer D-EF5 [SEQ ID NO: 66]:

5' -ata aga aga gca cat tgt tgt acc aga ccc tcc acc-3'

(8). reverse primer E998R3 [SEQ ID NO: 67]:

5'-gta ttg ttg ttg ggt ctt gta caa caa tat gct ttt ctt ata tct cc-3'

Clade F: (9). forward primer F888F5 [SEQ ID NO: 68]:

5'-gga gat ata aga aaa gca tat tgt tgt aca aga ccc aac aac aat ac-3'

(10). reverse primer F-GR3 [SEQ ID NO: 69]:

5'-gtt att agg tct ggt aca aca atg tgc ctt tct gat gtc-3'

Clade G: (11). forward primer F-GF5 [SEQ ID NO: 70]:

5'-gac atc aga aag gca cat tgt tgt acc aga cct aat aac-3'

(12). reverse primer G989R3 [SEQ ID NO: 71]:

5'-aat aaa cta gtc tag acc ccc gag tct aga aca atg tgc ttg tct tat atc tcc-3'

AvaI XbaI pRAd-ORF6-Gag/PI-RT pRAd-ORF6-Gag-PI-RT pRAd-ORF6-Gag/Pol pRAd-ORF6-Gag-Pol

SEQUENCE LISTING

```
<160> NUMBER OF SEQ ID NOS: 75

<210> SEQ ID NO 1
<211> LENGTH: 7
<212> TYPE: DNA
<213> ORGANISM: Ebola virus

<400> SEQUENCE: 1

ttttttt                                                                7


<210> SEQ ID NO 2
<211> LENGTH: 7
<212> TYPE: RNA
<213> ORGANISM: Ebola virus

<400> SEQUENCE: 2

uuuuuuu                                                                7


<210> SEQ ID NO 3
<211> LENGTH: 8
<212> TYPE: RNA
<213> ORGANISM: Artificial sequence
<220> FEATURE:
<223> OTHER INFORMATION: Modified RNA editing site

<400> SEQUENCE: 3

uucuucuu                                                               8


<210> SEQ ID NO 4
<211> LENGTH: 7
<212> TYPE: DNA
<213> ORGANISM: Ebola virus

<400> SEQUENCE: 4

aaaaaaa                                                                7


<210> SEQ ID NO 5
<211> LENGTH: 8
<212> TYPE: DNA
<213> ORGANISM: Artificial sequence
<220> FEATURE:
<223> OTHER INFORMATION: DNA of modified RNA editing site

<400> SEQUENCE: 5

aagaagaa                                                               8
```

-continued

<210> SEQ ID NO 6
<211> LENGTH: 6
<212> TYPE: RNA
<213> ORGANISM: Ebola virus

<400> SEQUENCE: 6 uuuuuu 6

<210> SEQ ID NO 7
<211> LENGTH: 6
<212> TYPE: RNA
<213> ORGANISM: Artificial sequence
<220> FEATURE:
<223> OTHER INFORMATION: Modified RNA editing site

<400> SEQUENCE: 7 uucuuc 6

<210> SEQ ID NO 8
<211> LENGTH: 6
<212> TYPE: DNA
<213> ORGANISM: Artificial sequence
<220> FEATURE:
<223> OTHER INFORMATION: DNA of modified RNA editing site

<400> SEQUENCE: 8 ttcttc 6

<210> SEQ ID NO 9
<211> LENGTH: 21
<212> TYPE: PRT
<213> ORGANISM: Homo sapiens

<400> SEQUENCE: 9

```
Ser Trp Leu Leu Leu Leu Leu Leu Ser Leu Ser Leu Leu Gln Ala Thr
1               5                   10                  15

Asp Phe Met Ser Leu
            20
```

<210> SEQ ID NO 10
<211> LENGTH: 5
<212> TYPE: PRT
<213> ORGANISM: Ebola virus

<400> SEQUENCE: 10

```
Arg Arg Thr Arg Arg
1               5
```

<210> SEQ ID NO 11
<211> LENGTH: 4
<212> TYPE: PRT
<213> ORGANISM: Human immunodeficiency virus type 1

<400> SEQUENCE: 11

```
Arg Glu Lys Arg
1
```

<210> SEQ ID NO 12
<211> LENGTH: 9
<212> TYPE: DNA
<213> ORGANISM: Artificial sequence
<220> FEATURE:
<223> OTHER INFORMATION: DNA of GAG site -continued

<400> SEQUENCE: 12 ggagctggt 9

<210> SEQ ID NO 13
<211> LENGTH: 3
<212> TYPE: PRT
<213> ORGANISM: Artificial sequence
<220> FEATURE:
<223> OTHER INFORMATION: GAG site

<400> SEQUENCE: 13

Gly Ala Gly
1

<210> SEQ ID NO 14
<211> LENGTH: 3157
<212> TYPE: DNA
<213> ORGANISM: Artificial sequence
<220> FEATURE:
<223> OTHER INFORMATION: Env/Tat/Rev

<400> SEQUENCE: 14
gaattctgca acaactgctg tttatccatt ttcagaattg ggtgtcgaca tagcagaata 60
ggcgttactc gacagaggag agcaagaaat ggagccagta gatcctagac tagagccctg 120
gaagcatcca ggaagtcagc ctaaaactgc ttgtaccaat tgctattgta aaaagtgttg 180
ctttcattgc caagtttgtt tcataacaaa agccttaggc atctcctatg gcaggaagaa 240
gcggagacag cgacgaagac ctcctcaagg cagtcagact catcaagttt ctctatcaaa 300
gcagtaagta gtacatgtaa tgcaacctat acaaatagca atagtagcat tagtagtagc 360
aataataata gcaatagttg tgtggtccat agtaatcata gaatatagga aaatattaag 420
acaaagaaaa atagacaggt taattgatag actaatagaa agagcagaag acagtggcaa 480
tgagagtgaa ggagaaatat cagcacttgt ggagatgggg gtggagatgg ggcaccatgc 540
tccttgggat gttgatgatc tgtagtgcta cagaaaaatt gtgggtcaca gtctattatg 600
gggtacctgt gtggaaggaa gcaaccacca ctctattttg tgcatcagat gctaaagcat 660
atgatacaga ggtacataat gtttgggcca cacatgcctg tgtacccaca gaccccaacc 720
cacaagaagt agtattggta aatgtgacag aaaattttaa catgtggaaa aatgacatgg 780
tagaacagat gcatgaggat ataatcagtt tatgggatca aagcctaaag ccatgtgtaa 840
aattaacccc actctgtgtt agtttaaagt gcactgattt gaagaatgat actaatacca 900
atagtagtag cgggagaatg ataatggaga aaggagagat aaaaaactgc tctttcaata 960
tcagcacaag cataagaggt aaggtgcaga aagaatatgc atttttttat aaacttgata 1020
taataccaat agataatgat actaccagct atacgttgac aagttgtaac acctcagtca 1080
ttacacaggc ctgtccaaag gtatcctttg agccaattcc catacattat tgtgccccgg 1140
ctggttttgc gattctaaaa tgtaataata agacgttcaa tggaacagga ccatgtacaa 1200
atgtcagcac agtacaatgt acacatggaa ttaggccagt agtatcaact caactgctgt 1260
taaatggcag tctggcagaa gaagaggtag taattagatc tgccaatttc acagacaatg 1320
ctaaaaccat aatagtacag ctgaaccaat ctgtagaaat taattgtaca agacccaaca 1380
acaatacaag aaaaagtatc cgtatccaga gaggaccagg gagagcattt gttacaatag 1440
gaaaaatagg aaatatgaga caagcacatt gtaacattag tagagcaaaa tggaataaca 1500
ctttaaaaca gatagatagc aaattaagag aacaatttgg aaataataaa acaataatct 1560

-continued ttaagcagtc ctcaggaggg gacccagaaa ttgtaacgca cagttttaat tgtggagggg 1620
aatttttcta ctgtaattca acacaactgt ttaatagtac ttggtttaat agtacttgga 1680
gtactaaagg gtcaaataac actgaaggaa gtgacacaat caccctccca tgcagaataa 1740
aacaaattat aaacatgtgg caggaagtag gaaaagcaat gtatgcccct cccatcagtg 1800
gacaaattag atgttcatca aatattacag ggctgctatt aacaagagat ggtggtaata 1860
gcaacaatga gtccgagatc ttcagacctg gaggaggaga tatgagggac aattggagaa 1920
gtgaattata taaatataaa gtagtaaaaa ttgaaccatt aggagtagca cccaccaagg 1980
caaagagaag agtggtgcag agagaaaaaa gagcagtggg aataggagct ttgttccttg 2040
ggttcttggg agcagcagga agcactatgg gcgcagcgtc aatgacgctg acggtacagg 2100
ccagacaatt attgtctggt atagtgcagc agcagaacaa tttgctgagg gctattgagg 2160
cgcaacagca tctgttgcaa ctcacagtct ggggcatcaa gcagctccag gcaagaatcc 2220
tggctgtgga aagataccta aaggatcaac agctcctggg gatttggggt tgctctggaa 2280
aactcatttg caccactgct gtgccttgga atgctagttg gagtaataaa tctctggaac 2340
agatttggaa taacatgacc tggatggagt gggacagaga aattaacaat tacacaagct 2400
taatacactc cttaattgaa gaatcgcaaa accagcaaga aaagaatgaa caagaattat 2460
tggaattaga taaatgggca agtttgtgga attggtttaa cataacaaat tggctgtggt 2520
atataaaatt attcataatg atagtaggag gcttggtagg tttaagaata gtttttgctg 2580
tactttctgt agtgaataga gttaggcagg gatattcacc attatcgttt cagacccacc 2640
tcccaatccc gaggggaccc gacaggcccg aaggaataga agaagaaggt ggagagagag 2700
acagagacag atccattcga ttagtgaacg gatccttagc acttatctgg gacgatctgc 2760
ggagcctgtg cctcttcagc taccaccgct tgagagactt actcttgatt gtaacgagga 2820
ttgtggaact tctgggacgc agggggtggg aagccctcaa atattggtgg aatctcctac 2880
agtattggag tcaggagcta aagaatagtg ctgttagctt gctcaatgcc acagctatag 2940
cagtagctga ggggacagat agggttatag aagtagtaca aggagcttat agagctattc 3000
gccacatacc tagaagaata agacagggct tggaaaggat tttgctataa gatgggtggc 3060
aagtggtcaa aaagtagtgt ggttggatgg cctgctgtaa gggaaagaat gagacgagct 3120
gagccagcag cagatggggt gggagcagca tctcgag 3157

<210> SEQ ID NO 15
<211> LENGTH: 508
<212> TYPE: DNA
<213> ORGANISM: Artificial sequence
<220> FEATURE:
<223> OTHER INFORMATION: Modified IL-2

<400> SEQUENCE: 15
tcactctctt taatcactac tcacagtaac ctcaactcct gccacaatgt acaggatgca 60
actcctgtct tgcattgcac taagtcttgc acttgtcaca aacagtgcac ctacttcaag 120
ttctacaaag aaaacacagc tacaactgga gcatttactg ctggatttac agatgatttt 180
gaatggaatt aataattaca agaatcccaa actcaccagg atgctcacat ttaagtttta 240
catgcccaag aaggccacag aactgaaaca tcttcagtgt cttgaagaag aactcaaacc 300
tctggaggaa gtgctaaatt tagctcaaag caaaaacttt cacttaagac ccagggactt 360
aatcagcaat atcaacgtaa tagttctgga actaaaggga tctgaaacaa cattcatgtg 420

-continued tgaatatgct gatgagacag caaccattgt agaatttctg aacagatgga ttaccttttg 480
tcaaagcatc atctcaacac taacttga 508

<210> SEQ ID NO 16
<211> LENGTH: 2280
<212> TYPE: DNA
<213> ORGANISM: Artificial sequence
<220> FEATURE:
<223> OTHER INFORMATION: Modified Env

<400> SEQUENCE: 16
gaattcgcca ccatgggagt gaaggagaaa tatcagcact tgtggagatg gggggtggaga 60 tggggcacca tgctccttgg gatgttgatg atctgtagtg ctacagaaaa attgtgggtc 120
acagtctatt atggggtacc tgtgtggaag gaagcaacca ccactctatt ttgtgcatca 180
gatgctaaag catatgatac agaggtacat aatgtttggg ccacacatgc ctgtgtaccc 240
acagacccca acccacaaga agtagtattg gtaaatgtga cagaaaattt taacatgtgg 300
aaaaatgaca tggtagaaca gatgcatgag gatataatca gtttatggga tcaaagccta 360
aagccatgtg taaaattaac cccactctgt gttagtttaa agtgcactga tttgaagaat 420
gatactaata ccaatagtag tagcgggaga atgataatgg agaaaggaga gataaaaaac 480
tgctctttca atatcagcac aagcataaga ggtaaggtgc agaaagaata tgcatttttt 540
tataaacttg atataatacc aatagataat gatactacca gctatacgtt gacaagttgt 600
aacacctcag tcattacaca ggcctgtcca aaggtatcct ttgagccaat tcccatacat 660
tattgtgccc cggctggttt tgcgattcta aaatgtaata ataagacgtt caatggaaca 720
ggaccatgta caaatgtcag cacagtacaa tgtacacatg gaattaggcc agtagtatca 780
actcaactgc tgttaaatgg cagtctggca gaagaagagg tagtaattag atctgccaat 840
ttcacagaca atgctaaaac cataatagta cagctgaacc aatctgtaga aattaattgt 900
acaagaccca acaacaatac aagaaaaagt atccgtatcc agagaggacc agggagagca 960
tttgttacaa taggaaaaat aggaaatatg agacaagcac attgtaacat tagtagagca 1020
aaatggaata acactttaaa acagatagat agcaaattaa gagaacaatt tggaaataat 1080
aaaacaataa tctttaagca gtcctcagga ggggacccag aaattgtaac gcacagtttt 1140
aattgtggag gggaattttt ctactgtaat tcaacacaac tgtttaatag tacttggttt 1200
aatagtactt ggagtactaa agggtcaaat aacactgaag gaagtgacac aatcaccctc 1260
ccatgcagaa taaaacaaat tataaacatg tggcaggaag taggaaaagc aatgtatgcc 1320
cctcccatca gtggacaaat tagatgttca tcaaatatta cagggctgct attaacaaga 1380
gatggtggta atagcaacaa tgagtccgag atcttcagac ctggaggagg agatatgagg 1440
gacaattgga gaagtgaatt atataaatat aaagtagtaa aaattgaacc attaggagta 1500
gcacccacca aggcaaagag aagagtggtg cagactagtg cagtgggaat aggagctttg 1560
ttccttgggt tcttgggagc agcaggaagc actatgggcg cagcgtcaat gacgctgacg 1620
gtacaggcca gacaattatt gtctggtata gtgcagcagc agaacaattt gctgagggct 1680
attgaggcgc aacagcatct gttgcaactc acagtctggg gcatcaagca gctccaggca 1740
agaatcctgg ctgtggaaag atacctaaag gatcaacagc tcctggggat ttggggttgc 1800
tctggaaaac tcatttgcac cactgctgtg ccttggaatg ctagttggag taataaatct 1860
ctggaacaga tttggaataa catgacctgg atggagtggg acagagaaat taacaattac 1920
acaagcttaa tacactcctt aattgaagaa tcgcaaaacc agcaagaaaa gaatgaacaa 1980

-continued gaattattgg aattagataa atgggcaagt ttgtggaatt ggtttaacat aacaaattgg 2040
ctgtggtata taaaattatt cataatgata gtaggaggct tggtaggttt aagaatagtt 2100
tttgctgtac tttctgtagt gaatagagtt aggcagggat attcaccatt atcgtttcag 2160
acccacctcc caatcccgag gggacccgac aggcccgaag gaatagaaga agaaggtgga 2220
gagagagaca gagacagatc cattcgatta gtgaacggat ccttagcact tatctggtaa 2280

<210> SEQ ID NO 17
<211> LENGTH: 1496
<212> TYPE: DNA
<213> ORGANISM: Artificial sequence
<220> FEATURE:
<223> OTHER INFORMATION: Full length Gag

<400> SEQUENCE: 17
ggctagaagg agagaggatg ggtgcgagag cgtcagtatt aagcggggga gaattagatc 60
gatgggaaaa aattcggtta aggccagggg gaaagaaaaa atataaatta aaacatatag 120
tatgggcaag cagggagcta gaacgactac aaccatccct tcagacagga tcagaagaac 180
ttagatcatt atataataca gtagcaaccc tctattgtgt gcatcaaagg atagagataa 240
aagacaccaa ggaagcttta gacaagatag aggaagagca aaacaaaagt aagaaaaaag 300
cacagcaagc agcagctgac acaggacaca gcagtcaggt cagccaaaat taccctatag 360
tgcagaacat ccaggggcaa atggtacatc aggccatatc acctagaact ttaaatgcat 420
gggtaaaagt agtagaagag aaggctttca gcccagaagt aatacccatg ttttcagcat 480
tatcagaagg agccacccca caagatttaa acaccatgct aaacacagtg gggggacatc 540
aagcagccat gcaaatgtta aaagagacca tcaatgagga agctgcagaa tgggatagag 600
tacatccagt gcatgcaggg cctattgcac caggccagat gagagaacca aggggaagtg 660
acatagcagg aactactagt acccttcagg aacaaatagg atggatgaca aataatccac 720
ctatcccagt aggagaaatt tataaaagat ggataatcct gggattaaat aaaatagtaa 780
gaatgtatag ccctaccagc attctggaca taagacaagg accaaaagaa ccttttagag 840
actatgtaga ccggttctat aaaactctaa gagccgagca agcttcacag gaggtaaaaa 900
attggatgac agaaaccttg ttggtccaaa atgcgaaccc agattgtaag actattttaa 960
aagcattggg accagcggct acactagaag aaatgatgac agcatgtcag ggagtaggag 1020
gacccggcca taaggcaaga gttttggctg aagcaatgag ccaagtaaca aatacagcta 1080
ccataatgat gcagagaggc aattttagga accaaagaaa gatggttaag tgtttcaatt 1140
gtggcaaaga agggcacaca gccagaaatt gcagggcccc taggaaaaag ggctgttgga 1200
aatgtggaaa ggaaggacac caaatgaaag attgtactga gagacaggct aatttttag 1260 ggaagatctg gccttcctac aagggaaggc cagggaattt tcttcagagc agaccagagc 1320
caacagcccc accatttctt cagagcagac cagagccaac agccccacca gaagagagct 1380
tcaggtctgg ggtagagaca acaactcccc ctcagaagca ggagccgata gacaaggaac 1440
tgtatccttt aacttccctc agatcactct ttggcaacga cccctcgtca caataa 1496

<210> SEQ ID NO 18
<211> LENGTH: 492
<212> TYPE: PRT
<213> ORGANISM: Human immunodeficiency virus type 1

-continued

<400> SEQUENCE: 18

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Leu Gln Pro Ser Leu
        35                  40                  45

Gln Thr Gly Ser Glu Glu Leu Arg Ser Leu Tyr Asn Thr Val Ala Thr
    50                  55                  60

Leu Tyr Cys Val His Gln Arg Ile Glu Ile Lys Asp Thr Lys Glu Ala
65                  70                  75                  80

Leu Asp Lys Ile Glu Glu Glu Gln Asn Lys Ser Lys Lys Lys Ala Gln
                85                  90                  95

Gln Ala Ala Ala Asp Thr Gly His Ser Ser Gln Val Ser Gln Asn Tyr
            100                 105                 110

Pro Ile Val Gln Asn Ile Gln Gly Gln Met Val His Gln Ala Ile Ser
        115                 120                 125

Pro Arg Thr Leu Asn Ala Trp Val Lys Val Val Glu Glu Lys Ala Phe
    130                 135                 140

Ser Pro Glu Val Ile Pro Met Phe Ser Ala Leu Ser Glu Gly Ala Thr
145                 150                 155                 160

Pro Gln Asp Leu Asn Thr Met Leu Asn Thr Val Gly Gly His Gln Ala
                165                 170                 175

Ala Met Gln Met Leu Lys Glu Thr Ile Asn Glu Glu Ala Ala Glu Trp
            180                 185                 190

Asp Arg Val His Pro Val His Ala Gly Pro Ile Ala Pro Gly Gln Met
        195                 200                 205

Arg Glu Pro Arg Gly Ser Asp Ile Ala Gly Thr Thr Ser Thr Leu Gln
    210                 215                 220

Glu Gln Ile Gly Trp Met Thr Asn Asn Pro Pro Ile Pro Val Gly Glu
225                 230                 235                 240

Ile Tyr Lys Arg Trp Ile Ile Leu Gly Leu Asn Lys Ile Val Arg Met
                245                 250                 255

Tyr Ser Pro Thr Ser Ile Leu Asp Ile Arg Gln Gly Pro Lys Glu Pro
            260                 265                 270

Phe Arg Asp Tyr Val Asp Arg Phe Tyr Lys Thr Leu Arg Ala Glu Gln
        275                 280                 285

Ala Ser Gln Glu Val Lys Asn Trp Met Thr Glu Thr Leu Leu Val Gln
    290                 295                 300

Asn Ala Asn Pro Asp Cys Lys Thr Ile Leu Lys Ala Leu Gly Pro Ala
305                 310                 315                 320

Ala Thr Leu Glu Glu Met Met Thr Ala Cys Gln Gly Val Gly Gly Pro
                325                 330                 335

Gly His Lys Ala Arg Val Leu Ala Glu Ala Met Ser Gln Val Thr Asn
            340                 345                 350

Thr Ala Thr Ile Met Met Gln Arg Gly Asn Phe Arg Asn Gln Arg Lys
        355                 360                 365

Met Val Lys Cys Phe Asn Cys Gly Lys Glu Gly His Thr Ala Arg Asn
    370                 375                 380

Cys Arg Ala Pro Arg Lys Lys Gly Cys Trp Lys Cys Gly Lys Glu Gly
385                 390                 395                 400

His Gln Met Lys Asp Cys Thr Glu Arg Gln Ala Asn Phe Leu Gly Lys
                405                 410                 415

-continued

```
Ile Trp Pro Ser Tyr Lys Gly Arg Pro Gly Asn Phe Leu Gln Ser Arg
            420                 425                 430

Pro Glu Pro Thr Ala Pro Pro Phe Leu Gln Ser Arg Pro Glu Pro Thr
        435                 440                 445

Ala Pro Pro Glu Glu Ser Phe Arg Ser Gly Val Glu Thr Thr Thr Pro
    450                 455                 460

Pro Gln Lys Gln Glu Pro Ile Asp Lys Glu Leu Tyr Pro Leu Thr Ser
465                 470                 475                 480

Leu Arg Ser Leu Phe Gly Asn Asp Pro Ser Ser Gln
                485                 490


<210> SEQ ID NO 19
<211> LENGTH: 2941
<212> TYPE: DNA
<213> ORGANISM: Artificial sequence
<220> FEATURE:
<223> OTHER INFORMATION: Modified Env from HIV strain pNL4-3

<400> SEQUENCE: 19

gaattctgca acaactgctg tttatccatt tcagaattgg gtgtcgacat agcagaatag     60

gcgttactcg acagaggaga gcaagaaatg gagccagtag atcctagact agagccctgg    120

aagcatccag gaagtcagcc taaaactgct tgtaccaatt gctattgtaa aaagtgttgc    180

tttcattgcc aagtttgttt catgacaaaa gccttaggca tctcctatgg caggaagaag    240

cggagacagc gacgaagagc tcatcagaac agtcagactc atcaagcttc tctatcaaag    300

cagtaagtag tacatgtaat gcaacctata atagtagcaa tagtagcatt agtagtagca    360

ataataatag caatagttgt gtggtccata gtaatcatag aatataggaa aatattaaga    420

caaagaaaaa tagacaggtt aattgataga ctaatagaaa gagcagaaga cagtggcaat    480

gagagtgaag gagaagtatc agcacttgtg gagatggggg tggaaatggg gcaccatgct    540

ccttgggata ttgatgatct gtagtgctac agaaaaattg tgggtcacag tctattatgg    600

ggtacctgtg tggaaggaag caaccaccac tctattttgt gcatcagatg ctaaagcata    660

tgatacagag gtacataatg tttgggccac acatgcctgt gtacccacag accccaaccc    720

acaagaagta gtattggtaa atgtgacaga aaattttaac atgtggaaaa atgacatggt    780

agaacagatg catgaggata taatcagttt atgggatcaa agcctaaagc catgtgtaaa    840

attaacccca ctctgtgtta gtttaaagtg cactgatttg aagaatgata ctaataccaa    900

tagtagtagc gggagaatga taatggagaa aggagagata aaaaactgct ctttcaatat    960

cagcacaagc ataagagata aggtgcagaa agaatatgca ttcttttata aacttgatat   1020

agtaccaata gataatacca gctataggtt gataagttgt aacacctcag tcattacaca   1080

ggcctgtcca aaggtatcct ttgagccaat tcccatacat tattgtgccc cggctggttt   1140

tgcgattcta aaatgtaata ataagacgtt caatggaaca ggaccatgta caaatgtcag   1200

cacagtacaa tgtacacatg gaatcaggcc agtagtatca actcaactgc tgttaaatgg   1260

cagtctagca gaagaagatg tagtaattag atctgccaat ttcacagaca atgctaaaac   1320

cataatagta cagctgaaca catctgtaga aattaattgt acaagaccca acaacaatac   1380

aagaaaaagt atccgtatcc agaggggacc agggagagca tttgttacaa taggaaaaat   1440

aggaaatatg agacaagcac attgtaacat tagtagagca aaatggaatg ccactttaaa   1500

acagatagct agcaaattaa gagaacaatt tggaaataat aaaacaataa tctttaagca   1560

atcctcagga ggggacccag aaattgtaac gcacagtttt aattgtggag gggaattttt   1620
```

-continued

```
ctactgtaat tcaacacaac tgtttaatag tacttggttt aatagtactt ggagtactga   1680

agggtcaaat aacactgaag gaagtgacac aatcacactc ccatgcagaa taaaacaatt   1740

tataaacatg tggcaggaag taggaaaagc aatgtatgcc cctcccatca gtggacaaat   1800

tagatgttca tcaaatatta ctgggctgct attaacaaga gatggtggta ataacaacaa   1860

tgggtccgag atcttcagac ctggaggagg cgatatgagg gacaattgga gaagtgaatt   1920

atataaatat aaagtagtaa aaattgaacc attaggagta gcacccacca aggcaaagag   1980

aagagtggtg cagactagtg cagtgggaat aggagctttg ttccttgggt tcttgggagc   2040

agcaggaagc actatgggct gcacgtcaat gacgctgacg gtacaggcca gacaattatt   2100

gtctgatata gtgcagcagc agaacaattt gctgagggct attgaggcgc aacagcatct   2160

gttgcaactc acagtctggg gcatcaaaca gctccaggca agaatcctgg ctgtggaaag   2220

atacctaaag gatcaacagc tcctggggat ttggggttgc tctggaaaac tcatttgcac   2280

cactgctgtg ccttggaatg ctagttggag taataaatct ctggaacaga tttggaataa   2340

catgacctgg atggagtggg acagagaaat taacaattac acaagcttaa tacactcctt   2400

aattgaagaa tcgcaaaacc agcaagaaaa gaatgaacaa gaattattgg aattagataa   2460

atgggcaagt ttgtggaatt ggtttaacat aacaaattgg ctgtggtata taaaattatt   2520

cataatgata gtaggaggct tggtaggttt aagaatagtt tttgctgtac tttctatagt   2580

gaatagagtt aggcagggat attcaccatt atcgtttcag acccacctcc caatcccgag   2640

gggacccgac aggcccgaag gaatagaaga agaaggtgga gagagagaca gagacagatc   2700

cattcgatta gtgaacggat ccttagcact tatctgggac gatctgcgga gcctgtgcct   2760

cttcagctac caccgcttga gagacttact cttgattgta acgaggattg tggaacttct   2820

gggacgcagg gggtgggaag ccctcaaata ttggtggaat ctcctacagt attggagtca   2880

ggaactaaag aatagtgctg ttaacttgct caatgccaca gccatagcag tagctgagta   2940

a                                                                   2941
```

<210> SEQ ID NO 20
<211> LENGTH: 2746
<212> TYPE: DNA
<213> ORGANISM: Artificial sequence
<220> FEATURE:
<223> OTHER INFORMATION: Modified Env/Tat/Rev from pNL4-3

<400> SEQUENCE: 20

```
gaattctgca acaactgctg tttatccatt tcagaattgg gtgtcgacat agcagaatag     60

gcgttactcg acagaggaga gcaagaaatg gagccagtag atcctagact agagccctgg    120

aagcatccag gaagtcagcc taaaactgct tgtaccaatt gctattgtaa aaagtgttgc    180

tttcattgcc aagtttgttt catgacaaaa gccttaggca tctcctatgg caggaagaag    240

cggagacagc gacgaagagc tcatcagaac agtcagactc atcaagcttc tctatcaaag    300

cagtaagtag tacatgtaat gcaacctata atagtagcaa tagtagcatt agtagtagca    360

ataataatag caatagttgt gtggtccata gtaatcatag aatataggaa aatattaaga    420

caaagaaaaa tagacaggtt aattgataga ctaatagaaa gagcagaaga cagtggcaat    480

gagagtgaag gagaagtatc agcacttgtg gagatggggg tggaaatggg gcaccatgct    540

ccttgggata ttgatgatct gtagtgctac agaaaaattg tgggtcacag tctattatgg    600

ggtacctgtg tggaaggaag caaccaccac tctattttgt gcatcagatg ctaaagcata    660

tgatacagag gtacataatg tttgggccac acatgcctgt gtacccacag accccaaccc    720
```

-continued

```
acaagaagta gtattggtaa atgtgacaga aaattttaac atgtggaaaa atgacatggt    780
agaacagatg catgaggata taatcagttt atgggatcaa agcctaaagc catgtgtaaa    840
attaacccca ctctgtgtta gttgtaacac ctcagtcatt acacaggcct gtccaaaggt    900
atcctttgag ccaattccca tacattattg tgccccggct ggttttgcga ttctaaaatg    960
taataataag acgttcaatg gaacaggacc atgtacaaat gtcagcacag tacaatgtac   1020
acatggaatc aggccagtag tatcaactca actgctgtta aatggcagtc tagcagaaga   1080
agatgtagta attagatctg ccaatttcac agacaatgct aaaaccataa tagtacagct   1140
gaacacatct gtagaaatta attgtacaag acccaacaac aatacaagaa aaagtatccg   1200
tatccagagg ggaccaggga gagcatttgt tacaatagga aaaataggaa atatgagaca   1260
agcacattgt aacattagta gagcaaaatg gaatgccact ttaaaacaga tagctagcaa   1320
attaagagaa caatttggaa ataataaaac aataatcttt aagcaatcct caggaggggga   1380
cccagaaatt gtaacgcaca gttttaattg tggaggggaa tttttctact gtaattcaac   1440
acaactgttt aatagtactt ggtttaatag tacttggagt actgaagggt caaataacac   1500
tgaaggaagt gacacaatca cactcccatg cagaataaaa caatttataa acatgtggca   1560
ggaagtagga aaagcaatgt atgcccctcc catcagtgga caaattagat gttcatcaaa   1620
tattactggg ctgctattaa caagagatgg tggtaataac aacaatgggt ccgagatctt   1680
cagacctgga ggaggcgata tgagggacaa ttggagaagt gaattatata aatataaagt   1740
agtaaaaatt gaaccattag gagtagcacc caccaaggca aagagaagag tggtgcagac   1800
tagtgcagtg ggaataggag ctttgttcct tgggttcttg ggagcagcag gaagcactat   1860
gggctgcacg tcaatgacgc tgacggtaca ggccagacaa ttattgtctg atatagtgca   1920
gcagcagaac aatttgctga gggctattga ggcgcaacag catctgttgc aactcacagt   1980
ctggggcatc aaacagctcc aggcaagaat cctggctgtg gaaagatacc taaaggatca   2040
acagctcctg gggatttggg gttgctctgg aaaactcatt tgcaccactg ctgtgccttg   2100
gaatgctagt tggagtaata aatctctgga acagatttgg aataacatga cctggatgga   2160
gtgggacaga gaaattaaca attacacaag cttaatacac tccttaattg aagaatcgca   2220
aaaccagcaa gaaaagaatg aacaagaatt attggaatta gataaatggg caagtttgtg   2280
gaattggttt aacataacaa attggctgtg gtatataaaa ttattcataa tgatagtagg   2340
aggcttggta ggtttaagaa tagtttttgc tgtactttct atagtgaata gagttaggca   2400
gggatattca ccattatcgt ttcagaccca cctcccaatc ccgaggggac ccgacaggcc   2460
cgaaggaata gaagaagaag gtggagagag agacagagac agatccattc gattagtgaa   2520
cggatcctta gcacttatct gggacgatct gcggagcctg tgcctcttca gctaccaccg   2580
cttgagagac ttactcttga ttgtaacgag gattgtggaa cttctgggac gcagggggtg   2640
ggaagccctc aaatattggt ggaatctcct acagtattgg agtcaggaac taaagaatag   2700
tgctgttaac ttgctcaatg ccacagccat agcagtagct gagtaa                  2746
```

<210> SEQ ID NO 21
<211> LENGTH: 3417
<212> TYPE: DNA
<213> ORGANISM: Artificial sequence
<220> FEATURE:
<223> OTHER INFORMATION: Modified Env/Tat/Rev/Nef from strain BH10

-continued

<400> SEQUENCE: 21

```
gaattctgca acaactgctg tttatccatt ttcagaattg ggtgtcgaca tagcagaata     60
ggcgttactc gacagaggag agcaagaaat ggagccagta gatcctagac tagagccctg    120
gaagcatcca ggaagtcagc ctaaaactgc ttgtaccaat tgctattgta aaaagtgttg    180
ctttcattgc caagtttgtt tcataacaaa agccttaggc atctcctatg gcaggaagaa    240
gcggagacag cgacgaagac ctcctcaagg cagtcagact catcaagttt ctctatcaaa    300
gcagtaagta gtacatgtaa tgcaacctat acaaatagca atagtagcat tagtagtagc    360
aataataata gcaatagttg tgtggtccat agtaatcata gaatatagga aaatattaag    420
acaaagaaaa atagacaggt taattgatag actaatagaa agagcagaag acagtggcaa    480
tgagagtgaa ggagaaatat cagcacttgt ggagatgggg gtggagatgg ggcaccatgc    540
tccttgggat gttgatgatc tgtagtgcta cagaaaaatt gtgggtcaca gtctattatg    600
gggtacctgt gtggaaggaa gcaaccacca ctctattttg tgcatcagat gctaaagcat    660
atgatacaga ggtacataat gtttgggcca cacatgcctg tgtacccaca gaccccaacc    720
cacaagaagt agtattggta aatgtgacag aaaattttaa catgtggaaa aatgacatgg    780
tagaacagat gcatgaggat ataatcagtt tatgggatca aagcctaaag ccatgtgtaa    840
aattaacccc actctgtgtt agtttaaagt gcactgattt gaagaatgat actaatacca    900
atagtagtag cgggagaatg ataatggaga aaggagagat aaaaaactgc tctttcaata    960
tcagcacaag cataagaggt aaggtgcaga aagaatatgc attttttat aaacttgata   1020
taataccaat agataatgat actaccagct atacgttgac aagttgtaac acctcagtca   1080
ttacacaggc ctgtccaaag gtatcctttg agccaattcc catacattat tgtgccccgg   1140
ctggttttgc gattctaaaa tgtaataata agacgttcaa tggaacagga ccatgtacaa   1200
atgtcagcac agtacaatgt acacatggaa ttaggccagt agtatcaact caactgctgt   1260
taaatggcag tctggcagaa gaagaggtag taattagatc tgccaatttc acagacaatg   1320
ctaaaaccat aatagtacag ctgaaccaat ctgtagaaat taattgtaca agacccaaca   1380
acaatacaag aaaaagtatc cgtatccaga gaggaccagg gagagcattt gttacaatag   1440
gaaaaatagg aaatatgaga caagcacatt gtaacattag tagagcaaaa tggaataaca   1500
ctttaaaaca gatagatagc aaattaagag aacaatttgg aaataataaa acaataatct   1560
ttaagcagtc ctcaggaggg gacccagaaa ttgtaacgca cagttttaat tgtggagggg   1620
aatttttcta ctgtaattca acacaactgt ttaatagtac ttggtttaat agtacttgga   1680
gtactaaagg gtcaaataac actgaaggaa gtgacacaat caccctccca tgcagaataa   1740
aacaaattat aaacatgtgg caggaagtag gaaaagcaat gtatgcccct cccatcagtg   1800
gacaaattag atgttcatca aatattacag ggctgctatt aacaagagat ggtggtaata   1860
gcaacaatga gtccgagatc ttcagacctg gaggaggaga tatgagggac aattggagaa   1920
gtgaattata taaatataaa gtagtaaaaa ttgaaccatt aggagtagca cccaccaagg   1980
caaagagaag agtggtgcag actagtgcag tgggaatagg agctttgttc cttgggttct   2040
tgggagcagc aggaagcact atgggcgcag cgtcaatgac gctgacggta caggccagac   2100
aattattgtc tggtatagtg cagcagcaga acaatttgct gagggctatt gaggcgcaac   2160
agcatctgtt gcaactcaca gtctggggca tcaagcagct ccaggcaaga atcctggctg   2220
tggaaagata cctaaaggat caacagctcc tggggatttg gggttgctct ggaaaactca   2280
tttgcaccac tgctgtgcct tggaatgcta gttggagtaa taaatctctg gaacagattt   2340
```

-continued

```
ggaataacat gacctggatg gagtgggaca gagaaattaa caattacaca agcttaatac   2400
actccttaat tgaagaatcg caaaaccagc aagaaaagaa tgaacaagaa ttattggaat   2460
tagataaatg ggcaagtttg tggaattggt ttaacataac aaattggctg tggtatataa   2520
aattattcat aatgatagta ggaggcttgg taggtttaag aatagttttt gctgtacttt   2580
ctgtagtgaa tagagttagg cagggatatt caccattatc gtttcagacc cacctcccaa   2640
tcccgagggg acccgacagg cccgaaggaa tagaagaaga aggtggagag agagacagag   2700
acagatccat tcgattagtg aacggatcct tagcacttat ctgggacgat ctgcggagcc   2760
tgtgcctctt cagctaccac cgcttgagag acttactctt gattgtaacg aggattgtgg   2820
aacttctggg acgcaggggg tgggaagccc tcaaatattg gtggaatctc ctacagtatt   2880
ggagtcagga gctaaagaat agtgctgtta gcttgctcaa tgccacagct atagcagtag   2940
ctgaggggac agatagggtt atagaagtag tacaaggagc ttatagagct attcgccaca   3000
tacctagaag aataagacag ggcttggaaa ggattttgct ataagatggg tggcaagtgg   3060
tcaaaaagta gtgtggttgg atggcctgct gtaagggaaa gaatgagacg agctgagcca   3120
gcagcagatg ggtgggagc agcatctcga gacctagaaa aacatggagc aatcacaagt   3180
agcaacacag cagctaacaa tgctgattgt gcctggctag aagcacaaga ggaggaggag   3240
gtgggttttc cagtcacacc tcaggtacct ttaagaccaa tgacttacaa ggcagctgta   3300
gatcttagcc actttttaaa agaaaagggg ggactggaag ggctaattca ctcccaacga   3360
agacaagata tccttgatct gtggatctac cacacacaag gctacttccc tgattag      3417
```

<210> SEQ ID NO 22
<211> LENGTH: 2950
<212> TYPE: DNA
<213> ORGANISM: Artificial sequence
<220> FEATURE:
<223> OTHER INFORMATION: Modified Env/Nef from strain BH10

<400> SEQUENCE: 22

```
gaattcgcca ccatgggagt gaaggagaaa tatcagcact tgtggagatg gggtggaga     60
tggggcacca tgctccttgg gatgttgatg atctgtagtg ctacagaaaa attgtgggtc    120
acagtctatt atggggtacc tgtgtggaag gaagcaacca ccactctatt ttgtgcatca    180
gatgctaaag catatgatac agaggtacat aatgtttggg ccacacatgc ctgtgtaccc    240
acagacccca acccacaaga agtagtattg gtaaatgtga cagaaaattt taacatgtgg    300
aaaaatgaca tggtagaaca gatgcatgag gatataatca gtttatggga tcaaagccta    360
aagccatgtg taaaattaac cccactctgt gttagtttaa agtgcactga tttgaagaat    420
gatactaata ccaatagtag tagcgggaga atgataatgg agaaaggaga gataaaaaac    480
tgctctttca atatcagcac aagcataaga ggtaaggtgc agaaagaata tgcatttttt    540
tataaacttg atataatacc aatagataat gatactacca gctatacgtt gacaagttgt    600
aacacctcag tcattacaca ggcctgtcca aaggtatcct ttgagccaat tcccatacat    660
tattgtgccc cggctggttt tgcgattcta aaatgtaata ataagacgtt caatggaaca    720
ggaccatgta caaatgtcag cacagtacaa tgtacacatg gaattaggcc agtagtatca    780
actcaactgc tgttaaatgg cagtctggca gaagaagagg tagtaattag atctgccaat    840
ttcacagaca atgctaaaac cataatagta cagctgaacc aatctgtaga aattaattgt    900
acaagaccca acaacaatac aagaaaaagt atccgtatcc agagaggacc agggagagca    960
```

-continued

```
tttgttacaa taggaaaaat aggaaatatg agacaagcac attgtaacat tagtagagca   1020

aaatggaata acactttaaa acagatagat agcaaattaa gagaacaatt tggaaataat   1080

aaaacaataa tctttaagca gtcctcagga ggggacccag aaattgtaac gcacagtttt   1140

aattgtggag gggaattttt ctactgtaat tcaacacaac tgtttaatag tacttggttt   1200

aatagtactt ggagtactaa agggtcaaat aacactgaag gaagtgacac aatcaccctc   1260

ccatgcagaa taaaacaaat tataaacatg tggcaggaag taggaaaagc aatgtatgcc   1320

cctcccatca gtggacaaat tagatgttca tcaaatatta cagggctgct attaacaaga   1380

gatggtggta atagcaacaa tgagtccgag atcttcagac ctggaggagg agatatgagg   1440

gacaattgga gaagtgaatt atataaatat aaagtagtaa aaattgaacc attaggagta   1500

gcacccacca aggcaaagag aagagtggtg cagactagtg cagtgggaat aggagctttg   1560

ttccttgggt tcttgggagc agcaggaagc actatgggcg cagcgtcaat gacgctgacg   1620

gtacaggcca gacaattatt gtctggtata gtgcagcagc agaacaattt gctgagggct   1680

attgaggcgc aacagcatct gttgcaactc acagtctggg gcatcaagca gctccaggca   1740

agaatcctgg ctgtggaaag atacctaaag gatcaacagc tcctggggat ttggggttgc   1800

tctggaaaac tcatttgcac cactgctgtg ccttggaatg ctagttggag taataaatct   1860

ctggaacaga tttggaataa catgacctgg atggagtggg acagagaaat taacaattac   1920

acaagcttaa tacactcctt aattgaagaa tcgcaaaacc agcaagaaaa gaatgaacaa   1980

gaattattgg aattagataa atgggcaagt ttgtggaatt ggtttaacat aacaaattgg   2040

ctgtggtata taaaattatt cataatgata gtaggaggct tggtaggttt aagaatagtt   2100

tttgctgtac tttctgtagt gaatagagtt aggcagggat attcaccatt atcgtttcag   2160

acccacctcc caatcccgag gggacccgac aggcccgaag gaatagaaga agaaggtgga   2220

gagagagaca gagacagatc cattcgatta gtgaacggat ccttagcact tatctgggac   2280

gatctgcgga gcctgtgcct cttcagctac caccgcttga gagacttact cttgattgta   2340

acgaggattg tggaacttct gggacgcagg gggtgggaag ccctcaaata ttggtggaat   2400

ctcctacagt attggagtca ggagctaaag aatagtgctg ttagcttgct caatgccaca   2460

gctatagcag tagctgaggg gacagatagg gttatagaag tagtacaagg agcttataga   2520

gctattcgcc acatacctag aagaataaga cagggcttgg aaaggatttt gctataagat   2580

gggtggcaag tggtcaaaaa gtagtgtggt tggatggcct gctgtaaggg aaagaatgag   2640

acgagctgag ccagcagcag atggggtggg agcagcatct cgagacctag aaaaacatgg   2700

agcaatcaca agtagcaaca cagcagctaa caatgctgat tgtgcctggc tagaagcaca   2760

agaggaggag gaggtgggtt ttccagtcac acctcaggta cctttaagac caatgactta   2820

caaggcagct gtagatctta gccacttttt aaaagaaaag gggggactgg aagggctaat   2880

tcactcccaa cgaagacaag atatccttga tctgtggatc taccacacac aaggctactt   2940

ccctgattag                                                          2950
```

<210> SEQ ID NO 23
<211> LENGTH: 2747
<212> TYPE: DNA
<213> ORGANISM: Artificial sequence
<220> FEATURE:
<223> OTHER INFORMATION: Modified Env/Tat from strain BH10

-continued

<400> SEQUENCE: 23
gaattctgca acaactgctg tttatccatt ttcagaattg ggtgtcgaca tagcagaata 60
ggcgttactc gacagaggag agcaagaaat ggagccagta gatcctagac tagagccctg 120
gaagcatcca ggaagtcagc ctaaaactgc ttgtaccaat tgctattgta aaaagtgttg 180
ctttcattgc caagtttgtt tcataacaaa agccttaggc atctcctatg gcaggaagaa 240
gcggagacag cgacgaagac ctcctcaagg cagtcagact catcaagttt ctctatcaaa 300
gcagtaagta gtacatgtaa tgcaacctat acaaatagca atagtagcat tagtagtagc 360
aataataata gcaatagttg tgtggtccat agtaatcata gaatatagga aaatattaag 420
acaaagaaaa atagacaggt taattgatag actaatagaa agagcagaag acagtggcaa 480
tgagagtgaa ggagaaatat cagcacttgt ggagatgggg gtggagatgg ggcaccatgc 540
tccttgggat gttgatgatc tgtagtgcta cagaaaaatt gtgggtcaca gtctattatg 600
gggtacctgt gtggaaggaa gcaaccacca ctctattttg tgcatcagat gctaaagcat 660
atgatacaga ggtacataat gtttgggcca cacatgcctg tgtacccaca gaccccaacc 720
cacaagaagt agtattggta aatgtgacag aaaattttaa catgtggaaa aatgacatgg 780
tagaacagat gcatgaggat ataatcagtt tatgggatca aagcctaaag ccatgtgtaa 840
aattaacccc actctgtgtt agtttaaagt gcactgattt gaagaatgat actaatacca 900
atagtagtag cgggagaatg ataatggaga aaggagagat aaaaaactgc tctttcaata 960
tcagcacaag cataagaggt aaggtgcaga aagaatatgc atttttttat aaacttgata 1020
taataccaat agataatgat actaccagct atacgttgac aagttgtaac acctcagtca 1080
ttacacaggc ctgtccaaag gtatcctttg agccaattcc catacattat tgtgccccgg 1140
ctggttttgc gattctaaaa tgtaataata agacgttcaa tggaacagga ccatgtacaa 1200
atgtcagcac agtacaatgt acacatggaa ttaggccagt agtatcaact caactgctgt 1260
taaatggcag tctggcagaa gaagaggtag taattagatc tgccaatttc acagacaatg 1320
ctaaaaccat aatagtacag ctgaaccaat ctgtagaaat taattgtaca agacccaaca 1380
acaatacaag aaaaagtatc cgtatccaga gaggaccagg gagagcattt gttacaatag 1440
gaaaaatagg aaatatgaga caagcacatt gtaacattag tagagcaaaa tggaataaca 1500
ctttaaaaca gatagatagc aaattaagag aacaatttgg aaataataaa acaataatct 1560
ttaagcagtc ctcaggaggg gacccagaaa ttgtaacgca cagttttaat tgtggagggg 1620
aatttttcta ctgtaattca acacaactgt ttaatagtac ttggtttaat agtacttgga 1680
gtactaaagg gtcaaataac actgaaggaa gtgacacaat caccctccca tgcagaataa 1740
aacaaattat aaacatgtgg caggaagtag gaaaagcaat gtatgcccct cccatcagtg 1800
gacaaattag atgttcatca aatattacag ggctgctatt aacaagagat ggtggtaata 1860
gcaacaatga gtccgagatc ttcagacctg gaggaggaga tatgagggac aattggagaa 1920
gtgaattata taaatataaa gtagtaaaaa ttgaaccatt aggagtagca cccaccaagg 1980
caaagagaag agtggtgcag actagtgcag tgggaatagg agctttgttc cttgggttct 2040
tgggagcagc aggaagcact atgggcgcag cgtcaatgac gctgacggta caggccagac 2100
aattattgtc tggtatagtg cagcagcaga acaatttgct gagggctatt gaggcgcaac 2160
agcatctgtt gcaactcaca gtctggggca tcaagcagct ccaggcaaga atcctggctg 2220
tggaaagata cctaaaggat caacagctcc tggggatttg gggttgctct ggaaaactca 2280
tttgcaccac tgctgtgcct tggaatgcta gttggagtaa taaatctctg gaacagattt 2340

-continued

```
ggaataacat gacctggatg gagtgggaca gagaaattaa caattacaca agcttaatac   2400

actccttaat tgaagaatcg caaaaccagc aagaaaagaa tgaacaagaa ttattggaat   2460

tagataaatg ggcaagtttg tggaattggt ttaacataac aaattggctg tggtatataa   2520

aattattcat aatgatagta ggaggcttgg taggtttaag aatagttttt gctgtacttt   2580

ctgtagtgaa tagagttagg cagggatatt caccattatc gtttcagacc cacctcccaa   2640

tcccgagggg acccgacagg cccgaaggaa tagaagaaga aggtggagag agagacagag   2700

acagatccat tcgattagtg aacggatcct tagcacttat ctggtaa                 2747
```

<210> SEQ ID NO 24
<211> LENGTH: 2583
<212> TYPE: DNA
<213> ORGANISM: Artificial sequence
<220> FEATURE:
<223> OTHER INFORMATION: Modified Env

<400> SEQUENCE: 24

```
gaattcgcca ccatgggagt gaaggagaaa tatcagcact tgtggagatg ggggtggaga     60

tggggcacca tgctccttgg gatgttgatg atctgtagtg ctacagaaaa attgtgggtc    120

acagtctatt atggggtacc tgtgtggaag gaagcaacca ccactctatt ttgtgcatca    180

gatgctaaag catatgatac agaggtacat aatgtttggg ccacacatgc ctgtgtaccc    240

acagacccca acccacaaga agtagtattg gtaaatgtga cagaaaattt taacatgtgg    300

aaaaatgaca tggtagaaca gatgcatgag gatataatca gtttatggga tcaaagccta    360

aagccatgtg taaaattaac cccactctgt gttagtttaa agtgcactga tttgaagaat    420

gatactaata ccaatagtag tagcgggaga atgataatgg agaaaggaga gataaaaaac    480

tgctctttca atatcagcac aagcataaga ggtaaggtgc agaaagaata tgcatttttt    540

tataaacttg atataatacc aatagataat gatactacca gctatacgtt gacaagttgt    600

aacacctcag tcattacaca ggcctgtcca aaggtatcct ttgagccaat tcccatacat    660

tattgtgccc cggctggttt tgcgattcta aaatgtaata ataagacgtt caatggaaca    720

ggaccatgta caaatgtcag cacagtacaa tgtacacatg gaattaggcc agtagtatca    780

actcaactgc tgttaaatgg cagtctggca gaagaagagg tagtaattag atctgccaat    840

ttcacagaca atgctaaaac cataatagta cagctgaacc aatctgtaga aattaattgt    900

acaagaccca acaacaatac aagaaaaagt atccgtatcc agagaggacc agggagagca    960

tttgttacaa taggaaaaat aggaaatatg agacaagcac attgtaacat tagtagagca   1020

aaatggaata acactttaaa acagatagat agcaaattaa gagaacaatt tggaaataat   1080

aaaacaataa tctttaagca gtcctcagga ggggacccag aaattgtaac gcacagtttt   1140

aattgtggag gggaattttt ctactgtaat tcaacacaac tgtttaatag tacttggttt   1200

aatagtactt ggagtactaa agggtcaaat aacactgaag gaagtgacac aatcaccctc   1260

ccatgcagaa taaaacaaat tataaacatg tggcaggaag taggaaaagc aatgtatgcc   1320

cctcccatca gtggacaaat tagatgttca tcaaatatta cagggctgct attaacaaga   1380

gatggtggta atagcaacaa tgagtccgag atcttcagac ctggaggagg agatatgagg   1440

gacaattgga gaagtgaatt atataaatat aaagtagtaa aaattgaacc attaggagta   1500

gcacccacca aggcaaagag aagagtggtg cagagagaaa aaagagcagt gggaatagga   1560

gctttgttcc ttgggttctt gggagcagca ggaagcacta tgggcgcagc gtcaatgacg   1620

ctgacggtac aggccagaca attattgtct ggtatagtgc agcagcagaa caatttgctg   1680
```

-continued

```
agggctattg aggcgcaaca gcatctgttg caactcacag tctggggcat caagcagctc   1740
caggcaagaa tcctggctgt ggaaagatac ctaaaggatc aacagctcct ggggatttgg   1800
ggttgctctg gaaaactcat ttgcaccact gctgtgcctt ggaatgctag ttggagtaat   1860
aaatctctgg aacagatttg gaataacatg acctggatgg agtgggacag agaaattaac   1920
aattacacaa gcttaataca ctccttaatt gaagaatcgc aaaaccagca agaaaagaat   1980
gaacaagaat tattggaatt agataaatgg gcaagtttgt ggaattggtt taacataaca   2040
aattggctgt ggtatataaa attattcata atgatagtag gaggcttggt aggtttaaga   2100
atagtttttg ctgtactttc tgtagtgaat agagttaggc agggatattc accattatcg   2160
tttcagaccc acctcccaat cccgaggggga cccgacaggc ccgaaggaat agaagaagaa   2220
ggtggagaga gagacagaga cagatccatt cgattagtga acggatcctt agcacttatc   2280
tgggacgatc tgcggagcct gtgcctcttc agctaccacc gcttgagaga cttactcttg   2340
attgtaacga ggattgtgga acttctggga cgcagggggt gggaagccct caaatattgg   2400
tggaatctcc tacagtattg gagtcaggag ctaaagaata gtgctgttag cttgctcaat   2460
gccacagcta tagcagtagc tgaggggaca gatagggtta tagaagtagt acaaggagct   2520
tatagagcta ttcgccacat acctagaaga ataagacagg gcttggaaag gattttgcta   2580
taa                                                                  2583
```

<210> SEQ ID NO 25
<211> LENGTH: 108
<212> TYPE: DNA
<213> ORGANISM: Human immunodeficiency virus type 1

<400> SEQUENCE: 25

```
tgtacaagac ccaacaacaa tacaagaaaa agtatccgta tccagagagg accagggaga     60
gcatttgtta caataggaaa aataggaaat atgagacaag cacattgt                 108
```

<210> SEQ ID NO 26
<211> LENGTH: 105
<212> TYPE: DNA
<213> ORGANISM: Human immunodeficiency virus type 1

<400> SEQUENCE: 26

```
tgtaccagac ctaacaacaa tacaagaaaa agtgtacgta taggaccagg acaaacattc     60
tatgcaacag gtgatataat aggggatata agacaagcac attgt                    105
```

<210> SEQ ID NO 27
<211> LENGTH: 105
<212> TYPE: DNA
<213> ORGANISM: Human immunodeficiency virus type 1

<400> SEQUENCE: 27

```
tgtacgagac ccaacaataa tacaagaaaa agtataagga taggaccagg acaagcattc     60
tatgcaacag gagaaataat aggagatata agacaagcac attgt                    105
```

<210> SEQ ID NO 28
<211> LENGTH: 102
<212> TYPE: DNA
<213> ORGANISM: Human immunodeficiency virus type 1

<400> SEQUENCE: 28

```
tgcacaaggc cctacaacaa tataagacaa aggacccccca taggactagg gcaagcactc     60
tatacaacaa gaagaataga agatataaga agagcacatt gt                       102
```

-continued

<210> SEQ ID NO 29
<211> LENGTH: 105
<212> TYPE: DNA
<213> ORGANISM: Human immunodeficiency virus type 1

<400> SEQUENCE: 29
tgtaccagac cctccaccaa tacaagaaca agtatacgta taggaccagg acaagtattc 60
tatagaacag gagacataac aggagatata agaaaagcat attgt 105

<210> SEQ ID NO 30
<211> LENGTH: 105
<212> TYPE: DNA
<213> ORGANISM: Human immunodeficiency virus type 1

<400> SEQUENCE: 30
tgtacaagac ccaacaacaa tacaagaaaa agaatatctt taggaccagg acgagtattt 60
tatacagcag gagaaataat aggagacatc agaaaggcac attgt 105

<210> SEQ ID NO 31
<211> LENGTH: 105
<212> TYPE: DNA
<213> ORGANISM: Human immunodeficiency virus type 1

<400> SEQUENCE: 31
tgtaccagac ctaataacaa tacaagaaaa agtataactt ttgcaccagg acaagcgctc 60
tatgcaacag gtgaaataat aggagatata agacaagcac attgt 105

<210> SEQ ID NO 32
<211> LENGTH: 2562
<212> TYPE: DNA
<213> ORGANISM: Artificial sequence
<220> FEATURE:
<223> OTHER INFORMATION: Env with multi-clade V3 loops

<400> SEQUENCE: 32
atgagagtga aggagaaata tcagcacttg tggagatggg ggtggagatg gggcaccatg 60
ctccttggga tgttgatgat ctgtagtgct acagaaaaat tgtgggtcac agtctattat 120
ggggtacctg tgtggaagga agcaaccacc actctatttt gtgcatcaga tgctaaagca 180
tatgatacag aggtacataa tgtttgggcc acacatgcct gtgtacccac agaccccaac 240
ccacaagaag tagtattggt aaatgtgaca gaaaatttta acatgtggaa aaatgacatg 300
gtagaacaga tgcatgagga tataatcagt ttatgggatc aaagcctaaa gccatgtgta 360
aaattaaccc cactctgtgt tggagctggt agttgtaaca cctcagtcat tacacaggcc 420
tgtccaaagg tatcctttga gccaattccc atacattatt gtgccccggc tggttttgcg 480
attctaaaat gtaataataa gacgttcaat ggaacaggac catgtacaaa tgtcagcaca 540
gtacaatgta cacatggaat taggccagta gtatcaactc aactgctgtt aaatggcagt 600
ctggcagaag aagaggtagt aattagatct gccaatttca cagacaatgc taaaaccata 660
atagtacagc tgaaccaatc tgtagaaatt aattgtacaa gacccaacaa caatacaaga 720
aaaagtatcc gtatccagag aggaccaggg agagcatttg ttacaatagg aaaaatagga 780
aatatgagac aagcacattg tctcgggtgt accagaccta acaacaatac aagaaaaagt 840
gtacgtatag gaccaggaca aacattctat gcaacaggtg atataatagg ggatataaga 900
caagcacatt gttgtacgag acccaacaat aatacaagaa aaagtataag gataggacca 960
ggacaagcat tctatgcaac aggagaaata ataggagata taagacaagc acattgttgc 1020

-continued

```
acaaggccct acaacaatat aagacaaagg acccccatag gactagggca agcactctat   1080

acaacaagaa gaatagaaga tataagaaga gcacattgtt gtaccagacc ctccaccaat   1140

acaagaacaa gtatacgtat aggaccagga caagtattct atagaacagg agacataaca   1200

ggagatataa gaaaagcata ttgtggatcc tgtacaagac ccaacaacaa tacaagaaaa   1260

agaatatctt taggaccagg acgagtattt tatacagcag gagaaataat aggagacatc   1320

agaaaggcac attgttgtac cagacctaat aacaatacaa gaaaaagtat aacttttgca   1380

ccaggacaag cgctctatgc aacaggtgaa ataataggag atataagaca agcacattgt   1440

ctcgggaaca ttagtagagc aaaatggaat aacactttaa aacagataga tagcaaatta   1500

agagaacaat ttggaaataa taaaacaata atctttaagc agtcctcagg aggggaccca   1560

gaaattgtaa cgcacagttt taattgtgga ggggaatttt tctactgtaa ttcaacacaa   1620

ctgtttaata gtacttggtt taatagtact tggagtacta aagggtcaaa taacactgaa   1680

ggaagtgaca caatcaccct cccatgcaga ataaaacaaa ttataaacat gtggcaggaa   1740

gtaggaaaag caatgtatgc ccctcccatc agtggacaaa ttagatgttc atcaaatatt   1800

acagggctgc tattaacaag agatggtggt aatagcaaca atgagtccga gatcttcaga   1860

cctggaggag gagatatgag ggacaattgg agaagtgaat tatataaata taaagtagta   1920

aaaattgaac cattaggagt agcacccacc aaggcaaaga gaagagtggt gcagactagt   1980

gcagtgggaa taggagcttt gttccttggg ttcttgggag cagcaggaag cactatgggc   2040

gcagcgtcaa tgacgctgac ggtacaggcc agacaattat tgtctggtat agtgcagcag   2100

cagaacaatt tgctgagggc tattgaggcg caacagcatc tgttgcaact cacagtctgg   2160

ggcatcaagc agctccaggc aagaatcctg gctgtggaaa gatacctaaa ggatcaacag   2220

ctcctgggga tttggggttg ctctggaaaa ctcatttgca ccactgctgt gccttggaat   2280

gctagttgga gtaataaatc tctggaacag atttggaata acatgacctg gatggagtgg   2340

gacagagaaa ttaacaatta cacaagctta atacactcct taattgaaga atcgcaaaac   2400

cagcaagaaa agaatgaaca agaattattg gaattagata aatgggcaag tttgtggaat   2460

tggtttaaca taacaaattg gctgtggtat ataaaatcgt ggctgctgct gctcctgctc   2520

tccctctccc tcctccaggc cacggatttc atgtccctgt ga                       2562
```

```
<210> SEQ ID NO 33
<211> LENGTH: 853
<212> TYPE: PRT
<213> ORGANISM: Artificial sequence
<220> FEATURE:
<223> OTHER INFORMATION: Modified Env with multi-clade V3 loops

<400> SEQUENCE: 33

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95
```

-continued

```
Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Gly
        115                 120                 125

Ala Gly Ser Cys Asn Thr Ser Val Ile Thr Gln Ala Cys Pro Lys Val
    130                 135                 140

Ser Phe Glu Pro Ile Pro Ile His Tyr Cys Ala Pro Ala Gly Phe Ala
145                 150                 155                 160

Ile Leu Lys Cys Asn Asn Lys Thr Phe Asn Gly Thr Gly Pro Cys Thr
                165                 170                 175

Asn Val Ser Thr Val Gln Cys Thr His Gly Ile Arg Pro Val Val Ser
            180                 185                 190

Thr Gln Leu Leu Leu Asn Gly Ser Leu Ala Glu Glu Glu Val Val Ile
        195                 200                 205

Arg Ser Ala Asn Phe Thr Asp Asn Ala Lys Thr Ile Ile Val Gln Leu
    210                 215                 220

Asn Gln Ser Val Glu Ile Asn Cys Thr Arg Pro Asn Asn Asn Thr Arg
225                 230                 235                 240

Lys Ser Ile Arg Ile Gln Arg Gly Pro Gly Arg Ala Phe Val Thr Ile
                245                 250                 255

Gly Lys Ile Gly Asn Met Arg Gln Ala His Cys Leu Gly Cys Thr Arg
            260                 265                 270

Pro Asn Asn Asn Thr Arg Lys Ser Val Arg Ile Gly Pro Gly Gln Thr
        275                 280                 285

Phe Tyr Ala Thr Gly Asp Ile Ile Gly Asp Ile Arg Gln Ala His Cys
    290                 295                 300

Cys Thr Arg Pro Asn Asn Asn Thr Arg Lys Ser Ile Arg Ile Gly Pro
305                 310                 315                 320

Gly Gln Ala Phe Tyr Ala Thr Gly Glu Ile Ile Gly Asp Ile Arg Gln
                325                 330                 335

Ala His Cys Cys Thr Arg Pro Tyr Asn Asn Ile Arg Gln Arg Thr Pro
            340                 345                 350

Ile Gly Leu Gly Gln Ala Leu Tyr Thr Thr Arg Arg Ile Glu Asp Ile
        355                 360                 365

Arg Arg Ala His Cys Cys Thr Arg Pro Ser Thr Asn Thr Arg Thr Ser
    370                 375                 380

Ile Arg Ile Gly Pro Gly Gln Val Phe Tyr Arg Thr Gly Asp Ile Thr
385                 390                 395                 400

Gly Asp Ile Arg Lys Ala Tyr Cys Gly Ser Cys Thr Arg Pro Asn Asn
                405                 410                 415

Asn Thr Arg Lys Arg Ile Ser Leu Gly Pro Gly Arg Val Phe Tyr Thr
            420                 425                 430

Ala Gly Glu Ile Ile Gly Asp Ile Arg Lys Ala His Cys Cys Thr Arg
        435                 440                 445

Pro Asn Asn Asn Thr Arg Lys Ser Ile Thr Phe Ala Pro Gly Gln Ala
    450                 455                 460

Leu Tyr Ala Thr Gly Glu Ile Ile Gly Asp Ile Arg Gln Ala His Cys
465                 470                 475                 480

Leu Gly Asn Ile Ser Arg Ala Lys Trp Asn Asn Thr Leu Lys Gln Ile
                485                 490                 495

Asp Ser Lys Leu Arg Glu Gln Phe Gly Asn Asn Lys Thr Ile Ile Phe
            500                 505                 510
```

-continued

```
Lys Gln Ser Ser Gly Gly Asp Pro Glu Ile Val Thr His Ser Phe Asn
        515                 520                 525

Cys Gly Gly Glu Phe Phe Tyr Cys Asn Ser Thr Gln Leu Phe Asn Ser
    530                 535                 540

Thr Trp Phe Asn Ser Thr Trp Ser Thr Lys Gly Ser Asn Asn Thr Glu
545                 550                 555                 560

Gly Ser Asp Thr Ile Thr Leu Pro Cys Arg Ile Lys Gln Ile Ile Asn
                565                 570                 575

Met Trp Gln Glu Val Gly Lys Ala Met Tyr Ala Pro Pro Ile Ser Gly
            580                 585                 590

Gln Ile Arg Cys Ser Ser Asn Ile Thr Gly Leu Leu Leu Thr Arg Asp
        595                 600                 605

Gly Gly Asn Ser Asn Asn Glu Ser Glu Ile Phe Arg Pro Gly Gly Gly
    610                 615                 620

Asp Met Arg Asp Asn Trp Arg Ser Glu Leu Tyr Lys Tyr Lys Val Val
625                 630                 635                 640

Lys Ile Glu Pro Leu Gly Val Ala Pro Thr Lys Ala Lys Arg Arg Val
                645                 650                 655

Val Gln Thr Ser Ala Val Gly Ile Gly Ala Leu Phe Leu Gly Phe Leu
            660                 665                 670

Gly Ala Ala Gly Ser Thr Met Gly Ala Ala Ser Met Thr Leu Thr Val
        675                 680                 685

Gln Ala Arg Gln Leu Leu Ser Gly Ile Val Gln Gln Gln Asn Asn Leu
    690                 695                 700

Leu Arg Ala Ile Glu Ala Gln Gln His Leu Leu Gln Leu Thr Val Trp
705                 710                 715                 720

Gly Ile Lys Gln Leu Gln Ala Arg Ile Leu Ala Val Glu Arg Tyr Leu
                725                 730                 735

Lys Asp Gln Gln Leu Leu Gly Ile Trp Gly Cys Ser Gly Lys Leu Ile
            740                 745                 750

Cys Thr Thr Ala Val Pro Trp Asn Ala Ser Trp Ser Asn Lys Ser Leu
        755                 760                 765

Glu Gln Ile Trp Asn Asn Met Thr Trp Met Glu Trp Asp Arg Glu Ile
    770                 775                 780

Asn Asn Tyr Thr Ser Leu Ile His Ser Leu Ile Glu Glu Ser Gln Asn
785                 790                 795                 800

Gln Gln Glu Lys Asn Glu Gln Glu Leu Leu Glu Leu Asp Lys Trp Ala
                805                 810                 815

Ser Leu Trp Asn Trp Phe Asn Ile Thr Asn Trp Leu Trp Tyr Ile Lys
            820                 825                 830

Ser Trp Leu Leu Leu Leu Leu Leu Ser Leu Ser Leu Leu Gln Ala Thr
        835                 840                 845

Asp Phe Met Ser Leu
    850
```

<210> SEQ ID NO 34
<211> LENGTH: 1092
<212> TYPE: DNA
<213> ORGANISM: Human immunodeficiency virus type 1

<400> SEQUENCE: 34

```
atgggtgcga gagcgtcagt attaagcggg ggagaattag atcgatggga aaaaattcgg      60

ttaaggccag ggggaaagaa aaaatataaa ttaaaacata tagtatgggc aagcagggag     120

ctagaacgat tcgcagttaa tcctggcctg ttagaaacat cagaaggctg tagacaaata     180
```

-continued

```
ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcagtca ggtcagccaa aattacccta tagtgcagaa catccagggg    420

caaatggtac atcaggccat atcacctaga actttaaatg catgggtaaa agtagtagaa    480

gagaaggctt tcagcccaga agtaataccc atgttttcag cattatcaga aggagccacc    540

ccacaagatt taaacaccat gctaaacaca gtggggggac atcaagcagc catgcaaatg    600

ttaaaagaga ccatcaatga ggaagctgca gaatgggata gagtacatcc agtgcatgca    660

gggcctattg caccaggcca gatgagagaa ccaaggggaa gtgacatagc aggaactact    720

agtacccttc aggaacaaat aggatggatg acaaataatc cacctatccc agtaggagaa    780

atttataaaa gatggataat cctgggatta aataaaatag taagaatgta tagccctacc    840

agcattctgg acataagaca aggaccaaaa gaacctttta gagactatgt agaccggttc    900

tataaaactc taagagccga gcaagcttca caggaggtaa aaaattggat gacagaaacc    960

ttgttggtcc aaaatgcgaa cccagattgt aagactattt taaaagcatt gggaccagcg   1020

gctacactag aagaaatgat gacagcatgt cagggagtag gaggacccgg ccataaggca   1080

agagttttgt aa                                                       1092
```

<210> SEQ ID NO 35
<211> LENGTH: 1179
<212> TYPE: DNA
<213> ORGANISM: Human immunodeficiency virus type 1

<400> SEQUENCE: 35

```
atgagagtga aggagaaata tcagcacttg tggagatggg ggtggagatg gggcaccatg     60

ctccttggga tgttgatgat ctgtagtgct ggtgcgagag cgtcagtatt aagcggggga    120

gaattagatc gatgggaaaa aattcggtta aggccagggg gaaagaaaaa atataaatta    180

aaacatatag tatgggcaag cagggagcta gaacgattcg cagttaatcc tggcctgtta    240

gaaacatcag aaggctgtag acaaatactg ggacagctac aaccatccct tcagacagga    300

tcagaagaac ttagatcatt atataataca gtagcaaccc tctattgtgt gcatcaaagg    360

atagagataa aagacaccaa ggaagcttta gacaagatag aggaagagca aaacaaaagt    420

aagaaaaaag cacagcaagc agcagctgac acaggacaca gcagtcaggt cagccaaaat    480

taccctatag tgcagaacat ccaggggcaa atggtacatc aggccatatc acctagaact    540

ttaaatgcat gggtaaaagt agtagaagag aaggctttca gcccagaagt aatacccatg    600

ttttcagcat tatcagaagg agccacccca caagatttaa acaccatgct aaacacagtg    660

gggggacatc aagcagccat gcaaatgtta aaagagacca tcaatgagga agctgcagaa    720

tgggatagag tacatccagt gcatgcaggg cctattgcac caggccagat gagagaacca    780

aggggaagtg acatagcagg aactactagt acccttcagg aacaaatagg atggatgaca    840

aataatccac ctatcccagt aggagaaatt tataaaagat ggataatcct gggattaaat    900

aaaatagtaa gaatgtatag ccctaccagc attctggaca taagacaagg accaaaagaa    960

ccttttagag actatgtaga ccggttctat aaaactctaa gagccgagca agcttcacag   1020

gaggtaaaaa attggatgac agaaaccttg ttggtccaaa atgcgaaccc agattgtaag   1080

actattttaa aagcattggg accagcggct acactagaag aaatgatgac agcatgtcag   1140

ggagtaggag gacccggcca taaggcaaga gttttgtaa                          1179
```

-continued

<210> SEQ ID NO 36
<211> LENGTH: 1308
<212> TYPE: DNA
<213> ORGANISM: Human immunodeficiency virus type 1

<400> SEQUENCE: 36
atgagagtga aggagaaata tcagcacttg tggagatggg ggtggagatg gggcaccatg 60
ctccttggga tgttgatgat ctgtagtgct ggtgcgagag cgtcagtatt aagcggggga 120
gaattagatc gatgggaaaa aattcggtta aggccagggg gaaagaaaaa atataaatta 180
aaacatatag tatgggcaag cagggagcta gaacgattcg cagttaatcc tggcctgtta 240
gaaacatcag aaggctgtag acaaatactg ggacagctac aaccatccct tcagacagga 300
tcagaagaac ttagatcatt atataataca gtagcaaccc tctattgtgt gcatcaaagg 360
atagagataa aagacaccaa ggaagcttta gacaagatag aggaagagca aaacaaaagt 420
aagaaaaaag cacagcaagc agcagctgac acaggacaca gcagtcaggt cagccaaaat 480
taccctatag tgcagaacat ccaggggcaa atggtacatc aggccatatc acctagaact 540
ttaaatgcat gggtaaaagt agtagaagag aaggctttca gcccagaagt aatacccatg 600
ttttcagcat tatcagaagg agccacccca caagatttaa acaccatgct aaacacagtg 660
gggggacatc aagcagccat gcaaatgtta aaagagacca tcaatgagga agctgcagaa 720
tgggatagag tacatccagt gcatgcaggg cctattgcac caggccagat gagagaacca 780
aggggaagtg acatagcagg aactactagt acccttcagg aacaaatagg atggatgaca 840
aataatccac ctatcccagt aggagaaatt tataaaagat ggataatcct gggattaaat 900
aaaatagtaa gaatgtatag ccctaccagc attctggaca taagacaagg accaaaagaa 960
ccttttagag actatgtaga ccggttctat aaaactctaa gagccgagca agcttcacag 1020
gaggtaaaaa attggatgac agaaaccttg ttggtccaaa atgcgaaccc agattgtaag 1080
actattttaa aagcattggg accagcggct acactagaag aaatgatgac agcatgtcag 1140
ggagtaggag gacccggcca taaggcaaga gttttgttat tcataatgat agtaggaggc 1200
ttggtaggtt taagaatagt ttttgctgta ctttctgtag tgaatagagt taggcaggga 1260
tattcaccat tatcgtttca gacccacctc ccaatcccga ggggataa 1308

<210> SEQ ID NO 37
<211> LENGTH: 363
<212> TYPE: PRT
<213> ORGANISM: Human immunodeficiency virus type 1

<400> SEQUENCE: 37

Met Gly Ala Arg Ala Ser Val Leu Ser Gly Gly Glu Leu Asp Arg Trp
1 5 10 15

Glu Lys Ile Arg Leu Arg Pro Gly Gly Lys Lys Lys Tyr Lys Leu Lys
20 25 30

His Ile Val Trp Ala Ser Arg Glu Leu Glu Arg Phe Ala Val Asn Pro
35 40 45

Gly Leu Leu Glu Thr Ser Glu Gly Cys Arg Gln Ile Leu Gly Gln Leu
50 55 60

Gln Pro Ser Leu Gln Thr Gly Ser Glu Glu Leu Arg Ser Leu Tyr Asn
65 70 75 80

Thr Val Ala Thr Leu Tyr Cys Val His Gln Arg Ile Glu Ile Lys Asp
85 90 95

Thr Lys Glu Ala Leu Asp Lys Ile Glu Glu Glu Gln Asn Lys Ser Lys
100 105 110

-continued

```
Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
        355                 360
```

<210> SEQ ID NO 38
<211> LENGTH: 410
<212> TYPE: PRT
<213> ORGANISM: Human immunodeficiency virus type 1

<400> SEQUENCE: 38

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Gly Ala
            20                  25                  30

Arg Ala Ser Val Leu Ser Gly Gly Glu Leu Asp Arg Trp Glu Lys Ile
        35                  40                  45

Arg Leu Arg Pro Gly Gly Lys Lys Lys Tyr Lys Leu Lys His Ile Val
    50                  55                  60

Trp Ala Ser Arg Glu Leu Glu Arg Phe Ala Val Asn Pro Gly Leu Leu
65                  70                  75                  80

Glu Thr Ser Glu Gly Cys Arg Gln Ile Leu Gly Gln Leu Gln Pro Ser
                85                  90                  95

Leu Gln Thr Gly Ser Glu Glu Leu Arg Ser Leu Tyr Asn Thr Val Ala
            100                 105                 110

Thr Leu Tyr Cys Val His Gln Arg Ile Glu Ile Lys Asp Thr Lys Glu
        115                 120                 125
```

-continued

```
Ala Leu Asp Lys Ile Glu Glu Glu Gln Asn Lys Ser Lys Lys Lys Ala
    130                 135                 140

Gln Gln Ala Ala Ala Asp Thr Gly His Ser Ser Gln Val Ser Gln Asn
145                 150                 155                 160

Tyr Pro Gln Gln Ala Ala Ala Asp Thr Gly His Ser Ser Gln Val Ser
                165                 170                 175

Gln Asn Tyr Pro Gln Gln Ala Ala Ala Asp Thr Gly His Ser Ser Gln
            180                 185                 190

Val Ser Gln Asn Tyr Pro Ile Val Gln Asn Ile Gln Gly Gln Met Val
        195                 200                 205

His Gln Ala Ile Ser Pro Arg Thr Leu Asn Ala Trp Val Lys Val Val
    210                 215                 220

Glu Glu Lys Ala Phe Ser Pro Glu Val Ile Pro Met Phe Ser Ala Leu
225                 230                 235                 240

Ser Glu Gly Ala Thr Pro Gln Asp Leu Asn Thr Met Leu Asn Thr Val
                245                 250                 255

Gly Gly His Gln Ala Ala Met Gln Met Leu Lys Glu Thr Ile Asn Glu
            260                 265                 270

Glu Ala Ala Glu Trp Asp Arg Val His Pro Val His Ala Gly Pro Ile
        275                 280                 285

Ala Pro Gly Gln Met Arg Glu Pro Arg Gly Ser Asp Ile Ala Gly Thr
    290                 295                 300

Thr Ser Thr Leu Gln Glu Gln Ile Gly Trp Met Thr Asn Asn Pro Pro
305                 310                 315                 320

Ile Pro Val Gly Glu Ile Tyr Lys Arg Trp Ile Ile Leu Gly Leu Asn
                325                 330                 335

Lys Ile Val Arg Met Tyr Ser Pro Thr Ser Ile Leu Asp Ile Arg Gln
            340                 345                 350

Gly Pro Lys Glu Pro Phe Arg Asp Tyr Val Asp Arg Phe Tyr Lys Thr
        355                 360                 365

Leu Arg Ala Glu Gln Ala Ser Gln Glu Val Thr Ile Leu Lys Ala Leu
    370                 375                 380

Gly Pro Ala Ala Thr Leu Glu Glu Met Met Thr Ala Cys Gln Gly Val
385                 390                 395                 400

Gly Gly Pro Gly His Lys Ala Arg Val Leu
                405                 410


<210> SEQ ID NO 39
<211> LENGTH: 453
<212> TYPE: PRT
<213> ORGANISM: Human immunodeficiency virus type 1

<400> SEQUENCE: 39

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Gly Ala
            20                  25                  30

Arg Ala Ser Val Leu Ser Gly Gly Glu Leu Asp Arg Trp Glu Lys Ile
        35                  40                  45

Arg Leu Arg Pro Gly Gly Leu Ser Gly Gly Glu Leu Asp Arg Trp Glu
    50                  55                  60

Lys Ile Arg Leu Arg Pro Gly Gly Lys Lys Lys Tyr Lys Leu Lys His
65                  70                  75                  80

Ile Val Trp Ala Ser Arg Glu Leu Glu Arg Phe Ala Val Asn Pro Gly
                85                  90                  95
```

-continued

```
Leu Leu Glu Thr Ser Glu Gly Cys Arg Gln Ile Leu Gly Gln Leu Gln
            100                 105                 110

Pro Ser Leu Gln Thr Gly Ser Glu Glu Leu Arg Ser Leu Tyr Asn Thr
        115                 120                 125

Val Ala Thr Leu Tyr Cys Val His Gln Arg Ile Glu Ile Lys Asp Thr
    130                 135                 140

Lys Glu Ala Leu Asp Lys Ile Glu Glu Glu Gln Asn Lys Ser Lys Lys
145                 150                 155                 160

Lys Ala Gln Gln Ala Ala Ala Asp Thr Gly His Ser Ser Gln Val Ser
                165                 170                 175

Gln Asn Tyr Pro Ile Val Gln Asn Ile Gln Gly Gln Met Val His Gln
            180                 185                 190

Ala Ile Ser Pro Arg Thr Leu Asn Ala Trp Val Lys Val Val Glu Glu
        195                 200                 205

Lys Ala Phe Ser Pro Glu Val Ile Pro Met Phe Ser Ala Leu Ser Glu
    210                 215                 220

Gly Ala Thr Pro Gln Asp Leu Asn Thr Met Leu Asn Thr Val Gly Gly
225                 230                 235                 240

His Gln Ala Ala Met Gln Met Leu Lys Glu Thr Ile Asn Glu Glu Ala
                245                 250                 255

Ala Glu Trp Asp Arg Val His Pro Val His Ala Gly Pro Ile Ala Pro
            260                 265                 270

Gly Gln Met Arg Glu Pro Arg Gly Ser Asp Ile Ala Gly Thr Thr Ser
        275                 280                 285

Thr Leu Gln Glu Gln Ile Gly Trp Met Thr Asn Asn Pro Pro Ile Pro
    290                 295                 300

Val Gly Glu Ile Tyr Lys Arg Trp Ile Ile Leu Gly Leu Asn Lys Ile
305                 310                 315                 320

Val Arg Met Tyr Ser Pro Thr Ser Ile Leu Asp Ile Arg Gln Gly Pro
                325                 330                 335

Lys Glu Pro Phe Arg Asp Tyr Val Asp Arg Phe Tyr Lys Thr Leu Arg
            340                 345                 350

Ala Glu Gln Ala Ser Gln Glu Val Lys Asn Trp Met Thr Glu Thr Leu
        355                 360                 365

Leu Val Gln Asn Ala Asn Pro Asp Cys Lys Thr Ile Leu Lys Ala Leu
    370                 375                 380

Gly Pro Ala Ala Thr Leu Glu Glu Met Met Thr Ala Cys Gln Gly Val
385                 390                 395                 400

Gly Gly Pro Gly His Lys Ala Arg Val Leu Leu Phe Ile Met Ile Val
                405                 410                 415

Gly Gly Leu Val Gly Leu Arg Ile Val Phe Ala Val Leu Ser Val Val
            420                 425                 430

Asn Arg Val Arg Gln Gly Tyr Ser Pro Leu Ser Phe Gln Thr His Leu
        435                 440                 445

Pro Ile Pro Arg Gly
    450
```

<210> SEQ ID NO 40
<211> LENGTH: 399
<212> TYPE: DNA
<213> ORGANISM: Human immunodeficiency virus type 1

-continued

<400> SEQUENCE: 40
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcagtca ggtcagccaa aattactaa 399

<210> SEQ ID NO 41
<211> LENGTH: 486
<212> TYPE: DNA
<213> ORGANISM: Human immunodeficiency virus type 1

<400> SEQUENCE: 41
atgagagtga aggagaaata tcagcacttg tggagatggg ggtggagatg gggcaccatg 60
ctccttggga tgttgatgat ctgtagtgct ggtgcgagag cgtcagtatt aagcggggga 120
gaattagatc gatgggaaaa aattcggtta aggccagggg gaaagaaaaa atataaatta 180
aaacatatag tatgggcaag cagggagcta gaacgattcg cagttaatcc tggcctgtta 240
gaaacatcag aaggctgtag acaaatactg ggacagctac aaccatccct tcagacagga 300
tcagaagaac ttagatcatt atataataca gtagcaaccc tctattgtgt gcatcaaagg 360
atagagataa aagacaccaa ggaagcttta gacaagatag aggaagagca aaacaaaagt 420
aagaaaaaag cacagcaagc agcagctgac acaggacaca gcagtcaggt cagccaaaat 480
tactaa 486

<210> SEQ ID NO 42
<211> LENGTH: 615
<212> TYPE: DNA
<213> ORGANISM: Human immunodeficiency virus type 1

<400> SEQUENCE: 42
atgagagtga aggagaaata tcagcacttg tggagatggg ggtggagatg gggcaccatg 60
ctccttggga tgttgatgat ctgtagtgct ggtgcgagag cgtcagtatt aagcggggga 120
gaattagatc gatgggaaaa aattcggtta aggccagggg gaaagaaaaa atataaatta 180
aaacatatag tatgggcaag cagggagcta gaacgattcg cagttaatcc tggcctgtta 240
gaaacatcag aaggctgtag acaaatactg ggacagctac aaccatccct tcagacagga 300
tcagaagaac ttagatcatt atataataca gtagcaaccc tctattgtgt gcatcaaagg 360
atagagataa aagacaccaa ggaagcttta gacaagatag aggaagagca aaacaaaagt 420
aagaaaaaag cacagcaagc agcagctgac acaggacaca gcagtcaggt cagccaaaat 480
tacttattca taatgatagt aggaggcttg gtaggtttaa gaatagtttt tgctgtactt 540
tctgtagtga atagagttag gcagggatat tcaccattat cgtttcagac ccacctccca 600
atcccgaggg gataa 615

<210> SEQ ID NO 43
<211> LENGTH: 132
<212> TYPE: PRT
<213> ORGANISM: Human immunodeficiency virus type 1

-continued

<400> SEQUENCE: 43

Met Gly Ala Arg Ala Ser Val Leu Ser Gly Gly Glu Leu Asp Arg Trp
1 5 10 15

Glu Lys Ile Arg Leu Arg Pro Gly Gly Lys Lys Lys Tyr Lys Leu Lys
20 25 30

His Ile Val Trp Ala Ser Arg Glu Leu Glu Arg Phe Ala Val Asn Pro
35 40 45

Gly Leu Leu Glu Thr Ser Glu Gly Cys Arg Gln Ile Leu Gly Gln Leu
50 55 60

Gln Pro Ser Leu Gln Thr Gly Ser Glu Glu Leu Arg Ser Leu Tyr Asn
65 70 75 80

Thr Val Ala Thr Leu Tyr Cys Val His Gln Arg Ile Glu Ile Lys Asp
85 90 95

Thr Lys Glu Ala Leu Asp Lys Ile Glu Glu Glu Gln Asn Lys Ser Lys
100 105 110

Lys Lys Ala Gln Gln Ala Ala Ala Asp Thr Gly His Ser Ser Gln Val
115 120 125

Ser Gln Asn Tyr
130

<210> SEQ ID NO 44
<211> LENGTH: 179
<212> TYPE: PRT
<213> ORGANISM: Human immunodeficiency virus type 1

<400> SEQUENCE: 44

Met Arg Val Lys Glu Lys Tyr Gln His Leu Trp Arg Trp Gly Trp Arg
1 5 10 15

Trp Gly Thr Met Leu Leu Gly Met Leu Met Ile Cys Ser Ala Gly Ala
20 25 30

Arg Ala Ser Val Leu Ser Gly Gly Glu Leu Asp Arg Trp Glu Lys Ile
35 40 45

Arg Leu Arg Pro Gly Gly Lys Lys Lys Tyr Lys Leu Lys His Ile Val
50 55 60

Trp Ala Ser Arg Glu Leu Glu Arg Phe Ala Val Asn Pro Gly Leu Leu
65 70 75 80

Glu Thr Ser Glu Gly Cys Arg Gln Ile Leu Gly Gln Leu Gln Pro Ser
85 90 95

Leu Gln Thr Gly Ser Glu Glu Leu Arg Ser Leu Tyr Gly Gln Leu Gln
100 105 110

Pro Ser Leu Gln Thr Gly Ser Glu Glu Leu Arg Ser Leu Tyr Asn Thr
115 120 125

Val Ala Thr Leu Tyr Cys Val His Gln Arg Ile Glu Ile Lys Asp Thr
130 135 140

Lys Glu Ala Leu Asp Lys Ile Glu Glu Glu Gln Asn Lys Ser Lys Lys
145 150 155 160

Lys Ala Gln Gln Ala Ala Ala Asp Thr Gly His Ser Ser Gln Val Ser
165 170 175

Gln Asn Tyr

<210> SEQ ID NO 45
<211> LENGTH: 186
<212> TYPE: PRT
<213> ORGANISM: Human immunodeficiency virus type 1

-continued

<400> SEQUENCE: 45

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Gly Ala
            20                  25                  30

Arg Ala Ser Val Leu Ser Gly Gly Glu Leu Asp Arg Trp Glu Lys Ile
        35                  40                  45

Arg Leu Arg Pro Gly Gly Lys Lys Lys Tyr Lys Leu Lys His Ile Val
    50                  55                  60

Trp Ala Ser Arg Glu Leu Glu Arg Gly Gln Leu Gln Pro Ser Leu Gln
65                  70                  75                  80

Thr Gly Ser Glu Glu Leu Arg Ser Leu Tyr Asn Thr Val Ala Thr Leu
                85                  90                  95

Tyr Cys Val His Gln Arg Ile Glu Ile Lys Asp Thr Lys Glu Ala Leu
            100                 105                 110

Asp Lys Ile Glu Glu Glu Gln Asn Lys Ser Lys Lys Lys Ala Gln Gln
        115                 120                 125

Ala Ala Ala Asp Thr Gly His Ser Ser Gln Val Ser Gln Asn Tyr Leu
    130                 135                 140

Phe Ile Met Ile Val Gly Gly Leu Val Gly Leu Arg Ile Val Phe Ala
145                 150                 155                 160

Val Leu Ser Val Val Asn Arg Val Arg Gln Gly Tyr Ser Pro Leu Ser
                165                 170                 175

Phe Gln Thr His Leu Pro Ile Pro Arg Gly
            180                 185
```

<210> SEQ ID NO 46
<211> LENGTH: 699
<212> TYPE: DNA
<213> ORGANISM: Human immunodeficiency virus type 1

<400> SEQUENCE: 46

```
atgcctatag tgcagaacat ccaggggcaa atggtacatc aggccatatc acctagaact     60
ttaaatgcat gggtaaaagt agtagaagag aaggctttca gcccagaagt aatacccatg    120
ttttcagcat tatcagaagg agccacccca caagatttaa acaccatgct aaacacagtg    180
gggggacatc aagcagccat gcaaatgtta aaagagacca tcaatgagga agctgcagaa    240
tgggatagag tacatccagt gcatgcaggg cctattgcac caggccagat gagagaacca    300
aggggaagtg acatagcagg aactactagt acccttcagg aacaaatagg atggatgaca    360
aataatccac ctatcccagt aggagaaatt tataaaagat ggataatcct gggattaaat    420
aaaatagtaa gaatgtatag ccctaccagc attctggaca taagacaagg accaaaagaa    480
ccttttagag actatgtaga ccggttctat aaaactctaa gagccgagca agcttcacag    540
gaggtaaaaa attggatgac agaaaccttg ttggtccaaa atgcgaaccc agattgtaag    600
actattttaa aagcattggg accagcggct acactagaag aaatgatgac agcatgtcag    660
ggagtaggag gacccggcca taaggcaaga gttttgtaa                           699
```

<210> SEQ ID NO 47
<211> LENGTH: 786
<212> TYPE: DNA
<213> ORGANISM: Human immunodeficiency virus type 1

-continued

<400> SEQUENCE: 47
atgagagtga aggagaaata tcagcacttg tggagatggg ggtggagatg gggcaccatg 60
ctccttggga tgttgatgat ctgtagtgct cctatagtgc agaacatcca ggggcaaatg 120
gtacatcagg ccatatcacc tagaacttta aatgcatggg taaaagtagt agaagagaag 180
gctttcagcc cagaagtaat acccatgttt tcagcattat cagaaggagc caccccacaa 240
gatttaaaca ccatgctaaa cacagtgggg ggacatcaag cagccatgca aatgttaaaa 300
gagaccatca atgaggaagc tgcagaatgg gatagagtac atccagtgca tgcagggcct 360
attgcaccag gccagatgag agaaccaagg ggaagtgaca tagcaggaac tactagtacc 420
cttcaggaac aaataggatg gatgacaaat aatccaccta tcccagtagg agaaatttat 480
aaaagatgga taatcctggg attaaataaa atagtaagaa tgtatagccc taccagcatt 540
ctggacataa gacaaggacc aaaagaacct tttagagact atgtagaccg gttctataaa 600
actctaagag ccgagcaagc ttcacaggag gtaaaaaatt ggatgacaga aaccttgttg 660
gtccaaaatg cgaacccaga ttgtaagact attttaaaag cattgggacc agcggctaca 720
ctagaagaaa tgatgacagc atgtcaggga gtaggaggac ccggccataa ggcaagagtt 780
ttgtaa 786

<210> SEQ ID NO 48
<211> LENGTH: 915
<212> TYPE: DNA
<213> ORGANISM: Human immunodeficiency virus type 1

<400> SEQUENCE: 48
atgagagtga aggagaaata tcagcacttg tggagatggg ggtggagatg gggcaccatg 60
ctccttggga tgttgatgat ctgtagtgct cctatagtgc agaacatcca ggggcaaatg 120
gtacatcagg ccatatcacc tagaacttta aatgcatggg taaaagtagt agaagagaag 180
gctttcagcc cagaagtaat acccatgttt tcagcattat cagaaggagc caccccacaa 240
gatttaaaca ccatgctaaa cacagtgggg ggacatcaag cagccatgca aatgttaaaa 300
gagaccatca atgaggaagc tgcagaatgg gatagagtac atccagtgca tgcagggcct 360
attgcaccag gccagatgag agaaccaagg ggaagtgaca tagcaggaac tactagtacc 420
cttcaggaac aaataggatg gatgacaaat aatccaccta tcccagtagg agaaatttat 480
aaaagatgga taatcctggg attaaataaa atagtaagaa tgtatagccc taccagcatt 540
ctggacataa gacaaggacc aaaagaacct tttagagact atgtagaccg gttctataaa 600
actctaagag ccgagcaagc ttcacaggag gtaaaaaatt ggatgacaga aaccttgttg 660
gtccaaaatg cgaacccaga ttgtaagact attttaaaag cattgggacc agcggctaca 720
ctagaagaaa tgatgacagc atgtcaggga gtaggaggac ccggccataa ggcaagagtt 780
ttgttattca taatgatagt aggaggcttg gtaggtttaa gaatagtttt tgctgtactt 840
tctgtagtga atagagttag gcagggatat tcaccattat cgtttcagac ccacctccca 900
atcccgaggg gataa 915

<210> SEQ ID NO 49
<211> LENGTH: 232
<212> TYPE: PRT
<213> ORGANISM: Human immunodeficiency virus type 1

-continued

<400> SEQUENCE: 49

Met Pro Ile Val Gln Asn Ile Gln Gly Gln Met Val His Gln Ala Ile
1 5 10 15

Ser Pro Arg Thr Leu Asn Ala Trp Val Lys Val Val Glu Glu Lys Ala
20 25 30

Phe Ser Pro Glu Val Ile Pro Met Phe Ser Ala Leu Ser Glu Gly Ala
35 40 45

Thr Pro Gln Asp Leu Asn Thr Met Leu Asn Thr Val Gly Gly His Gln
50 55 60

Ala Ala Met Gln Met Leu Lys Glu Thr Ile Asn Glu Glu Ala Ala Glu
65 70 75 80

Trp Asp Arg Val His Pro Val His Ala Gly Pro Ile Ala Pro Gly Gln
85 90 95

Met Arg Glu Pro Arg Gly Ser Asp Ile Ala Gly Thr Thr Ser Thr Leu
100 105 110

Gln Glu Gln Ile Gly Trp Met Thr Asn Asn Pro Pro Ile Pro Val Gly
115 120 125

Glu Ile Tyr Lys Arg Trp Ile Ile Leu Gly Leu Asn Lys Ile Val Arg
130 135 140

Met Tyr Ser Pro Thr Ser Ile Leu Asp Ile Arg Gln Gly Pro Lys Glu
145 150 155 160

Pro Phe Arg Asp Tyr Val Asp Arg Phe Tyr Lys Thr Leu Arg Ala Glu
165 170 175

Gln Ala Ser Gln Glu Val Lys Asn Trp Met Thr Glu Thr Leu Leu Val
180 185 190

Gln Asn Ala Asn Pro Asp Cys Lys Thr Ile Leu Lys Ala Leu Gly Pro
195 200 205

Ala Ala Thr Leu Glu Glu Met Met Thr Ala Cys Gln Gly Val Gly Gly
210 215 220

Pro Gly His Lys Ala Arg Val Leu
225 230

<210> SEQ ID NO 50
<211> LENGTH: 261
<212> TYPE: PRT
<213> ORGANISM: Human immunodeficiency virus type 1

<400> SEQUENCE: 50

Met Arg Val Lys Glu Lys Tyr Gln His Leu Trp Arg Trp Gly Trp Arg
1 5 10 15

Trp Gly Thr Met Leu Leu Gly Met Leu Met Ile Cys Ser Ala Pro Ile
20 25 30

Val Gln Asn Ile Gln Gly Gln Met Val His Gln Ala Ile Ser Pro Arg
35 40 45

Thr Leu Asn Ala Trp Val Lys Val Val Glu Glu Lys Ala Phe Ser Pro
50 55 60

Glu Val Ile Pro Met Phe Ser Ala Leu Ser Glu Gly Ala Thr Pro Gln
65 70 75 80

Asp Leu Asn Thr Met Leu Asn Thr Val Gly Gly His Gln Ala Ala Met
85 90 95

Gln Met Leu Lys Glu Thr Ile Asn Glu Glu Ala Ala Glu Trp Asp Arg
100 105 110

Val His Pro Val His Ala Gly Pro Ile Ala Pro Gly Gln Met Arg Glu
115 120 125

-continued

```
Pro Arg Gly Ser Asp Ile Ala Gly Thr Thr Ser Thr Leu Gln Glu Gln
    130                 135                 140

Ile Gly Trp Met Thr Asn Asn Pro Pro Ile Pro Val Gly Glu Ile Tyr
145                 150                 155                 160

Lys Arg Trp Ile Ile Leu Gly Leu Asn Lys Ile Val Arg Met Tyr Ser
                165                 170                 175

Pro Thr Ser Ile Leu Asp Ile Arg Gln Gly Pro Lys Glu Pro Phe Arg
            180                 185                 190

Asp Tyr Val Asp Arg Phe Tyr Lys Thr Leu Arg Ala Glu Gln Ala Ser
        195                 200                 205

Gln Glu Val Lys Asn Trp Met Thr Glu Thr Leu Leu Val Gln Asn Ala
    210                 215                 220

Asn Pro Asp Cys Lys Thr Ile Leu Lys Ala Leu Gly Pro Ala Ala Thr
225                 230                 235                 240

Leu Glu Glu Met Met Thr Ala Cys Gln Gly Val Gly Gly Pro Gly His
                245                 250                 255

Lys Ala Arg Val Leu
            260


<210> SEQ ID NO 51
<211> LENGTH: 286
<212> TYPE: PRT
<213> ORGANISM: Human immunodeficiency virus type 1

<400> SEQUENCE: 51

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Pro Ile
            20                  25                  30

Val Gln Asn Ile Gln Gly Gln Met Val His Gln Ala Ile Ser Pro Arg
        35                  40                  45

Thr Leu Asn Ala Trp Val Lys Val Val Glu Glu Lys Ala Phe Ser Pro
    50                  55                  60

Glu Val Ile Pro Met Phe Ser Ala Leu Ser Glu Gly Ala Thr Pro Gln
65                  70                  75                  80

Asp Leu Asn Thr Met Leu Asn Thr Val Gly Gly His Gln Ala Ala Met
                85                  90                  95

Gln Met Leu Lys Glu Thr Ile Asn Glu Glu Ala Ala Arg Glu Pro Arg
            100                 105                 110

Gly Ser Asp Ile Ala Gly Thr Thr Ser Thr Leu Gln Glu Gln Ile Gly
        115                 120                 125

Trp Met Thr Asn Asn Pro Pro Ile Pro Val Gly Glu Ile Tyr Lys Arg
    130                 135                 140

Trp Ile Ile Leu Gly Leu Asn Lys Ile Val Arg Met Tyr Ser Pro Thr
145                 150                 155                 160

Ser Ile Leu Asp Ile Arg Gln Gly Pro Lys Glu Pro Phe Arg Asp Tyr
                165                 170                 175

Val Asp Arg Phe Tyr Lys Thr Leu Arg Ala Glu Gln Ala Ser Gln Glu
            180                 185                 190

Val Lys Asn Trp Met Thr Glu Thr Leu Leu Val Gln Asn Ala Asn Pro
        195                 200                 205

Asp Cys Lys Thr Ile Leu Lys Ala Leu Gly Pro Ala Ala Thr Leu Glu
    210                 215                 220

Glu Met Met Thr Ala Cys Gln Gly Val Gly Gly Pro Gly His Lys Ala
225                 230                 235                 240
```

-continued

```
Arg Val Leu Leu Phe Ile Met Ile Val Gly Gly Leu Val Gly Leu Arg
                245                 250                 255

Ile Val Phe Ala Val Leu Ser Val Val Asn Arg Val Arg Gln Gly Tyr
            260                 265                 270

Ser Pro Leu Ser Phe Gln Thr His Leu Pro Ile Pro Arg Gly
        275                 280                 285


<210> SEQ ID NO 52
<211> LENGTH: 3839
<212> TYPE: DNA
<213> ORGANISM: Artificial sequence
<220> FEATURE:
<223> OTHER INFORMATION: Modified Env/Tat

<400> SEQUENCE: 52

gaattctgca acaactgctg tttatccatt ttcagaattg ggtgtcgaca tagcagaata     60

ggcgttactc gacagaggag agcaagaaat ggagccagta gatcctagac tagagccctg    120

gaagcatcca ggaagtcagc ctaaaactgc ttgtaccaat tgctattgta aaaagtgttg    180

ctttcattgc caagtttgtt tcataacaaa agccttaggc atctcctatg gcaggaagaa    240

gcggagacag cgacgaagac ctcctcaagg cagtcagact catcaagttt ctctatcaaa    300

gcagtaagta gtacatgtaa tgcaacctat acaaatagca atagtagcat tagtagtagc    360

aataataata gcaatagttg tgtggtccat agtaatcata gaatatagga aaatattaag    420

acaaagaaaa atagacaggt taattgatag actaatagaa agagcagaag acagtggcaa    480

tgagagtgaa ggagaaatat cagcacttgt ggagatgggg gtggagatgg ggcaccatgc    540

tccttgggat gttgatgatc tgtagtgcta cagaaaaatt gtgggtcaca gtctattatg    600

gggtacctgt gtggaaggaa gcaaccacca ctctattttg tgcatcagat gctaaagcat    660

atgatacaga ggtacataat gtttgggcca cacatgcctg tgtacccaca gaccccaacc    720

cacaagaagt agtattggta aatgtgacag aaaattttaa catgtggaaa aatgacatgg    780

tagaacagat gcatgaggat ataatcagtt tatgggatca aagcctaaag ccatgtgtaa    840

aattaacccc actctgtgtt ggagctggta gttgtaacac ctcagtcatt acacaggcct    900

gtccaaaggt atcctttgag ccaattccca tacattattg tgccccggct ggttttgcga    960

ttctaaaatg taataataag acgttcaatg gaacaggacc atgtacaaat gtcagcacag   1020

tacaatgtac acatggaatt aggccagtag tatcaactca actgctgtta aatggcagtc   1080

tggcagaaga agaggtagta attagatctg ccaatttcac agacaatgct aaaaccataa   1140

tagtacagct gaaccaatct gtagaaatta attgtacaag acccaacaac aatacaagaa   1200

aaagtatccg tatccagaga ggaccaggga gagcatttgt tacaatagga aaaataggaa   1260

atatgagaca agcacattgt ctcgggtgta ccagacctaa caacaataca agaaaaagtg   1320

tacgtatagg accaggacaa acattctatg caacaggtga tataataggg gatataagac   1380

aagcacattg ttgtacgaga cccaacaata atacaagaaa aagtataagg ataggaccag   1440

gacaagcatt ctatgcaaca ggagaaataa taggagatat aagacaagca cattgttgca   1500

caaggcccta caacaatata agacaaagga cccccatagg actagggcaa gcactctata   1560

caacaagaag aatagaagat ataagaagag cacattgttg taccagaccc tccaccaata   1620

caagaacaag tatacgtata ggaccaggac aagtattcta tagaacagga gacataacag   1680

gagatataag aaaagcatat tgtggatcct gtacaagacc caacaacaat acaagaaaaa   1740

gaatatcttt aggaccagga cgagtatttt atacagcagg agaaataata ggagacatca   1800
```

-continued

```
gaaaggcaca ttgttgtacc agacctaata acaatacaag aaaaagtata acttttgcac   1860

caggacaagc gctctatgca acaggtgaaa taataggaga tataagacaa gcacattgtc   1920

tcgggtgtac cagacctaac aacaatacaa gaaaaagtgt acgtatagga ccaggacaaa   1980

cattctatgc aacaggtgat ataatagggg atataagaca agcacattgt tgtacgagac   2040

ccaacaataa tacaagaaaa agtataagga taggaccagg acaagcattc tatgcaacag   2100

gagaaataat aggagatata agacaagcac attgttgcac aaggccctac aacaatataa   2160

gacaaaggac ccccatagga ctagggcaag cactctatac aacaagaaga atagaagata   2220

taagaagagc acattgttgt accagaccct ccaccaatac aagaacaagt atacgtatag   2280

gaccaggaca agtattctat agaacaggag acataacagg agatataaga aaagcatatt   2340

gtggatcctg tacaagaccc aacaacaata caagaaaaag aatatcttta ggaccaggac   2400

gagtatttta tacagcagga gaaataatag gagacatcag aaaggcacat tgttgtacca   2460

gacctaataa caatacaaga aaaagtataa cttttgcacc aggacaagcg ctctatgcaa   2520

caggtgaaat aataggagat ataagacaag cacattgtct cgggaacatt agtagagcaa   2580

aatggaataa cactttaaaa cagatagata gcaaattaag agaacaattt ggaaataata   2640

aaacaataat ctttaagcag tcctcaggag gggacccaga aattgtaacg cacagtttta   2700

attgtggagg ggaatttttc tactgtaatt caacacaact gtttaatagt acttggttta   2760

atagtacttg gagtactaaa gggtcaaata acactgaagg aagtgacaca atcaccctcc   2820

catgcagaat aaaacaaatt ataaacatgt ggcaggaagt aggaaaagca atgtatgccc   2880

ctcccatcag tggacaaatt agatgttcat caaatattac agggctgcta ttaacaagag   2940

atggtggtaa tagcaacaat gagtccgaga tcttcagacc tggaggagga gatatgaggg   3000

acaattggag aagtgaatta tataaatata aagtagtaaa aattgaacca ttaggagtag   3060

cacccaccaa ggcaaagaga agagtggtgc agactagtgc agtgggaata ggagctttgt   3120

tccttgggtt cttgggagca gcaggaagca ctatgggcgc agcgtcaatg acgctgacgg   3180

tacaggccag acaattattg tctggtatag tgcagcagca gaacaatttg ctgagggcta   3240

ttgaggcgca acagcatctg ttgcaactca cagtctgggg catcaagcag ctccaggcaa   3300

gaatcctggc tgtggaaaga tacctaaagg atcaacagct cctggggatt tggggttgct   3360

ctggaaaact catttgcacc actgctgtgc cttggaatgc tagttggagt aataaatctc   3420

tggaacagat ttggaataac atgacctgga tggagtggga cagagaaatt aacaattaca   3480

caagcttaat acactcctta attgaagaat cgcaaaacca gcaagaaaag aatgaacaag   3540

aattattgga attagataaa tgggcaagtt tgtggaattg gtttaacata acaaattggc   3600

tgtggtatat aaaattattc ataatgatag taggaggctt ggtaggttta agaatagttt   3660

ttgctgtact ttctgtagtg aatagagtta ggcagggata ttcaccatta tcgtttcaga   3720

cccacctccc aatcccgagg ggacccgaca ggcccgaagg aatagaagaa gaaggtggag   3780

agagagacag agacagatcc attcgattag tgaacggatc cttagcactt atctggtaa    3839
```

<210> SEQ ID NO 53
<211> LENGTH: 1101
<212> TYPE: PRT
<213> ORGANISM: Artificial sequence
<220> FEATURE:
<223> OTHER INFORMATION: Modified Env/Tat -continued

<400> SEQUENCE: 53

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Gly
        115                 120                 125

Ala Gly Ser Cys Asn Thr Ser Val Ile Thr Gln Ala Cys Pro Lys Val
    130                 135                 140

Ser Phe Glu Pro Ile Pro Ile His Tyr Cys Ala Pro Ala Gly Phe Ala
145                 150                 155                 160

Ile Leu Lys Cys Asn Asn Lys Thr Phe Asn Gly Thr Gly Pro Cys Thr
                165                 170                 175

Asn Val Ser Thr Val Gln Cys Thr His Gly Ile Arg Pro Val Val Ser
            180                 185                 190

Thr Gln Leu Leu Leu Asn Gly Ser Leu Ala Glu Glu Glu Val Val Ile
        195                 200                 205

Arg Ser Ala Asn Phe Thr Asp Asn Ala Lys Thr Ile Ile Val Gln Leu
    210                 215                 220

Asn Gln Ser Val Glu Ile Asn Cys Thr Arg Pro Asn Asn Asn Thr Arg
225                 230                 235                 240

Lys Ser Ile Arg Ile Gln Arg Gly Pro Gly Arg Ala Phe Val Thr Ile
                245                 250                 255

Gly Lys Ile Gly Asn Met Arg Gln Ala His Cys Leu Gly Cys Thr Arg
            260                 265                 270

Pro Asn Asn Asn Thr Arg Lys Ser Val Arg Ile Gly Pro Gly Gln Thr
        275                 280                 285

Phe Tyr Ala Thr Gly Asp Ile Ile Gly Asp Ile Arg Gln Ala His Cys
    290                 295                 300

Cys Thr Arg Pro Asn Asn Asn Thr Arg Lys Ser Ile Arg Ile Gly Pro
305                 310                 315                 320

Gly Gln Ala Phe Tyr Ala Thr Gly Glu Ile Ile Gly Asp Ile Arg Gln
                325                 330                 335

Ala His Cys Cys Thr Arg Pro Tyr Asn Asn Ile Arg Gln Arg Thr Pro
            340                 345                 350

Ile Gly Leu Gly Gln Ala Leu Tyr Thr Thr Arg Arg Ile Glu Asp Ile
        355                 360                 365

Arg Arg Ala His Cys Cys Thr Arg Pro Ser Thr Asn Thr Arg Thr Ser
    370                 375                 380

Ile Arg Ile Gly Pro Gly Gln Val Phe Tyr Arg Thr Gly Asp Ile Thr
385                 390                 395                 400

Gly Asp Ile Arg Lys Ala Tyr Cys Gly Ser Cys Thr Arg Pro Asn Asn
                405                 410                 415

-continued

```
Asn Thr Arg Lys Arg Ile Ser Leu Gly Pro Gly Arg Val Phe Tyr Thr
            420                 425                 430

Ala Gly Glu Ile Ile Gly Asp Ile Arg Lys Ala His Cys Cys Thr Arg
        435                 440                 445

Pro Asn Asn Asn Thr Arg Lys Ser Ile Thr Phe Ala Pro Gly Gln Ala
    450                 455                 460

Leu Tyr Ala Thr Gly Glu Ile Ile Gly Asp Ile Arg Gln Ala His Cys
465                 470                 475                 480

Leu Gly Cys Thr Arg Pro Asn Asn Asn Thr Arg Lys Ser Val Arg Ile
                485                 490                 495

Gly Pro Gly Gln Thr Phe Tyr Ala Thr Gly Asp Ile Ile Gly Asp Ile
            500                 505                 510

Arg Gln Ala His Cys Cys Thr Arg Pro Asn Asn Asn Thr Arg Lys Ser
        515                 520                 525

Ile Arg Ile Gly Pro Gly Gln Ala Phe Tyr Ala Thr Gly Glu Ile Ile
    530                 535                 540

Gly Asp Ile Arg Gln Ala His Cys Cys Thr Arg Pro Tyr Asn Asn Ile
545                 550                 555                 560

Arg Gln Arg Thr Pro Ile Gly Leu Gly Gln Ala Leu Tyr Thr Thr Arg
                565                 570                 575

Arg Ile Glu Asp Ile Arg Arg Ala His Cys Cys Thr Arg Pro Ser Thr
            580                 585                 590

Asn Thr Arg Thr Ser Ile Arg Ile Gly Pro Gly Gln Val Phe Tyr Arg
        595                 600                 605

Thr Gly Asp Ile Thr Gly Asp Ile Arg Lys Ala Tyr Cys Gly Ser Cys
    610                 615                 620

Thr Arg Pro Asn Asn Asn Thr Arg Lys Arg Ile Ser Leu Gly Pro Gly
625                 630                 635                 640

Arg Val Phe Tyr Thr Ala Gly Glu Ile Ile Gly Asp Ile Arg Lys Ala
                645                 650                 655

His Cys Cys Thr Arg Pro Asn Asn Asn Thr Arg Lys Ser Ile Thr Phe
            660                 665                 670

Ala Pro Gly Gln Ala Leu Tyr Ala Thr Gly Glu Ile Ile Gly Asp Ile
        675                 680                 685

Arg Gln Ala His Cys Leu Gly Asn Ile Ser Arg Ala Lys Trp Asn Asn
    690                 695                 700

Thr Leu Lys Gln Ile Asp Ser Lys Leu Arg Glu Gln Phe Gly Asn Asn
705                 710                 715                 720

Lys Thr Ile Ile Phe Lys Gln Ser Ser Gly Gly Asp Pro Glu Ile Val
                725                 730                 735

Thr His Ser Phe Asn Cys Gly Gly Glu Phe Phe Tyr Cys Asn Ser Thr
            740                 745                 750

Gln Leu Phe Asn Ser Thr Trp Phe Asn Ser Thr Trp Ser Thr Lys Gly
        755                 760                 765

Ser Asn Asn Thr Glu Gly Ser Asp Thr Ile Thr Leu Pro Cys Arg Ile
    770                 775                 780

Lys Gln Ile Ile Asn Met Trp Gln Glu Val Gly Lys Ala Met Tyr Ala
785                 790                 795                 800

Pro Pro Ile Ser Gly Gln Ile Arg Cys Ser Ser Asn Ile Thr Gly Leu
                805                 810                 815

Leu Leu Thr Arg Asp Gly Gly Asn Ser Asn Asn Glu Ser Glu Ile Phe
            820                 825                 830
```

-continued

```
Arg Pro Gly Gly Gly Asp Met Arg Asp Asn Trp Arg Ser Glu Leu Tyr
        835                 840                 845

Lys Tyr Lys Val Val Lys Ile Glu Pro Leu Gly Val Ala Pro Thr Lys
    850                 855                 860

Ala Lys Arg Arg Val Val Gln Thr Ser Ala Val Gly Ile Gly Ala Leu
865                 870                 875                 880

Phe Leu Gly Phe Leu Gly Ala Ala Gly Ser Thr Met Gly Ala Ala Ser
                885                 890                 895

Met Thr Leu Thr Val Gln Ala Arg Gln Leu Leu Ser Gly Ile Val Gln
            900                 905                 910

Gln Gln Asn Asn Leu Leu Arg Ala Ile Glu Ala Gln Gln His Leu Leu
        915                 920                 925

Gln Leu Thr Val Trp Gly Ile Lys Gln Leu Gln Ala Arg Ile Leu Ala
    930                 935                 940

Val Glu Arg Tyr Leu Lys Asp Gln Gln Leu Leu Gly Ile Trp Gly Cys
945                 950                 955                 960

Ser Gly Lys Leu Ile Cys Thr Thr Ala Val Pro Trp Asn Ala Ser Trp
                965                 970                 975

Ser Asn Lys Ser Leu Glu Gln Ile Trp Asn Asn Met Thr Trp Met Glu
            980                 985                 990

Trp Asp Arg Glu Ile Asn Asn Tyr  Thr Ser Leu Ile His  Ser Leu Ile
        995                 1000                 1005

Glu Glu  Ser Gln Asn Gln Gln  Glu Lys Asn Glu Gln  Glu Leu Leu
    1010                 1015                 1020

Glu Leu  Asp Lys Trp Ala Ser  Leu Trp Asn Trp Phe  Asn Ile Thr
    1025                 1030                 1035

Asn Trp  Leu Trp Tyr Ile Lys  Leu Phe Ile Met Ile  Val Gly Gly
    1040                 1045                 1050

Leu Val  Gly Leu Arg Ile Val  Phe Ala Thr His Leu  Pro Ile Pro
    1055                 1060                 1065

Arg Gly  Pro Asp Arg Pro Glu  Gly Ile Glu Glu Glu  Gly Gly Glu
    1070                 1075                 1080

Arg Asp  Arg Asp Arg Ser Ile  Arg Leu Val Asn Gly  Ser Leu Ala
    1085                 1090                 1095

Leu Ile  Trp
    1100
```

<210> SEQ ID NO 54
<211> LENGTH: 4040
<212> TYPE: DNA
<213> ORGANISM: Artificial sequence
<220> FEATURE:
<223> OTHER INFORMATION: Modified Env/Tat/Rev

<400> SEQUENCE: 54

```
gaattctgca acaactgctg tttatccatt ttcagaattg ggtgtcgaca tagcagaata     60

ggcgttactc gacagaggag agcaagaaat ggagccagta gatcctagac tagagccctg    120

gaagcatcca ggaagtcagc ctaaaactgc ttgtaccaat tgctattgta aaaagtgttg    180

ctttcattgc caagtttgtt tcataacaaa agccttaggc atctcctatg gcaggaagaa    240

gcggagacag cgacgaagac ctcctcaagg cagtcagact catcaagttt ctctatcaaa    300

gcagtaagta gtacatgtaa tgcaacctat acaaatagca atagtagcat tagtagtagc    360

aataataata gcaatagttg tgtggtccat agtaatcata gaatatagga aaatattaag    420

acaaagaaaa atagacaggt taattgatag actaatagaa agagcagaag acagtggcaa    480
```

-continued

```
tgagagtgaa ggagaaatat cagcacttgt ggagatgggg gtggagatgg ggcaccatgc    540
tccttgggat gttgatgatc tgtagtgcta cagaaaaatt gtgggtcaca gtctattatg    600
gggtacctgt gtggaaggaa gcaaccacca ctctattttg tgcatcagat gctaaagcat    660
atgatacaga ggtacataat gtttgggcca cacatgcctg tgtacccaca gaccccaacc    720
cacaagaagt agtattggta aatgtgacag aaaattttaa catgtggaaa aatgacatgg    780
tagaacagat gcatgaggat ataatcagtt tatgggatca aagcctaaag ccatgtgtaa    840
aattaacccc actctgtgtt ggagctggta gttgtaacac ctcagtcatt acacaggcct    900
gtccaaaggt atcctttgag ccaattccca tacattattg tgccccggct ggttttgcga    960
ttctaaaatg taataataag acgttcaatg gaacaggacc atgtacaaat gtcagcacag   1020
tacaatgtac acatggaatt aggccagtag tatcaactca actgctgtta aatggcagtc   1080
tggcagaaga agaggtagta attagatctg ccaatttcac agacaatgct aaaaccataa   1140
tagtacagct gaaccaatct gtagaaatta attgtacaag acccaacaac aatacaagaa   1200
aaagtatccg tatccagaga ggaccaggga gagcatttgt tacaatagga aaaataggaa   1260
atatgagaca agcacattgt ctcgggtgta ccagacctaa caacaataca agaaaaagtg   1320
tacgtatagg accaggacaa acattctatg caacaggtga tataataggg gatataagac   1380
aagcacattg ttgtacgaga cccaacaata atacaagaaa aagtataagg ataggaccag   1440
gacaagcatt ctatgcaaca ggagaaataa taggagatat aagacaagca cattgttgca   1500
caaggcccta caacaatata agacaaagga cccccatagg actagggcaa gcactctata   1560
caacaagaag aatagaagat ataagaagag cacattgttg taccagaccc tccaccaata   1620
caagaacaag tatacgtata ggaccaggac aagtattcta tagaacagga gacataacag   1680
gagatataag aaaagcatat tgtggatcct gtacaagacc caacaacaat acaagaaaaa   1740
gaatatcttt aggaccagga cgagtatttt atacagcagg agaaataata ggagacatca   1800
gaaaggcaca ttgttgtacc agacctaata acaatacaag aaaaagtata acttttgcac   1860
caggacaagc gctctatgca acaggtgaaa taataggaga tataagacaa gcacattgtc   1920
tcgggtgtac cagacctaac aacaatacaa gaaaaagtgt acgtatagga ccaggacaaa   1980
cattctatgc aacaggtgat ataatagggg atataagaca agcacattgt tgtacgagac   2040
ccaacaataa tacaagaaaa agtataagga taggaccagg acaagcattc tatgcaacag   2100
gagaaataat aggagatata agacaagcac attgttgcac aaggccctac aacaatataa   2160
gacaaaggac ccccatagga ctagggcaag cactctatac aacaagaaga atagaagata   2220
taagaagagc acattgttgt accagaccct ccaccaatac aagaacaagt atacgtatag   2280
gaccaggaca agtattctat agaacaggag acataacagg agatataaga aaagcatatt   2340
gtggatcctg tacaagaccc aacaacaata caagaaaaag aatatcttta ggaccaggac   2400
gagtatttta tacagcagga gaaataatag gagacatcag aaaggcacat tgttgtacca   2460
gacctaataa caatacaaga aaaagtataa cttttgcacc aggacaagcg ctctatgcaa   2520
caggtgaaat aataggagat ataagacaag cacattgtct cgggaacatt agtagagcaa   2580
aatggaataa cactttaaaa cagatagata gcaaattaag agaacaattt ggaaataata   2640
aaacaataat ctttaagcag tcctcaggag gggacccaga aattgtaacg cacagtttta   2700
attgtggagg ggaatttttc tactgtaatt caacacaact gtttaatagt acttggttta   2760
atagtacttg gagtactaaa gggtcaaata acactgaagg aagtgacaca atcaccctcc   2820
catgcagaat aaaacaaatt ataaacatgt ggcaggaagt aggaaaagca atgtatgccc   2880
```

-continued

```
ctcccatcag tggacaaatt agatgttcat caaatattac agggctgcta ttaacaagag   2940

atggtggtaa tagcaacaat gagtccgaga tcttcagacc tggaggagga gatatgaggg   3000

acaattggag aagtgaatta tataaatata aagtagtaaa aattgaacca ttaggagtag   3060

cacccaccaa ggcaaagaga agagtggtgc agactagtgc agtgggaata ggagctttgt   3120

tccttgggtt cttgggagca gcaggaagca ctatgggctg cacgtcaatg acgctgacgg   3180

tacaggccag acaattattg tctgatatag tgcagcagca gaacaatttg ctgagggcta   3240

ttgaggcgca acagcatctg ttgcaactca cagtctgggg catcaaacag ctccaggcaa   3300

gaatcctggc tgtggaaaga tacctaaagg atcaacagct cctggggatt tggggttgct   3360

ctggaaaact catttgcacc actgctgtgc cttggaatgc tagttggagt aataaatctc   3420

tggaacagat ttggaataac atgacctgga tggagtggga cagagaaatt aacaattaca   3480

caagcttaat acactcctta attgaagaat cgcaaaacca gcaagaaaag aatgaacaag   3540

aattattgga attagataaa tggcaagtt tgtggaattg gtttaacata acaaattggc   3600

tgtggtatat aaaattattc ataatgatag taggaggctt ggtaggttta agaatagttt   3660

ttgctgtact ttctatagtg aatagagtta ggcagggata ttcaccatta tcgtttcaga   3720

cccacctccc aatcccgagg ggacccgaca ggcccgaagg aatagaagaa gaaggtggag   3780

agagagacag agacagatcc attcgattag tgaacggatc cttagcactt atctgggacg   3840

atctgcggag cctgtgcctc ttcagctacc accgcttgag agacttactc ttgattgtaa   3900

cgaggattgt ggaacttctg ggacgcaggg ggtgggaagc cctcaaatat tggtggaatc   3960

tcctacagta ttggagtcag gaactaaaga atagtgctgt taacttgctc aatgccacag   4020

ccatagcagt agctgagtaa                                               4040
```

<210> SEQ ID NO 55
<211> LENGTH: 1186
<212> TYPE: PRT
<213> ORGANISM: Artificial sequence
<220> FEATURE:
<223> OTHER INFORMATION: Modified Env/Tat/Rev

<400> SEQUENCE: 55

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Gly
        115                 120                 125

Ala Gly Ser Cys Asn Thr Ser Val Ile Thr Gln Ala Cys Pro Lys Val
    130                 135                 140

Ser Phe Glu Pro Ile Pro Ile His Tyr Cys Ala Pro Ala Gly Phe Ala
145                 150                 155                 160
```

-continued

```
Ile Leu Lys Cys Asn Asn Lys Thr Phe Asn Gly Thr Gly Pro Cys Thr
                165                 170                 175

Asn Val Ser Thr Val Gln Cys Thr His Gly Ile Arg Pro Val Val Ser
            180                 185                 190

Thr Gln Leu Leu Leu Asn Gly Ser Leu Ala Glu Glu Glu Val Val Ile
        195                 200                 205

Arg Ser Ala Asn Phe Thr Asp Asn Ala Lys Thr Ile Ile Val Gln Leu
    210                 215                 220

Asn Gln Ser Val Glu Ile Asn Cys Thr Arg Pro Asn Asn Asn Thr Arg
225                 230                 235                 240

Lys Ser Ile Arg Ile Gln Arg Gly Pro Gly Arg Ala Phe Val Thr Ile
                245                 250                 255

Gly Lys Ile Gly Asn Met Arg Gln Ala His Cys Leu Gly Cys Thr Arg
            260                 265                 270

Pro Asn Asn Asn Thr Arg Lys Ser Val Arg Ile Gly Pro Gly Gln Thr
        275                 280                 285

Phe Tyr Ala Thr Gly Asp Ile Ile Gly Asp Ile Arg Gln Ala His Cys
    290                 295                 300

Cys Thr Arg Pro Asn Asn Asn Thr Arg Lys Ser Ile Arg Ile Gly Pro
305                 310                 315                 320

Gly Gln Ala Phe Tyr Ala Thr Gly Glu Ile Ile Gly Asp Ile Arg Gln
                325                 330                 335

Ala His Cys Cys Thr Arg Pro Tyr Asn Asn Ile Arg Gln Arg Thr Pro
            340                 345                 350

Ile Gly Leu Gly Gln Ala Leu Tyr Thr Thr Arg Arg Ile Glu Asp Ile
        355                 360                 365

Arg Arg Ala His Cys Cys Thr Arg Pro Ser Thr Asn Thr Arg Thr Ser
    370                 375                 380

Ile Arg Ile Gly Pro Gly Gln Val Phe Tyr Arg Thr Gly Asp Ile Thr
385                 390                 395                 400

Gly Asp Ile Arg Lys Ala Tyr Cys Gly Ser Cys Thr Arg Pro Asn Asn
                405                 410                 415

Asn Thr Arg Lys Arg Ile Ser Leu Gly Pro Gly Arg Val Phe Tyr Thr
            420                 425                 430

Ala Gly Glu Ile Ile Gly Asp Ile Arg Lys Ala His Cys Cys Thr Arg
        435                 440                 445

Pro Asn Asn Asn Thr Arg Lys Ser Ile Thr Phe Ala Pro Gly Gln Ala
    450                 455                 460

Leu Tyr Ala Thr Gly Glu Ile Ile Gly Asp Ile Arg Gln Ala His Cys
465                 470                 475                 480

Leu Gly Cys Thr Arg Pro Asn Asn Asn Thr Arg Lys Ser Val Arg Ile
                485                 490                 495

Gly Pro Gly Gln Thr Phe Tyr Ala Thr Gly Asp Ile Ile Gly Asp Ile
            500                 505                 510

Arg Gln Ala His Cys Cys Thr Arg Pro Asn Asn Asn Thr Arg Lys Ser
        515                 520                 525

Ile Arg Ile Gly Pro Gly Gln Ala Phe Tyr Ala Thr Gly Glu Ile Ile
    530                 535                 540

Gly Asp Ile Arg Gln Ala His Cys Cys Thr Arg Pro Tyr Asn Asn Ile
545                 550                 555                 560

Arg Gln Arg Thr Pro Ile Gly Leu Gly Gln Ala Leu Tyr Thr Thr Arg
                565                 570                 575
```

-continued

```
Arg Ile Glu Asp Ile Arg Arg Ala His Cys Cys Thr Arg Pro Ser Thr
            580                 585                 590

Asn Thr Arg Thr Ser Ile Arg Ile Gly Pro Gly Gln Val Phe Tyr Arg
        595                 600                 605

Thr Gly Asp Ile Thr Gly Asp Ile Arg Lys Ala Tyr Cys Gly Ser Cys
    610                 615                 620

Thr Arg Pro Asn Asn Asn Thr Arg Lys Arg Ile Ser Leu Gly Pro Gly
625                 630                 635                 640

Arg Val Phe Tyr Thr Ala Gly Glu Ile Ile Gly Asp Ile Arg Lys Ala
                645                 650                 655

His Cys Cys Thr Arg Pro Asn Asn Asn Thr Arg Lys Ser Ile Thr Phe
            660                 665                 670

Ala Pro Gly Gln Ala Leu Tyr Ala Thr Gly Glu Ile Ile Gly Asp Ile
        675                 680                 685

Arg Gln Ala His Cys Leu Gly Asn Ile Ser Arg Ala Lys Trp Asn Asn
    690                 695                 700

Thr Leu Lys Gln Ile Asp Ser Lys Leu Arg Glu Gln Phe Gly Asn Asn
705                 710                 715                 720

Lys Thr Ile Ile Phe Lys Gln Ser Ser Gly Gly Asp Pro Glu Ile Val
                725                 730                 735

Thr His Ser Phe Asn Cys Gly Gly Glu Phe Phe Tyr Cys Asn Ser Thr
            740                 745                 750

Gln Leu Phe Asn Ser Thr Trp Phe Asn Ser Thr Trp Ser Thr Lys Gly
        755                 760                 765

Ser Asn Asn Thr Glu Gly Ser Asp Thr Ile Thr Leu Pro Cys Arg Ile
    770                 775                 780

Lys Gln Ile Ile Asn Met Trp Gln Glu Val Gly Lys Ala Met Tyr Ala
785                 790                 795                 800

Pro Pro Ile Ser Gly Gln Ile Arg Cys Ser Ser Asn Ile Thr Gly Leu
                805                 810                 815

Leu Leu Thr Arg Asp Gly Gly Asn Ser Asn Asn Glu Ser Glu Ile Phe
            820                 825                 830

Arg Pro Gly Gly Gly Asp Met Arg Asp Asn Trp Arg Ser Glu Leu Tyr
        835                 840                 845

Lys Tyr Lys Val Val Lys Ile Glu Pro Leu Gly Val Ala Pro Thr Lys
    850                 855                 860

Ala Lys Arg Arg Val Val Gln Thr Ser Ala Val Gly Ile Gly Ala Leu
865                 870                 875                 880

Phe Leu Gly Phe Leu Gly Ala Ala Gly Ser Thr Met Gly Cys Thr Ser
                885                 890                 895

Met Thr Leu Thr Val Gln Ala Arg Gln Leu Leu Ser Asp Ile Val Gln
            900                 905                 910

Gln Gln Asn Asn Leu Leu Arg Ala Ile Glu Ala Gln Gln His Leu Leu
        915                 920                 925

Gln Leu Thr Val Trp Gly Ile Lys Gln Leu Gln Ala Arg Ile Leu Ala
    930                 935                 940

Val Glu Arg Tyr Leu Lys Asp Gln Gln Leu Leu Gly Ile Trp Gly Cys
945                 950                 955                 960

Ser Gly Lys Leu Ile Cys Thr Thr Ala Val Pro Trp Asn Ala Ser Trp
                965                 970                 975

Ser Asn Lys Ser Leu Glu Gln Ile Trp Asn Asn Met Thr Trp Met Glu
            980                 985                 990
```

-continued

```
Trp Asp Arg Glu Ile Asn Asn Tyr  Thr Ser Leu Ile His  Ser Leu Ile
        995                 1000                 1005

Glu Glu  Ser Gln Asn Gln Gln  Glu Lys Asn Glu Gln  Glu Leu Leu
    1010                 1015                 1020

Glu Leu  Asp Lys Trp Ala Ser  Leu Trp Asn Trp Phe  Asn Ile Thr
    1025                 1030                 1035

Asn Trp  Leu Trp Tyr Ile Lys  Leu Phe Ile Met Ile  Val Gly Gly
    1040                 1045                 1050

Leu Val  Gly Leu Arg Ile Val  Phe Ala Val Leu Ser  Ile Val Asn
    1055                 1060                 1065

Arg Val  Arg Gln Gly Tyr Ser  Pro Leu Ser Phe Gln  Thr His Leu
    1070                 1075                 1080

Pro Ile  Pro Arg Gly Pro Asp  Arg Pro Glu Gly Ile  Glu Glu Glu
    1085                 1090                 1095

Gly Gly  Glu Arg Asp Arg Asp  Arg Ser Ile Arg Leu  Val Asn Gly
    1100                 1105                 1110

Ser Leu  Ala Leu Ile Trp Asp  Asp Leu Arg Ser Leu  Cys Leu Phe
    1115                 1120                 1125

Ser Tyr  His Arg Leu Arg Asp  Leu Leu Leu Ile Val  Thr Arg Ile
    1130                 1135                 1140

Val Glu  Leu Leu Gly Arg Arg  Gly Trp Glu Ala Leu  Lys Tyr Trp
    1145                 1150                 1155

Trp Asn  Leu Leu Gln Tyr Trp  Ser Gln Glu Leu Lys  Asn Ser Ala
    1160                 1165                 1170

Val Asn  Leu Leu Asn Ala Thr  Ala Ile Ala Val Ala  Glu
    1175                 1180                 1185


<210> SEQ ID NO 56
<211> LENGTH: 507
<212> TYPE: DNA
<213> ORGANISM: Human immunodeficiency virus type 1

<400> SEQUENCE: 56

atgttcttta gggaagatct ggccttccta caagggaagg ccagggaatt ttcttcagag     60

cagaccagag ccaacagccc caccatttct tcagagcaga ccagagccaa cagccccacc    120

agaagagagc ttcaggtctg gggtagagac aacaactccc cctcagaagc aggagccgat    180

agacaaggaa ctgtatcctt taacttccct cagatcactc tttggcaacg acccctcgtc    240

acaataaaga taggggggca actaaaggaa gctctattag atacaggagc agatgataca    300

gtattagaag aaatgagttt gccaggaaga tggaaaccaa aaatgatagg gggaattgga    360

ggttttatca aagtaagaca gtatgatcag atactcatag aaatctgtgg acataaagct    420

ataggtacag tattagtagg acctacacct gtcaacataa ttggaagaaa tctgttgact    480

cagattggtt gcactttaaa tttttaa                                        507


<210> SEQ ID NO 57
<211> LENGTH: 168
<212> TYPE: PRT
<213> ORGANISM: Human immunodeficiency virus type 1

<400> SEQUENCE: 57

Met Phe Phe Arg Glu Asp Leu Ala Phe Leu Gln Gly Lys Ala Arg Glu
1               5                   10                  15

Phe Ser Ser Glu Gln Thr Arg Ala Asn Ser Pro Thr Ile Ser Ser Glu
            20                  25                  30
```

-continued

```
Gln Thr Arg Ala Asn Ser Pro Thr Arg Arg Glu Leu Gln Val Trp Gly
        35                  40                  45

Arg Asp Asn Asn Ser Pro Ser Glu Ala Gly Ala Asp Arg Gln Gly Thr
    50                  55                  60

Val Ser Phe Asn Phe Pro Gln Ile Thr Leu Trp Gln Arg Pro Leu Val
65                  70                  75                  80

Thr Ile Lys Ile Gly Gly Gln Leu Lys Glu Ala Leu Leu Asp Thr Gly
                85                  90                  95

Ala Asp Asp Thr Val Leu Glu Glu Met Ser Leu Pro Gly Arg Trp Lys
            100                 105                 110

Pro Lys Met Ile Gly Gly Ile Gly Gly Phe Ile Lys Val Arg Gln Tyr
        115                 120                 125

Asp Gln Ile Leu Ile Glu Ile Cys Gly His Lys Ala Ile Gly Thr Val
    130                 135                 140

Leu Val Gly Pro Thr Pro Val Asn Ile Ile Gly Arg Asn Leu Leu Thr
145                 150                 155                 160

Gln Ile Gly Cys Thr Leu Asn Phe
                165


<210> SEQ ID NO 58
<211> LENGTH: 1800
<212> TYPE: DNA
<213> ORGANISM: Artificial sequence
<220> FEATURE:
<223> OTHER INFORMATION: Gag-PI

<400> SEQUENCE: 58

atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcagtca ggtcagccaa aattacccta tagtgcagaa catccagggg    420

caaatggtac atcaggccat atcacctaga actttaaatg catgggtaaa agtagtagaa    480

gagaaggctt tcagcccaga agtaataccc atgttttcag cattatcaga aggagccacc    540

ccacaagatt taaacaccat gctaaacaca gtggggggac atcaagcagc catgcaaatg    600

ttaaaagaga ccatcaatga ggaagctgca gaatgggata gagtacatcc agtgcatgca    660

gggcctattg caccaggcca gatgagagaa ccaaggggaa gtgacatagc aggaactact    720

agtacccttc aggaacaaat aggatggatg acaaataatc cacctatccc agtaggagaa    780

atttataaaa gatggataat cctgggatta aataaaatag taagaatgta tagccctacc    840

agcattctgg acataagaca aggaccaaaa gaacctttta gagactatgt agaccggttc    900

tataaaactc taagagccga gcaagcttca caggaggtaa aaaattggat gacagaaacc    960

ttgttggtcc aaaatgcgaa cccagattgt aagactattt taaaagcatt gggaccagcg   1020

gctacactag aagaaatgat gacagcatgt cagggagtag gaggacccgg ccataaggca   1080

agagttttgg ctgaagcaat gagccaagta acaaatacag ctaccataat gatgcagaga   1140

ggcaatttta ggaaccaaag aaagatggtt aagtgtttca attgtggcaa agaagggcac   1200

acagccagaa attgcagggc ccctaggaaa aagggctgtt ggaaatgtgg aaaggaagga   1260
```

-continued

```
caccaaatga aagattgtac tgagagacag gctaatttct ttagggaaga tctggccttc   1320

ctacaaggga aggccaggga attttcttca gagcagacca gagccaacag ccccaccatt   1380

tcttcagagc agaccagagc caacagcccc accagaagag agcttcaggt ctggggtaga   1440

gacaacaact ccccctcaga agcaggagcc gatagacaag gaactgtatc ctttaacttc   1500

cctcagatca ctctttggca acgacccctc gtcacaataa agataggggg gcaactaaag   1560

gaagctctat tagatacagg agcagatgat acagtattag aagaaatgag tttgccagga   1620

agatggaaac caaaaatgat agggggaatt ggaggtttta tcaaagtaag acagtatgat   1680

cagatactca tagaaatctg tggacataaa gctataggta cagtattagt aggacctaca   1740

cctgtcaaca taattggaag aaatctgttg actcagattg gttgcacttt aaatttttaa   1800
```

<210> SEQ ID NO 59
<211> LENGTH: 599
<212> TYPE: PRT
<213> ORGANISM: Artificial sequence
<220> FEATURE:
<223> OTHER INFORMATION: Gag-PI

<400> SEQUENCE: 59

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255
```

-continued

```
Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
    370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Phe Arg Glu Asp Leu Ala Phe Leu Gln Gly Lys Ala Arg Glu Phe
        435                 440                 445

Ser Ser Glu Gln Thr Arg Ala Asn Ser Pro Thr Ile Ser Ser Glu Gln
    450                 455                 460

Thr Arg Ala Asn Ser Pro Thr Arg Arg Glu Leu Gln Val Trp Gly Arg
465                 470                 475                 480

Asp Asn Asn Ser Pro Ser Glu Ala Gly Ala Asp Arg Gln Gly Thr Val
                485                 490                 495

Ser Phe Asn Phe Pro Gln Ile Thr Leu Trp Gln Arg Pro Leu Val Thr
            500                 505                 510

Ile Lys Ile Gly Gly Gln Leu Lys Glu Ala Leu Leu Asp Thr Gly Ala
        515                 520                 525

Asp Asp Thr Val Leu Glu Glu Met Ser Leu Pro Gly Arg Trp Lys Pro
    530                 535                 540

Lys Met Ile Gly Gly Ile Gly Gly Phe Ile Lys Val Arg Gln Tyr Asp
545                 550                 555                 560

Gln Ile Leu Ile Glu Ile Cys Gly His Lys Ala Ile Gly Thr Val Leu
                565                 570                 575

Val Gly Pro Thr Pro Val Asn Ile Ile Gly Arg Asn Leu Leu Thr Gln
            580                 585                 590

Ile Gly Cys Thr Leu Asn Phe
        595
```

<210> SEQ ID NO 60
<211> LENGTH: 51
<212> TYPE: DNA
<213> ORGANISM: Artificial sequence
<220> FEATURE:
<223> OTHER INFORMATION: PCR primer

<400> SEQUENCE: 60
aaatcaaccg gaattgaatt ccctcgggtg taccagacct aacaacaata c 51

-continued

<210> SEQ ID NO 61
<211> LENGTH: 42
<212> TYPE: DNA
<213> ORGANISM: Artificial sequence
<220> FEATURE:
<223> OTHER INFORMATION: PCR primer

<400> SEQUENCE: 61
attgttgggt ctcgtacaac aatgtgcttg tcttatatcc cc 42

<210> SEQ ID NO 62
<211> LENGTH: 41
<212> TYPE: DNA
<213> ORGANISM: Artificial sequence
<220> FEATURE:
<223> OTHER INFORMATION: PCR primer

<400> SEQUENCE: 62
ggggatataa gacaagcaca ttgtacgaga cccaacaata c 41

<210> SEQ ID NO 63
<211> LENGTH: 39
<212> TYPE: DNA
<213> ORGANISM: Artificial sequence
<220> FEATURE:
<223> OTHER INFORMATION: PCR primer

<400> SEQUENCE: 63
gttgtagggc cttgtgcaac aatgtgcttg tcttatatc 39

<210> SEQ ID NO 64
<211> LENGTH: 39
<212> TYPE: DNA
<213> ORGANISM: Artificial sequence
<220> FEATURE:
<223> OTHER INFORMATION: PCR primer

<400> SEQUENCE: 64
gatataagac aagcacattg ttgcacaagg ccctacaac 39

<210> SEQ ID NO 65
<211> LENGTH: 36
<212> TYPE: DNA
<213> ORGANISM: Artificial sequence
<220> FEATURE:
<223> OTHER INFORMATION: PCR primer

<400> SEQUENCE: 65
ggtggagggt ctggtacaac aatgtgctct tcttat 36

<210> SEQ ID NO 66
<211> LENGTH: 36
<212> TYPE: DNA
<213> ORGANISM: Artificial sequence
<220> FEATURE:
<223> OTHER INFORMATION: PCR primer

<400> SEQUENCE: 66
ataagaagag cacattgttg taccagaccc tccacc 36

<210> SEQ ID NO 67
<211> LENGTH: 47
<212> TYPE: DNA
<213> ORGANISM: Artificial sequence
<220> FEATURE:
<223> OTHER INFORMATION: PCR primer -continued

<400> SEQUENCE: 67
gtattgttgt tgggtcttgt acaacaatat gcttttctta tatctcc 47

<210> SEQ ID NO 68
<211> LENGTH: 47
<212> TYPE: DNA
<213> ORGANISM: Artificial sequence
<220> FEATURE:
<223> OTHER INFORMATION: PCR primer

<400> SEQUENCE: 68
ggagatataa gaaaagcata ttgttgtaca agacccaaca acaatac 47

<210> SEQ ID NO 69
<211> LENGTH: 39
<212> TYPE: DNA
<213> ORGANISM: Artificial sequence
<220> FEATURE:
<223> OTHER INFORMATION: PCR primer

<400> SEQUENCE: 69
gttattaggt ctggtacaac aatgtgcctt tctgatgtc 39

<210> SEQ ID NO 70
<211> LENGTH: 39
<212> TYPE: DNA
<213> ORGANISM: Artificial sequence
<220> FEATURE:
<223> OTHER INFORMATION: PCR primer

<400> SEQUENCE: 70
gacatcagaa aggcacattg ttgtaccaga cctaataac 39

<210> SEQ ID NO 71
<211> LENGTH: 54
<212> TYPE: DNA
<213> ORGANISM: Artificial sequence
<220> FEATURE:
<223> OTHER INFORMATION: PCR primer

<400> SEQUENCE: 71
aataaactag tctagacccc cgagtctaga acaatgtgct tgtcttatat ctcc 54

<210> SEQ ID NO 72
<211> LENGTH: 7
<212> TYPE: DNA
<213> ORGANISM: Artificial sequence
<220> FEATURE:
<223> OTHER INFORMATION: MMLV SD site

<400> SEQUENCE: 72 aggtaag 7

<210> SEQ ID NO 73
<211> LENGTH: 9
<212> TYPE: DNA
<213> ORGANISM: Artificial sequence
<220> FEATURE:
<223> OTHER INFORMATION: MMLV SA site

<400> SEQUENCE: 73 ctgctgcag 9

-continued

```
<210> SEQ ID NO 74
<211> LENGTH: 90
<212> TYPE: DNA
<213> ORGANISM: Artificial sequence
<220> FEATURE:
<223> OTHER INFORMATION: DNA encoding gp120 signal peptide

<400> SEQUENCE: 74

atgagagtga aggagaaata tcagcacttg tggagatggg ggtggagatg gggcaccatg     60

ctccttggga tgttgatgat ctgtagtgct                                      90


<210> SEQ ID NO 75
<211> LENGTH: 129
<212> TYPE: DNA
<213> ORGANISM: Artificial sequence
<220> FEATURE:
<223> OTHER INFORMATION: DNA encoding gp41 transmembrane domain

<400> SEQUENCE: 75

ttattcataa tgatagtagg aggcttggta ggtttaagaa tagtttttgc tgtactttct     60

gtagtgaata gagttaggca gggatattca ccattatcgt ttcagaccca cctcccaatc    120

ccgagggga                                                            129
```

METHOD OF VACCINATION THROUGH SEROTYPE ROTATION

RELATIONSHIP TO PARENT AND CO-PENDING APPLICATIONS

This application is a continuation-in-part of U.S. patent application entitled "GENETIC VACCINE AGAINST HUMAN IMMUNODEFICIENCY VIRUS", application Ser. No. 10/003,035, Filed: Nov. 1, 2001, now abandoned which is a continuation-in-part of PCT application entitled "GENETIC VACCINE THAT MIMICS NATURAL VIRAL INFECTION AND INDUCES LONG-LASTING IMMUNITY TO PATHOGEN", application Ser. No.: PCT US01/18238, Filed: Jun. 4, 2001, which is a continuation-in-part of U.S. patent application entitled "GENETIC VACCINE THAT MIMICS NATURAL VIRAL INFECTION AND INDUCES LONG-LASTING IMMUNITY TO PATHOGEN", application Ser. No. 09/585,599, Filed: Jun. 2, 2000 now U.S. Pat. No. 6,544,780. The above applications are incorporated herein by reference.

BACKGROUND OF THE INVENTION

1. Field of the Invention

This invention relates to vaccines for stimulating immune responses in human and other hosts, and, in particular, relates to recombinant viruses that express heterologous antigens of human immunodeficiency virus (HIV) in a host and elicit immune response to HIV infection.

2. Background of the Invention

Current techniques for developing vaccines are largely based on the concept of using denatured virus or purified viral proteins made from bacteria. These types of vaccines may be effective for only a limited number of infectious agents, and the protection rates are limited.

For viruses that contain membrane (envelope) glycoproteins (GPs), including the Ebola virus and the HIV virus, use of denatured virus or purified viral proteins often does not work satisfactorily. There may be several reasons for this. First, the GPs of these viruses are sensitive to the denaturing procedures so that the epitopes of the proteins are altered by the denaturing process. Second, the sugar moieties of the GPs are important antigenic determinants for neutralizing antibodies. In comparison, proteins made in bacteria are not properly glycosylated and can fold into somewhat different structures that can have antigenecities different from those of the natural viral proteins. Further, many vaccines that are based on attenuated or denatured virus provide a weak immune response to poorly immunogenic antigens. In addition, the vaccine preparations frequently offer only limited protection, not life-long immunity as desired.

Other vaccine approaches express antigens by plasmids directly injected into the body, the so-called naked DNA or DNA vaccine technology. These methods involve the deliberate introduction of a DNA plasmid carrying an antigen-coding gene by transfecting cells with the plasmid in vivo. The plasmid expresses the antigen that causes an immune response. The immune response stimulated by DNA vaccine can be very inefficient, presumably due to low levels of uptake of the plasmid and low levels of antigen expression in the cells. DNA vaccines are also characterized by an extremely short antigen expression period due to vector degradation. In addition, DNA vaccines are difficult and costly to produce in large amounts.

Replication-competent, live vaccinia viruses have also been modified for expression of the genes for hepatitis B (HBV), human immunodeficiency virus (HIV), influenza and malaria antigens. In some instances, though, the immune response of recombinant vaccines is often of limited nature and magnitude. Thus, for example, while peripheral immunization with vaccinia influenza recombinants provides good protection against lower respiratory tract infections, it fails to induce immunity in the upper respiratory tract. On the other hand, peripheral immunization with recombinant vaccines may prove ineffective when local rather than systemic immunity is required, as in, for example, the gastrointestinal tract.

Vaccination with recombinant vaccinia virus expressing Ebola virus GP has been attempted to confer partial protection in guinea pigs. Gilligan, K. J., et al., *Vaccines,* 97:87-92 (1997). Vaccination with DNA constructs expressing either GP or nucleocapsid protein (NP) protects mice from lethal challenge with Ebola virus. Vanderzanden, L., et al., *Virology,* 246(1):134-44 (1998). However, each of these approaches has its own set of limitations that make them less then ideal choices for Ebola virus vaccines in humans. For example, vaccinia virus rapidly kills vector-infected cells. Consequently, the vaccine antigen is expressed for only a short time. However, the major limitation for this type of approaches is that the replication of vaccina virus causes the immune system to react mainly to the vaccinia proteins, only small portion of the immune responses is targeted to the antigen of the pathogenic virus. This phenomenon has been termed "antigen dilution".

Previous attempts to remedy these deficiencies, including expression of vaccine antigens through viruses having stronger promoters, such as poxyirus, have not met with significant success.

As yet, no vaccine has been effective in conferring protection against HIV infection. Attempts to develop vaccines have thus far failed. Certain antibodies reactive with HIV, notably anti-GP160/120 are present at high levels throughout both the asymptomatic and symptomatic phases of the HIV infection, suggesting that rather than playing a protective role, such antibodies may in fact promote the attachment and penetration of the virus into the host cell. More significantly, current vaccines do not induce efficient cellular responses against the infected cells, the source of newly released virions.

SUMMARY OF THE INVENTION

Genetic viral vaccines are provided. These vaccines are designed to mimic natural infection of pathogenic viruses without causing diseases that are naturally associated with the pathogenic viruses in a host to be immunized, such as human, domestic animals and other mammals.

The vaccines are recombinant benign viruses that are replication deficient or incompetent. The benign viruses may be designed to express antigens from a wide variety of pathogens such as viruses, bacteria and parasites, and thus may be used to treat this wide variety of viruses, bacteria, and parasites that natively express these antigens. Infection of the benign virus causes host cells to express the antigens of the pathogenic virus and presents the antigen in its natural conformation and pathway as if the cell were infected by the pathogenic virus, and induces a strong and long-lasting immune response in the host.

In one embodiment, a recombinant benign virus is provided for eliciting an immune response in a host infected by the virus. The recombinant virus comprises: an antigen sequence heterologous to the benign virus that encodes a viral antigen from a pathogenic virus, expression of the viral antigen eliciting an immune response directed against the pathogenic virus and cells expressing the viral antigen in the host upon infection of the host by the recombinant virus; and an immuno-stimulator sequence heterologous to the benign virus that encodes an immuno-stimulator whose expression in the host enhances the immunogenicity of the viral antigen. The recombinant virus is replication-incompetent and does not cause disease that is associated with the pathogenic virus in the host In a variation of the this embodiment, the recombinant benign virus may be a replication-incompetent virus such as adenovirus, adeno-associated virus, SV40 virus, retrovirus, herpes simplex virus or vaccinia virus. Preferably, the benign virus does not have the pathologic regions of the native progenitor of the benign virus but retains its infectivity.

In a preferred embodiment, the benign virus is a replication-incompetent adenovirus, more preferably adenovirus type 5. The heterologous antigen sequence may be positioned in the E1, E3 or E4 region of the adenovirus. The immuno-stimulator sequence may be positioned in the E4, E3 or E1 region of the adenovirus.

In a variation of the preferred embodiment, the heterologous antigen sequence and the immuno-stimulator sequence are positioned in the E1, E3 or E4 region of the adenovirus, where the heterologous antigen sequence and the immuno-stimulator sequence are expressed from a promoter bicistronically via an internal ribosomal entry site or via a splicing donor-acceptor mechanism.

Expression of the viral antigen or the immuno-stimulator may be controlled by a promoter homologous to the native progenitor of the recombinant virus. Alternatively, expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

The pathogenic virus may be any pathogenic virus that causes pathogenic effects or disease in human or other animals. Thus, the recombinant benign virus can be used as a vaccine for protecting the host from infection of the pathogenic virus.

In a variation, the pathogenic virus may be various strains of human immunodeficiency virus (HIV), such as HIV-1 and HIV-2. The viral antigen may be an HIV glycoprotein (or surface antigen) such as HIV GP120 and GP41, or a capsid protein (or structural protein) such as HIV P24 protein.

In another variation, the pathogenic virus may be Ebola virus. The viral antigen may be an Ebola glycoprotein or surface antigen such as Ebola GP1 or GP2 protein.

In yet another variation, the pathogenic virus may be hepatitis virus such as hepatitis A, B, C, D or E virus. For example, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may be a surface antigen or core protein of hepatitis C virus such as NS3, NS4 and NS5 antigens.

In yet another variation, the pathogenic virus may be a respiratory syncytial virus (RSV). For example, the RSV viral antigen may be the glycoprotein (G-protein) or the fusion protein (F-protein) of RSV, for which the sequences are available from GenBank.

In yet another variation, the pathogenic virus may be a herpes simplex virus (HSV) such as HSV-1 and HSV-2. For example, the HSV viral antigen may be the glycoprotein D from HSV-2.

In yet another variation, the viral antigen may be a tumor antigen, such as Her 2 of breast cancer cells and CD20 on lymphoma cells, a viral oncogene such as E6 and E7 of human papilloma virus, or a cellular oncogene such as mutated ras.

It is noted that, other virus-associated proteins or antigens are readily available to those of skill in the art. Selection of the pathogenic virus and the viral antigen associated with the pathogenic virus is not a limiting factor in this invention.

The recombinant virus also expresses an immuno-stimulator to mimic cytokine-releasing response of a host cell upon viral infection and further augments the immune response to the viral antigen co-expressed from the recombinant virus. The immuno-stimulator may preferably be a cytokine. Examples of cytokine include, but are not limited to, interleukin-2, interleukin-8, interleukin-12, β-interferon, λ-interferon, γ-interferon, granulocyte colony stimulating factor (G-CSF), and granulocyte-macrophage colony stimulating factor (GM-CSF).

The viral antigen may be a full-length antigenic viral protein or a portion of the antigenic viral protein that contains the predominant antigen, neutralizing antigen, or epitope of the pathogenic virus. Alternatively, the viral antigen contains the constant region of glycoproteins of at least two strains of the pathogenic virus.

In a variation, the viral antigen may be a modified antigen that is mutated from a glycoprotein of the pathogenic virus such that the viral antigen is rendered non-functional as a viral component but retains its antigenicity. Such modification of the viral antigen includes deletions in the proteolytic cleavage site of the glycoprotein, and duplications and rearrangement of immunosuppressive peptide regions of the glycoprotein.

In another embodiment, a recombinant adenovirus is provided for eliciting an immune response in a host infected by the virus. The recombinant virus comprises: an antigen sequence heterologous to adenovirus and encoding a viral antigen from a pathogenic virus, expression of the viral antigen eliciting an immune response directed against the viral antigen upon infection of the host by the recombinant adenovirus.

In a preferred variation of the embodiment, the recombinant virus is a replication-incompetent adenovirus. In particular, the pathogenic virus is HIV, including various types (e.g., HIV-1 and HIV-2), strains (e.g., strain BH10 and pNL4-3 of HIV-1), isolates, clades within a group of isolates (e.g., clade A, B, C, D, E, F, and G of group M of HIV-1 isolates) of HIV. The viral antigen may be a 1) HIV glycoprotein (or surface antigen) such as HIV envelope protein Env, either full length wild type (gp160), truncated (e.g, gp120 and gp41), or modified with insertions, deletions or substitutions; 2) HIV structural protein Gag, either full length wild type, modified, or protease-processed products or fragments in various forms (e.g., natural, secreted, or membrane bound forms of HIV capsid proteins such as HIV p24 and p17; and 3) HIV regulatory proteins such as Tat, Vif, Nef, and Rev.

According to this variation, the HIV antigen is an HIV envelop protein encoded by a polynucleotide selected from the group consisting of SEQ ID NOs: 14, 16, 20, 21, 22, 23, and 24. The polynucleotide may further encode HIV regulatory proteins such as Tat, Vif, Nef, and Rev.

Also according to the variation, the HIV antigen is a modified HIV envelope protein that includes multiclade variable loops. Preferably, the multiclade variable loops are V3 loops from various clades such as clade A, B, C, D, E, F, and G of group M of HIV-1 isolates. The modified HIV envelope protein that includes multiclade variable loops may include two or more V3 loops from different HIV clades, preferably V3 loops encoded by polynucleotides selected from the group consisting of SEQ ID NOs: 25, 26, 27, 28, 29, 30, and 31. More preferably, the modified HIV envelope protein that includes multiclade variable loops is encoded by a polynucleotide selected from the group consisting of SEQ ID NOs: 32, 52, and 54.

Also according to the variation, the HIV antigen is an HIV structural protein. The HIV structural protein may be a full length wild type Gag encoded by SEQ ID NO: 17, or a proteolytic fragment of Gag such as p17/24, p17 and p24. The fragment p17/24 may be in natural form and encoded by SEQ ID NO: 34, in secreted form and encoded by SEQ ID NO: 34, or in membrane bound form and encoded by SEQ ID NO: 36. The fragment p17 may be in natural form and encoded by SEQ ID NO: 40, in secreted form and encoded by SEQ ID NO: 41, or in membrane bound form and encoded by SEQ ID NO: 42. Similarly, p24 may be in natural form and encoded by SEQ ID NO: 46, in secreted form and encoded by SEQ ID NO: 47, or in membrane bound form and encoded by SEQ ID NO: 48.

The recombinant virus may further comprise a polynucleotide encoding an HIV protease PI such as SEQ ID NO: 56, expression of which facilitates proteolytic processing of Gag expressed from the same recombinant virus or from another vector. PI may be expressed as a fusion protein with Gag, or separately from a different promoter or from the same promoter for Gag via an IRES or splicing donor/acceptor mechanism.

The recombinant virus may further comprise a polynucleotide encoding a fusion protein of HIV protease PI and HIV reverse transcriptase RT, PI-RT. PI may be expressed as a fusion protein with Gag, or separately from a different promoter or from the same promoter for Gag via an IRES or splicing donor/acceptor mechanism.

The recombinant virus may further comprise a polynucleotide which is an HIV Pol gene and encodes the HIV enzyme proteins: HIV protease PI, reverse transcriptase RT, and integrase IN. Pol may be expressed as a fusion protein with Gag, or separately from a different promoter or from the same promoter for Gag via an IRES or splicing donor/acceptor mechanism.

Optionally, the recombinant virus may further comprise an immuno-stimulator sequence heterologous to the recombinant virus that encodes an immuno-stimulator whose expression in the host enhances the immunogenicity of the viral antigen.

The present invention also provides viral vaccines that present multiple antigens to the host to further mimic natural infection of a native pathogenic virus and induce strong and long-lasting immune response to various strains or types of the pathogenic virus in the host.

In one embodiment, a recombinant virus is provided as a viral vaccine for eliciting an immune response in a host infected by the virus. The recombinant virus comprises: a plurality of antigen sequences heterologous to the recombinant virus, each encoding a viral antigen from a same pathogenic virus, different strains of a pathogenic virus, or different kinds of pathogenic viruses, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy in the host naturally associated with pathogenic virus.

According to the embodiment, the recombinant virus may be any virus, preferably replication-incompetent adenovirus, adeno-associated virus, SV40 virus, retrovirus, herpes simplex virus or vaccinia virus. The benign virus may also preferably have the pathologic regions of the native progenitor of the benign virus deleted but retain its infectivity.

Also according to the embodiment, the plurality of the antigen sequences may be multiple copies of the same antigen sequence or multiple antigen sequences that differ from each another.

In a variation of the embodiment, at least two of the plurality of the antigen sequences are expressed from a promoter bicistronically via an internal ribosomal entry site or via a splicing donor-acceptor mechanism.

Optionally, at least two of the plurality of the antigen sequences are expressed from a promoter to produce a fusion protein.

Also according to the embodiment, the viral genome further comprises at least one promoter heterologous to the native progenitor of the recombinant virus that controls the expression of at least two of the plurality of the antigen sequences. Examples of the promoter heterologous to the native progenitor of the recombinant virus include, but are not limited to, insulin promoter, CMV promoter and its early promoter, SV40 promoter, retrovirus LTR promoter/enhancer, the chicken cytoplasmic β-actin promoter, and inducible promoters such as tetracycline-inducible promoter.

Also according to the embodiment, the plurality of antigen sequences may be a combination of antigens from at least two strains of the pathogenic virus.

Optionally, the plurality of antigen sequences may be a combination of antigens from at least two different pathogenic viruses. For example, the plurality of antigen sequences may be a combination of antigens from HIV-1, HIV-2, herpes simplex virus type 1, herpes simplex virus type 2, Ebola virus, Marburg virus, Arbovirus (a group of viruses carried by mosquitoes that cause encephalitis, yellow fever, and dengue), and hepatitis A, B, C, D, and E viruses.

In a variation of the embodiment, the recombinant virus may further comprise one or more immuno-stimulator sequences that are heterologous to the benign virus and encodes an immuno-stimulator whose expression in the host enhances the immunogenicity of the viral antigen. For example, the immuno-stimulator may be a cytokine. Examples of the cytokine include, but are not limited to, interleukin-2, interleukin-4, interleukin-12, β-interferon, α-interferon, γ-interferon, G-CSF, and GM-CSF.

According to the variation, the one or more immuno-stimulator sequences may be multiple copies of the same immuno-stimulator sequence or multiple immuno-stimulator sequences that differ from each other.

Optionally, at least two of the immuno-stimulator sequences may be expressed from a promoter multicistronically via an internal ribosomal entry site or via a splicing donor-acceptor mechanism. Alternatively, at least two of the immuno-stimulator sequences may be expressed from a promoter to form a fusion protein.

The present invention also provides genetic vaccines that elicit strong and long-lasting immune response to pathogenic bacteria. In one embodiment, a recombinant virus is provided as a genetic bacteria vaccine for eliciting an immune response in a host infected by the recombinant virus. The recombinant virus comprises: a plurality of antigen sequences heterologous to the recombinant virus, each encoding a bacterial antigen from a pathogenic bacteria, expression of the plurality of the bacterial antigen sequences eliciting an immune response directed against the bacterial antigen and cells expressing the bacterial antigen in the host upon infection of the host by the recombinant virus. The recombinant virus may preferably be replication-incompetent and not cause malignancy naturally associated with the pathogenic bacteria in the host.

The pathogenic bacteria may be any pathogenic bacteria that causes pathogenic effects or diseases in a host, such as *bacillus tuberculoses, bacillus anthracis* (causing vegetative anthrax), and spirochete *Borrelia burgdorferi* that causes the Lyme disease in animals. The plurality of antigen sequences may encode lethal factors, protective antigen, edema factors of the pathogenic bacteria, or combinations thereof.

The present invention also provides vaccines against parasites that elicit strong and long-lasting immune response to pathogenic parasites. In one embodiment, a recombinant virus is provided as a parasite vaccine for eliciting an immune response in a host infected by the recombinant virus. The recombinant virus comprises: a plurality of antigen sequences heterologous to the benign virus, each encoding a parasitic antigen from a pathogenic parasite, expression of the plurality of the parasitic antigen sequences eliciting an immune response directed against the parasitic antigen and cells expressing the parasitic antigen in the host upon infection of the host by the recombinant virus. The recombinant virus may preferably be replication-incompetent and not cause a malignancy naturally associated with the pathogenic parasite in the host.

The pathogenic parasite may be any pathogenic parasites that cause pathogenic effects or diseases in a host, such as malaria and protozoa such as Cryptosporidium, Eimeria, Histomonas, Leucocytozoon, Plasmodium, Toxoplasma, Trichomonas, Leishmania, Trypanosoma, Giardia, Babesia, and Theileria. The plurality of antigen sequences may encode coat proteins, attachment proteins of the pathogenic parasites, or combinations thereof.

The present invention also provides pharmaceutical compositions that include the viral vaccines of the present invention. The pharmaceutical composition may include any of the recombinant viruses described above and a pharmaceutically acceptable carrier or diluent.

The pharmaceutical composition may also include an adjuvant for augmenting the immune response to the viral antigen expressed from the recombinant virus. Examples of the adjuvant include, but are not limited to, bacillus Calmette-Guerin, endotoxin lipopolysaccharide, keyhole limpet hemocyanin, interleukin-2, GM-CSF, and cytoxan.

The present invention also relates to kits. These kits may include any one or more vaccines according to the present invention in combination with a composition for delivering the vaccine to a host and/or a device, such as a syringe, for delivering the vaccine to a host.

The present invention also provides methods for enhancing the immunity of a host with the recombinant viruses described above.

In one embodiment, the method comprises: administering to the host a recombinant virus in an amount effective to induce an immune response. The in the recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the benign virus that encodes an immunostimulator whose expression in the host enhances the immunogenicity of the viral antigen. The recombinant virus may preferably be replication-incompetent and not cause malignancy naturally associated with the pathogenic virus in the host.

The recombinant virus may be administered to the host via any pharmaceutically acceptable route of administration. The recombinant virus may be administered to the host via a route of intramuscular, intratracheal, subcutaneous, intranasal, intradermal, intramucosally, rectal, oral and parental administration.

In another embodiment, a method is provided for enhancing the immunity of a host to a pathogenic virus with multiple antigens. The method comprises: administering to the host a recombinant virus in an amount effective to induce an immune response. The recombinant virus comprises: a plurality of antigen sequences heterologous to the benign virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy naturally associated with the pathogenic virus in the host.

Optionally, the recombinant virus may further comprise one or more immuno-stimulator sequences heterologous to the recombinant virus that encodes an immuno-stimulator whose expression in the host enhances the immunogenicity of the viral antigen.

In yet another embodiment, a method is provided for enhancing the immunity of a host to a pathogenic virus by using multiple recombinant viral vaccines (or viruses). Multiple recombinant viruses may carry different antigens in each recombinant virus. The multiple recombinant viruses may be administered simultaneously or step-wise to the host.

The method comprises: administering to a host a first and second recombinant viruses in an amount effective to induce an immune response. The first recombinant virus comprises: an antigen sequence heterologous to the first recombinant virus that encodes a viral antigen from a pathogenic virus, expression of the viral antigen eliciting an immune response directed against the viral antigen and cells expressing the viral antigen in the host upon infection of the host by the recombinant virus. The second recombinant virus comprises: an immuno-stimulator sequence heterologous to the recombinant virus that encodes an immuno-stimulator whose expression in the host enhances the immunogenicity of the viral antigen. The first and second recombinant viruses may preferably be replication-incompetent and not cause a malignancy naturally associated with the pathogenic virus in the host.

According to the embodiment, the first and second recombinant virus may be any benign virus, such as replication-incompetent adenovirus, adeno-associated virus (AAV), SV40 virus, retrovirus, herpes simplex virus, Alpha virus, Venezuelan Equine Encephalitis (VEE) virus and vaccinia virus.

Optionally, both the first and second recombinant viruses may be replication-incompetent adenovirus. Also optionally, one of the first and second recombinant viruses may be recombinant adenovirus and the other may be recombinant AAV, SV40 virus, retrovirus, herpes simplex virus, Alpha virus, Venezuelan Equine Encephalitis (VEE) virus or vaccinia virus.

In yet another embodiment, a method is provided for enhancing the immunity of a host to a pathogen. The method comprises: administering to the host a recombinant virus and one or more immuno-stimulators. The recombinant virus may be any of the recombinant viruses described above. In particular, the recombinant virus comprises one or more antigen sequences heterologous to the recombinant virus that encode one or more antigens from the pathogen. Expression of the antigen elicits an immune response directed against the antigen and cells expressing the antigen in the host upon infection of the host by the recombinant virus. The recombinant virus is preferably replication-incompetent and does not cause a malignancy naturally associated with the pathogen in the host. The pathogen may be a pathogenic virus such as HIV, hepatitis virus and Ebola virus, a pathogenic bacteria or parasite.

According to this embodiment, the immuno-stimulator may be any molecule that enhances the immunogenicity of the antigen expressed by the cell infected by the recombinant virus. Preferably, the immuno-stimulator is a cytokine, including, but not limited to interleukin-2, interleukin-8, interleukin-12, β-interferon, λ-interferon, γ-interferon, granulocyte colony stimulating factor, granulocyte-macrophage colony stimulating factor, and combinations thereof. The cytokine may be administered into the host in a form of purified protein alone or formulated with one or more pharmaceutically acceptable excipients. Alternatively, the cytokine may be administered in a form of expression vector that expresses the coding sequence of the cytokine upon transfecting or transducing the cells of the host.

According to any of the above embodiments of the methods, the method may further comprise: administering to the host the recombinant virus again to boost the immune response. Such a booster inoculation with the recombinant virus is preferably conducted several weeks to several months after the primary inoculation. To insure sustained high levels of protection against infection or an efficacious treatment of the disease(s) caused by infection of the pathogen, it may be helpful to re-administer the booster immunization to the host at regular intervals, for example, once every several years. The recombinant virus administered in the booster immunization may be the same as or different from the recombinant virus administered in the primary immunization.

Also according to any of the above embodiments of the methods, the method may further comprise: administering to the host a plasmid vector that encodes the same or different antigen(s) as that (or those) encoded by the recombinant virus. The plasmid vector is preferably a eukaryotic plasmid expression vector that expresses the antigen(s) upon transfection of the cells in the host.

Also according to any of the above embodiments of the methods, the method may further comprise: administering to the host a second recombinant virus to boost the immune response and/or to minimize neutralizing effects of the host's immune system on the recombinant viruses.

Optionally, the second recombinant virus comprises a second antigen sequence from a second pathgen that is different from the first antigen sequence comprised in the first recombinant virus administered in the primary immunization. Preferably, the second antigen sequence encodes the same type of antigen as that encoded by the first antigen sequence but from a different strain, serotype, or subtype/clade of the same pathogen. Alternatively, the second antigen may be a different type of antigen compared to the first antigen, for example, the first antigen being a surface protein and second antigen being a core protein of the same or different pathogen.

Also according to any of the above embodiments of the methods, the method may further comprise: administering to the host a viral vector prior to, concurrently, or post the administration of any of the above embodiment of the recombinant virus to minimize neutralizing effects of the host's immune system on the recombinant virus. Preferably, the viral vector is administered post the administration of the recombinant virus.

The viral vector may be the native progeny of the recombinant virus. For example, the viral vector may be the wildtype adenovirus type 5 (Ad5) whereas the recombinant virus is a genetically modified Ad5.

Optionally, the viral vector may be the wildtype of or a genetically modified virus that is a different serotype of the recombinant virus. For example, the recombinant virus may be a genetically modified Ad5 whereas the viral vector is the wildtype of or a genetically modified adenoviral vector serotype other than Ad5, for example, serotype 1-4 or 6-51. It is noted that other serotypes discovered and/or classified later also fall within the scope of the invention.

Also optionally, the viral vector may be a different virus from the recombinant virus. For example, the recombinant virus may be a genetically modified Ad5 whereas the viral vector is a genetically modified AAV, SV40 virus, retrovirus, herpes simplex virus, Alpha virus, Venezuelan Equine Encephalitis (VEE) virus or vaccinia virus. The viral vector may or may not comprise a heterologou antigen sequence. Preferably, the viral vector may comprise another antigen sequence which is the same or different from the antigen sequence carried by the recombinant virus.

Also optionally, the viral vector may be a chimeric vector modified based on the native progenitor of the recombinant virus. For example, if the native progenitor of the recombinant virus is adenovirus type 5, the viral vector may be a chimeric adenovirus type 5 with certain regions of the backbone changed from type 5 to the corresponding regions from other adenovirus serotypes. For example, the fiber knob, shaft, and/or penton base in the backbone of adenovirus type 5 can be replaced by the corresponding region(s) of the backbone from adenovirus serotype 1-4, and 6-51.

Also optionally, the viral vector also comprises one or more heterologous antigen sequence and/or immuno-stimulator sequence which are the same or different from those in the recombinant virus.

The methods described above may be used for prevention or treatment of diseases. In the method of treatment, the administration of the recombinant viruses of the present invention may be for either "prophylactic" or "therapeutic" purpose. When provided prophylactically, the recombinant virus is provided in advance of any symptom. The prophylactic administration of the recombinant virus serves to prevent or ameliorate any subsequent infection or disease. When provided therapeutically, the recombinant virus is provided at (or after) the onset of a symptom of infection or disease. Thus, the present invention may be provided either prior to the anticipated exposure to a disease-causing agent or after the initiation and/or progression of the infection or disease.

It is noted that the innovative approaches of the present invention may also be employed in construction of cancer vaccines. For example, sequences encoding tumor-specific antigens may substitute the antigen sequence encoding viral antigen in any of the above embodiments of the recombinant virus and methods of using the same. Expression of tumor-specific antigens in the host should elicit specific immune response for prevention in patients with an increased risk of cancer development (i.e., preventive immunization) or to enhance the treatment of cancer with other therapeutics, prevention of disease recurrence after primary surgery (anti-metastatic vaccination), or as a tool to expand the number of CTL in vivo, thus improving their effectiveness in eradication of diffuse tumors (treatment of established disease). In addition, the methods of the present invention may elicit an immune response in a patient that is enhanced ex vivo prior to being transferred back to the tumor bearer (i.e., the adoptive immunotherapy).

Also according to any of the above embodiments of the methods, the method may further comprise: harvesting serum from the host after the administration of the recombinant virus. The harvested serum should contain antibodies against the antigen(s) encoded by the recombinant virus. Optionally, the method may further comprise: isolating antibody or antibodies against the pathogen from the host after the administration of the recombinant virus. The harvested serum or isolated antibody can be stored for certain periods of time for further uses. For example, a healthy human volunteer can serve as the host and the serum or antibody collected from him/her may be administered back to him/herself or a different person later to in anticipation or in the event of infection of the pathogen as prophylactic or therapeutic agent by eliciting passive immunity against the pathogen. Optionally, the host may be a non-human animal and the serum harvested or antibody isolated from the animal immunized by the recombinant virus may be used as a prophylactic or therapeutic agent to treat a human or non-human animal in anticipation or in the event of infection of the pathogen such as in the outbreak of biological warfare.

It should be noted that modifications and changes can be made in the DNA sequence of any of the above-described antigens and immuno-stimulators included in the recombinant virus and still maintain functional equivalence of the mutant. For example, wildtype codons for the above-described antigens can be replaced with codons that are preferred by the host to be immunized, e.g., a human. The resulting mutants fall within the scope of the present invention.

BRIEF DESCRIPTION OF THE FIGURES

FIG. 1A illustrates an example of a shuttle vector pLAd.Antigen carrying multiple antigen genes such as Antigen 1 and Antigen 2 which can be expressed from a $CMV_{ie}$ promoter bicistronically via a splicing donor-acceptor mechanism at the SD and SA sites.

FIG. 1B illustrates an example of a shuttle vector pRAd.Cytokines carrying multiple cytokine genes such as IL-2, INF, and IL-8 genes which can be expressed from a $CMV_{ie}$ promoter bicistronically via an internal ribosomal entry site IRES and a splicing donor-acceptor mechanism at the SD and SA sites.

FIG. 1C illustrates an example of constructing a genetic vaccine by ligating with an adenoviral backbon with a fragment that is derived from the shuttle vector pLAd.Antigen and contains multiple antigen genes and a fragment that is derived from the shuttle vector pRAd.Cytokines and contains multiple cytokine genes.

FIG. 2 also depicts the modifications made to the RNA to prevent the synthesis of sGP. The RNA editing site is modified from UUU UUU U (SEQ ID NO. 2) to UUC UUC UU (SEQ ID NO. 3). This modification removes the editing signal and results in the mRNA coding only for the GP.

FIG. 3 illustrates the modification of the immunosuppressive peptide (IS) located in GP2.

FIG. 4A illustrates a shuttle vector pLAd/EBO-GP carrying the GP gene of Ebola virus an antigen, and a shuttle vector pRAdIL2,4 carrying the IL-2 and IL-4 gene.

FIG. 4B illustrates the construction of a recombinant adenoviral vector by ligating an adenoviral backbone with a fragment that is derived from the shuttle vector pLAd/EBO-GP and contains the GP gene and a fragment that is derived from the shuttle vector pRAdIL2,4 and contains IL-2 and IL-4 genes.

FIG. 12A shows relative titers of antibody against HIV Gag in mice in week 10 post-immunization with Ad-3C/$E'''$Δ-CΔ$T^{300}$-G.

FIG. 12B shows relative titers of antibody against HIV Gag in mice in week 14 post-immunization/week 3 post-boost with Ad-3C/$E'''$ΔCΔ$T^{300}$-G.

FIG. 14A shows results of the granzyme A assays for serie 1 mice at week 4, 6, 8 post-immunization and week 12/1, 13/2,14/3 (prime/boost) post-secondary inoculation with Ad.3C.env.gag.

FIG. 14B shows the results of the granzyme A assays for serie 2 mice at week 2, 4, 6, 8 post-immunization with Ad.3C.env.gag.

FIG. 15A shows the ELISPOT results for the four mice in serie 1 at week 13/2 post-prime/boost with Ad.3C.env.gag.

FIG. 15B shows the ELISPOT results for the four mice in serie 1 at week 13/2 post-prime/boost with Ad.3C.env.rev.gag.

FIG. 24 illustrates a process for constructing a multi-clade insert by PCR.

FIG. 38 shows DNA sequence encoding Env/Tat/Rev from HIV-1 strain BH10.

FIG. 39 shows DNA sequence encoding a mutated IL-2 (IL-2ΔX).

FIG. 40 shows DNA sequence encoding a modified Env ($E'''\Delta C\Delta T$ (BH10).

FIG. 41A shows DNA sequence encoding the full length HIV Gag.

FIG. 41B shows amino acid sequence of the full length HIV Gag.

FIG. 42 shows DNA sequence encoding Env, and full length Tat and Rev.

FIG. 43 shows DNA sequence encoding $E'''\Delta V_{1,2}\Delta C\Delta T$.T.R.

FIG. 44 shows DNA sequence encoding $E'''\Delta C$.T.R.N.

FIG. 45 shows DNA sequence encoding $E'''\Delta C$.N.

FIG. 46 shows DNA sequence encoding $E'''\Delta C\Delta T^{300}$.T.

FIG. 47 shows DNA sequence encoding $E'''/E'''$.

FIG. 48 shows DNA sequences of V3 loops of clade B, A, C, D, E, F, and G.

FIG. 49A shows DNA sequence encoding a modified Env including multi-clade V3 loops.

FIG. 49B shows amino acid sequence encoding a modified Env including multi-clade V3 loops.

FIG. 50A shows DNA sequence encoding p17/p24 in natural form, secreted form, and membrane bound form, respectively.

FIG. 50B shows amino acid sequence of p17/p24 in natural form, secreted form, and membrane bound form, respectively.

FIG. 51A shows DNA sequence encoding p17 in natural form, secreted form, and membrane bound form, respectively.

FIG. 51B shows amino acid sequence of p17 in natural form, secreted form, and membrane bound form, respectively.

FIG. 52A shows DNA sequence encoding p24 in natural form, secreted form, and membrane bound form, respectively.

FIG. 52B shows amino acid sequence of p24 in natural form, secreted form, and membrane bound form, respectively.

FIG. 53A shows DNA sequence encoding a modified Env including multi-clade V3 loops, and Tat.

FIG. 53B shows amino acid sequence of a modified Env including multi-clade V3 loops, and Tat.

FIG. 54A shows DNA sequence encoding a modified Env including multi-clade V3 loops, Tat, and Rev.

FIG. 54B shows amino acid sequence of a modified Env including multi-clade V3 loops, Tat, and Rev.

FIG. 55A shows DNA sequence encoding an HIV protease PI.

FIG. 55B shows amino acid sequence of an HIV protease PI.

FIG. 56A shows DNA sequence encoding HIV Gag-PI.

FIG. 56B shows amino acid sequence of HIV Gag-PI.

FIG. 57 shows PCR primers for cloning V3 loops from multiple HIV clades.

DETAILED DESCRIPTION OF THE INVENTION

Figure 1A:
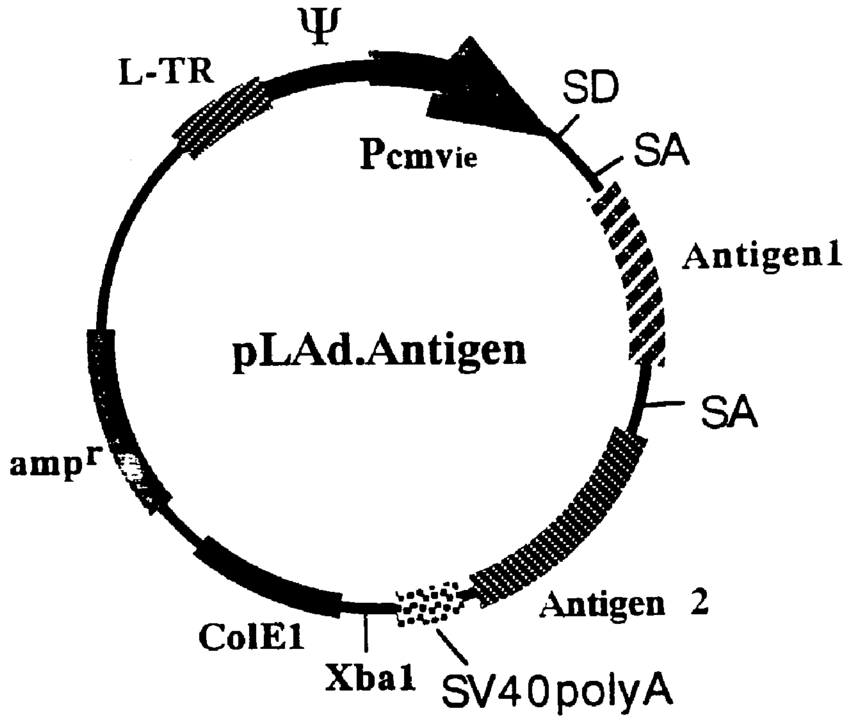
FIGS. 1A-1C illustrate an example of how to construct a genetic vaccine of the present invention.

The present invention provides genetic vaccines, pharmaceutical compositions including the vaccines and methods of immunizing a host against infection of a wide range of pathogenic viruses, bacteria and parasites. The genetic vaccines are recombinant benign viruses that are replication deficient and do not cause malignancy in the host to be immunized. Vaccination using the genetic vaccines of the present invention mimics natural viral infection in that the antigen(s) expressed by the cell infected by the genetic vaccine is presented to the host immune system in its natural conformation and by a "inside-out" mechanism, as compared with the conventional "outside-in" approach of vaccination using denatured protein or virus as a vaccine. The recombinant virus is capable of expressing multiple pathogenic antigens, mimicking natural pathogen infection. In particular, multiple pathogenic antigens such as a combination of an HIV envelop protein Env and structural protein Gag, either wildtype or mutant, can be expressed by the recombinant virus to elicit not only humoral immune response (i.e., production of antibody from B cells, helper T cells, and suppressor T cells), but also cellular response by producing cytotoxic T lymphocytes (CTL) directed specifically to these antigens. Further, the pathogenic antigen that is naturally expressed as an intracellular protein can be modified to be secretable and rendered bound to the cell surface, thus better presenting the antigen to the body's immune system. In addition, the cell infected by the genetic vaccine may also release high levels of cytokine, thereby further mimicking the natural response of the cell under stress induced by viral infection and yet not causing pathogenic effects on the cells. Mistaken by such a "signal of pathogenic viral infection", the host immune system mounts a strong immune defense against the antigen presented by the infected cell. Therefore, in a sense, the genetic vaccine of the present invention behaves like a "sheep in wolf's clothing", presenting the viral antigen to induce a strong immune response and yet not causing the detrimental effects that the pathogens would cause on the host. The recombinant viruses of the present invention can not only be used as a vaccine to prevent infection of the pathogen but also as a therapeutic agent to treat diseases associated with the infection of the pathogen.

In one embodiment, a recombinant virus is provided for eliciting an immune response in a host infected by the virus. The recombinant virus comprises: an antigen sequence heterologous to the recombinant virus and encoding a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the recombinant virus and encoding an immuno-stimulator whose expression in the host enhances the immunogenicity of the viral antigen. The recombinant virus is replication-incompetent and does not cause the malignancy naturally associated with the pathogenic virus in the host.

In another embodiment, a recombinant virus is provided as a viral vaccine for eliciting an immune response against multiple antigens in a host infected by the virus. The recombinant virus comprises: a plurality of antigen sequences heterologous to the benign virus, each encoding a different viral antigen from one or more pathogenic viruses, expression of the plurality of the antigen sequences eliciting an immune response directed against the viral antigens and cells expressing the viral antigen in the host upon infection of the host by the recombinant virus. The recombinant virus may preferably be replication-incompetent and not cause the malignancy that is naturally associated with the pathogenic virus(es) in the host.

The vaccines of the present invention can be used to immunize the host against a wide variety and different strains of pathogenic viruses such as HIV-1, HIV-2, herpes simplex virus type 1, herpes simplex virus type 2, Ebola virus, Ebola virus, and hepatitis A, B, C, D, and E viruses, or pathogenic bacteria such as *bacillus tumerculoses* and *bacillus anthracis*.

The recombinant vaccine of the present invention is a recombinant virus that contains nucleic acid sequences encoding one or more viral antigens in the viral genome. When a host is immunized by the recombinant vaccine, i.e., infected by the recombinant virus, the infection of the virus in a host cell results in expression of the viral antigen which is present on the surface of the infected cell. Since expression of the viral antigen is driven by a strong promoter, expession can be maintained at a high level. Upon recognizing the large amount viral antigen on the cell surface, the host immune system mounts a strong defense against the viral antigen, thereby achieving long-lasting immunity against the pathogenic virus from which the viral antigen is derived.

Compared with immunization with vaccines that are isolated proteins expressed by bacteria, yeast or insect cells, the viral antigen expressed from the recombinant virus of the present invention better mimics the natural viral antigen in its structure and function. Isolated protein vaccine may not adopt the native conformation of the natural viral antigen and may not be properly glycosylated in the bacteria, yeast or insect cells. When such an isolated protein vaccine is injected into the host, this antigen is presented from the outside of the host cell. This conventional "outside-in" approach often does not generate strong, long-lasting immune response, presumably due to the altered antigenicity of the vaccine and quick clearance of the protein vaccine by the immune scavenging cells.

In contrast, the genetic vaccine of the present invention, i.e., the recombinant virus, presents the viral antigen by an "inside-out" mechanism. The viral antigen is expressed after infection of the recombinant virus in the host cells. This better mimics the natural production and presentation of the viral antigen by the pathogenic virus.

By using a replication incompetent virus that is incapable of spreading beyond initially infected cells, the present invention dramatically reduces the risk of side effects that may potentially be generated by using replication-competent, live virus. For example, vaccines based on live vaccinia virus can replicate in the host cells, which can impose a high level of stress on the host cell and eventually lead to cell death.

Moreover, compared to the approach of using attenuated or inactive virus as a vaccine, the process of making the genetic vaccine of the present invention is much safer. Vaccination of a large population of people or animals demand large amounts of vaccines. For virulent viruses such as Ebola virus and HIV, large-scale production of attenuated or inactive virus from the live virus can pose a great danger to the environment and people who handle the live virus.

The recombinant virus of the present invention can be used to express multiple antigen sequences simultaneously from the same viral vector. Thus, the recombinant virus may encode multiple antigens from the same strain of pathogenic virus, from different strains of the same pathogenic viruses, or from different antigens from different kind of viruses, bacteria or parasites. This enables the vaccines of the present invention to be utilized to immunize against a broad-spectrum of viruses and other infectious agents. Since these multiple antigen sequences are rearranged in the recombinant viral genome, the risk of potential recombination of these viral sequences to generate a pathogenic virus is virtually eliminated.

The genetic vaccine of the present invention also preferably express large amount of immunuo-stimulator, such as cytokine. In a natural process of viral infection, virus-infected cells display viral antigens on their surface in the context of the MHC-I receptor, while viral particles are digested by the professional antigen-presenting cells which display antigens in association with MHC-II receptors. In response to viral infection, a full range of cytokines and interferons are produced, resulting in a strong humoral and cellular response to the viral antigens. At the same, large numbers of memory cells remain to defeat any new infection. In vaccinations using isolated protein vaccines, the protein is quickly cleared by the immune scavenging cells. During this process, only MHC-II antigen presentation occurs and the cytokine-releasing response is absent or greatly diminished. As a result, little cellular response is generated and few "memory" cells are produced.

In comparison, co-expression of viral antigen and cytokine from the recombinant virus of the present invention effectively mimics the natural response of the host cell to viral infection by presenting the antigen on the surface of the infected and producing large amount of immuno-modulating cytokines. With the high levels of cytokine expressed from the host cells infected by the genetic vaccine, the host immune system would be "tricked" to mount a strong response to vaccine, thereby resulting in a longer-lasting immunity.

Additionally, although vaccination with the genetic vaccine mimics the natural viral infection of a pathogenic virus, the vaccine itself is a benign virus that does not have the detrimental effects of the pathogenic virus. For example, infection of a pathogenic virus such as HIV, influenza virus and Ebola virus has profound immuno-suppressing effects on the host, presumably due to the immuno-suppressing functions of the glycoproteins of the virus. According to the present invention, the viral antigen sequence carried by the genetic vaccine is preferred to have its pathogenic or immuno-suppressing regions deleted. In a sense, the genetic vaccine of the present invention behaves like a "sheep in wolf's clothing", presenting the viral antigen to induce strong immune response and yet not causing detrimental effects on the host.

1. The Genetic Vaccines of the Present Invention

The present invention is directed to vaccines that mimic the features of a native pathogenic virus, but without eliciting immuno-suppression and pathogenicity, thus causing the host to mount an effective defense, while not being in any actual danger of infection. The genetic vaccines are replication incompetent or defective viruses into which one or more DNA sequences encoding one or more viral antigens are inserted into the regions of the viral genome non-essential to its infectivity. The recombinant virus expresses the viral antigens and elicits a cell-mediated immune response in vivo directed against the antigens and cells expressing the antigens.

In one embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viralantigen in the host upon infection of the host by the recombinant virus; and an immuno-stimulator sequence heterologous to the recombinant virus that encodes an immuno-stimulator whose expression in the host enhances the immunogenicity of the viral antigen. The recombinant virus is replication-incompetent and does not cause a malignancy naturally associated with the pathogenic virus in the host.

The recombinant virus may be constructed from any virus as long as the native progenitor is rendered replication incompetent. For example, replication-incompetent adenovirus, adeno-associated virus, SV40 virus, retrovirus, herpes simplex virus or vaccinia virus may be used to generate the recombinant virus by inserting the viral antigen into the region non-essential to the infectivity of the recombinant virus. Therefore, it is preferred that the recombinant virus does not have the pathologic regions of the native progenitor of the benign virus but retains its infectivity to the host.

In a preferred embodiment, the recombinant virus is a replication-incompetent adenovirus.

The recombinant adenovirus of the present invention can direct high levels of antigen expression that provide strong stimulation of the immune system. The antigen expressed by cells infected by adenovirus is processed and displayed in the infected cells in a way that mimics pathogen-infected cells. This phase is believed to be very important in inducing cellular immunity against infected cells, and is completely lacking when conventional vaccination approaches are used. Further, the recombinant adenovirus may infect dendritic cells which are very potent antigen-presenting cells. Further, the recombinant adenovirus may also carry genes encoding immuno-enhancing cytokines to further boost immunity. Moreover, the recombinant adenovirus may naturally infect airway and gut epithelial cells in humans, and therefore the vaccine may be delivered through nasal spray or oral ingestion. In addition, the recombinant adenovirus of the present invention should be safe because it is replication-incompetent.

The heterologous antigen sequence may be positioned in the E1, E3 or E4 region of the adenovirus. The immuno-stimulator sequence may be positioned in the E1, E3 or E4 region of the adenovirus.

In a variation of the preferred embodiment, the heterologous antigen sequence and the immuno-stimulator sequence are positioned in the E1, E3 or E4 region of the adenovirus, where the heterologous antigen sequence and the immuno-stimulator sequence are expressed from a promoter bicistronically via an internal ribosomal entry site or via a splicing donor-acceptor mechanism.

The expression of the viral antigen or the immuno-stimulator may be controlled by a promoter homologous to the native progenitor of the recombinant virus. Alternatively, the expression of the viral antigen may be controlled by a promoter heterologous to the native progenitor of the recombinant virus. For example, the promoter heterologous to the native progenitor of the recombinant virus may be a eukaryotic promoter such as insulin promoter, human cytomegalovirus (CMV) promoter and its early promoter, simian virus SV40 promoter, Rous sarcoma virus LTR promoter/enhancer, the chicken cytoplasmic β-actin promoter, and inducible promoters such as the tetracycline-inducible promoter.

The pathogenic virus may be any pathogenic virus that causes pathogenic effects or disease in a host such as human, domestic animals or other mammals. Thus, the recombinant virus can be used as a vaccine for protecting the host from infection of the pathogenic virus.

In a variation, the pathogenic virus may be various strains of human immunodeficiency virus (HIV), such as HIV-1 and HIV-2. The viral antigen may be a HIV glycoprotein (or surface antigen) such as HIV GP120 and GP41, a capsid protein (or structural protein) such as HIV P24 protein, or other HIV regulatory proteins such as Tat, Vif and Rev proteins.

In another variation, the pathogenic virus may be influenza virus. The viral antigen may be an influenza glycoprotein such as influenza HA1, HA2 and NA.

In another variation, the pathogenic virus may be Ebola virus. The viral antigen may be an Ebola glycoprotein or surface antigen such as Ebola GP1 and GP2 protein.

In yet another variation, the pathogenic virus may be hepatitis virus such as hepatitis A, B, C, D or E virus. The viral antigen may be a surface antigen or core protein of hepatitis A, B, C, D or E virus. For example, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may also be a surface antigen or core protein of hepatitis C virus such as NS3, NS4 and NS5 antigens.

In yet another variation, the pathogenic virus may be a respiratory syncytial virus (RSV). For example, the RSV viral antigen may be the glycoprotein (G-protein) or the fusion protein (F-protein) of RSV, for which the sequences are available from GenBank.

In yet another variation, the pathogenic virus may be a herpes simplex virus (HSV) such as HSV-1 and HSV-2. For example, the HSV viral antigen may be the glycoprotein D from HSV-2.

In yet another variation, the viral antigen may be a tumor antigen or viral oncogene such as E6 and E7 of human papilloma virus, or cellular oncogenes such as mutated ras or p53.

It is noted that, other virus-associated proteins or antigens are readily available to those of skill in the art. Selection of the pathogenic virus and the viral antigen is not a limiting factor in this invention.

The viral antigen may be a full-length antigenic viral protein or a portion of the antigenic viral protein that contains the predominant antigen, neutralizing antigen, or epitope of the pathogenic virus. Alternatively, the viral antigen contains the conserved region of glycoproteins between at least two strains of the same pathogenic virus.

In a variation, the viral antigen may be a modified antigen that is mutated from a glycoprotein of the pathogenic virus such that the viral antigen is rendered non-functional as a viral component but retains its antigenicity. Such modification of the viral antigen includes deletions in the proteolytic cleavage site of the glycoprotein, and duplications and rearrangement of immunosuppressive peptide regions of the glycoprotein.

The recombinant virus also expresses an immuno-stimulator to mimic cytokine-releasing response of a host cell upon viral infection and further augments immune response to the viral antigen co-expressed from the recombinant virus. The immuno-stimulator may preferably be a cytokine. Examples of cytokine include, but are not limited to, interleukin-2, interleukin-4, interleukin-12, β-interferon, λ-interferon, =γ-interferon, granulocyte colony stimulating factor (G-CSF), and granulocyte-macrophage colony stimulating factor (GM-CSF).

In another embodiment, a recombinant virus is provided for eliciting an immune response in a host infected by the virus. The recombinant virus comprises: an antigen sequence heterologous to the recombinant virus that encodes a viral antigen from a pathogenic virus, expression of the viral antigen eliciting an immune response directed against the viral antigen and cells expressing the viral antigen in the host upon infection of the host by the recombinant virus.

According to this embodiment, the recombinant virus is preferably be replication-incompetent adeno-associated virus, SV40 virus, retrovirus, herpes simplex virus or vaccinia virus. The benign virus may preferably have the pathologic regions of the native progenitor of the benign virus deleted but retains its infectivity to the host.

Optionally, the recombinant virus includes an immuno-stimulator sequence heterologous to the recombinant virus that encodes an immuno-stimulator whose expression in the host enhances the immunogenicity of the viral antigen.

The present invention also provides genetic vaccines that elicit strong and long-lasting immune response to pathogenic bacteria. In one embodiment, a recombinant virus is provided as a genetic bacteria vaccine for eliciting an immune response in a host infected by the recombinant virus. The viral genome of the recombinant virus comprises: a plurality of antigen sequences heterologous to the recombinant virus, each encoding a bacterial antigen from a pathogenic bacteria, expression of the plurality of the bacterial antigen sequences eliciting an immune response directed against the bacterial antigen and cells expressing the bacterial antigen in the host upon infection of the host by the recombinant virus. The recombinant virus may preferably be replication-incompetent and not cause a malignancy naturally associated with the pathogenic bacteria in the host.

The pathogenic bacteria may be any pathogenic bacteria that causes pathogenic effects or diseases in a host, such as *bacillus tuberculoses, bacillus anthracis*, and spirochete *Borrelia burgdorferi* that causes the Lyme disease in animals. The plurality of antigen sequences may encode lethal factors, protective antigen, edema factors of the pathogenic bacteria, or combination thereof.

The present invention also provides parasites vaccines that elicit strong and long-lasting immune response to pathogenic parasites. In one embodiment, a recombinant virus is provided as a parasite vaccine for eliciting an immune response in a host infected by the benign virus. The recombinant virus comprises: a plurality of antigen sequences heterologous to the recombinant virus, each encoding a parasitic antigen from a pathogenic parasite, expression of the plurality of the parasitic antigen sequences eliciting an immune response directed against the parasitic antigen and cells expressing the parasitic antigen in the host upon infection of the host by the recombinant virus. The recombinant virus may preferably be replication-incompetent and not a cause malignancy naturally associated with the pathogenic parasite in the host.

The pathogenic parasite may be any pathogenic parasite that causes pathogenic effects or diseases in a host, such as malaria and protozoa such as Cryptosporidium, Eimeria, Histomonas, Leucocytozoon, Plasmodium, Toxoplasma, Trichomonas, Leishmania, Trypanosoma, Giardia, Babesia, and Theileria. The plurality of antigen sequences may encode coat proteins, attachment proteins of the pathogenic parasites, or combinations thereof.

The present invention also provides viral vaccines that present multiple antigens to the host to further mimic natural infection of a native pathogenic virus and induce strong and long-lasting immune response to various strains or types of the pathogenic virus in the host.

In one embodiment, a recombinant virus is provided as a viral vaccine for eliciting an immune response in a host infected by the virus. The recombinant virus comprises: a plurality of antigen sequences heterologous to the recombinant virus, each encoding a viral antigen from a pathogenic virus, expression of the plurality of the antigen sequences eliciting an immune response directed against the viral antigen and cells expressing the viral antigen in the host upon infection of the host by the recombinant virus. The recombinant virus may preferably be replication-incompetent and not cause a malignancy naturally associated with the pathogenic virus in the host.

According to the embodiment, the recombinant virus may be any virus, preferably replication-incompetent adenovirus, adeno-associated virus, SV40 virus, retrovirus, herpes simplex virus or vaccinia virus. The recombinant virus may also preferably have the pathologic regions of the native progenitor of the benign virus deleted but retain its infectivity to the host.

Also according to the embodiment, the plurality of the antigen sequences may be multiple copies of the same antigen sequence or multiple antigen sequences that differ from each another.

In a variation of the embodiment, at least two of the plurality of the antigen sequences are expressed from a promoter bicistronically via an internal ribosomal entry site or via a splicing donor-acceptor mechanism.

Alternatively, at least two of the plurality of the antigen sequences are expressed from a promoter to form a fusion protein.

Also according to the embodiment, the recombinant virus further comprises at least one promoter heterologous to the native progenitor of the recombinant virus that controls the expression of at least two of the plurality of the antigen sequences. Examples of the promoter heterologous to the native progenitor of the recombinant virus include, but are not limited to, insulin promoter, CMV promoter and its early promoter, SV40 promoter, Rous sarcoma virus LTR promoter/enhancer, the chicken cytoplasmic β-actin promoter, and inducible promoters such as tetracycline-inducible promoter.

Also according to the embodiment, the plurality of antigen sequences may be a combination of antigens from at least two strains of the pathogenic virus.

Optionally, the plurality of antigen sequences may be a combination of antigens from at least two different pathogenic viruses. For example, the plurality of antigen sequences may be a combination of antigens from HIV-1, HIV-2, herpes simplex virus type 1, herpes simplexvirus type 2, influenza virus, Marburg virus, Ebola virus, Arbovirus (a group of viruses carried by mosquitoes that cause encephalitis, yellow fever, and dengue), and hepatitis A, B, C, D, and E viruses.

In a variation of the embodiment, the viral genome of the recombinant virus may further comprise one or more immuno-stimulator sequences that is heterologous to the recombinant virus and encodes an immuno-stimulator whose expression in the host enhances the immunogenicity of the viral antigen. For example, the immuno-stimulator may be a cytokine. Examples of the cytokine include, but are not limited to, interleukin-2, interleukin-4, interleukin-12, β-interferon, λ-interferon, γ-interferon, G-CSF, and GM-CSF.

According to the variation, the one or more immuno-stimulator sequences may be multiple copies of the same immuno-stimulator sequence or multiple immuno-stimulator sequences that differ from each other.

Optionally, at least two of the immuno-stimulator sequences may be expressed from a promoter bicistronically via an internal ribosomal entry site or via a splicing donor-acceptor mechanism. Alternatively, at least two of the immuno-stimulator sequences may be expressed from a promoter to form a fusion protein.

The DNA sequence encoding viral antigen(s) is inserted into any non-essential region of the replication defective virus. In the case of adenovirus, for example, the nucleic acid is preferably inserted into the E1, E3 and/or E4 region of the adenovirus and most preferably into the E4 region. Because the E1, E3 and E4 regions are available as insertion sites, the present invention also contemplates separate insertion of more than one encoding sequence.

In the recombinant viral vector vaccines of the present invention, the selected nucleotide sequences of the viral antigens are operably linked to control elements that direct transcription or expression thereof in the subject in vivo. Either homologous or heterologous viral control sequences can be employed. Useful heterologous control sequences generally include those derived from sequences encoding hostian or viral genes. Examples include, but are not limited to a cytomegalovirus (CMV) promoter such as the CMV immediate early promoter region ($CMV_{ie}$), SV40 early promoter, mouse mammary tumor virus LTR promoter, adenovirus major late promoter (AdMLP), a herpes simplex virus promoter, and a retrovirus LTR promoter. Preferably, any strong constitutive promoter may be operatively linked to viral antigens or cytokines. More preferably the viral promoter is CMV immediate early promoter ($CMV_{ie}$).

Figure 1B:
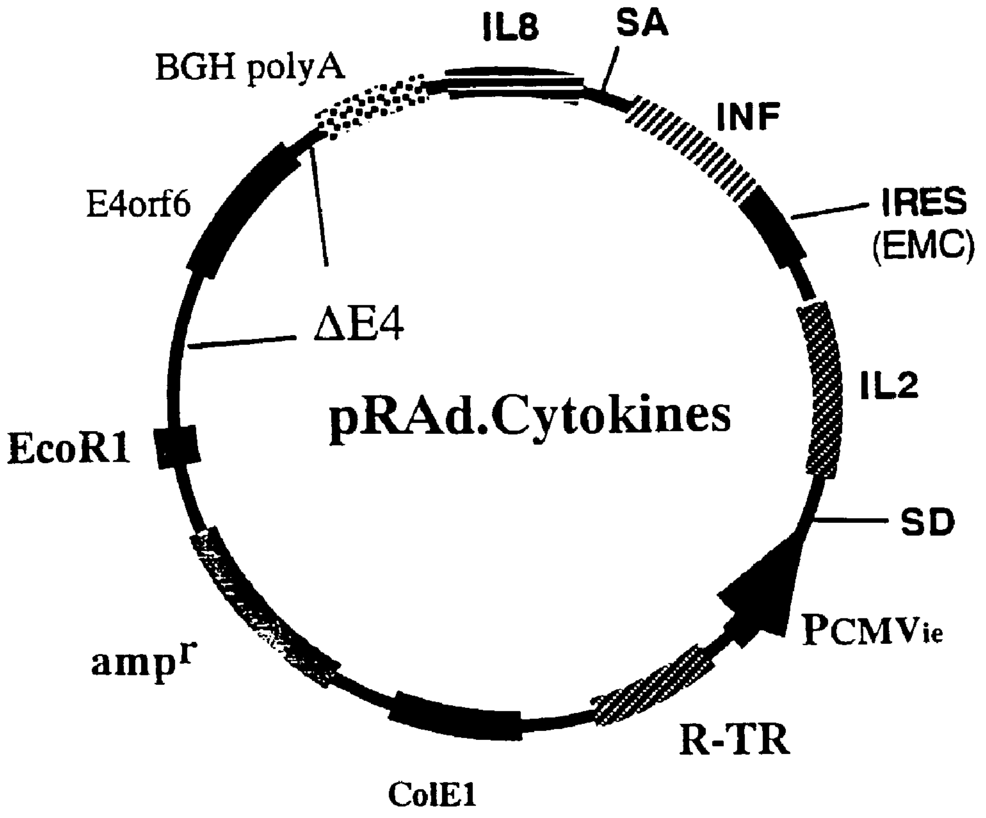
Figure 1C:
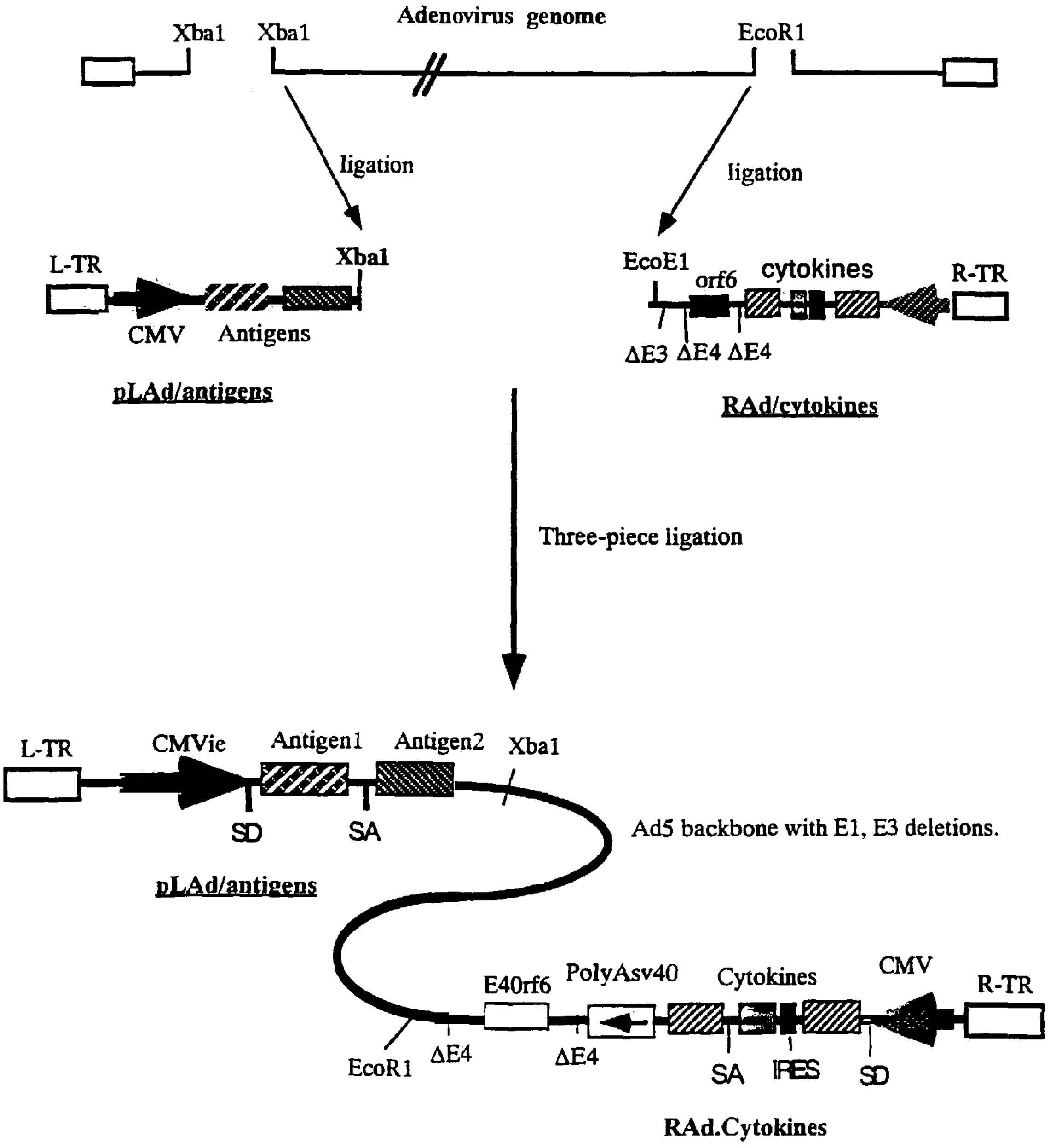

FIGS. 1A-1C illustrate a method for constructing a recombinant adenoviral vector as a genetic vaccine of the present invention. The recombinant adenoviral vector of the present invention is constructed by using shuttle plasmids or vectors carrying multiple antigen genes and multiple cytokine genes.

FIG. 1A illustrates a shuttle plasmid (pLAd.Antigen) containing two antigen genes, Antigen 1 and Antigen 2. The shuttle plasmid pLAd.Antigen contains the left end of the adenoviral genome including the left long terminal repeats L-TR, and an adenoviral packaging signal (ψ). The E1 region of the adenovirus is replaced by a multiple gene expression cassette and CMVie promoter.

Genes encoding Antigen 1 and Antigen 2 are placed under the transcriptional control of the $CMV_{ie}$ promoter by a splicing mechanism at the SD and SA sites. The plasmid pLAd.Antigen also contains a SV40 polyadenylation site, as well as prokaryotic replication origin and ampicillin-resistance gene for DNA propagation in bacteria.

FIG. 1B illustrates another shuttle plasmid (pRAd.Cytokines) containing multiple cytokine genes such as IL-2, INF, and IL-8. The shuttle plasmid pRAd.Cytokines contains the right end of the adenoviral genome including the right long terminal repeats R-TR. Most of the E4 region (except orf6) is replaced by the cytokine genes. Expression of cytokine genes is under the transcriptional control of the $CMV_{ie}$ promoter via an internal ribosomal entry site (IRES) and by a splicing mechanism at the SD and SA sites. The plasmid pRAd.Cytokines also contains a bovine growth hormone (BGH) polyadenylation site, as well as a prokaryotic replication origin and ampicillin-resistance gene for DNA propagation in bacteria.

The recombinant adenoviral genome is assembled from the two shuttle plasmids, pLAd.Antigen and pRAd.Cytokines, which carries the left and right end of the adenoviral genome, respectively. The shuttle plasmids pLAd.Antigen and pRAd.Cytokines are digested with restriction enzymes such as XbaI and EcoRI, respectively.

As illustrated in FIG. 1C, the fragments corresponding to the left end and right end of adenovirus from these two shuttle plasmids, pLAd.Antigen and pRAd.Cytokines, are isolated and ligated to the middle section of the adenoviral genome (the adenovirus backbone).

The ligated vector genome DNA is then transfected into 293HK cells that express the E1 proteins of adenovirus. In the presence of E1 proteins, the vector genome in which the E1 has been deleted can replicate and be packaged into viral particle, i.e. producing the recombinant adenoviral vector that can be used as a genetic vaccine of the present invention. The E1 region which is preserved in a native adenoviral genome but deleted from the recombinant viral genome is an example of the pathologic region native to the native progenitor of the recombinant virus: the wild type adenovirus.

Figure 5:
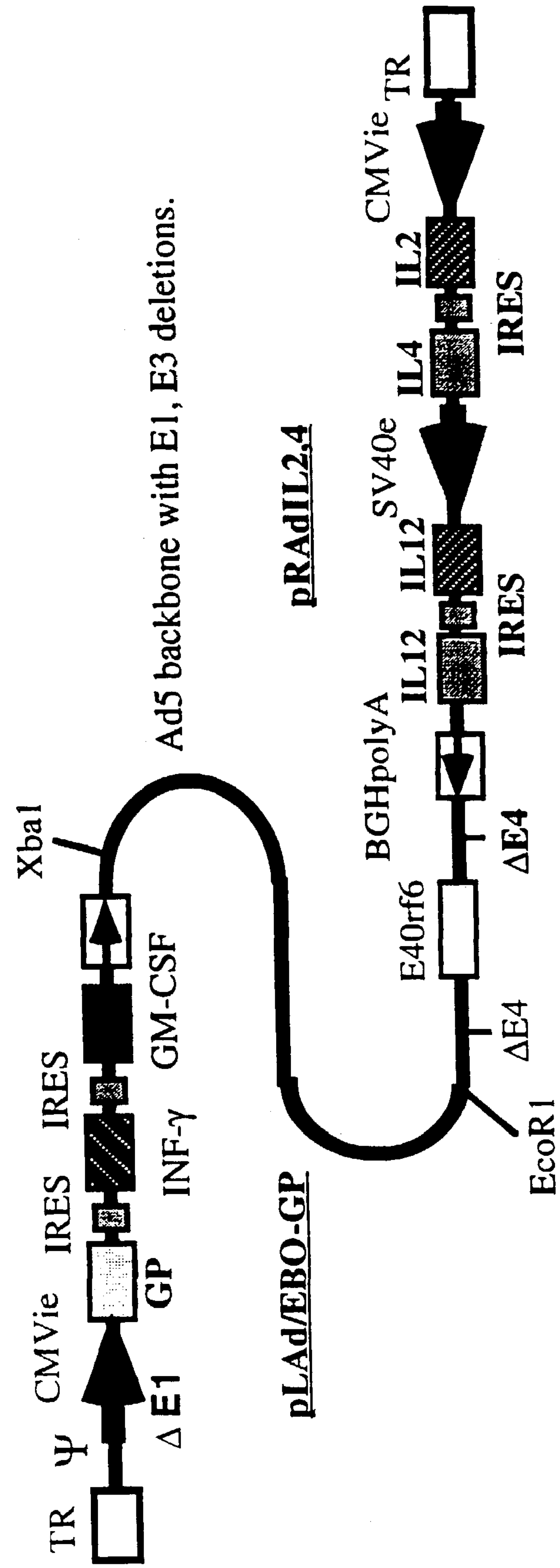
FIG. 5 illustrates a complex adenoviral vector as an example of the genetic vaccine of the present invention. The Ebola viral GP gene is expressed by a CMVie promoter in the E1 region. The GP gene is followed by INF-γ and GM-CSF which are expressed by two IRES sequences. This configuration allows for the expression of three proteins from a single mRNA. Expression of IL-2 and IL-4 is controlled by a second CMVie promoter as a bi-cistronic cassette, and followed by a second bi-cistronic cassette that expressed the two subunits of IL12 in the E4 region by a SV40 early promoter.

FIG. 5 illustrates an example of a genetic vaccine constructed by using the method described above. The replication defective adenovirus, type 5, is the vector backbone into which viral antigen and cytokines are inserted in the E1 region. The viral antigens are expressed using the CMVie promoter. The gene for the viral antigen is followed by the gene encoding INF-γ and GM-CSF, utilizing 2 IRES sequences to achieve expression of the three proteins from a single mRNA. IL2 and IL4 are controlled by a second $CMV_{ie}$ promoter as a bi-cistronic cassette, followed by a second bi-cistronic cassette that express the two subunits of IL12 in the E4 region. Those skilled in the art will appreciate that the present invention is not limited to the structure discussed above, but that alternative cytokines may be used alone or in combination with these and/or other cytokines. The detailed information about of these cytokines are described in the following section.

2. Cytokines Co-Expressed with Viral Antigens

The recombinant virus of the present invention may also express an immuno-stimulator to mimic cytokine-releasing response of a host cell upon viral infection and further augment immune response to the viral antigen co-expressed from the recombinant virus. The immuno-stimulator may be an immunoenhancing cytokine to further stimulate the immune system. The recombinant virus may encode one or multiple cytokines in any combination. Alternatively, multiple cytokines may be expressed by more than one recombinant virus or delivered to the host by using other techniques such as delivery via naked DNA plasmids or injection of cytokine proteins.

Examples of cytokine include, but are not limited to, interleukin-2, interleukin-4, interleukin-8, interleukin-12, β-interferon, λ-interferon, γ-interferon, granulocyte colony stimulating factor (G-CSF), and granulocyte-macrophage colony stimulating factor (GM-CSF).

Cytokines are immunodmodulatory molecules particularly useful in the vaccines of the invention as they are pleitropic mediators that modulate and shape the quality and intensity of the immune response. Cytokines are occasionally autocrines or endocrines, but are largely paracrine hormones produced in nature by lymphocytes and monocytes.

As used herein, the term "cytokine" refers to a member of the class of proteins or peptides that are produced by cells of the immune system and that regulate or modulate an immune response. Such regulation can occur within the humoral or the cell mediated immune response and includes modulation of the effector function of T cells, B cells, NK cells, macrophages, antigen-presenting cells or other immune system cells.

Cytokines are typically small proteins or glycoproteins having a molecular mass of less than about 30 kDa. As used herein the term cytokine encompasses those cytokines secreted by lyphocytes and other cell types (often designated as lymphokines) as well as cytokines secreted by monocytes and macrophages and other cell types (often designated as monokines). As used herein, the term cytokine encompasses those cytokines secreted by lymphocytes and other cell types as well as cyotkines secreted by monocytes and macrophages and other cell types. The term cytokine includes the interleukins, such as IL-2, IL-4, IL-5, IL-8, IL-10, IL-11, IL-12, IL-15, and IL-18, which are molecules secreted by leukocytes that primarily affect the growth and differentiation of hematopoietic and immune system cells, and human proinflammatory cytokines such as IL-1a, TNF-a and TNF-b). The term cytokine also includes hematopoietic growth factors and, in particular, colony stimulating factors such as colony stimulating factor-1, granulocyte colony stimulating factor and granulocyte macrophage colony stimulating factor.

The cytokines can have the sequence of a naturally occurring cytokine or can have an amino acid sequence with substantial amino acid sequence similarity, e.g., 60-95% amino acid sequence similarity, preferably 70-98% amino acid sequence, and most preferably 75-95% amino acid sequence similarity to the sequence of a naturally occurring cytokine.

Thus, it is understood that limited modifications to a naturally occurring sequence can be made without destroying the biological function of the cytokine. For example, minor modifications of gamma interferon that do not destroy its function fall within the definition of gamma interferon. These modifications can be deliberate, as through site-directed mutagenesis, or can be accidental such as through mutation. The preferred cytokines are IL-2, IL-8, IL-12, or γ-interferon, β-interferon, λ-interferon, GM-CSF, or G-CSF or a combination thereof.

Interleukin-2 is a lymphokine produced by helper T cells and is active in controlling the magnitude and type of the immune response. Smith, K. A., *Ann. Rev. Immunol.* 2, 319-333 (1984). Other functions have also been ascribed to IL-2 including the activation of NK cells (Minato, N. et al., *J. Exp. Med.* 154, 750 (1983)) and the stimulation of cell division in large granular lymphocytes and B cells. Tsudo, M. et al. *J. Exp. Med.* 160, 612-616 (1984). Studies in mice and humans have demonstrated that deficient immune responsiveness both in vivo and in vitro can be augmented by IL-2. For example, exogenous IL-2 can restore the immune response in cyclophosphamide-induced immunosuppressed mice (Merluzzi, V. J. et al. *Cancer Res.* 41, 850-853 (1981)) and athymic (nude) mice. Wagner, H. et al. *Nature* 284, 278-80 (1982). Furthermore, IL-2 can restore responsiveness of lymphocytes from patients with various immunodeficiency states such as leprosy and cancer. Vose, B. M. et al. *Cancer Immuno.* 13, 105-111 (1984). The genes for murine (Yokota, T. et al. *Proc. Natl. Acad. Sci. USA* 82, 68-72 (1985)) and human (Taniguchi, T. et al. *Nature,* 302, 305-307 (1983)) IL-2 have been cloned and sequenced.

Interleukin-4 is a T cell derived factor that acts as an induction factor on resting B cells, as a B cell differentiation factor and as a B cell growth factors. Sevenusar, E. Eur. J. Immunol. 17, 67-72 (1987). The gene for human IL-4 has been isolated and sequenced. Lee, F. et al. Proc. Natl. Acad. Sci. USA 83, 2061-2065 (1986).

IL-12 is a recently characterized heterodimeric cytokine that has a molecular weight of 75 kDa and is composed of disulfide-bonded 40 kDa and 35 kDa subunits. It is produced by antigen presenting cells such as macrophages, and binds to receptors on activated T, B and NK cells (Desai, B. B., et al., *J. Immunol.,* 148:3125-3132 (1992); Vogel, L. A., et al., *Int. Immunol.,* 8:1955-1962 (1996)). It has several effects including 1) enhanced proliferation of T cells and NK cells, 2) increased cytolytic activities of T cells, NK cells, and macrophages, 3) induction of IFN-γ production and to a lesser extent, TNF-α and GM-CSF, and 4) activation of TH1 cells. (Trinchieri, G., et al., Blood, 84:4008-4027 (1994). IL-12 has been shown to be an important costimulator of proliferation in Th1 clones (Kennedy et al., *Eur. J. Immunol.* 24:2271-2278 (1994)) and leads to increased production of IgG2a antibodies in serum (Morris, S. C., et al., *J. Immunol.* 152:1047-1056 (1994); Germann, T. M., et al., *Eur. J. Immunol.,* 25:823-829 (1995); Sher, A., et al., Ann. N.Y. Acad. Sci., 795:202-207 (1996); Buchanan, J. M., et al., *Int. Immunol.,* 7:1519-1528 (1995); Metzger, D. W. et al., *Eur. J. Imunol.,* 27:1958-1965 (1997)). Administration of IL-12 can also temporarily decrease production of IgG1 antibodies (Morris, S. C., et al., *J. Immunol.* 152:1047-1056 (1994); McKnight, A. J., *J. Immunol.* 152:2172-2179 (1994); Buchanan, J. M., et al., *Int. Immunol.,* 7:1519-1528 (1995)), indicating suppression of the Th2 response. The purification and cloning of IL-12 are disclosed in WO 92/05256 and WO 90/05147, and in EP 322,827 (identified as "CLMF"). All of the above effects were observed in adult animals.

Interferons (IFNs) are relatively small, species-specific, single chain polypeptides, produced by hostian cells in response to exposure to a variety of inducers such as viruses, polypeptides, mitogens and the like. They exhibit antiviral, antiproliferative and immunoregulatory properties and are, therefore, of great interest as therapeutic agents in the control of cancer and various other antiviral diseases (J. Desmyter et al., *Lancet* 11, 645-647 (1976); R. Derynck et al., *Nature* 287, 193 (1980)). Human interferons are grouped into three classes based on their cellular origin and antigenicity: α-interferon (leukocytes), β-interferon (fibroblasts) and γ-interferon (B cells). Recombinant forms of each group have been developed and are commercially available.

γ-interferon is also a T cell derived molecule which has profound effects on the immune response. The molecule promotes the production of immunoglobulin by activated B cells stimulated with interleukin-2. γ-interferon also increases the expression of histocompatability antigens on cells which associated with viral antigens to stimulate cytotoxic T cells. The gene for human y-interferon has been isolated and sequenced. Gray, P. W. et al., *Nature* 295, 503-508 (1982).

Human alpha interferons (also known as Leukocyte interferons) comprise a family of about 30 protein species, encoded by at least 14 different genes and about 16 alleles. Some of these alpha interferon protein species have been shown to have antiviral, antigrowth and immunoregulatory activities. See, e.g., Pestka et al., *Ann. Rev. Biochem.,* 56:727 (1987). The therapeutic efficacy of human alpha interferons has been established for human cancers and viral diseases. For example, recombinant interferons (IFN alpha-2a, IFN alpha-2b, IFN alpha-2c), cell-line derived interferon (IFN alpha-n1) and interferon derived from leukocytes (IFN alpha-n3) are currently used for the treatment of Condyloma acuminata, hepatitis (Weck et al., *Am. J. Med.,* 85(Suppl 2A):159 (1988); Korenman et al., *Annal. Intern. Med.,* 114:629 (1991); Friedman-Kien et al., *JAMA,* 259:533 (1988)), for the regression of some malignancies (Baron et al., *JAMA,* 266: 1375 (1991)), for the treatment of AIDS related Kaposi's sarcoma (Physicians Desk Reference, 47th edit., eds. Medical Economics Data, Montvale, N.J., p. 2194 and 2006 (1993)) and are currently being considered for the treatment of human acquired immunodeficiency syndrome (AIDS) either alone or in combination with other antiviral agents (Hirsch, *Am. J. Med.,* 85 (Suppl 2A):182 (1988)).

β-interferon has been shown to be a glycoprotein by chemical measurement of its carbohydrate content. It has one N-glycosidyl attachment site (E. Knight, Jr., *Proc. Natl. Acad. Sci.,* 73, 520 (1976); E. Knight, Jr., and D. Fahey, *J. Interferon Res.,* 2 (3), 421 (1982)). Even though not much is known about the kinds of sugars which make up the carbohydrate moiety of β-interferon, it has been shown that the carbohydrate moiety is not essential for its antigenicity, biological activity or hydrophobicity (T. Taniguchi et al., supra; E. Knight, Jr., supra; and E. Knight, Jr. and D. Fahey, supra). Beta-interferon can be induced in fibroblasts by viral challenge and contains about 165 amino acids. The sequence of beta-interferon is known. Fiers et al. *Philos. Trnas. R. Soc. Lond., B, Biol. Sci.* 299:29-38 (1982).

GM-CSF is a cytokine important in the maturation and function of dendritic cells. It binds receptors on dendritic cells and stimulates these cells to mature, present antigen, and prime naive T cells. Dendritic cells form a system of highly efficient antigen-presenting cells. After capturing antigen in the periphery, dendritic cells migrate to lymphoid organs and present antigens to T cells. These potent antigen-presenting cells are unique in their ability to interact with active naive T cells. The potent antigen-presenting capacity of dendritic cells may be due in part to their unique life cycle and high level expression of major histocompatibility complex class I and II molecules and co-stimulatory molecules. The sequence of human GM-CSF is known. Wong et al., *Science* 228:810-815 (1985).

Granulocyte colony stimulating factor (G-CSF) is one of the hematopoietic growth factors, also called colony stimulating factors, that stimulate committed progenitor cells to proliferate and to form colonies of differentiating blood cells. G-CSF preferentially stimulates the growth and development of neutrophils, and is useful for treating in neutropenic states. Welte et al., *PNAS-USA* 82: 1526-1530 (1985); Souza et al., *Science* 232: 61-65 (1986) and Gabrilove, *J. Seminars in Hematology* 26: (2) 1-14 (1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection. See, e.g., Wendel et al., *J. Immunol.,* 149:918-924 (1992). The cDNAs for human (Nagata et al., *Nature* 319;415, 1986) and mouse G-CSF (Tsuchiya et al., *PNAS* 83, 7633, 1986) have been isolated, permitting further structural and biological characterization of G-CSF.

In humans, endogenous G-CSF is detectable in blood plasma. Jones et al., *Bailliere's Clinical Hematology* 2 (1): 83-111 (1989). G-CSF is produced by fibroblasts, macrophages, T cells trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids. Nagata et al., *EMBO J.* 5: 575-581(1986). The form comprised of 174 amino acids has been found to have the greatest specific in vivo biological activity. G-CSF is species cross-reactive, such that when human G-CSF is administered to another host such as a mouse, Canine or monkey, sustained neutrophil leukocytosis is elicited. Moore et al. *PNAS-USA* 84: 7134-7138(1987).

The present invention provides an effective means for enhancing the immune response to the specific foreign antigenic polypeptides of recombinant viruses. Although any foreign antigenic polypeptide can be used in the vaccine of the present invention, the vaccine is particularly useful in vaccines against the HIV virus and the Ebola virus, since these viruses have a negative effect on the host's immune system. The vaccine is also very useful for immunization against hepatitis B and C virus.

3. Genetic Vaccines Against HIV Infection

The genetic vaccine of the present invention also addresses the need for an efficient vaccine against the HIV virus. According to the present invention the genetic vaccine may be a recombinant benign virus in which the viral genome carries one or more antigens from HIV, such as HIV glycoproteins (e.g. GP120 and GP41) or capsid proteins (e.g. P24). Sequences of these HIV antigens may be modified such as deletion of the immunosuppressive regions of the HIV glycoproteins.

The HIV virus causes the disease known as Acquired Immune Deficiency Syndrome (AIDS). AIDS has been described as a modern plague since its first description in 1981, it has claimed over 60,000 victims, and accounted for over 32,000 deaths in the United States alone. The disease is characterized by a long aysmptomatic period followed by a progressive degeneration of the immune system and the central nervous system. The virus may remain latent in infected individuals for five or more years before symptoms appear, and thus, the true impact of the disease has yet to be felt. Many Americans may unknowingly be infected and capable of infecting others who might come into contact with their body fluids. Thus, if unchecked, the personal, social and economic impact of AIDS will be enormous.

The HIV virus is a retrovirus. Thus, its genetic matierial is RNA, which encodes the information for viral replication. Upon infection of a host cell, the RNA acts as a template for the transcription to DNA, which is catalyzed by an enzyme called reverse transcriptase. The DNA so produced enters the cell nucleus where it is integrated into the host DNA as a provirus. When properly activated, the retroviral-derived DNA is transcribed and translated to produce RNA containing virions, which are then released from the cell by a budding process.

When an individual becomes infected with HIV, the virus preferentially attaches to and enters a particular class, of white blood cells, called T4 lymphocytes, which are characterized by the presence of a cell surface marker termed CD4. These white blood cells play an integral role in the immune system, functioning as critical components of both the humoral and cellular immune response. Much of the deleterious effect of HIV can be attributed to the functional depression or destruction of T4 lymphocytes.

The intact HIV virion is roughly spherical and is approximately 110 nm in diameter. The virion has an outer membrane covered with spike-like structures made up of glycoprotein, gp160/120. In addition, there exists a transmembrane protein termed gp41. Inside the virion are two structural proteins: an outer shell composed of the phosphoprotein, p17, and an inner nucleoid or central core made up of the phosphoprotein, p24. The viral RNA is present inside the core along with two copies of the reverse transcriptase enzyme, p66/51, which is necessary for the synthesis of viral DNA from the RNA template. The HIV RNA genome encodes three major structural genes: gag, pol and env, which are flanked at either end by long terminal repeat (LTR) sequences. The gag gene codes for the group-specific core proteins, p55, p39, p24, p17 and p15. The pol genes code for the reverse transcriptase, p66/p51, and the protease, p31. The env genes encode the outer envelope glycoprotein, gp120, and its precursor, gp160, and the transmembrane glycoprotein, gp41. Some of the genes tend to be highly variable, particularly the env genes. In addition, there are five other genes, not shared by other retroviruses, which are either involved in transcriptional or translational regulation or encode other structural proteins. The entire HIV genome has now been sequenced. See Ratner et al. Nature 313:277 (1985), which is incorporated herein by reference.

The HIV envelope protein has been extensively described, and the amino acid and RNA sequences encoding HIV envelope from a number of HIV strains are known. See Myers, G. et al., *Human Retroviruses and AIDS: A compilation and analysis of nucleic acid and amino acid sequences*, Los Alamos National Laboratory, Los Alamos, N.M. (1992). The env genes of various strains of HIV are predicted to encode proteins of 850 to 880 amino acids. Extensive glycosylation of the Env precursor polyprotein during synthesis produces gp160 (about 160 kilodaltons) which is also the major form of the env gene product detected in infected cells. Gp160 forms a homotrimers and undergoes glycosylation with the Golgi apparatus.

The functional domains of gp160 includes, starting from N-terminus, Signal peptide, Variable regions 1 through 5 which encompass CD4 binding sites (e.g., $Thr^{257}$, $Trp^{427}$, $Asp^{368}/Glu^{370}$, and $Asp^{457}$), Proteolytic processing site (also called the cleavage site between gp120 and gp41), Fusion domain, Leucine zipper motif, transmembrane domain, and Lentivirus lytic peptides (LLP) 1 and 2. Although the nucleotide and amino acid sequences of gp120 and the numbering thereof from various isolates and strains of HIV may differ, the region encoding the functional domains can be readily identified by the teaching in Luciw (1996) in "Fundamental Virology", 3rd ed., eds., Fields et al., Lippincott-Raven Publishers, Philadelphia, Chapter 27, pp. 845-916.

The signal peptide at the N-terminus of the Env precursor gp160 directs ribosomes translating the nascent protein to the endoplasmic reticulum; an intracellular proteinase removes this signal peptide during Env gp biogenesis. The Env precursor gp160 is cleaved at the processing site by a cellular protease to produce gp120 (designated SU subunit) and gp41 (designated TM subunit). Gp120 contains most of the external, surface-exposed, domains of the envelope glycoprotein complex. Gp41 contains a transmembrane domain and remains in a trimeric configuration, and it interacts with gp120 in a non-covalent manner. The subunits of gp41 include: Fusion peptide, Leucine zipper-like region, transmembrane domain (TM), LLP1 and LLP2.

The gp120 subunit contains five variable regions and six conserved regions. The variable (V) domains and conserved (C) domains of gp120 are specified according to the nomenclature of Modrow et al. (1987) "Computer-assisted analysis of envelope protein sequences of seven human immunodeficiency virus isolates: predictions of antigenic epitopes in conserved and variable regions", J. Virol. 61:570-578.

The gp120 molecule consists of a polypeptide core of 60,000 daltons, which is extensively modified by N-linked glycosylation to increase the apparent molecular weight of the molecule to 120,000 daltons. The positions of the 18 cysteine residues in the gp120 primary sequence, and the positions of 13 of the approximately 24 N-linked glycosylation sites in the gp120 sequence are common to all gp120 sequences. The hypervariable domains contain extensive amino acid substitutions, insertions and deletions. Sequence variations in these domains result in up to 30% overall sequence variability between gp120 molecules from the various viral isolates. Despite this variation, all gp120 sequences preserve the virus's ability to bind to the viral receptor CD4 and to interact with gp41 to induce fusion of the viral and host cell membranes.

The HIV virus attaches to host cells by an interaction of the envelope glycoproteins with a cell surface receptor. It appears that when HIV makes contact with a T4 cell, gp120 interacts with the CD4 receptor. Recently, the crystal structure of the core domain of HIV-1 gp120 (strain HXB-2, a clade B virus) has been solved by complexing the protein with a fragment of human CD and an antigen-binding fragment from a virus-neutralizing antibody that blocks chemokine-receptor binding. Kwong et al. (1998) "Structure of an HIV gp120 envelope glycoprotein in complex with the CD4 receptor and a neutralizing human antibody", Nature 393:648-659. These studies revealed that the gp120 core has a unique molecular structure that comprises two domains—an "inner domain" (which faces gp41) and an "outer" domain (which is mostly exposed on the surface of the oligomeric envelope glycoprotein complex). The two gp120 domains are separated by a "bridging sheet" that is not part of either domain. Binding to CD4 causes a conformational change in gp120 which exposes the bridging sheet and may move the inner and outer domains relative to each other. It was also found that most of the carbohydrate molecules which are added to gp120 are added to the outer domain. This is consistent with the idea that that virus uses carbohydrate molecules to mask external antigenic epitopes on gp120.

Gp120 not only binds to the cellular CD4 receptor but also to HIV coreceptors such as the cellular chemokine receptors (e.g. CCR5). Upon binding to the receptor and/or coreceptor, the viral envelope is then fused with the cell membrane and the inner core of the virus enters the infected cell where the transcription of RNA into a DNA provirus is catalyzed by reverse transcriptase. The provirus may remain in the cell in a latent form for some months or years, during which time the infected individual is asymptomatic. However, if the virus is later activated causing viral replication and immuno-suppression the individual will than be susceptible to the opportunistic infections associated with AIDS.

In one embodiment of the HIV vaccine of the present invention, a recombinant virus is provided for eliciting strong immune response against infection of HIV. The recombinant virus comprises: an antigen sequence heterologous to the recombinant virus that encodes an antigen from human immunodeficiency virus (HIV), expression of the HIV antigen eliciting an immune response directed against the HIV antigen and cells expressing the HIV antigen in a host upon infection of the host by the recombinant virus; and an immuno-stimulator sequence heterologous to the recombinant virus that encodes an immuno-stimulator whose expression in the host enhances the immunogenicity of the HIV antigen. In a preferred embodiment, the recombinant virus is replication-incompetent and does not cause a malignancy naturally associated with HIV in the host. The recombinant virus is used as a genetic vaccine to be administered to a host to induce or elicit strong and long-lasting immunity against HIV infection.

In comparison with other approaches for developing HIV vaccine using denatured or attenuated HIV virion, the approach of the present invention should be safer and more efficient in eliciting strong immune response but not creating risks of reactivation of HIV, probably through recombination with the wild type HIV infecting the host.

According to the present invention, the HIV antigen expressed by the genetic vaccine may be any antigen derived from a HIV virus, such as HIV surface, core/capsid, regulatory, enzyme and accessory proteins. Examples of HIV surface protein include, but are limited to the products of the env gene such as gp120 and gp41. Examples of HIV capsid protein include, but are limited to the products of the gag gene such as the cleavage products of the $Pr55^{gag}$ by the viral encoded protease PR: the mature capsid proteins MA (p17), CA (p24), p2, NC (p7), p1 and p6. Herderson et al. (1992) J. Virol. 66:1856-1865. Examples of viral regulatory proteins include, but are not limited to the products of the tat and rev genes: Tat and Rev. Examples of viral enzyme proteins include, but are not limited to the products of the pol gene: p11 (protease or PR), p51 (reverse transcriptase or RT), and p32 (integrase or IN). Examples of viral accessory proteins include, but are not limited to the products of the vif, vpr, vpx, vpu and nef genes: Vif, Vpr, Vpx, Vpu and Nef.

In one embodiment, HIV Nef protein may serve as the HIV antigen expressed by the recombinant virus of the present invention. For example, sequence encoding Nef (e.g., the nef sequence at position 8152-8523 for BH10 strain of HIV and at position 8787-9407 for pNL4-3 strain of HIV) may be inserted into the vector.

In another embodiment, HIV Rev protein may serve as the HIV antigen expressed by the recombinant virus of the present invention. For example, sequence encoding Rev (e.g., the rev1 sequence at position 5969-6044 and the rev2 sequence at position 8369-8643 for pNL4-3 strain of HIV) may be inserted into the vector.

In yet another embodiment, full length HIV Gag protein may serve as the HIV antigen expressed by the recombinant virus of the present invention. For example, sequence encoding full length Gag (e.g., the gag sequence at position 112-1650 for BH10 strain of HIV and at position 790-2292 for pNL4-3 strain of HIV) may be inserted into the vector.

Alternatively, capsid protein from HIV Gag protein (e.g. p24 CA) may serve as the HIV antigen expressed by the recombinant virus of the present invention. For example, sequence encoding p24CA (e.g., the sequence at position 1186-1878 for BH10 strain of HIV and at position 508-1200 for pNL4-3 strain of HIV) may be inserted into the vector.

In yet another embodiment, the HIV antigen expressed by the recombinant virus is derived from the env gene products. For example, the antigen is derived from the Env protein.

According to the embodiment, modifications or mutagenesis may be used to delete or mutate in certain region(s) of Env to render it non-functional and yet still contains neutralizing epitopes for its natural genicity. For example, the proteolytic processing site of Env may be deleted or mutated to render it resistant to cleavage by cellular protease to produce gp120 and gp41 fragments. Deletion or mutation may also be carried out on the transmembrane and cytoplasmic domains of gp41 such as the TM, LLP-1 and LLP-2 domains. Compared to the wild type Env, the mutated Env protein should have a reduced risk of being incorporated into a wild type HIV that infects the host and being exploited by HIV in its furtherance of the goal: destruction the host's immune system.

For example, wildtype HIV Env can be modified in the following ways. Wildtype gp120 sequence from BH10 strain of HIV and containing Env, Tat, and Rev coding sequences can be digested with restriction enzymes EcoR I and Xho I to produce a fragment starting from nucleotide 5101 and ending at nucleotide 8252. The cytosolic domain of Env can be removed by deleting nucleotides from the coding sequence at position 7848-8150 for BH10 strain, and 8610-8785 for pNL4-3 strain of HIV. The cleavage site of Env can be removed by deleting 12 nucleotides encoding amino acid sequence REKR at position 7101-7112 for BH10 strain, and 7736-7747 for pNL4-3 strain of HIV.

Also according to this embodiment, the modified Env protein may contain deletions in the regions that do not contain neutralizing epitopes. For example, the V1 and V5 domains of gp120 may be deleted without sacrificing the natural antigenicity of gp120. Portions of the V2 and V3 domains of gp120 that do not contain neutralizing epitopes may also be deleted. Although the principle neutralizing domain (PND) has been found in the V3 domain, V2 and C4 domains of gp120 have also been found to contain neutralizing epitopes. Among various strains or clades of HIV, the amino acid sequences of the neutralizing epitopes may be variable. However, it has been found that the amount of variation is highly constrained. Thus, the sequences not containing the neutralizing epitopes should be readily determined.

For example, sequence encoding V1 region of Env can be deleted at position 5961-6032 for BH10 strain, and 6602-6673 for pNL4-3 strain of HIV. Sequence encoding V2 region of Env can be deleted at position 6060-6161 for BH10 strain, and 6700-6796 for pNL4-3 strain of HIV. Optionally, sequence encoding both V1 and V2 regions of Env can be deleted at position 5961-6161 for BH10 strain, and 6602-6796 for pNL4-3 strain of HIV.

Alternatively, the HIV antigen expressed by the recombinant virus may be a subunit of gp120 which contains one or more selected variable (V) and/or conserved (C) domains. For example, the HIV antigen may be a gp120 subunit containing V2, V3 and C4 domains, or V3 and C4 domains. The location of neutralizing epitopes in the V3 domain is well known. It has been found that neutralizing epitopes in the V2 and C4 domains are located between residues 163 and 200 and between about 420 and 440, respectively. In addition, residues for antibody binding also include residues 171, 174, 177, 181, 183, 187, 188 in the V2 domain and residues 429 and 432 in the C4 domains. Berman et al. (1999) Virology 265:1-9; and Berman (1998) AIDS Res. Human Retroviruses 15:115-132.

In another embodiment, the HIV antigen expressed by the recombinant virus of the present invention may be a modified Env protein that contains deletions and/or mutations in the glycosylation sites. The gp120 of HIV-1 contains 24 potential sites for N-linked glycosylation (Asn-X-Ser/Thr); about 13 of the 24 glycosylation motifs are conserved in the different viral isolates. Analysis of HIV-1 Env gp proteins has demonstrated that 17 of 24 potential glycosylation sites are modified with carbohydrate side chains. Mizuochi et al. (1990) J. Biol. Chem. 265:8519-8524; and Leonard et al. (1990) J. Biol. Chem. 265:10373-10382. Because of the extensive glycosylation of Env gp proteins, very few regions of the peptide backbone of gp120 protrude from the carbohydrate mass. Some of the glycosylation sites have been found in non-neutralizing epitopes that dilute the immunity against true neutralizing epitopes or serve as decoy epitopes. Thus, deletion or mutation of these glycosylation sites may enhance immunity of the antigen by unmasking the true neutralizing epitopes.

In another embodiment, the different HIV antigens may be expressed by the same recombinant virus of the present invention. For example, both Env, Tat and Rev proteins may be expressed from the same promoter such as a CMV early promoter via a retroviral splicing donor-acceptor mechanism. Optionally, HIV Gag protein, either in full length or a truncated or modified form (e.g., capsid protein p24), may also be expressed together with other HIV antigens such as Env, Tat and Rev. Further, these HIV antigens may be expressed together with the immuno-stimulator(s) (e.g., IL-2, IL-12, INF-γ, and GMCSF) in single or multiple copies by the same recombinant viral vector.

For example, the sequences encoding the HIV antigens may be inserted into E1 region of an adenoviral vector and expressed from a CMV early promoter via a retroviral splicing donor-acceptor mechanism or an IRES mechanism. The sequences encoding the immuno-stimulators may be inserted into E4 region of the same adenoviral vector and expressed from another CMV early promoter via a retroviral splicing donor-acceptor mechanism or an IRES mechanism.

In yet another embodiment, the sequence encoding the HIV antigen in the recombinant virus of the present invention is a mosaic antigen that contains sequences from different strains, isolates and/or clades of HIV viruses. A strain of HIV is the HIV isolated from an individual (an isolate), characterized and given a strain name (e.g., MN, LAI). Because of the heterogenecity of HIV, not two isolates are exactly the same. A group of related HIV isolates are classified according to their degree of genetic similarity such as of their envelop proteins. There are currently two groups of HIV-1 isolates, M and O. The M group consists of at least 9 clades (also called subtypes), A through I. The O group may consist of a similar number of clades. Clades are genetically distinct but are all infectious. It is believed that by using a mosaic HIV antigen in the design of the genetic vaccine of the present invention the vaccine produced should have an enhanced ability to stimulate the production of anti-HIV antibodies and HIV-specific cytotoxic T lymphocytes (CTLs) against a wider spectrum of "wild type" HIV strains.

In one embodiment, the mosaic HIV antigen in the recombinant virus contains antigens from multiple clades of HIV-1, including clade A (Accession No: HIV-1 92UG037WHO.0108HED), B (Accession No: pNL4-3), C (Accession No: HIV-1 92BR025WHO.109HED), D (Accession No: HIV-1 92UG024.2), E (Accession No: HIV-1 93TH976.17), F (Accession No: HIV-1 93BR020.17), and G (Accession No: HIV-1 92RU131.9). Optionally, multiple repeats of restriction fragments of HIV antigen (e.g., Ava I fragments) from different clades may be linked head-to-tail to generate an even more complex mosaic HIV antigen.

For example, an adenoviral vector may be constructed to the V3 loops of multiple clades as the mosaic HIV antigen. Optionally, HIV antigens with gp41 deletion from multiple clades may serve as the mosaic HIV antigen. Alternatively, HIV antigens from multiple clades with V1 and V2 loops deleted from clade B (pNL4-3) may serve as the mosaic HIV antigen.

Yet optionally, a human gene Thy-1 GPA anchor sequence encoding amino acid sequence SWLLLLLLSLSLLQATD-FMSL [SEQ ID NO: 9] may be added to the recombinant viral construct.

In another embodiment, the mosaic HIV antigen contains an Env protein which comprises variable and constant domains of gp120 derived from different strains, isolates and/or clades of HIV viruses. For example, V2 domain from clade B of the M group may be mixed with V3 and C4 domains from clade C of the O group to generate a mosaic HIV antigen. Vaccination of individuals with such a mosaic antigen may stimulate CTLs with cross-clade activity. In another word, these CTLs can recognize and kill target cells infected HIV from different clades.

Alternatively, the recombinant virus may express a plurality of HIV antigens, each of which is an antigen from a different strain, isolate or clade of HIV. For example, env genes from different clades of HIV can be cloned into the recombinant virus and expressed in tandem to produces various Env proteins from these clades in the host cells. It is believed that expressing various Env proteins from different strains, isolates or clades of HIV in the host cells should enhance the ability of the genetic vaccine of the present invention to stimulate the production of anti-HIV antibodies and HIV-specific cytotoxic T lymphocytes (CTLs) against a wider spectrum of "wild type" HIV strains. The host vaccinated with such a vaccine would be able to be immunized from infection of various strains of HIV.

By using the genetic vaccine of the present invention, individuals not infected by HIV may be immunized against HIV. For HIV-infected individuals the vaccine may also be used boost their immune response and help fight against this virulent virus. Since the genetic vaccine can express high level of antigens and/or a variety of HIV glycoproteins and capsid proteins simultaneously, the vaccinated individuals should be immunized against various strains of HIV, such as HIV-1 and HIV-2. Additionally, since the genetic vaccine can express high levels of cytokines to mimic the body's response to natural viral infection, the body's immune response to such a genetic vaccine against HIV should be strong and long-lasting, thereby achieving a life-long immunity against this deadly virus.

4. Genetic Vaccines Against Hepatitis Viruses

The genetic vaccine of the present invention also addresses the need for an efficient vaccine against hepatitis viruses such as hepatitis A, B, C, D, and E viruses. According to the present invention the genetic vaccine may be a recombinant benign virus in which the viral genome carries one or more antigens from a hepatitis virus, such as glycoproteins and core proteins of the hepatitis virus. Sequences of these HIV antigens may be modified such as deletion of the pathogenic regions of the hepatitis glycoproteins or coreproteins.

In particular, the recombinant virus of the present invention can be used as a vaccine to immunize individuals against Hepatitis B infections. Viral hepatitis B is caused by the Hepatitis B virus (HBV). HBV is estimated to have infected 400 million people throughout the world, making HBV one of the most common humanpathogens. Hepatocellular carcinomas (HCC), one of the most common cancers afflicting humans, is primarily caused by chronic HBV infection.

HBV is a mostly double-stranded DNA virus in the Hepadnaviridae family. The HBV genome is unique in the world of viruses due to its compact form, use of overlapping reading frames, and dependence on a reverse-transcriptase step, though the virion contains primarily DNA. The HBV genome has four genes: pol, env, pre-core and X that respectively encode the viral DNA polymerase, envelope protein, pre-core protein (which is processed to viral capsid) and protein X. The function of protein X is not clear but it may be involved in the activation of host cell genes and the development of cancer.

The diagnosis of HBV infection is generally made on the basis of serology. Virtually all individuals infected with HBV will have detectable serum hepatitis surface antigens (HBsAg). Despite notable successes of vaccines against HBV infection, it is still an on-going task. A review on modern hepatitis vaccines, including a number of key references, may be found in the Eddleston, The Lancet, p. 1142, May 12, 1990. See also *Viral Hepatitis and Liver Disease*, Vyas, B. N., Dienstag, J. L., and Hoofnagle, J. H., eds., Grune and Stratton, Inc. (1984) and *Viral Hepatitis and Liver Disease*, Proceedings of the 1990 International Symposium, eds F. B. Hollinger, S. M. Lemon and H. Margolis, published by Williams and Wilkins. According to the present invention, the viral antigen may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg).

Antigens of different types of HBV, such as Asian type C and America type A, may be expressed by the recombinant virus to elicit immune response to these types of HBV. The HBV surface antigen (HBsAg) or the core antigen (HBcAg) may be expressed by the recombinant virus of the present invention, separately or in combination (HBsAg+HBcAg).

For example, the sequences encoding multiple HBV antigens may be inserted into E1 or E4 region of an adenoviral vector and expressed from a CMV early promoter via a retroviral splicing donor-acceptor mechanism or an IRES mechanism. Further, these HBV antigens may be expressed in combination with one or more immuno-stimulators such as IL-2, IFN-γ and GMCSF in single or multiple copies. Sequences encoding these cytokines may be inserted into E4 or E1 region that is not occupied by the antigen sequences and expressed from another CMV early promoter via a retroviral splicing donor-acceptor mechanism or an IRES mechanism.

Specific combinations of inserts include, but are not limited to, HBsAg+HBcAg; HBsAg+HBcAg+IL-2; HBsAg+HBcAg+IFN-γ+GMCSF; and HBsAg+IFN-γ+IFN-γ+GMCSF.

The sequences encoding the immuno-stimulators may be inserted into E4 region of the same adenoviral vector and expressed from another CMV early promoter via a retroviral splicing donor-acceptor mechanism or an IRES mechanism.

Also according to the present invention, the viral antigen may be a surface antigen or core protein of hepatitis C virus such as NS3, NS4 and NS5 antigens.

For example, sequence(s) encoding the HCV antigen(s) may be inserted into E1 or E4 region of an adenoviral vector and expressed separately or in combination with one or more immuno-stimulators such as IL-2, IL-12, IFN-γ and GMCSF in single or multiple copies.

Specific combinations include, but are not limited to, (1) HCV wildtype E2+wildtype E1;

(2) core of HCV;

(3) HCV E2+E1+core;

(4) HCV E2+E1+core+IL-2;

(5) HCV E2+E1+core+IL-2+IFN-γ+GMCSF; and (6) HCV E2+E1+core+IL-2+IFN-γ+IL-12.

In another embodiment, multi copies of hypervariable regions (HVR) of HCV E1 and E2, e.g., five copies of HVR (5×HVR), may serve as the viral antigen in the recombinant virus, and may be expressed alone or in combination with one or more immuno-stimulators such as IL-2, IL-12, IFN-γ and GMCSF in single or multiple copies.

Specific combinations include, but are not limited to, (1) E2-5xHVR+E1;

(2) E2-5xHVR+E1+IL-2;

(3) E2-5xHVR+E1+core+IL-2;

(4) E2-5xHVR+E1+core+IL-2+IFN-γ+GMCSF; and (5) E2-5xHVR+E1+core+IL-2+IL-12.

By using the genetic vaccine of the present invention, non-hepatitis-infected individuals may be immunized against hepatitis virus. For hepatitis virus-infected individuals the vaccine may also be used boost their immune response and help fight against the hepatitis virus. Since the genetic vaccine can express high level of antigens and/or a variety of hepatitis glycoproteins and coreproteins simultaneously, the vaccinated individuals should be immunized against various strains and/or types of hepatitis virus, such as hepatitis A, B, C, D, and E virus. Additionally, since the genetic vaccine can express high levels of cytokines to mimic the body's response to natural viral infection, the body's immune response to such a genetic vaccine against hepatitis should be strong and long-lasting, thereby achieving a life-long immunity against the hepatitis virus.

5. Genetic Vaccines Against Ebola Virus

The genetic vaccine of the present invention also addresses the need for an efficient vaccine against the deadly virus, Ebola virus. According to the present invention the genetic vaccine may be a recombinant benign virus in which the viral genome carries one or more antigens from Ebola hepatitis, such as glycoproteins (e.g. GP1 and GP2) of Ebola virus. Sequences of these Ebola antigens may be modified such as deletion of the immunosuppressive regions and/or other pathogenic regions of the Ebola virus.

Ebola virus is one of the most lethal viruses known to mankind with a mortality rate of up to 90%. Johnson, K. M., *Ann Intern Med* 91(1):117-9 (1979). Victims of Ebola virus infection are subjected to a horrible hemorrhagic diseases which kills in a matter of days. The natural reservoir of the virus remains unknown, as do the specifics of pathogenesis of the infection. The virus has a very specific tropism for liver cells and cells of the reticuloendothelial system, such as macrophages. Massive destruction of the liver is hallmark feature of the disease.

Although Ebola virus infection is rare, there is concern by public health officials about the potential for the disease to become an international epidemic as the Ebola virus is easily transmitted through human contact and is extremely contagious. Outbreaks like those that have recently occurred in Africa could happen in industrialized countries due to the rapid and extensive nature of modern travel. Recent cases of Ebola virus infection in Africa send strong warnings to be prepared for the outbreaks of this extremely dangerous infectious disease. In addition, Ebola virus has a terrifying potential if used as a biological weapon by terrorist nations or organizations. As in most cases of viral infection, the best approach to prevent an outbreak of Ebola virus is through vaccination. However, currently there is no effective vaccine nor treatment available against Ebola virus infection.

Ebola viruses are enveloped, negative strand RNA viruses, which belong to the family Filoviridae. There are three strains of filoviruses: Ebola, Marburg and Reston. The Ebola virus can enter the body a number of different ways such as an opening through which air is taken in because the virus can travel on airborne particles and it can also enter the body through any opening in the skin, such as cuts.

The Ebola virus has a non-segmented RNA genome that encodes all the viral structural proteins (nucleoprotein, matrix proteins VP24 and VP40), non-structural proteins (VP30, VP35) and viral polymerase. Peters, C. J., *West J Med* 164(1):36-8 (1996). Among the viral proteins, the envelope glycoproteins (GP) exist in two forms, a secreted glycoprotein (50-70 kDa) and a transmembrane glycoprotein (130-170 kDa) generated by transcriptional editing. Sanchez, A. et al., *Proc Natl Acad Sci U.S.A.,* 93(8):3602-7 (1996). Although the two forms of GP share 295 amino acid homology, they have distinct binding specificities, suggesting that they play different roles in the course of viral infection. The secreted glycoprotein (sGP) is the predominant form synthesized and secreted by the infected cells. It may play a role in suppressing the host immune system (Yang, Z., et al., *Science* 279(5353): 1034-7 (1998)) and may serve as a decoy to allow the virus particle to escape from neutralizing antibodies, since the two forms of GPs partly share their antigenicity. Analysis of monoclonal antibodies from the human survivors of Ebola virus Zaire infection has revealed that the vast majority of them were specific to the sGP, and only a few bound weakly to GP. Maruyama, T., et al., *J Infect Dis,* 179 Suppl 1:S235-9 (1999), Maruyama, T., et al., *J Virol,* 73(7):6024-30 (1999). Although the exact mechanism by which the sGP may suppress the immune system is not clearly understood, the large amounts of sGP synthesized in the early phase of the infection are probably responsible for the inhibition of neutrophil infiltration of the infected sites (Yang, Z., et al., *Science* 279 (5353):1034-7 (1998)) and the absence of humoral immune response in Ebola virus infected patients. Baize, S., et al., *Nat Med,* 5(4):423-6 (1999). This protein may also act to overactivate many types of immune cells which can lead to massive intravascular apoptosis—essentially a shut-down of the immune system. Baize, S., et al., *Nat Med,* 5(4):423-6 (1999). The importance of the sGP to the Ebola virus life-cycle is also suggested by the fact it is present in all Ebola virus strains examined to date. Feldmann, H., et al., *Arch Virol Suppl,* 15:159-69 (1999).

The membrane glycoproteins are responsible for the attachment and penetration of the virions into target cells by mediating receptor binding and viral-cellular membrane fusion. Wool-Lewis, et al., *J. Virol,* 72(4):3155-60 (1998), Ito H., et al., *J. Virol,* 73(10):8907-12 (1999). They are synthesized as a single peptide precursor and cleaved by cellular enzymes (furin or cathepsin B) into the two mature forms, GP1 and GP2. The two GPs remain associated through a disulfide bond linkage and remain anchored in the viral membrane by a transmembrane (TM) domain. Ito H., et al., *J. Virol,* 73(10):8907-12 (1999); Malashkevich, V. N., et al., *Proc Natl Acad Sci U.S.A.,* 96(6):2662-7 (1999). The proteolytic cleavage site is composed of 4-5 basic amino acid residues that are similar to those found in the GPs of retrovirus, influenza, and paramyxoviruses. Garten, W., et al., Biochimie, 76(3-4):217-25 (1994). The cleavage event is essential for viral infectivity and is likely carried out by the same enzymes that cleave GPs of retrovirus or influenza viruses. Garten, W., et al., *Biochimie,* 76(3-4):217-25 (1994); Volchkov, V. E., et al., *Virology,* 245(1):110-9 (1994). In addition, Ebola virus GP may share a common mechanism of mediating viral infection with retroviral and influenza glycoproteins. Weissenhorn, W., et al., *Mol Membr Biol,* 16(1):3-9 (1999). Because membrane-bound GPs play critical roles in initiating virus infection and are also the predominant proteins exposed on the surface of the virions, they are the primary targets for neutralizing antibodies against the virus.

One of the properties of Ebola viruses that make them lethal to the host is their ability to suppress the host immune system. Serologic analysis of patients who died of the Ebola virus infection showed no signs of humoral or cellular immune responses. Baize, S., et al., *Nat Med,* 5(4):423-6 (1999). In contrast, antibodies against viral proteins and virus-specific T-cell activities were detected in a few survivors. Baize, S., et al., *Nat Med,* 5(4):423-6 (1999). Although the immunosuppressive mechanisms are yet to be understood, it is probable that the high levels of sGP and the immunosuppressive peptide in the GP are to blame for the absence of humoral and cellular immune responses in Ebola virus-infected patients.

The proteins that are responsible for the initial inflection of Ebola virus are the viral glycoproteins. Therefore, they are the target for neutralizing antibodies. However, Ebola virus has evolved "tricks" to prevent or delay the host immune response until it is too late to recover from the infection. Conventional approaches in producing vaccines against Ebola virus are likely to be ineffective for the following reasons: (1) viral glycoproteins produced in bacteria, yeast or insect cells are not properly glycosylated and therefore do not have the true antigenicity of the viral proteins; (2) Ebola virus is too dangerous to be produced in large amounts as an inactivated-virus vaccine; and (3) procedures of inactivating the virus often destroy the conformation of the proteins, and therefore alter their antigenicity.

A preferred embodiment of the present invention is a recombinant viral vaccine having nucleic acids encoding one or more antigens of Ebola virus. Restriction maps and full sequence information of the Ebola virus, including the Zaire strain, is available through GenBank.

The genetic vaccine is a recombinant benign virus which is replication defective or incompetent and therefore is incapable of spreading beyond initially infected cells. For example, a recombinant adenoviral vaccine of the present invention mediates high levels of Ebola viral antigen expression for a period of two or more weeks, even though Ebola viral proteins have no functional relevance to recombinant virus function.

In another embodiment of the invention, the recombinant virus expresses one or more modified Ebola virus antigens. The modified Ebola virus antigens are preferably Ebola virus envelope glycoproteins and/or immunogically active parts thereof. Preferably the glycoproteins are modified GP and sGP glycoproteins. The Ebola virus GP and sGP glycoproteins are modified to destroy their pathogenic and immunosuppressive functions, but retain most of their natural antigenicity, since they are expressed, folded, glycosylated, and targeted to the cellular membrane inside the cells that can be productively infected by the Ebola virus. The modifications are carried out using standard molecular genetic manipulation techniques such as restriction digests and polymerase chain reaction.

A preferred modification of the Ebola virus envelope glycoprotein destroys the infective function of the Ebola virus GP. Any modification that destroys the infective function of Ebola virus can be used, but preferably the modification is a five amino acid deletion in the cleavage site of the GP. See Example 1. This cleavage site is composed of five basic amino acid residues, RRTRR, at position 501 from the start of the open reading frame. This deletion may be introduced into the Ebola virus GP cDNA using PCR amplification, which is performed by methods well known in the art.

Another preferred modification of the Ebola virus viral genome prevents synthesis of the sGP. Any modification that prevents synthesis may be employed. Preferably the modification is directed to altering the RNA editing site from UUUUUUU (SEQ ID NO. 2) to UUCUUCUU (SEQ ID NO. 3). See example 1.

Figure 2:
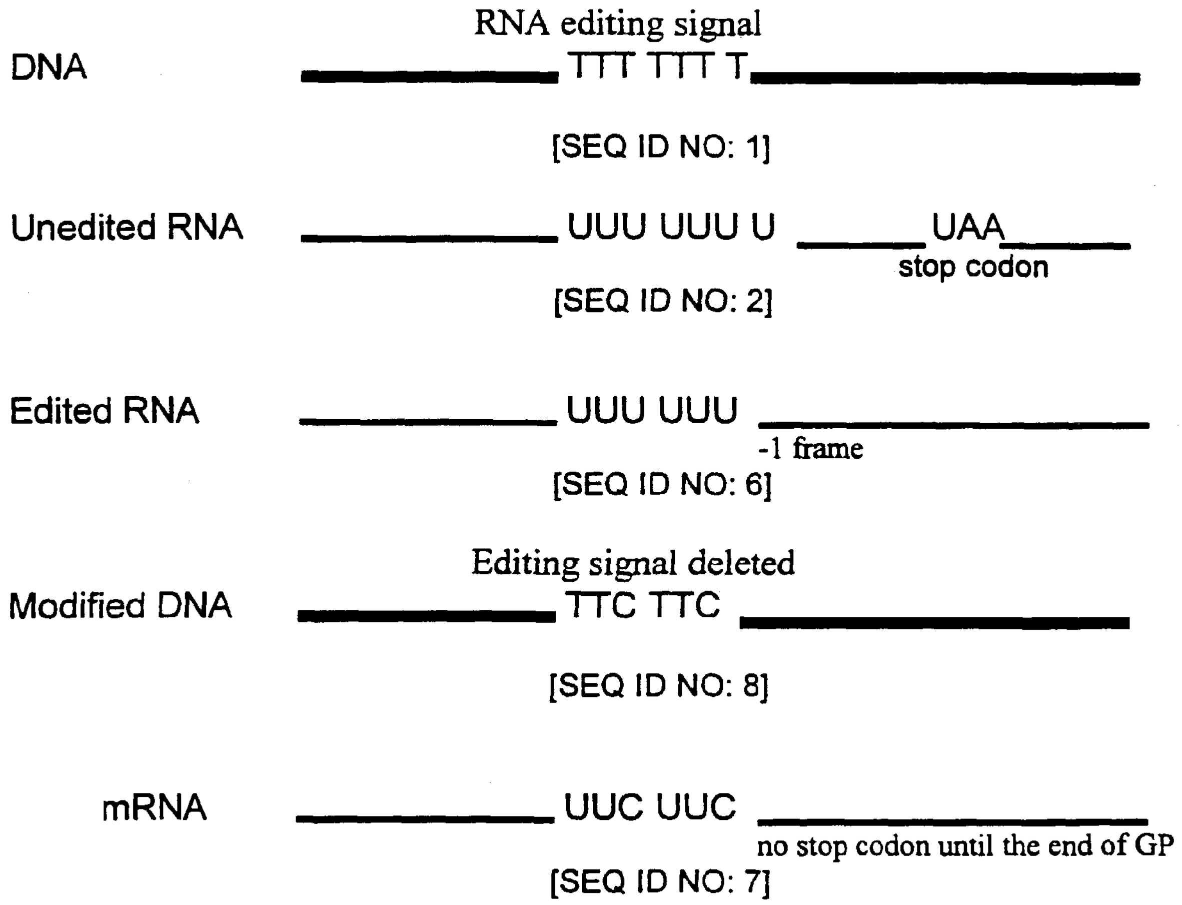
FIG. 2 illustrates the wild-type GP gene, which encodes the two forms of glycoproteins (sGP and GP), contains a RNA editing signal that results in un-edited and edited mRNAs. The sGP is synthesized from an un-edited mRNA and the GP is synthesized from an edited mRNA (having an insertion on one of the seven uridines).

Another preferred modification to Ebola virus antigen used in the present vaccines is immunosuppressive (IS) peptide located in GP2. The IS peptide motif is located at amino acids 585-609. A ten amino acid deletion between amino acide 590-600 removes its function. Second, each half of the IS peptide motif is reversed and duplicated. See FIG. 2. This further ensures that its function has been destroyed and also increases its antigenicity.

Further it is readily apparent to those skilled in the art that variations or derivatives of the nucleotide sequences encoding Ebola virus antigen(s) of the present invention can be produced, which alter the amino acid sequence of the encoded protein. The altered expressed antigen(s) may have an altered amino acid sequence, yet still elicit immuneresponses that react with Ebola virus antigen(s), and are considered functional equivalents. In addition, fragments of the full-length genes that encode portions of the full-length protein may also be constructed. These fragments may encode a protein or peptide which elicits antibodies which react with Ebola virus antigen(s), and are considered functional equivalents.

Vaccination of an individual with the vaccines of the present invention results in entrance of adenoviral particles into cells and expression of Ebola virus antigen(s), such as the envelope glycoproteins, and the immune-stimulating cytokines. The expression of Ebola virus antigen(s) in cells induces strong and persistent immune responses as if an infection has occurred. The genetic vaccine has all of the immunogenicity of a natural infection, including expression of the natural viral proteins and long-lasting antigen stimulation, but does not have the pathogenicity of a true viral infection. In the vaccines of the present invention, the immunosuppressive mechanisms of Ebola virus are disabled, the antigens occur in their natural forms and are associated with the cell membrane, and immune stimulation lasts for weeks. The effects of this novel vaccine are long lasting and provide high rates of protection against Ebola virus infection.

The present invention is also directed to a method of immunizing a human against Ebola virus infection comprising administering the vaccines described above. The techniques for administering these vaccines to humans are known to those skilled in the health fields.

By using the genetic vaccine of the present invention, individuals may be immunized against Ebola virus. Since the genetic vaccine can express high levels of antigens and/or a variety of glycoproteins simultaneously, the vaccinated individuals should be immunized against various strains Ebola virus. Additionally, since the genetic vaccine can express high levels of cytokines to mimic the body's response to natural viral infection, the body's immune response to such a genetic vaccine against Ebola virus should be strong and long-lasting, thereby achieving a life-long immunity against the Ebola virus.

6. Formulation and Routes of Administration

The present invention also relates to a pharmaceutical composition comprising the vaccine(s) described above, and a pharmaceutically acceptable diluent, carrier, or excipient carrier. Additionally the vaccine may also contain an aqueous medium or a water containing suspension, often mixed with other constituents in order to increase the activity and/or the shelf life. These constituents may be salt, pH buffers, stabilizers (such as skimmed milk or casein hydrolysate), emulsifiers, and preservatives.

An adjuvant may be included in the pharmaceutical composition to augment the immune response to the viral antigen expressed from the recombinant virus. Examples of the adjuvant include, but are not limited to, muramyl dipeptide, aluminum hydroxide, saponin, polyanions, anamphipatic substances, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believed to reduce tumor-induced suppression when given in low doses.

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention can be administered in a conventional active immunization scheme: single or repeated administration in a manner compatible with the dosage formulation, and in such amount as will be prophylactically effective, i.e. the amount of immunizing antigen or recombinant microorganism capable of expressing the antigen that will induce immunity in humans against challenge by the pathogenic virus or bacteria, such virulent Ebola virus, HIV, hepatitis A, B, C, D, and E virus, and bacillus tuberculous. Immunity is defined as the induction of a significant level of protection after vaccination compared to an unvaccinated human.

The vaccine of the present invention, i.e. the recombinant virus, may be administered to a host, preferably a human subject, via any pharmaceutically acceptable routes of administration. The routes of administration include, but are not limited to, intramuscular, intratracheal, subcutaneous, intranasal, intradermal, rectal, intramucusally, oral and parental route of administration. Routes of administration may be combined, if desired, or adjusted depending upon the type of the pathogenic virus to be immunized against and the desired body site of protection.

The route of administration can be particularly important in influencing the nature of induced immunity, and the degree of protection. For example, while parenteral administration may only activate a systemic immune response, whereas the oral route provides, in addition, mucosal immune response. The ability of the recombinant viruses of the present invention to elicit a mucosal immunity renders its application important in mucosally and sexually transmitted infection.

Doses or effective amounts of the recombinant virus may depend on factors such as the condition, the selected viral or bacterial antigen, the age, weight and health of the host, and may vary among hosts. In general, one skilled in the art understands that the amount of virus particles to be administered depends, for example, on the number of times the vaccine is administered and the level of response desired.

The appropriate titer of the recombinant virus of the present invention to be administered to an individual is the titer that can modulate an immune response against the viral or bacterial antigen and elicits antibodies against the pathogenic virus or bacteria from which the antigen is derived. An effective titer can be determined using an assay for determining the activity of immunoeffector cells following administration of the vaccine to the individual or by monitoring the effectiveness of the therapy using well known in vivo diagnostic assays. For example, a prophylactically effective amount or dose of a recombinant adenovirus of the present invention may be in the range of from about 100 μl to about 10 ml of saline solution containing concentrations of from about $1\times10^4$ to $1\times10^8$ plaque forming units (pfu) virus/ml. When other plasmid DNA vectors are used, 1-1000 μg per administration is the preferred dose range. The dose may be the same for priming and boosting immunizations or it may be desired to alter quantity of recombinant viruses provided in the boosting phase as compared to the initial priming dose. The dose of an inoculum of the recombinant virus of the present invention is dictated by and dependent upon the unique characteristics of the particular recombinant virus and the particular immunologic effect to be achieved, as is well-recognized by the skilled artisan.

7. Methods of Enhancing the Immunity of a Host to Pathogens

The present invention also provides methods for enhancing the immunity of a host to pathogens with the recombinant viruses described above.

In one embodiment, the method is provided for enhancing the immunity of a host to a pathogenic virus. The method comprises: administering to the host a recombinant virus in an amount effective to induce an immune response. The recombinant virus comprises: an antigen sequence heterologous to the benign virus and encoding a viral antigen from a pathogenic virus, expression of the viral antigen eliciting an immune response directed against the viral antigen and cells expressing the viral antigen in the host upon infection of the host by the recombinant virus; and an immuno-stimulator sequence heterologous to the benign virus that encodes an immuno-stimulator whose expression in the host enhances the immunogenicity of the viral antigen. The recombinant virus may preferably be replication-incompetent and not cause a malignancy naturally associated with the pathogenic virus in the host.

The recombinant virus may be administered to the host via any pharmaceutically acceptable route of administration. The recombinant virus may be administered to the host via a route of intramuscular, intratracheal, subcutaneous, intranasal, intradermal, intramucosally, rectal, oral and parental administration.

In another embodiment, a method is provided for immunizing a host against a pathogenic virus with multiple antigens that elicit strong and long-lasting immune response to the multiple antigens. The method comprises: administering to the host a recombinant virus in an amount effective to induce an immune response. The recombinant virus comprises: a plurality of antigen sequences heterologous to the recombinant virus, each encoding a different viral antigen from one or more pathogenic viruses, expression of the plurality of the antigen sequences eliciting an immune response directed against the viral antigen and cells expressing the viral antigen in the host upon infection of the host by the recombinant virus. The recombinant virus may preferably be replication-incompetent and not cause malignancy that is naturally associated with the pathogenic virus(es) in the host.

Optionally, the recombinant virus may also comprise one or more immuno-stimulator sequences heterologous to the recombinant virus that encodes an immuno-stimulator whose expression in the host enhances the immunogenicity of the viral antigen.

In yet another embodiment, a method is provided for immunizing a host against a pathogenic virus by using multiple genetic vaccines or viruses. Multiple recombinant viruses may carry different antigens in each recombinant virus. The multiple recombinant viruses may be administered simultaneously or step-wise to the host.

The method comprises: administering to a host a first and second recombinant viruses in an amount effective to induce an immune response, wherein antibodies are produced. The first recombinant benign virus comprises: an antigen sequence heterologous to the first recombinant virus that encodes a viral antigen from a pathogenic virus, expression of the viral antigen eliciting an immune response directed against the viral antigen and cells expressing the viral antigen in the host upon infection of the host by the recombinant virus. The second recombinant virus comprises: an immuno-stimulator sequence heterologous to the second recombinant virus that encodes an immuno-stimulator whose expression in the host enhances the immunogenicity of the viral antigen. The first and second recombinant viruses may preferably be replication-incompetent and not cause malignancy naturally associated with the pathogenic virus in the host.

According to the embodiment, the first and second recombinant virus may be any of a benign virus, such as replication-incompetent adenovirus, adeno-associated virus, SV40 virus, retrovirus, herpes simplex virus, Alpha virus, Venezuelan Equine Encephalitis (VEE) virus and vaccinia virus. Optionally, both the first and second recombinant viruses may be replication-incompetent adenovirus. Also optionally, one of the first and second recombinant viruses may be recombinant adenovirus and the other may be recombinant vaccinia virus.

In yet another embodiment, a method is provided for enhancing the immunity of a host to a pathogen. The method comprises: administering to the host a recombinant virus and one or more immuno-stimulators. The recombinant virus may be any of the recombinant viruses described above. In particular, the recombinant virus comprises one or more antigen sequences heterologous to the recombinant virus that encode one or more antigens from the pathogen. Expression of the antigen elicits an immune response directed against the antigen and cells expressing the antigen in the host upon infection of the host by the recombinant virus. The recombinant virus is preferably replication-incompetent and does not cause a malignancy naturally associated with the pathogen in the host. The pathogen may be a pathogenic virus such as HIV, hepatitis virus and Ebola virus, a pathogenic bacteria or parasite.

According to this embodiment, the immuno-stimulator may be any molecule that enhances the immunogenicity of the antigen expressed by the cell infected by the recombinant virus. Preferably, the immuno-stimulator is a cytokine, including, but not limited to interleukin-2, interleukin-8, interleukin-12, β-interferon, λ-interferon, γ-interferon, granulocyte colony stimulating factor, granulocyte-macrophage colony stimulating factor, and combinations thereof.

The cytokine may be administered into the host in a form of purified protein. Alternatively, the cytokine may be administered in a form of expression vector that expresses the coding sequence of the cytokine upon transfecting or transducing the cells of the host.

According to any of the above embodiments of the methods, the method may further comprise: administering to the host the recombinant virus again to boost the immune response. Such a booster inoculation with the recombinant virus is preferably conducted several weeks to several months after the primary inoculation. To insure sustained high levels of protection against infection or an efficacious treatment of the disease(s) caused by infection of the pathogen, it may be helpful to re-administer the booster immunization to the host at regular intervals, for example, once every several years. The recombinant virus administered in the booster immunization may be the same as or different from the recombinant virus administered in the primary immunization.

Also according to any of the above embodiments of the methods, the method may further comprise: administering to the host a plasmid vector that encodes the same or different antigen(s) as that (or those) encoded by the recombinant virus. The plasmid vector is preferably a eukaryotic plasmid expression vector that expresses the antigen(s) upon transfection of the cells in the host.

Also according to any of the above embodiments of the methods, the method may further comprise: administering to the host a second recombinant virus to boost the immune response and/or to minimize neutralizing effects of the host's immune system on the recombinant viruses.

Optionally, the second recombinant virus comprises a second antigen sequence from a second pathogen that is different from the first antigen sequence comprised in the first recombinant virus administered in the primary immunization. Preferably, the second antigen sequence encodes the same type of antigen as that encoded by the first antigen sequence but from a different strain, serotype, or subtype/clade of the same pathogen. Alternatively, the second antigen may be a different type of antigen compared to the first antigen, for example, the first antigen being a surface protein and second antigen being a core protein of the same or different pathogen.

Also according to any of the above embodiments of the methods, the method may further comprise: administering to the host a viral vector prior to, concurrently, or post the administration of any of the above embodiment of the recombinant virus to minimize neutralizing effects of the host's immune system on the recombinant virus. Preferably, the viral vector is administered post the administration of the recombinant virus.

The viral vector may be the native progenitor of the recombinant virus. For example, the viral vector may be the wildtype adenovirus type 5 (Ad5) whereas the recombinant virus is a genetically modified Ad5.

Optionally, the viral vector may be the wildtype of or a genetically modified virus that is a different serotype of the recombinant virus. For example, the recombinant virus may be a genetically modified Ad5 whereas the viral vector is the wildtype of or a genetically modified adenoviral vector serotype other than Ad5, for example, serotype 1-4 or 6-51. It is noted that other serotypes discovered and/or classified later also fall within the scope of the invention.

For example, the recombinant virus is a recombinant Ad5 encoding one or more heterologous antigens and/or an immunostimulator while the viral vector may also be a recombinant adenovirus encoding the same or different antigens and/or the immunostimulator but of different serotype (e.g., Ad2, Ad4, Ad9, Ad12, Ad35 and Ad40). Such a serotype rotation is believed to enhance expression of the transgenes and increase immunogenicity of the vaccines. To verify this belief, a wildtype non-Ad5 vector can be administered to mice first and the levels of anti-adenovirus antibody are measured by ELISA 3 weeks after the injection. The recombinant Ad5 encoding a heterologous antigen (e.g., HBV core protein) is then administered to the mice 4-5 weeks after the primary injection. The levels of antibody against the heterologous antigen (e.g., the HBV core protein) can be measured 4-5 weeks after the secondary injection.

Also optionally, the viral vector may be a different virus from the recombinant virus. For example, the recombinant virus may be a genetically modified Ad5 whereas the viral vector is a genetically modified MV, SV40 virus, retrovirus, herpes simplex virus, Alpha virus, Venezuelan Equine Encephalitis (VEE) virus or vaccinia virus. The viral vector may or may not comprise a heterologou antigen sequence. Preferably, the viral vector may comprise another antigen sequence which is the same or different from the antigen sequence carried by the recombinant virus.

Figure 62:
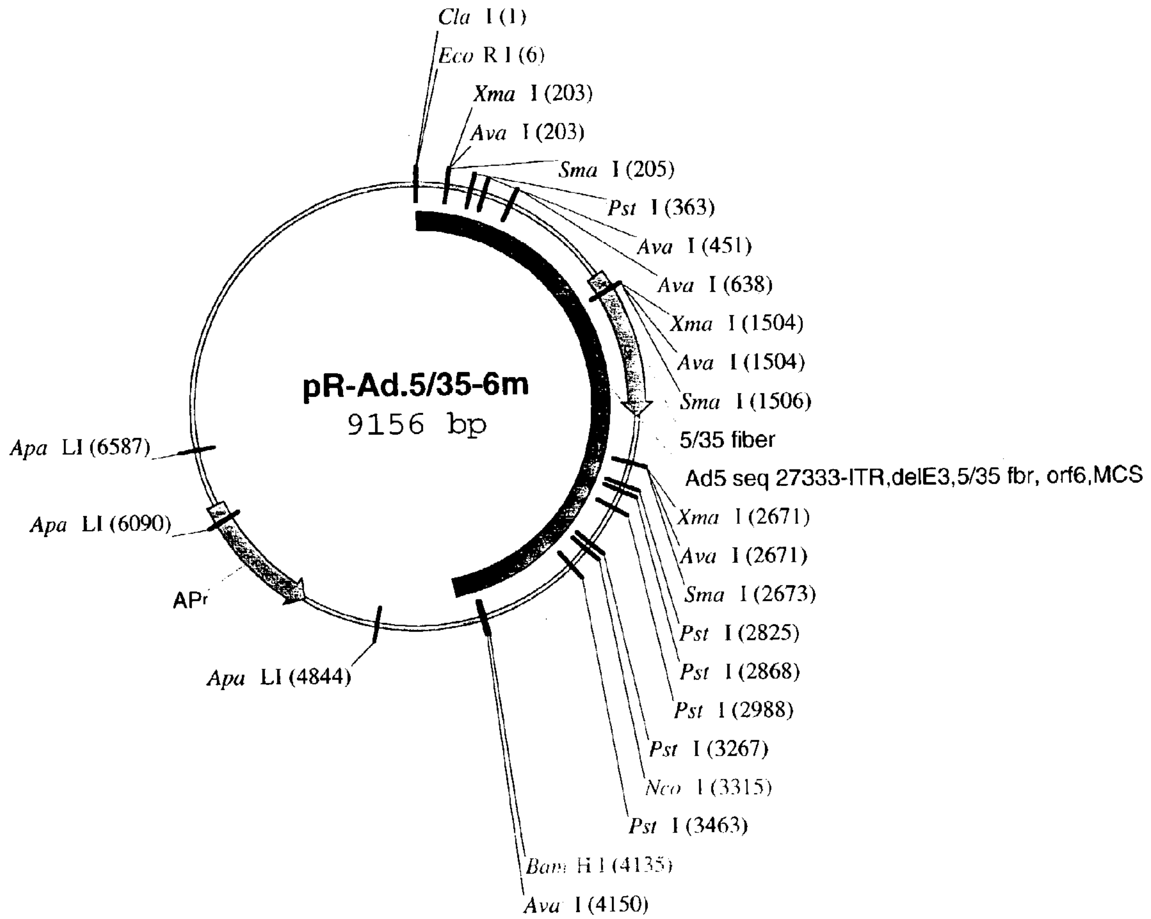
FIG. 62 illustrates a right shuttle vector pR-Ad.5/35-6m.

Also optionally, the viral vector may be a chimeric vector modified based on the native progenitor of the recombinant virus. For example, if the native progenitor of the recombinant virus is adenovirus type 5, the viral vector may be a chimeric adenovirus type 5 with certain regions of the backbone changed from type 5 to the corresponding regions from other adenovirus serotypes. This approach is believed to be advantageous because of the ease of cloning when only a portion of the backbone with the corresponding one of another serotype. This may be accomplished by constructing a shuttle vector by including Ad5 fiber DNA and switching the Ad5 fiber DNA partially or completely with that from another serotype of adenovirus. As shown in FIG. 62, a right shuttle vector pR-Ad.5/35-6m is constructed to the replace the fiber region of Ad5 with that of Ad35. This right shuttle vector can be combined with a left shuttle vector and the Ad5 backbone to generate a chimeric Ad5 vector.

Up to date, 51 serotype of human adenovirus have been identified and divided into six subgroups from A to F. The adenovirus entry into the cells is a two-step process consisting of virus attachment to the membrane via the Ad fiber knob, followed by internalization upon binding of the penton base RGD motifs to $\alpha v\beta 3$ and $\alpha v\beta 5$ integrins on the cell surface. De Long et al. (1999) J. Clin. Microbiol. 37:3940; Sallusto et al. (1994) J. Exp. Med. 179:1109; Huang et al. (1995) J. Virol. 69:2257-2263; and Mathias et al. (1994) J. Virol. 68:6811-6814.

The adenovirus fiber is considered to be a crucial mediator for high efficiency binding to target cells. Subgroup C, Ad5 fiber uses the coxsackievirus and adenovirus receptor (CAR) to mediate the high affinity binding. Nemerow (1999) Mol. Biol. Rev. 63:725-734. In CAR-deficient cells, Ad5 attachment occurs at much lower efficiency through alternative pathways involving interactions between the fiber and the MHC class I heavy chain $\alpha 2$ domain or between the penton and cellular integrins. Bergelson et al. (1997) Science 275: 1320-1323.

The adenovirus fiber can be divided into three domains. The conserved N-terminal tail contains the sequences responsible for association with the penton base. De Long et al. (1999) *J. Clin. Microbiol.* 37:3940. The rod-like fiber shafts contains number of repeats ranging from 6 to 23 form the $\beta$ sheets. Davison et al. (1999) J. Virol. 73:4513. The C-terminal contains globular knob domains, which both fiber shaft and knob are involved in the primary receptor interaction. Huang et al. (1996) J. Virol. 70:4502.

Figure 63:
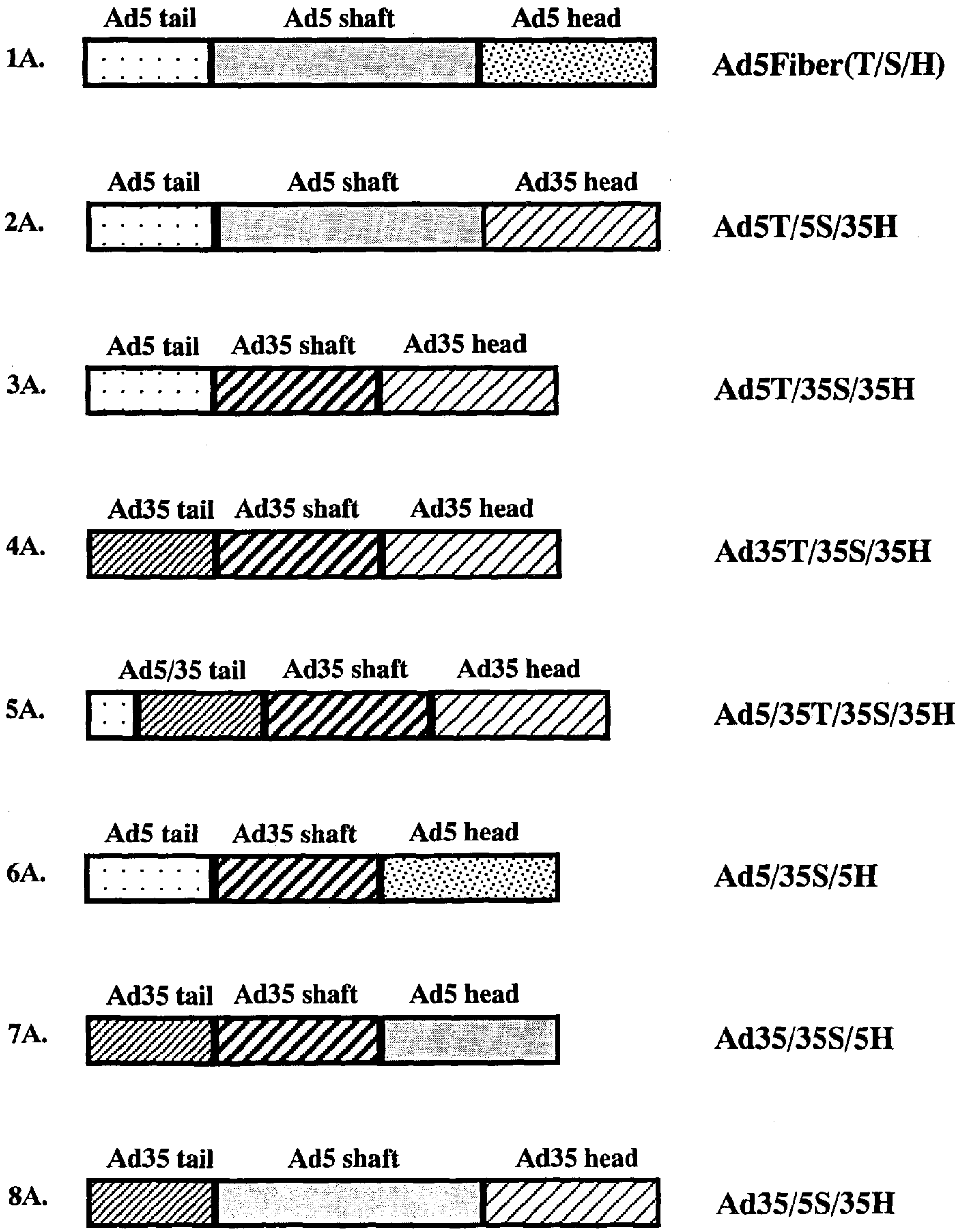
FIG. 63 shows various embodiments of chimeric vectors having the individual domains of the Ad5 fiber regions substituted with the corresponding domains of Ad35 fiber region.

According to the present invention, for example, the fiber knob (i.e., the head), shaft, and/or penton base (i.e., the tail) in the backbone of adenovirus type 5 can be replaced by the corresponding region(s) of the backbone from adenovirus serotype 1-4, and 6-51. FIG. 63 shows various embodiments of the chimeric vectors having the individual domains of the Ad5 fiber regions substituted with the corresponding domains of Ad35 fiber region. Preferably, the knob domain of the fiber region of Ad5 is swapped with the corresponding one from another serotype of adenovirus since the knob domain is believed to determine the receptor-ligand interaction.

For example, the recombinant virus is a recombinant Ad5 encoding one or more heterologous antigens and/or an immunostimulator while the chimeric viral vector may also be a recombinant Ad5 encoding the same or different antigens and/or the immunostimulator but having a fiber region from adenovirus of different serotype (e.g., Ad2, Ad4, Ad9, Ad12, Ad35 and Ad40). Such a serotype rotation is believed to enhance expression of the transgenes and increase immunogenicity of the vaccines. To verify this belief, an Ad5 vector carrying GFP can be administered to mice first and the levels of anti-GFP antibody are measured by ELISA 4 weeks after the injection. Another recombinant Ad5 also carrying GFP but having a fiber region from different serotype adenovirus (e.g, Ad9, Ad11, or Ad35) is then administered to the mice 4-5 weeks after the primary injection. The levels of antibody against GFP can be measured 4-5 weeks after the secondary injection.

The methods described above may be used for prevention or treatment of diseases. In the method of treatment, the administration of the recombinant viruses of the present invention may be for either "prophylactic" or "therapeutic" purpose. When provided prophylactically, the recombinant virus is provided in advance of any symptom. The prophylactic administration of the recombinant virus serves to prevent or ameliorate any subsequent infection.or disease. When provided therapeutically, the recombinant virus is provided at (or after) the onset of a symptom of infection or disease. Thus, the present invention may be provided either prior to the anticipated exposure to a disease-causing agent or after the initiation and/or progression of the infection or disease.

It is noted that the innovative approaches of the present invention may also be employed in the construction of cancer vaccines. For example, sequences encoding tumor-specific antigens may substitute the antigen sequence encoding viral antigen in any of the above embodiments of the recombinant virus and methods of using the same. Expression of tumor-specific antigens in the host should elicit specific immune response for prevention in patients with an increased risk of cancer development (i.e., preventive immunization) or to enhance the treatment of cancer with other therapeutics, prevention of disease recurrence after primary surgery (anti-metastatic vaccination), or as a tool to expand the number of CTL in vivo, thus improving their effectiveness in eradication of diffuse tumors (treatment of established disease). In addition, the methods of the present invention may elicit an immune response in a patient that is enhanced ex vivo prior to being transferred back to the tumor bearer (i.e., the adoptive immunotherapy).

Also according to any of the above embodiments of the methods, the method may further comprise: harvesting serum from the host after the administration of the recombinant virus. The harvested serum should contain antibodies against the antigen(s) encoded by the recombinant virus. Optionally, the method may further comprise: isolating antibody or antibodies against the pathogen from the host after the administration of the recombinant virus. The harvested serum or isolated antibody can be stored for certain periods of time for further uses. For example, a healthy human volunteer can serve as the host and the serum or antibody collected from him/her may be administered back to him/herself or a different person later to in anticipation or in the event of infection of the pathogen as prophylactic or therapeutic agent by eliciting passive immunity against the pathogen. Optionally, the host may be a non-human animal and the serum harvested or antibody isolated from the animal immunized by the recombinant virus may be used as a prophylactic or therapeutic agent to treat a human or non-human animal in anticipation or in the event of infection of the pathogen such as in the outbreak of biological warfare.

It should be noted that modifications and changes can be made in the DNA sequence of any of the above-described antigens and immuno-stimulators included in the recombinant virus and still maintain functional equivalence of the mutant. For example, wildtype codons for the above-described antigens can be replaced with codons that are preferred by the host to be immunized, e.g., a human. Synthetic polynucleotide can be made to include the preferred codons for the "humanized" antigens. Such a humanization process may be advantageous in that by using the preferred codons, translation efficiency of the antigens expressed by the recombinant virus can be significantly improved, which in turn can result in higher levels of humoral and/or cellular immune responses in the host. All of the above-described mutants fall within the scope of the present invention.

Standard procedures for endonuclease digestion, ligation and electrophoresis are carried out in accordance with the manufacturer's or supplier's instructions. Standard techniques are not described in detail and will be well understood by persons skilled in the art. Practicing the present invention employs, unless otherwise indicated, conventional methods of virology, microbiology, molecular biology and recombinant DNA techniques within the skill of the art. Such techniques are explained fully in the literature. See e.g. Sambrook, et al. *Molecular Cloning: A laboratory Manual; DNA Cloning: A Practical Approach*, vol I & II (D. Glover ed.); *Oligonucleotide Synthesis* (N. Giat, ed.); *Nucleic Acid Hybridization* (B. Hames & S. Higgins, eds., Current Edition); *Transcription and Translation* (B. Hames & S. Higgins, eds., Current Edition); *Fundamental Virology*, 2nd Edition, vol. I & II (B. N. Fields and D. M. Knipe, eds.)

The following examples are provided to illustrate the present invention without, however limiting the same thereto.

EXAMPLES

The following procedures are described to illustrate how to make a genetic vaccine of the present invention against various pathogenic viruses. The genetic vaccine is based on an adenoviral vector with modified antigens derived from the pathogenic virus (e.g., Ebola virus, Hepatitis B virus and HIV) inserted into the adenoviral backbone. Additionally, the recombinant adenovirus also carries multiple genes encoding various cytokines. The recombinant adenovirus is replication-incompetent but still retains adenoviral infectivity. It is noted that genetic vaccine against other pathogenic viruses, bacteria and parasites may be constructed by one with ordinary skill in the art following similar procedures described in details below.

1. Genetic Vaccine Against Ebola Virus

Embodiments of the genetic vaccine against Ebola virus and methods of their construction are described in detail as follows.

1) Genetic Modification of the Ebola Virus Membrane Glycoproteins

The modifications are carried out using standard molecular genetic manipulation techniques, such as restriction enzyme digests and polymerase chain reaction (PCR).

The glycoproteins of Ebola virus are modified to produce the optimal antigen for Ebola virus vaccine. Two modified forms of the GP proteins are constructed to have inactivated immunosuppressive and infectious mechanisms, but retain full natural antigenicity of the wild-type glycoproteins. The mRNA editing signal is deleted to prevent the production of the secreted glycoprotein (sGP), which is immunosuppressive; and (2) the proteolytic cleavage site of the glycoprotein precursor is deleted to prevent the formation of the functional glycoproteins (GP1 and GP2). Sanchez, A., et al., *Proc Natl Acad Sci U.S.A.* 93(8):3602-7 (1996). In one form the immunosuppressive peptide region is deleted to prevent its function, and in the other form, the immunosuppressive peptide motif is split in order to destroy its function, but retain its immunogenicity. These steps produce effective and safe antigens for the vaccine.

The envelope glycoproteins (GP) of the Ebola virus are synthesized as a single precursor protein and cleaved into the two subunits (GP1 and GP2) by a cellular enzyme (furin) during transport. Volchkov, V. E., et al., *Proc Natl Acad Sci U.S.A.,* 95(10):5762-7 (1998). This proteolytic cleavage is essential for the formation of the mature glycoproteins and the release of the fusion peptide located at the C-Terminus of the cleavage site. The mature glycoproteins are incorporated into virions as trimers (each monomer is a heterodimer of GP1 and GP2 linked by a disulfide bond). Sanchez, A., et al., *J. Virol* 72(8):6442-7 (1998). The glycoproteins of Ebola virus are the major proteins exposed on the viral membrane surface, and are responsible for initiating virus entry into host cells. Therefore, they are a primary target for neutralizing antibodies.

The glycoprotein cleavage site is composed of five basic amino acid residues (RRTRR [SEQ ID NO: 10]) at position 501 from the start site of the open reading frame. The Ebola virus glycoprotein cleavage site is similar to the conserved sequences found in glycoproteins of other viruses, such as in the envelope protein of RSV or MuLV. We have previously shown that deletions or point mutations at these basic amino acid residues can block cleavage and render the glycoproteins non-functional in RSV. Dong, J. Y, et al., *J. Virol* 66(2):865-74 (1992).

To destroy the infective functions of the Ebola virus glycoprotein, the five basic amino acid residues in the cleavage site are deleted. This deletion is introduced into the Ebola virus GP cDNA using PCR amplification. Alternatively, the cleavage site can be altered, such as by site specific mutation resulting in elimination of cleavage.

Another important feature of the Ebola virus is that two forms of glycoproteins are synthesized from a single gene, a secreted from (sGP) and a membrane-bound form (GP). The two forms are generated as a result of an alternative RNA editing event at a sequence of seven uridines (at location 1020-1028 from the start site), which is highly conserved among all four Ebola virus subtypes. Sanchez, A., et al., *Proc Natl Acad Sci U.S.A.* 93(8):3602-7 (1996). The sGP is synthesized from un-edited mRNA and likely has immunosuppressive functions. The GP is synthesized from an edited mRNA and likely has immunosuppressive functions. The GP is synthesized from an edited mRNA with insertion in one of the seven uridines. This RNA editing causes a frame-shift and results in a translation of the second reading frame that encodes the complete transmembrane glycoprotein (GP2).

To prevent the synthesis of sGP, the RNA editing site is modified from UUUUUUU [SEQ ID NO: 2] to UUCUUCUU [SEQ ID NO: 3]. In the cDNA, the equivalent sequence is AAAAAAA [SEQ ID NO: 4] and AAGAAGAA [SEQ ID NO: 5], respectively. This modification accomplishes two things: (1) all mRNAs encode only the GP (equivalent to the edited form with −1 frame shift); and (2) UUUUUU [SEQ ID NO: 6] encodes the same animo acid residues as UUCUUC [SEQ ID NO: 7], but prevents the possibility of further polymerase slipping at the stretch of the six uridines. The additional editing would cause deletion of one more uridine and further (−2) frame shifting. The mechanism of this modification is diagramed in FIG. 2.

A third modification may be introduced into the Ebola virus glycoprotein relating to a deletion of the immunosuppressive (IS) peptide located in GP2. The IS peptide motif (amino acid 585-609, form the start site) is highly conserved in filoviruses and has a high degree of homologywith a motif in the glycoproteins of oncogenic retroviruses that has been shown to be immunosuppressive. Volchkov, V. E., et al., *FEBS Lett* 305(3):181-4 (1992); Will, C., et al., *J. Virol* 67(3):1203-10 (1993); Mitani, M., et al., *Proc Natl Acad Sci U.S.A.* 84(1):237-40 (1987); Gatot, J. S., et al., *J. Biol Chem* 273(21):12870-80 (1998); Denner, J., et al., *J Acquir Immune Defic Syndr Hum Retrovirol* 12(5):442-50 (1996). First, a ten amino acid deletion is introduced in the core region of the motif (between amino acid 590-600) to remove its function. Second, each half of the motif is reversed and duplicated to destroy function and increase antigenicity. It is believed that antibodies against the IS peptide may inhibit the immunosuppressive function of the Ebola viruses during an infection. The basic strategy of this modification is diagrammed in FIGS. 3A-3C.

Figures 3A, 3B, 3C:
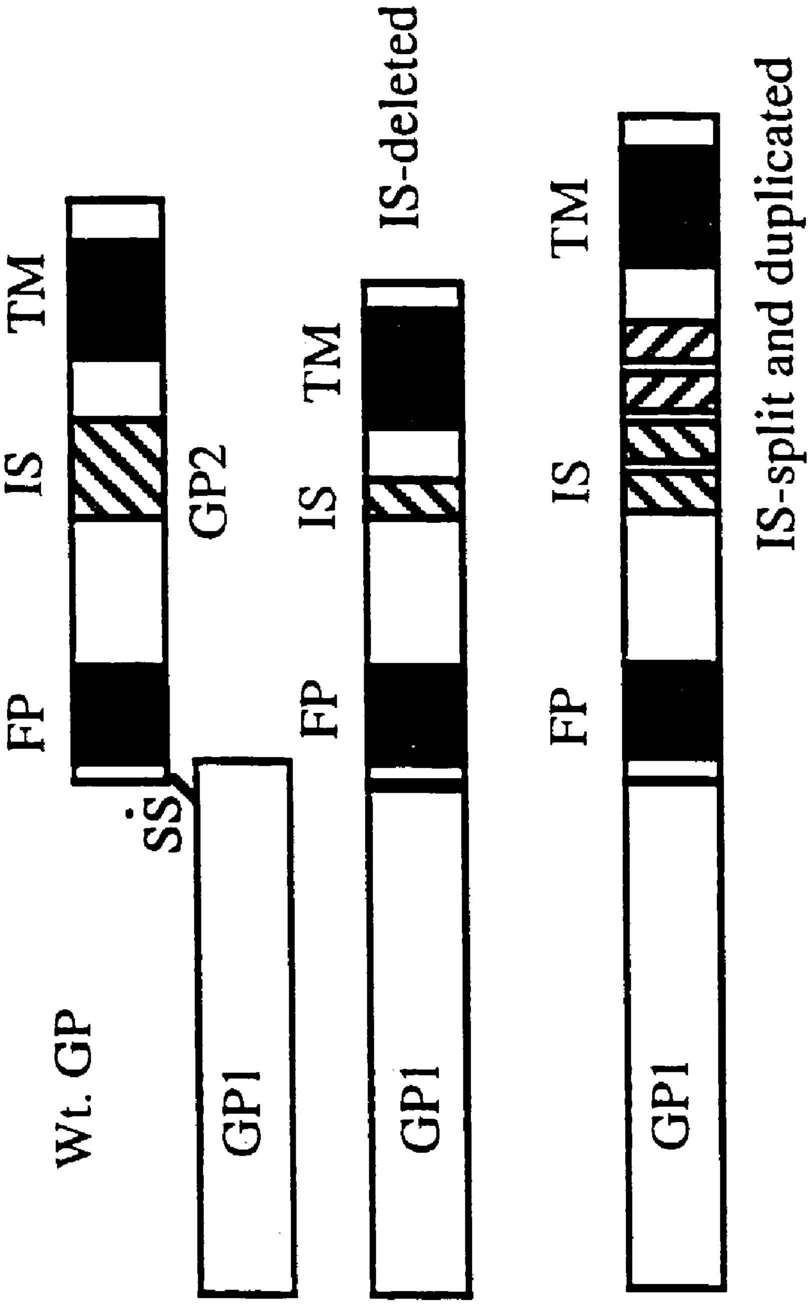
FIG. 3A shows the wild type GP.
FIG. 3B shows GP with the 10 amino acid deletion of the IS peptide.
FIG. 3C shows the IS peptide, which is split, reversed and duplicated. Abbreviations: FP, Fusion peptide; IS, Immunosuppressive peptide; TM, Transmembrane domain.

As illustrated in FIGS. 3A-3C, modification of the immunosuppressive peptide (IS) is made on the GP2 gene. FIG. 3A illustrates the wild type GP. FIG. 3B illustrates GP with the 10 amino acid deletion of the IS peptide. FIG. 3C illustrates the IS peptide, which is split, reversed and duplicated.

With these modifications, Ebola virus glycoproteins are generated that are non-functional, not immunosuppressive, yet they retain the natural antigenicity of GP. These modified GP sequences are used to generate antigens in the vaccines of the present invention against Ebola virus.

DNA sequences of the resulting altered GP genes are confirmed by sequence analysis. The modified GP sequences are then cloned intoplasmid vectors containing DNA elements necessary for efficient expression of these GPs in hostian cells. Expression and correct localization to the cellular membrane is determined by transient transfections of HeLa or 293 cells and analyzed by Western blot and FACS, using polyclonal antibodies from hyperimmunized equine serum and anti-horse secondary antibodies labeled with horse radish peroxidase (HRP) or fluorescent tags, respectively.

2) Construction of a Series of Replication-Defective Adenoviral Vaccines that Mediate High Levels of Expression of the Modified Ebola Virus GPs The vaccines of the present invention utilize a recombinant benign virus to carry modified antigens of Ebola virus to trick the host into mounting a robust immune defense against the Ebola virus. The preferred benign virus is a replication-defective adenovirus. These vectors are an excellent choice for vaccine expression, for several reasons. First, adenoviral vectors direct high levels of antigen expression that provides strong stimulation of the immune system. Second, the antigen that they express is processed and displayed in the transduced cells in a way that mimics pathogen-infected cells. This phase is believed to be very important in inducing cellular immunity against infected cells, and is completely lacking when conventional vaccination approaches are used. Third, adenoviral vectors infect dendritic cells which are very potent antigen-presenting cells. Diao, J. et al., *Gene Ther* 6(5):845-53 (1999); Zhong, L., et al., *Eur J Immunol* 29(3):964-72 (1999); Wan, Y., et al., *Int J Oncol* 14(4):771-6 (1999); Wan, Y., et al., *Hum Gene Ther* 8(11):1355-63 (1997). Fourth, these vectors can be engineered to carry immunoenhancing cytokine genes to further boost immunity. Fifth, adenoviruses naturally infect airway and gut epithelial cells in humans, and therefore the vaccine may be delivered through nasal spray or oral ingestion. And finally, the adenoviral vectors of this invention are safe because they are replication-defective and have been used in high doses ($10^9$ to $10^{12}$ i.p./dose) in clinical trials for gene therapy studies. Gahery-Segard, H., et al., *J. Clin Invest* 100(9):2218-26 (1997); Bellon, G., et al., *Hum Gene Ther* 8(1):15-25 (1997); Boucher, R. C., et al., *Hum Gene Ther* 5(5):615-39 (1994). Indeed, even live viruses have been safely used in military recruits to prevent common colds.

This vector-construction system is also used to establish complex vectors that express multiple genes or regulatory mechanisms. For example, the vector construct is used to express multiple cytokines along with Ebola GP antigens in a single complex vector to further enhance the immune induction. Alternatively, antigens and cytokines are placed in separate vectors. This enables the manipulation of different combinations of cytokines and antigens by co-transduction (infection) with two or three vectors.

Figure 4A:
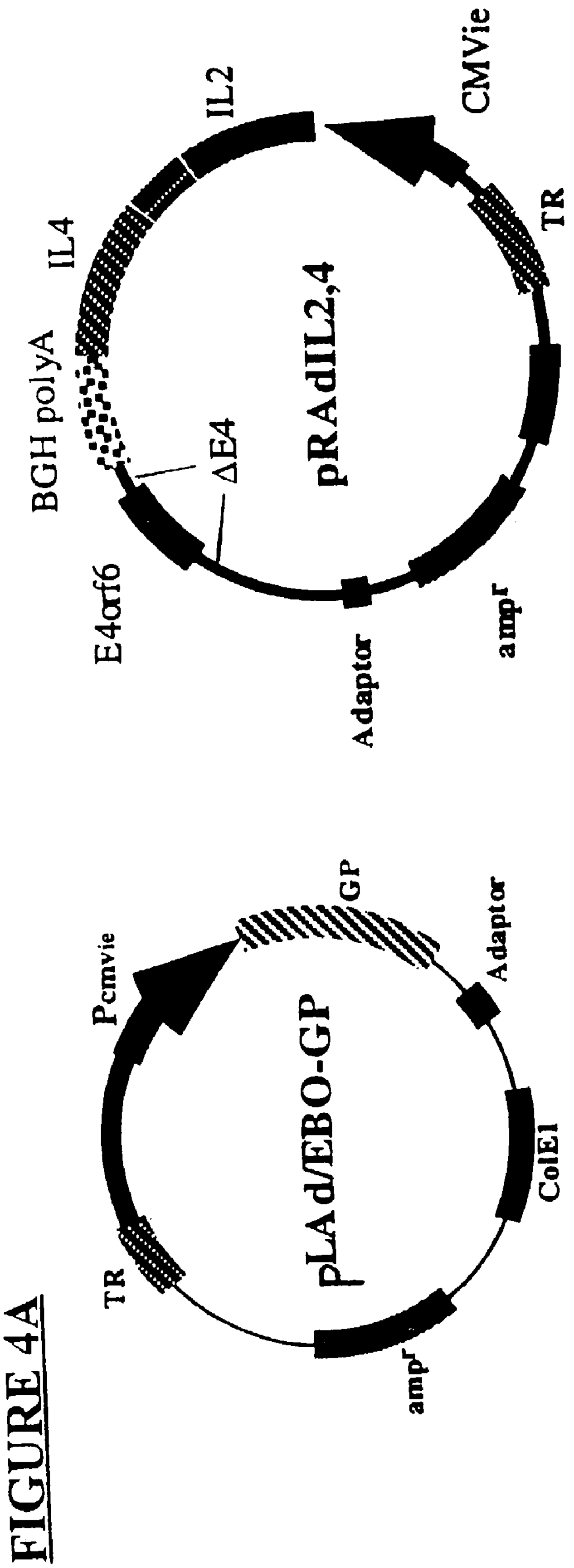
FIGS. 4A and 4B illustrate a procedure used to create a recombinant adenoviral vector as a genetic vaccine against Ebola virus.

Construction of the adenoviral vectors is diagramed in FIG. 4. The cDNA encoding a modified GP(s) is cloned into the left-end (E1 region) of the adenovirus genome using a shuttle vector pLAd (FIG. 4A left side), resulting in a shuttle vector pLAd/EBO-GP. The pLAd/EBO-GP vector contains the left end of the adenoviral genome including the left long terminal repeats L-TR and the adenoviral packaging signal ψ. Genes encoding cytokines such as IL-2 and IL-4 are inserted into E4 region of the adenovirus vector using the shuttle vector pRAd (FIG. 4A, right side), resulting in a shuttle vector pRAdIL2,4. The pRAdIL2,4 contains the right end of the adenoviral genome including the right long terminal repeats R-TR.

To construct an adenoviral vector carrying the GP gene only, the shuttle vector pLAd/EBO-GP is digested with appropriate restriction enzymes such as Xba I. The fragment containing the GP gene is ligated to an adenoviral backbone and pRAd vector.

Figure 4B:
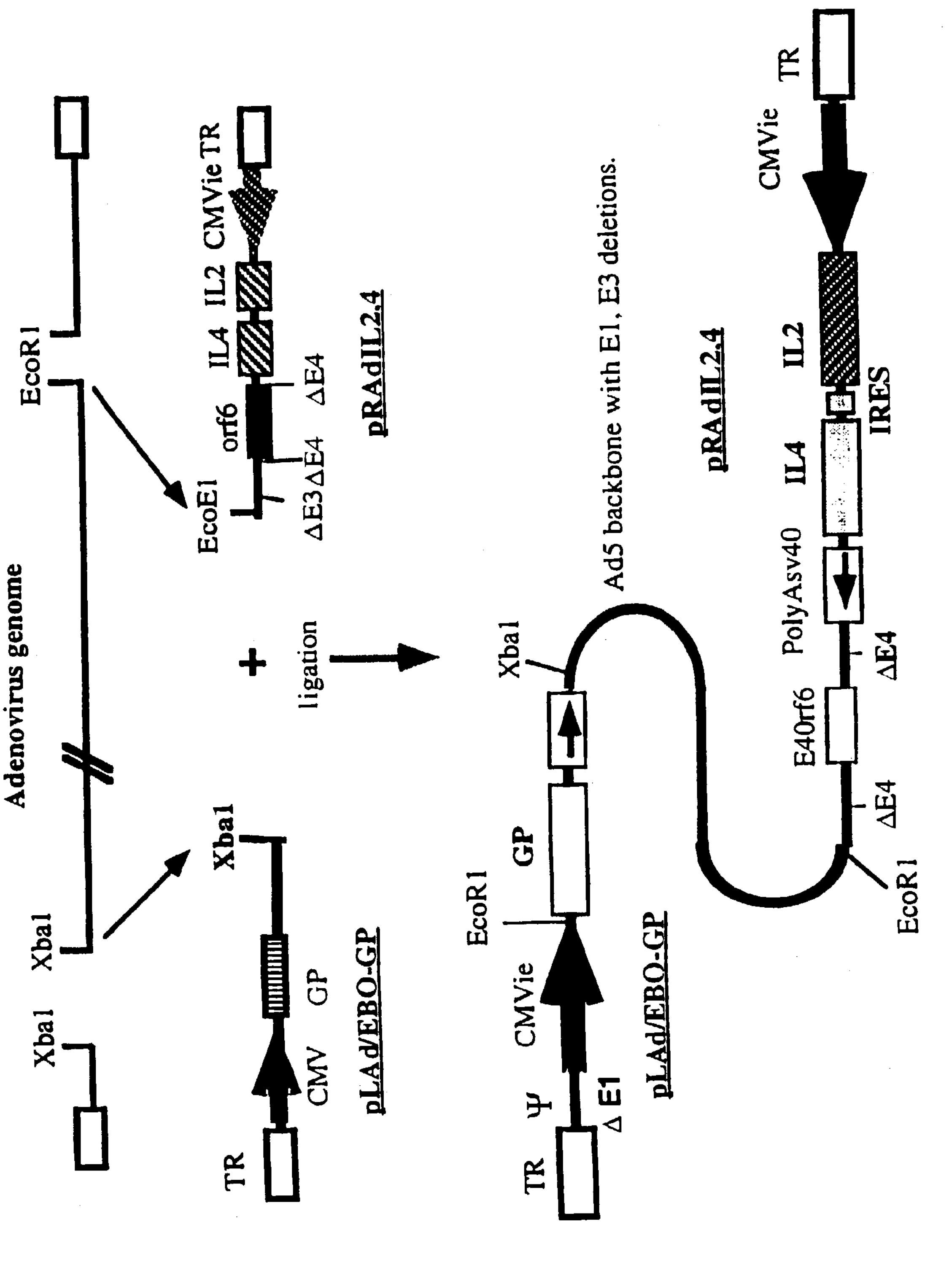

To construct an adenoviral vector carrying both the GP gene in the E1 region and cytokine genes in the E4 region, both pLAd/EBO-GP and pRAdIL2, 4 are linearized and ligated to the backbone of the adenovirus (FIG. 4B).

To generate recombinant adenoviral vectors, the ligated vector genome is transfected into 293 cells, in which only the correctly ligated genome with the two adenoviral terminal repeats can replicate and generate infectious viral particles. Human 293 cells (Graham et al., *J. Gen. Virol.,* 36: 59-72 (1977)), available from the ATCC under Accession No.: CRL1573), has adenovirus E1a and E1b genes stably integrated in its genome. The 293 cells supplement the essential E1 gene of adenovirus that has been deleted from the vector backbone. The final vector has E1, E3 and partial E4 deleted and can only replicate in 293 cells, but not in target cells. The adenoviral vectors are amplified in 293 cells and purified by ultracentrifugation in cesium chloride gradients. Titers of vectors are determined by serial dilutions and counting of the infectious particle (ip) after infection of 293 cells.

3) Determination of Immune Respones to the Genetic Vaccine

An in vitro assay is used to quantitate the amount of neutralizing antibodies developed in response to the vaccine. The assay is based on a retroviral vector system which is based on a Moloney Murine Leukemia virus system. Vectors and packaging cells expressing GAG and POL proteins have been extensively characterized and are commercially available. A packaging vector construct that carries a β-galactosidase gene as a reporter is used. A novel vector construct expressing the membrane form of the Ebola virus GP is co-transfected with the β-Gal reporter vector resulting in a GAG-POL packaging cell line, which generates retroviral vector particles with the Ebola virus GP instead of its original envelope protein.

4) Determination of which Modified GP Antigen Provides Better Production of Neutralizing Antibodies in Animal Models The adenoviral vaccine vectors carrying the two GP variants are tested for their ability to induce an immune response to the Ebola virus GP in CD-1 mice (Charles River Laboratories; outbred stock of Swiss mice from Rockefeller Institute). Specifically, the neutralizing antibody titers and cytolytic T-lymphocyte (CTL) activities to the Ebola virus GP antigens induced by the GP variants with and without the IS motif are compared. Three groups of 30 8-week old mice are injected subcutaneously with $10^5$ ip of adenoviral vectors expressing GP variant 1 (with IS peptide deleted), GP variant 2 (with IS peptide split and inverted) and β-Galactosidase (control vector), respectively. Six mice from each group are sacrificed (by $CO_2$ asphyxiation and cervical dislocation) at 1, 2, 4, 8 and 16 weeks post-vaccination, and their blood and spleens are harvested. In addition, 6 mice are mock-vaccinated with saline and sacrificed 2 days later to provide pre-immunization controls.

From mice injected with the control β-Gal vector, tissue sections from the sites of the vector injection are taken, fixed, and stained with the X-gal solution to determine the number and type of vector-transduced cells at various time-points post-infection. In addition, hemolysin staining is performed to determine the degree of infiltration of various immune cells (neutrophils, macrophages, monocytes, etc.) at the site of the vector delivery.

Sera from vaccinated animals is assayed for total GP-binding antibodies using a standard 96-well plate ELISA protocol, as has been described. Van Ginkel, F. W., et al., *Hum Gene Ther* 6(7):895-903 (1995); Van Ginkel, F. W., et al., *J Immunol* 159(2):685-93 (1997). Neutralizing activity of the sera is analyzed by monitoring the infectious activity of the Ebola virus GP-pseudotyped retroviral vector (Wool-Lewis, et al., *J. Virol,* 72(4):3155-60 (1998)) on HeLa cells after the vector has been incubated with various serum concentrations. Expression of β-galactosidase in infected cell lysates serves as an indicator of the neutralizing activity of the serum (the lower the β-gal activity, the more EBO-β-Gal vectors have been neutralized) and is measured using a very sensitive fluorogenic substrate (Galacto-Light kit J) and a fluorescence plate reader. Anti-GP serum-neutralized infection rates are compared to infection rates in the absence of serum and in the presence of non-GP activated serum.

Cytotoxic lymphocytes (CTLs) are extracted from mouse spleen as previously described. Van Ginkel, F. W., et al., *Hum Gene Ther* 1995; 6(7):895-903; Dong, J. Y., et al., *Hum Gene Ther* 1996;7(3):319-31. They are mixed with a constant number of detached LnCaP cells (prostate carcinoma cells of epithelial origin) transduced with an adenoviral vector carrying an unmodified Ebola virus GP protein. Ratios of effector: target cells of 10:1, 3:1, and 1:1 are used. The cells are seeded into 96-well plates, and 24 hour later all unattached cells (which include all of the effector CTLs and dead or dying LnCaP cells) are removed, and the remaining viable (adherent) cells are quantitated by the MTT (3-(4,5-dimethylthiazol-20-yl) 2,5-diphenyl tetrazolium bromide) cleavage assay. This assay has been employed in detecting the lymphocyte cytotoxic activity (Ni, J., et al., *J Clin Lab Anal* 1996;10 (1):42-52) and compares favorably with the radioactive assays in terms of sensitivity, reliability and speed.

5) Immuno-Enhancing Functions of Multiple Cytokines and their Effects on the Efficacy of the Genetic Vaccines To augment the effects of the vaccine, a vector-mediated gene transfer to express the immunoenhancing cytokines, such as IL2, IL4, IL12, INF-γ, and GM-CSF is used. Initially, each cytokine is separately cloned or the cytokines are cloned in various combinations into adenoviral vectors separate from the vectors encoding viral antigens. The immunoenhancing effects of individual cytokines or their combinations are studied by co-infecting with a vector encoding the cytokine and the vector carrying the antigens. The titers of serum antibodies are compared, as well as the time it takes to reach effective titers in animals inoculated with vaccines in combination with different cytokine-expressing vectors. These experiments allow the determination of whether immunoenhancing cytokines induce higher levels of antibodies, shorten the induction time, and prolong the immunity against the Ebola virus.

After determining the best-performing modified GP variant, the extent that the immune response elicited by it is enhanced by co-delivery to the immunization site of vectors carrying various cytokines is analyzed. Interleukin-2, either by itself or in combination with IL-4 or IL-1 2, has been demonstrated to strongly enhance the activation and proliferation of cytotoxic T-cells, natural killer (NK) cells and B-cells. Michael, B. N., et al., *Cell Immunol* 1994;158(1); 105-15; Bruserud, O., et al., *Eur J. Haematol* 1992;48(4); 221-7; Jacobsen, S. E., et al., *Res Immunol* 1995;146(7-8): 506-14; Wolf, S. F., et al., *Res Immunol* 1995;146(7-8);486-9; Tepper, R. I., *Res Immunol* 1993;144(8):633-7; O'Garra A., et al., *Res Immunol* 1993;144(8):620-5; Ohe, Y., et al., *Int J Cancer* 1993;53(3):432-7; Delespesse, G., et al., *Res Immunol* 1995;146(7-8):461-6. [36-43]. INF-γ stimulates the humoral immune response and increases the permeability of the blood vessel walls at the site of its secretion (Chensue, S. W., et al., *J Immunol* 154(11):5969-76 (1995); Szente, B. E., et al., *Biochem Biophys Res Commun* 203(3):1645-54 (1994); Adams, R. B., et al., *J. Immunol* 150(6):2356-63(1993)), while Gm-CSF activates and attracts macrophages and other professional APCs to the site of the infection. Bober, L. A., et al., *Immunopharmacology* 29(2):111-9 (1995); Dale, D. C., et al., *Am J. Hematol* 57(1):7-15 (1998); Zhao, Y., et al., *Chung Hua I Hsueh Tsa Chih* 77(10): 32-6 (1997).

Six groups of 30 8-week old mice are injected subcutaneously with a mixture of $5\times10^4$ ip of the selected GP variant vector and $5\times10^4$ ip of one of the following vectors: Ad-β-Gal, Ad-IL2, Ad-IL2/IL4, Ad-IL2/IL12, Ad-IFN-γ and Ad-GM-CSF.

Six mice from each group are sacrificed and analyzed at 1, 2, 4, 8 and 16 weeks as described in Example 4. Analysis of total IgG is peformed using ELISA, neutralizing activity is assayed as interference with the ability of EBO-GP pseudotyped retroviral vector to infect HeLa cells, and anti-GP CTL activity is performed by mixing spleen-extracted CTLs with target LnCaP cells transduced with Ad-EBO-GP construct as described in Example 4. Levels of various cytokines in the serum are also quantitated by ELISA using available commercial assays. In some cases, these assays can distinguish between human and murine versions of the same cytokine, providing direct information on the expression levels of cytokines delivered using Adenovirus vectors and how they correlate with the development of the immune response.

After the individual cytokines are analyzed, those that performed best are tested in combinations. Four groups of 30 8-week old mice are injected subcutaneously with a mixture of $5\times10^4$ i.p. of the selected GP variant vector and $5\times10^4$ i.p. of up to 3 selected cytokine-expressing vectors (if fewer than 3 cytokine vectors are used, i.p. counts are made up with Ad-β-Gal vector). Six mice from each group are sacrificed at weeks 1, 2, 4, 8 and 16, and analyzed as described above.

To verify the robust and reproducible nature of the immune response to the GP vector and multiple cytokines in different species, the experiment as described above is reproduced in rabbits. Five groups of six white New Zealand rabbits are injected into the thigh muscle with one of the following vector combinations: the Ad-β-Gal vector ($10^6$ ip), the selected GP vector ($2.5\times10^5$ ip plus $7.5\times10^5$ ip of Ad-β-Gal), and three cytokine vector combinations ($2.5\times10^5$ of each cytokine vector) plus the GP vector ($2.5\times10^5$ ip), as described above. The animals are bled 2 days prior to vaccination (pre-immune bleed) and then according to the schedule described above. 5 to 10 ml of blood will be extracted per session. Analysis is performed in a similar fashion to that of mice (see above).

Because genes coding for human cytokines are used in mouse and rabbit models, it is possible that their immune systems will have a non-identical (to human) response to those proteins. However, a high degree of homology exists between human and mouse cytokines and their receptors, and published reports on experiments using human or other hostian cytokines in mice indicate a high level of equivalency. If necessary, species-specific versions of these cytokines can be obtained and cloned into the adenoviral vectors of the present invention for species-targeted cytokine activity studies.

6) Optimizing the Efficiency and Rates of Administration of the Vaccine and Conducting Safety and Pathogen Challenge Studies in Non-Primate and Primate Animal Models After determining the best combinations of the cytokines and antigens, the final version of the vaccine vectors are constructed. These complex recombinant adenoviral vectors deliver combinations of cytokines and antigens into target cells using a single vector. Dose-titer analysis in mice and rabbits are conducted to identify the lowest dose required to generate maximallevels of immune responses. Different routes of vaccine administration, such as intramuscular and intravenous injection, oral ingestion and nasal sprays are compared. For safety studies, dose escalation experiments in mice and rabbits are conducted until toxicity is observed or until levels ten times the effective dose have been reached. Finally, additional safety and pathogen challenge experiments are conducted in primates.

2. Genetic Vaccine Against HIV

Specific embodiments of the genetic vaccines against HIV and methods of their construction are described in detail as follows.

A. Construction of Replication-Defective Adenoviral Vaccines Against HIV

1) Ad-E.T.R/IL2

An adenoviral vector, Ad-E.T.R/IL2, was constructed to carry coding sequences for multiple HIV antigens including Env, Tat, and Rev proteins, and interleukin-2 (IL-2) in the same vector. Expression of the HIV antigens and IL-2 is separately controlled by promoters located in different regions of the adenoviral vector. This design is believed to be able to ensure high level expression of both the viral antigens and the immuno-stimulator IL-2 and to enhance immunogenicity of the adenoviral vaccine. As shown by experimental data presented in the next section, this adenoviral vector is capable of eliciting strong humoral immune response in animals against HIV antigens.

Figure 16A:
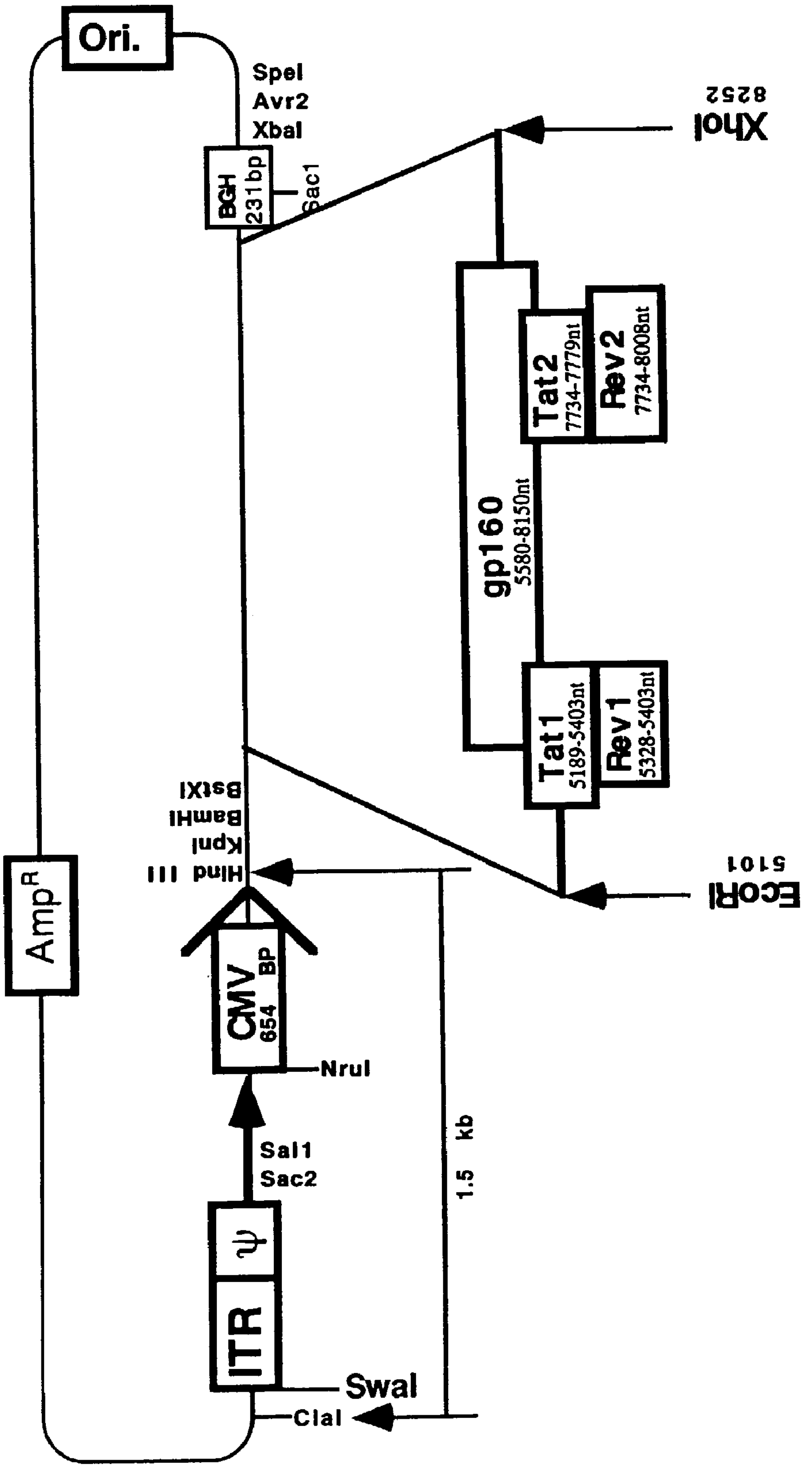
FIG. 16A illustrates a shuttle vector pLAd-E.T.R.

The adenoviral vector, Ad-E.T.R/IL2, was constructed using strategies similar to those for constructing the adenoviral vaccines against Ebola virus as described in detail above. Briefly, EcoRI/XhoI restriction fragment from HIV-1 strain BH10 (HIV-1 or HTLV-IIIB, clade B, Accession No: M15654), which encodes wildtype envelope gp160 (full length gp 120 and gp41), full length wildtype Tat and full length wild type Rev, was inserted into the left end (E1 region) of the adenoviral genome using a shuttle vector, resulting in a shuttle vector pLAd-E.T.R (FIG. 16A). DNA sequence of this EcoRI/XhoI restriction fragment [SEQ ID NO: 14] is shown in FIG. 38.

Figure 16B:
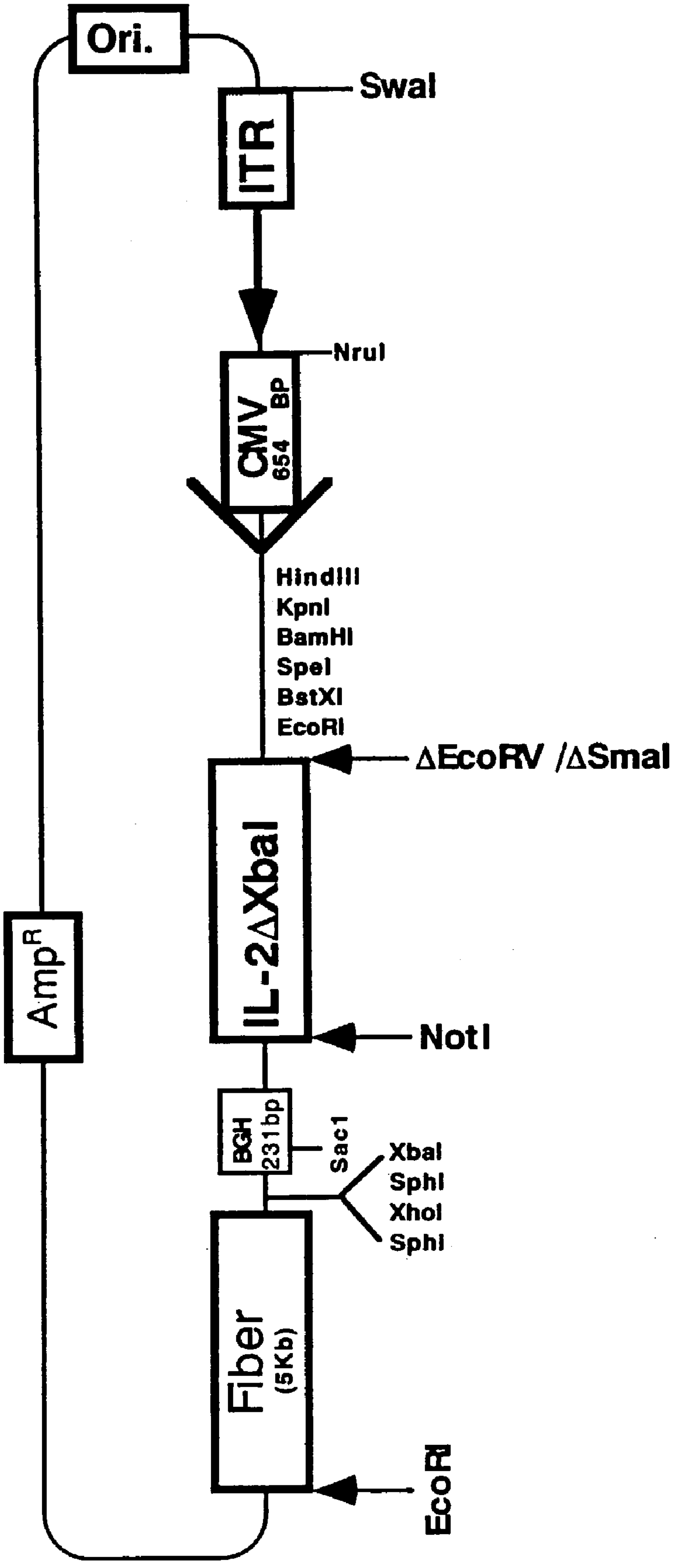
FIG. 16B illustrates a shuttle vector pRAd-ORF6-IL2.

The sequence encoding IL-2 (with a silent mutation CTA to CTT at amino acid position 79 to delete the XbaI site) was inserted into E4 region of the adenoviral genome using a shuttle vector, resulting in a shuttle vector pRAd-ORF6-IL2 (FIG. 16B). DNA sequence encoding this mutated IL-2 (IL-2ΔX) [SEQ ID NO: 15] is shown in FIG. 39.

Both pLAd-E.T.R and pRAd-OFR6-IL2 were linearized using appropriate restriction enzymes such as Xba I and EcoRI and ligated to the backbone of the adenovirus (FIG. 4B), resulting in the recombinant adenoviral vector Ad-E.T.R/IL2.

2) Ad-3C/E‴ΔCΔT$^{300}$-G

Another adenoviral vector, Ad-3C/E‴ΔCΔT$^{300}$-G, was constructed to carry coding sequences for multiple HIV antigens including a modified Env (gp160) with deletion of the cleavage site between gp120 and gp41 and the cytosolic domain and Gag proteins, and three different cytokines (IL-2 with silent mutation CTA to CTT at amino acid position 79 to delete the XbaI site, INF-γ, and GMCSF) in the same vector. Expression of the HIV antigens and the cytokines is separately controlled by promoters located in different regions of the adenoviral vector. This design is believed to be able to ensure high level expression of both the viral antigens and the immuno-stimulators and to enhance immunogenicity of the adenoviral vaccine. As shown by experimental data presented in the next section, this adenoviral vector is capable of eliciting strong humoral immune response in animals against HIV antigens.

The adenoviral vector, Ad-3C/E‴ΔCΔT$^{300}$-G, was constructed using strategies similar to those for constructing the adenoviral vaccines against Ebola virus as described in detail above. Briefly, the sequence from HIV-1 strain BH10 that encodes Env/gp160 (nucleotide position 5580-7850) was modified to delete the sequences encoding the cleavage site (REKR [SEQ ID NO: 11] encoded by nucleotide at position 7101-7112) and the cytosolic domain of 100 amino acids in length (encoded by nucleotide at position 7850-8150), and then, along with the sequence encoding a full length Gag, inserted into the right end (E4 region) of the adenoviral genome using a shuttle vector. DNA sequence of this modified Env (E‴ΔCΔT (BH10) [SEQ ID NO: 16] and that of the full length Gag [SEQ ID NO: 17] (amino acid sequence of which is SEQ ID NO: 18, FIG. 41B) are shown in FIGS. 40 and 41A, respectively.

These two HIV antigens are expressed separately from a CMV promoter via a retroviral splicing donor (SD) and acceptor (SA) mechanism at two splicing acceptor sites, $SA_1$, and $SA_2$. To facilitate efficient cloning of various gene fragments, a cloning vector SD/SA1.2.3 was constructed to include a retroviral SD site and multiple retroviral SA sites, $SA_1$, $SA_2$, $SA_3$ and $SA_4$. In this example, the SD and SA sites were derived from Moloney murine leukemia virus (MMLV) and their sequences are shown below:

SD site (MMLV nt 204-210): AGGTAAG [SEQ ID NO: 72]; and $SA_{1-4}$ site (MMLV nt 560-568): CTGCTGCAG [SEQ ID NO: 73].

Figure 37:
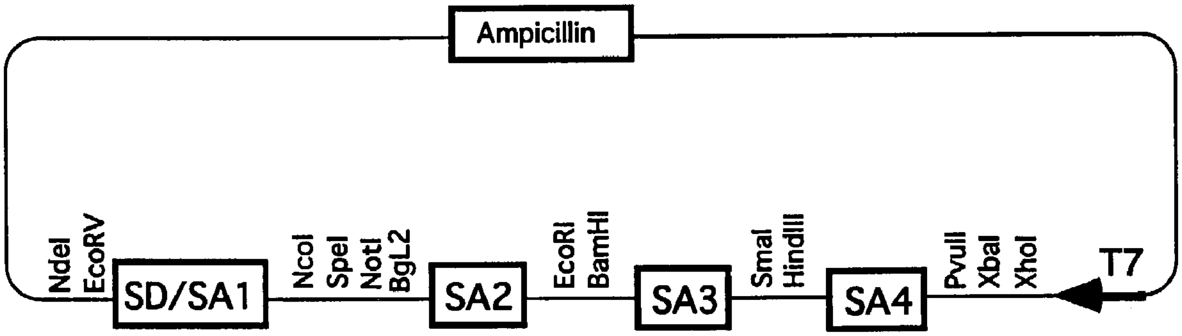
FIG. 37 illustrates a cloning vector SD/SA1.2.3

Each of the SD site, and the $SA_1$, $SA_2$, $SA_3$ and $SA_4$ ($SA_{1-4}$) sites which share the same sequence was inserted into the multiple cloning site of a cloning vector pSP73 by using standard PCR mutagenesis. As illustrated in FIG. 37, SA, was inserted immediately downstream from SD site, followed by $SA_2$, $SA_3$ and $SA_4$. To test the levels of expression of multiple genes via the SD/SA mechanism, the GFP (green fluorescence protein) gene was inserted between SD/$SA_1$ and $SA_2$, $SA_2$ and $SA_3$, $SA_3$ and $SA_4$, and after $SA_4$. The ratio of expression levels in these four sites is 10:1:5:4.

Figure 17A:
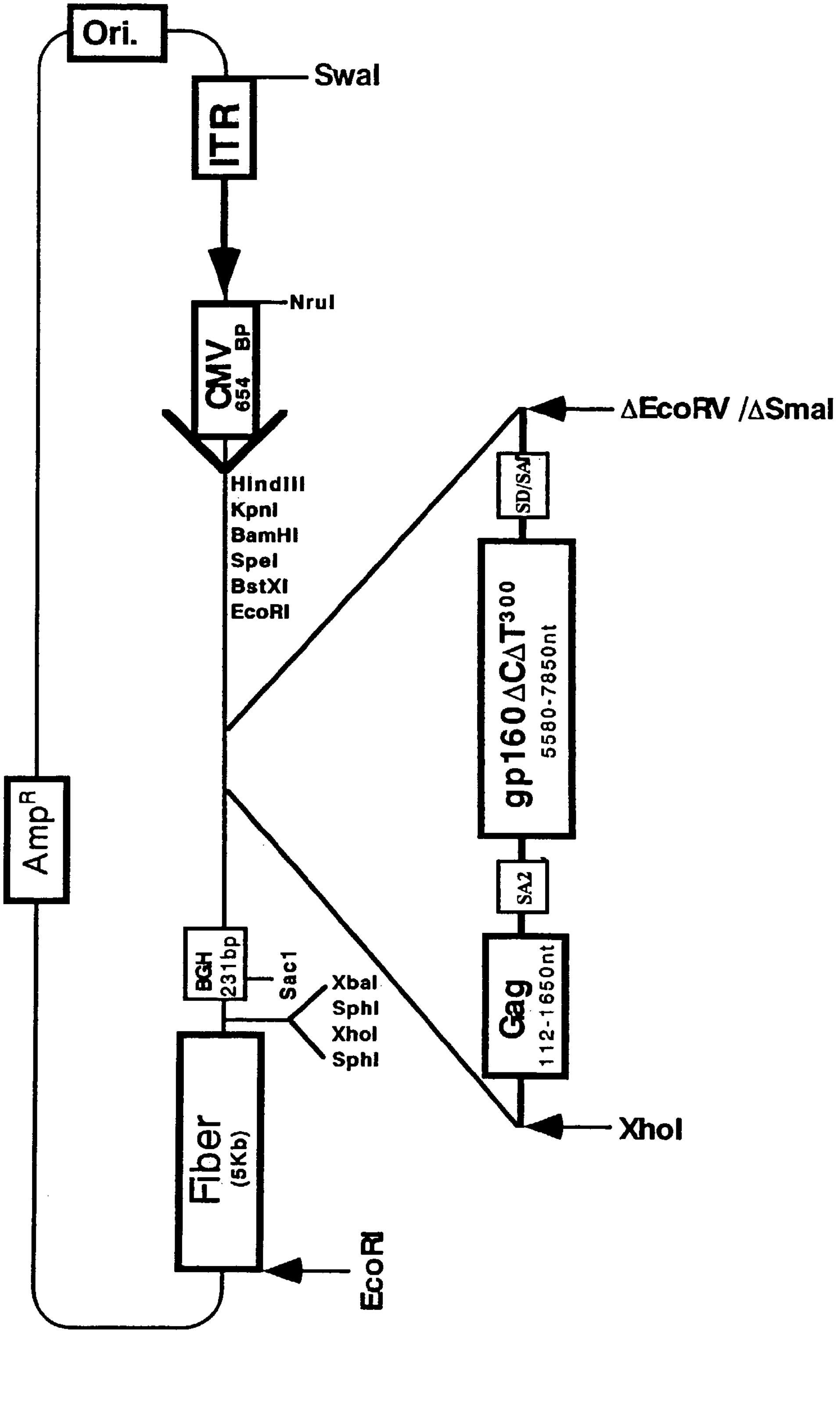
FIG. 17A illustrates a shuttle vector pRAd-ORF6-cmv-$E'''\Delta C\Delta T^{300}$-G.

DNA sequences encoding E‴ΔCΔT and Gag were inserted into the cloning vector SD/SA1.2.3 after SD/$SA_1$, and $SA_2$, respectively. The resulting vector was digested with EcoRV and XhoI and the fragment containing E‴ΔCΔT and Gag was inserted into an adenoviral shuttle vector, resulting in pRAd-ORF6-cmv-E‴ΔCΔT$^{300}$-G (FIG. 17A). Shuttle vectors capable of expressing other proteins (as shown below) via the retroviral SD/SA mechanism were constructed using the same strategy.

Figure 17B:
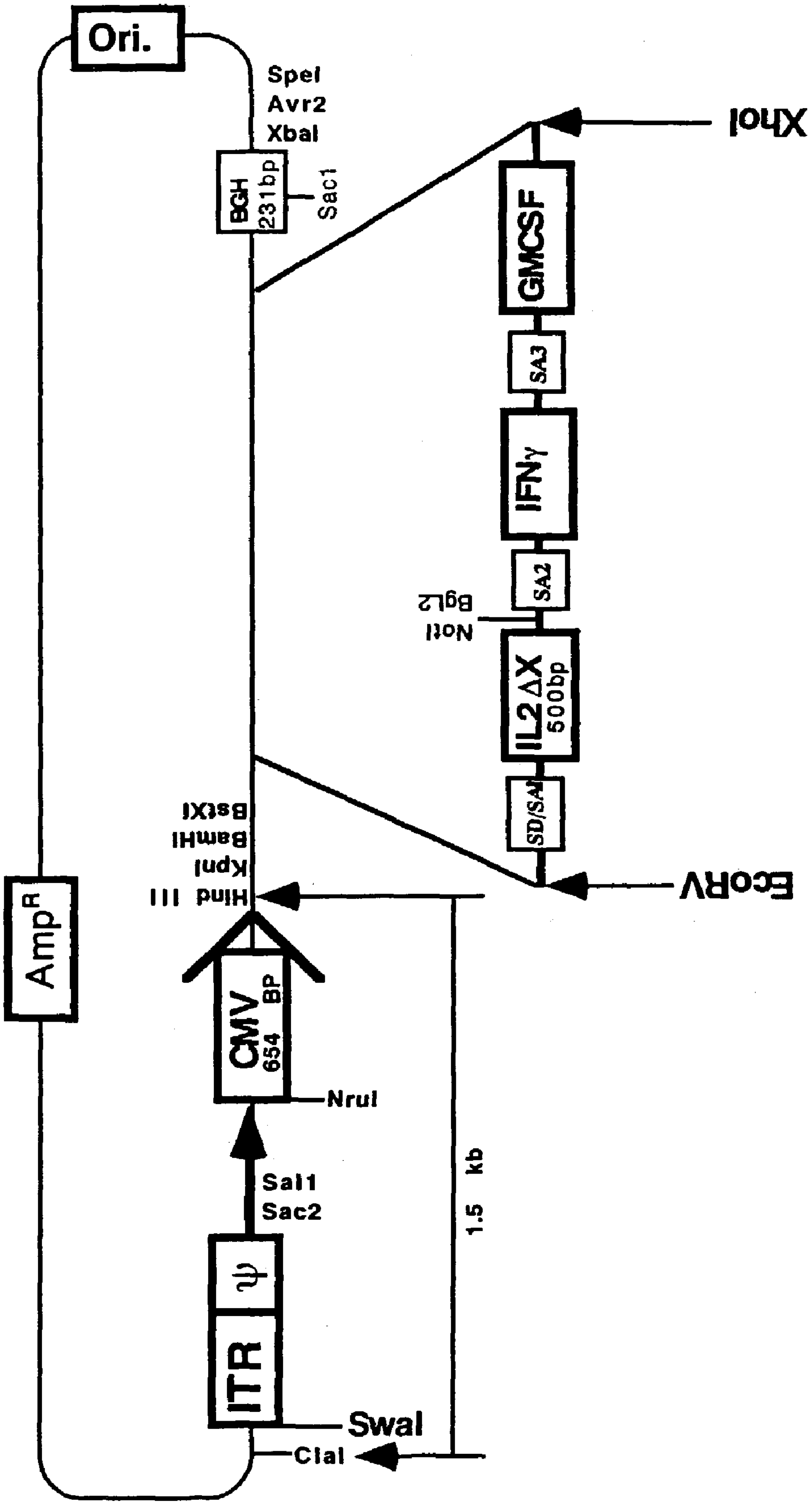
FIG. 17B illustrates a shuttle vector pLAd-3C.

Sequences encoding multiple immuno-stimulators, including IL-2 (with a silent mutation caused by deletion of Xba I site), INF-γ, and GMCSF, were inserted into E1 region of the adenoviral genome using a shuttle vector. These three immuno-stimulators are expressed separately from another CMV promoter via a retroviral splicing donor (SD) and acceptor (SA) mechanism at three splicing acceptor sites, $SA_1$, $SA_2$, and $SA_3$. The shuttle vector produced is designated pLAd-3C (FIG. 17B).

Both pRAd-ORF6-cmv-E‴ΔCΔT$^{300}$-G and pLAd-3C were linearized using appropriate restriction enzymes such as Xba I and EcoRI and ligated to the backbone of the adenovirus (FIG. 4B), resulting in the recombinant adenoviral vector Ad-3C/E‴ΔCΔT$^{300}$-G.

3) Ad-3C/E‴ΔCΔT$^{99}$.T.R-G

Yet another adenoviral vector, Ad-3C/E‴ΔCΔT$^{99}$.T.R-G, was constructed to carry coding sequences for multiple HIV antigens from strain pNL4-3 (Accession No: M19921) including a modified Env (gp160 with deletion of the cleavage site and the cytoplasmic domain of 33 amino acids in length), full length Rev and Gag proteins, and three different cytokines (IL-2 with silent mutation CTA to CTT at amino acid position 79 to delete the XbaI site, INF-γ, and GMCSF) in the same vector. Expression of the HIV antigens and the cytokines is separately controlled by promoters located in different regions of the adenoviral vector. This design is believed to be able to ensure high level expression of both the viral antigens and the immuno-stimulators and to enhance immunogenicity of the adenoviral vaccine. As shown by experimental data presented in the next section, this adenoviral vector is capable of eliciting strong humoral immune response in animals against HIV antigens.

The adenoviral vector, Ad-3C/E‴ΔCΔT$^{99}$.T.R-G, was constructed using strategies similar to those for constructing the adenoviral vaccines against Ebola virus as described in detail above. Briefly, the sequence from HIV-1 strain pNL4-3 that encodes Env/gp160 (nucleotide position 6221-8686) was modified to delete the sequences encoding the cleavage site (encoded by nucleotide at position 7736-7747) and the cytosolic domain (encoded by nucleotide at position 8687-8785) in length, and then, along with sequences encoding full length Tat, Rev, and Gag (from HIV strain BH10), inserted into the right end (E4 region) of the adenoviral genome using a shuttle vector.

Figure 18:
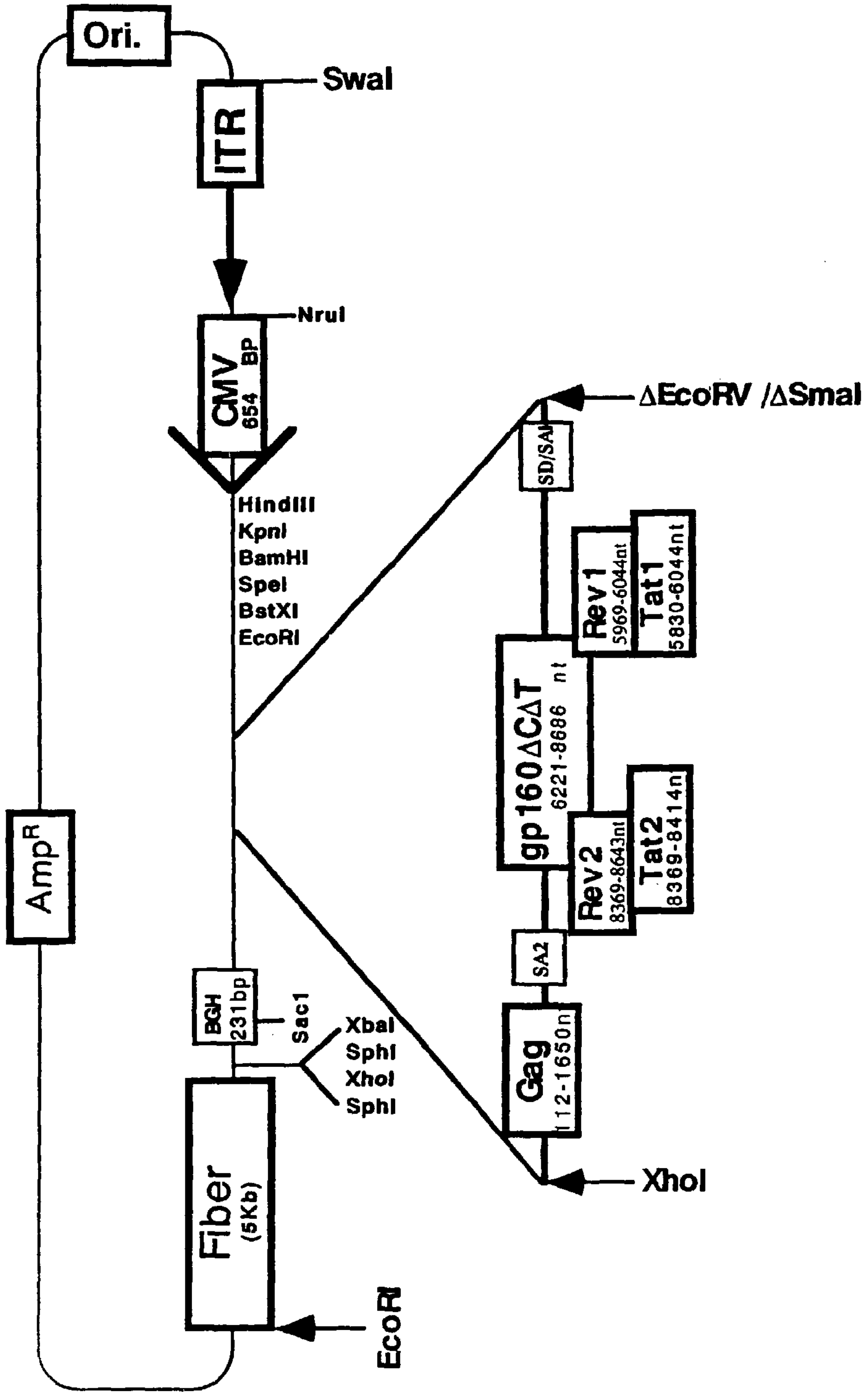
FIG. 18 illustrates a shuttle vector pRAd-$E'''\Delta C\Delta T^{99}$.T.R-G

These three HIV antigens are expressed separately from a CMV promoter via a retroviral splicing donor (SD) and acceptor (SA) mechanism at three splicing acceptor sites, SA, SA$_2$, and SA$_3$. The shuttle vector produced is designated pRAd-E$^m$ΔCΔT$^{99}$.T.R-G (FIG. 18). DNA sequence encoding the modified Env, and full length Tat and Rev [SEQ ID NO: 19] is shown in FIG. 42. DNA and amino acid sequences of the full length Gag from HIV strain BH10 [SEQ ID NO: 17] are shown in FIGS. 41A and 41B, respectively.

The shuttle vectors, pRAd-E$^m$ΔCΔT$^{99}$.T.R.-G and pLAd-3C (FIG. 17B) were linearized using appropriate restriction enzymes such as Xba I and EcoRI and ligated to the backbone of the adenovirus (FIG. 4B), resulting in the recombinant adenoviral vector Ad-3C/E$^m$ΔCΔT$^{99}$.T.R.-G.

4) Ad-E$^m$ΔV$_{1,2}$ΔCΔT$^{99}$.T.R-IL2/G.IL2

Yet another adenoviral vector, Ad-E$^m$ΔV$_{1,2}$ΔCΔT$^{99}$.T.R/G.IL2, was constructed to carry coding sequences for multiple HIV antigens from HIV-1 strain pNL4-3. The sequence from HIV-1 strain pNL4-3 that encodes Env/gp160 (nucleotide position 6221-8686) was modified to delete the sequences encoding the V1 and V2 loops at position 6602-6796 nt and insert nucleotide sequence GGA GCT GGT [SEQ ID NO: 12] that encodes amino acid sequence GAG [SEQ ID NO: 13]. This HIV Env/gp160 was also modified to delete the cleavage site encoded by nucleotide at position 7736-7747 (ΔC) and the 33-aa cytosolic domain encoded by nucleotide at position 8687-8785 (ΔT$^{99}$). Along with the sequences encoding full length Rev (R) and Tat (T), the modified env was inserted into the left end (E1 region) of the adenoviral genome using a shuttle vector. DNA sequence encoding the insert (E$^m$ΔV$_{1,2}$ΔCΔT.T.R) [SEQ ID NO: 20] is shown in FIG. 43.

Figure 19A:
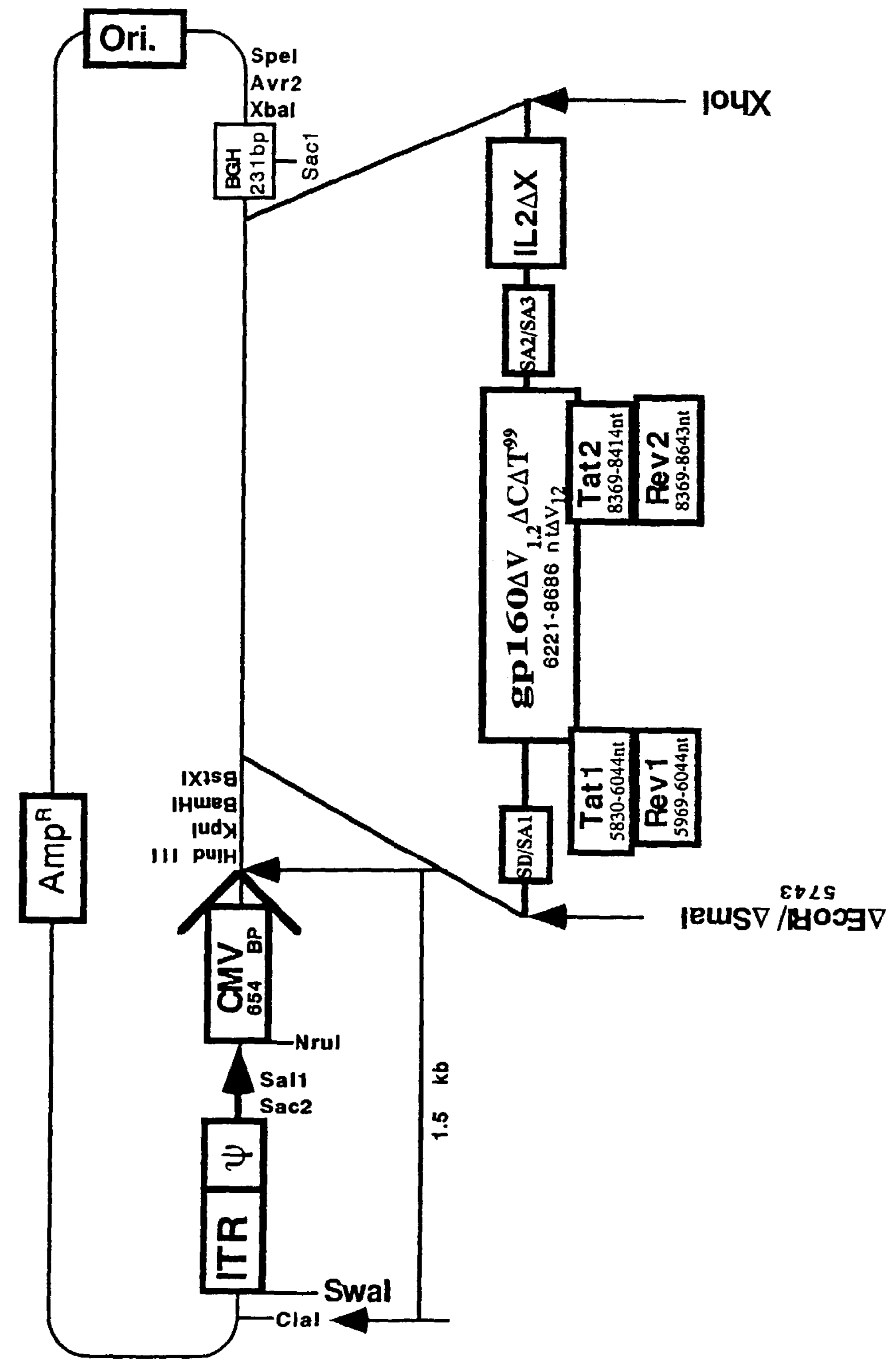
FIG. 19A illustrates a shuttle vector pLAd-$E'''\Delta V_{1,2}\Delta C\Delta T$.T.R.-IL2.

Additionally, IL-2 (with a silent mutation caused by deletion of Xba I site, DNA SEQ ID NO: 15) was inserted downstream from the modified env. Both the modified Env and IL-2 are expressed separately from a CMV promoter via a retroviral splicing donor (SD) and acceptor (SA) mechanism at two splicing acceptor sites, SA$_1$ and SA$_2$/SA$_3$. The shuttle vector produced is designated pLAd-E$^m$ΔV$_{1,2}$ΔCΔT.T.R-IL2 (FIG. 19A).

Figure 19B:
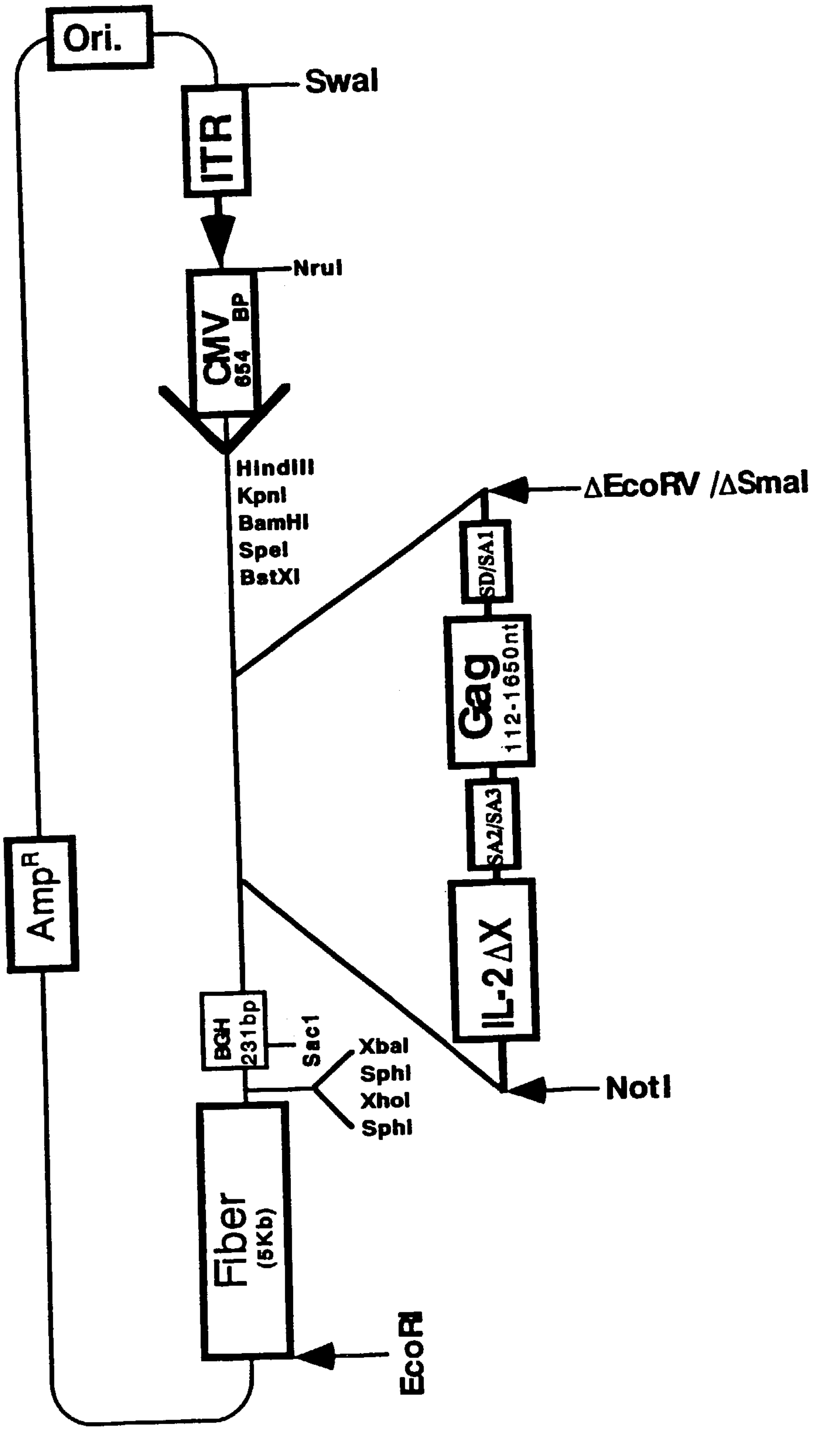
FIG. 19B illustrates a shuttle vector pRAd-ORF6-G.IL2.

Sequences encoding IL-2 (with a silent mutation caused by deletion of Xba I site, DNA SEQ ID NO: 15) and Gag from HIV-1 strain BH10 (nt 112-1650, DNA SEQ ID NO: 17) were inserted into E4 region of the adenoviral genome using a shuttle vector. These two proteins are expressed separately from a CMV promoter via a retroviral splicing donor (SD) and acceptor (SA) mechanism at two splicing acceptor sites, SA$_1$ and SA$_2$. The shuttle vector produced is designated pRAd-ORF6-G.IL2 (FIG. 19B).

Both pLAd-cmv-E$^m$ΔV$_{1,2}$ΔCΔT.T.R-G and pRAd-ORF6-G.IL2 were linearized using appropriate restriction enzymes and ligated to the backbone of the adenovirus (FIG. 4B), resulting in the recombinant adenoviral vector Ad-E$^m$ΔV$_{1,2}$ΔCΔT.T.R-G/G.IL2.

5) Ad-E$^m$ΔC.T.R.N/G.IL2

Figure 20:
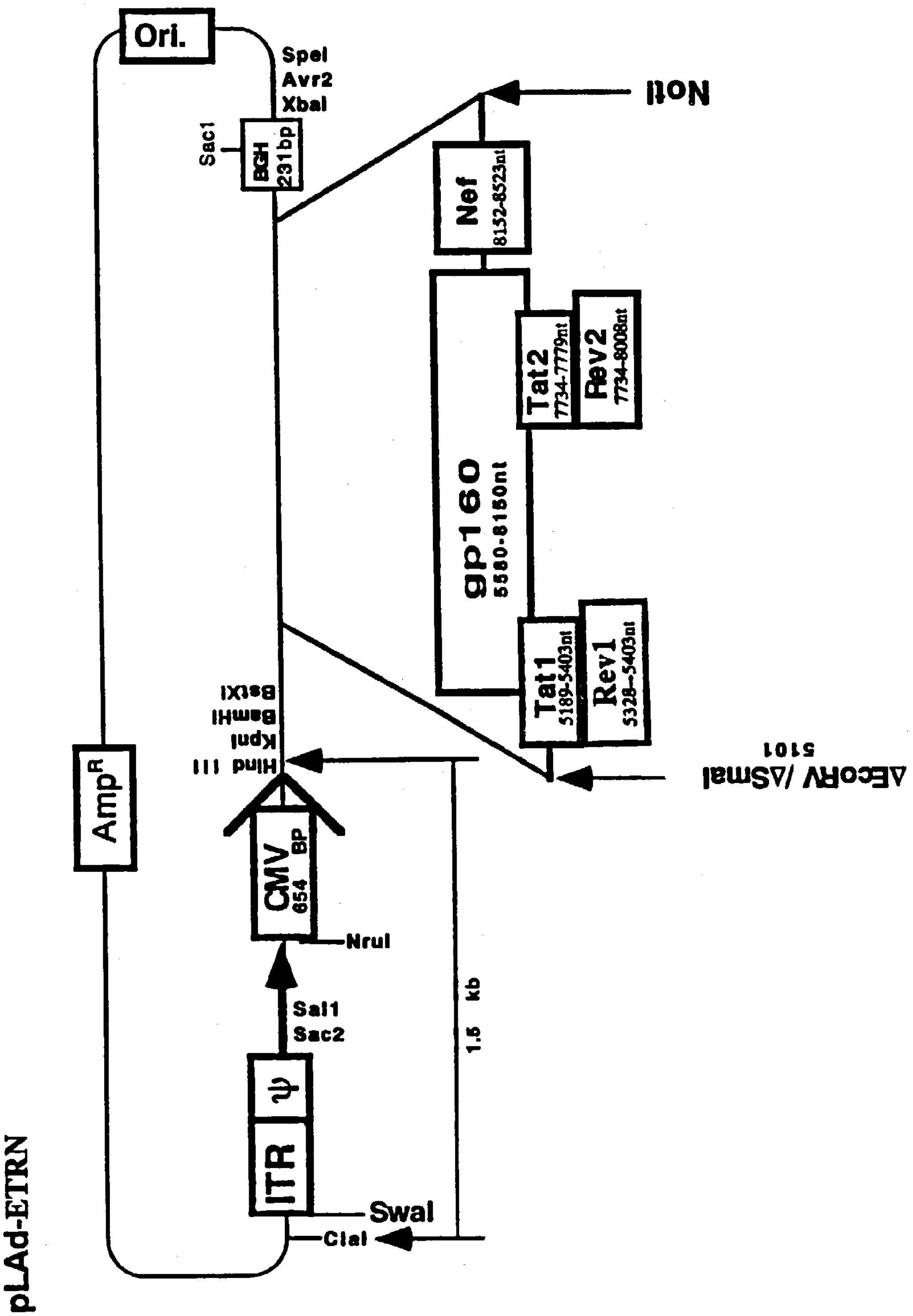
FIG. 20 illustrates a shuttle vector pLAd-$E'''\Delta C$.T.R.N.

Yet another adenoviral vector, Ad-E$^m$ΔC.T.R.N/G.IL2, was constructed to carry coding sequences for multiple HIV antigens from HIV-1 strain BH10. The sequence from HIV-1 strain BH10 that encodes full length Env/gp160 (nucleotide position 5580-8150), Tat, Rev, and Nef was modified by deleting the sequence encoding the cleavage site of Env and inserting a SpeI restriction site. DNA sequence of this insert [SEQ ID NO: 21] is shown in FIG. 44, and was inserted into the left end (E1 region) of the adenoviral genome using a shuttle vector, resulting in a shuttle vector pLAd-E$^m$ΔC.T.R.N (FIG. 20).

Both pLAd-E$^m$ΔC.T.R.N and pRAd-ORF6-G.IL2 (FIG. 19B) were linearized using appropriate restriction enzymes and ligated to the backbone of the adenovirus (FIG. 4B), resulting in the recombinant adenoviral vector Ad-E$^m$ΔC.T.R.N/G.IL2.

6) Ad-E$_m$ΔC.N/G.IL2

Figure 21:
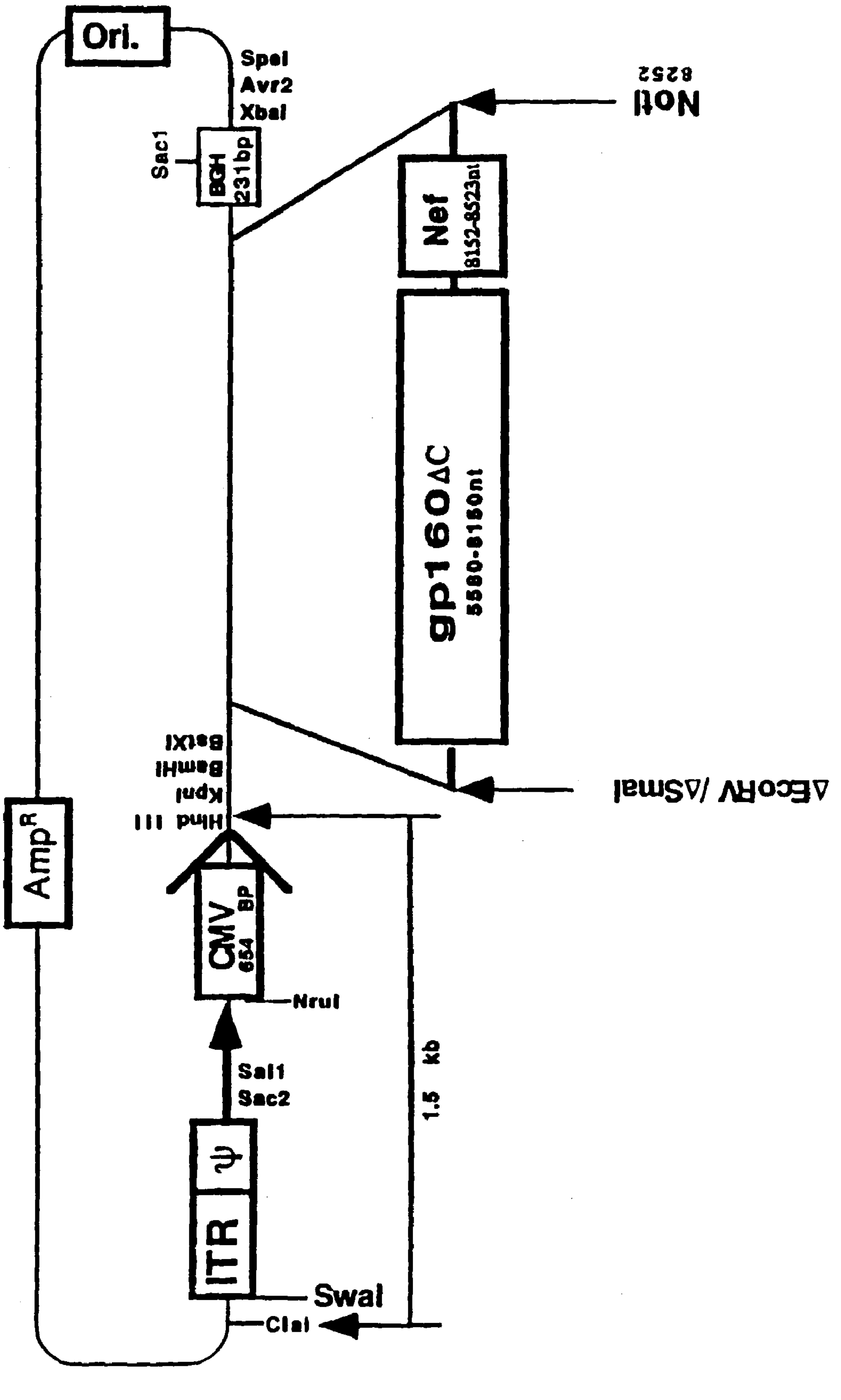
FIG. 21 illustrates a shuttle vector pLAd-$E'''\Delta C$.N.

Yet another adenoviral vector, Ad-E$^m$ΔC.N/G.IL2, was constructed to carry coding sequences for multiple HIV antigens from HIV-1 strain BH10. The sequence from HIV-1 strain BH10 that encodes full length Env/gp160 (nucleotide position 5580-8150, with preceding Kozak sequence), Tat, Rev, and Nef was modified by deleting the sequences encoding the cleavage site of Env, Tat and Rev, and inserting a SpeI restriction site. DNA sequence of this insert [SEQ ID NO: 22] is shown in FIG. 45, and was inserted into the left end (E1 region) of the adenoviral genome using a shuttle vector, resulting in a shuttle vector pLAd-E$^m$ΔC.N (FIG. 21).

Both pLAd-E$^m$ΔC.N and pRAd-ORF6-G.IL2 (FIG. 19B) were linearized using appropriate restriction enzymes and ligated to the backbone of the adenovirus (FIG. 4B), resulting in the recombinant adenoviral vector Ad-E$^m$ΔC.N/G.IL2.

7) Ad-E$^m$ΔCΔT$^{300}$.T/G.IL2

Figure 22:
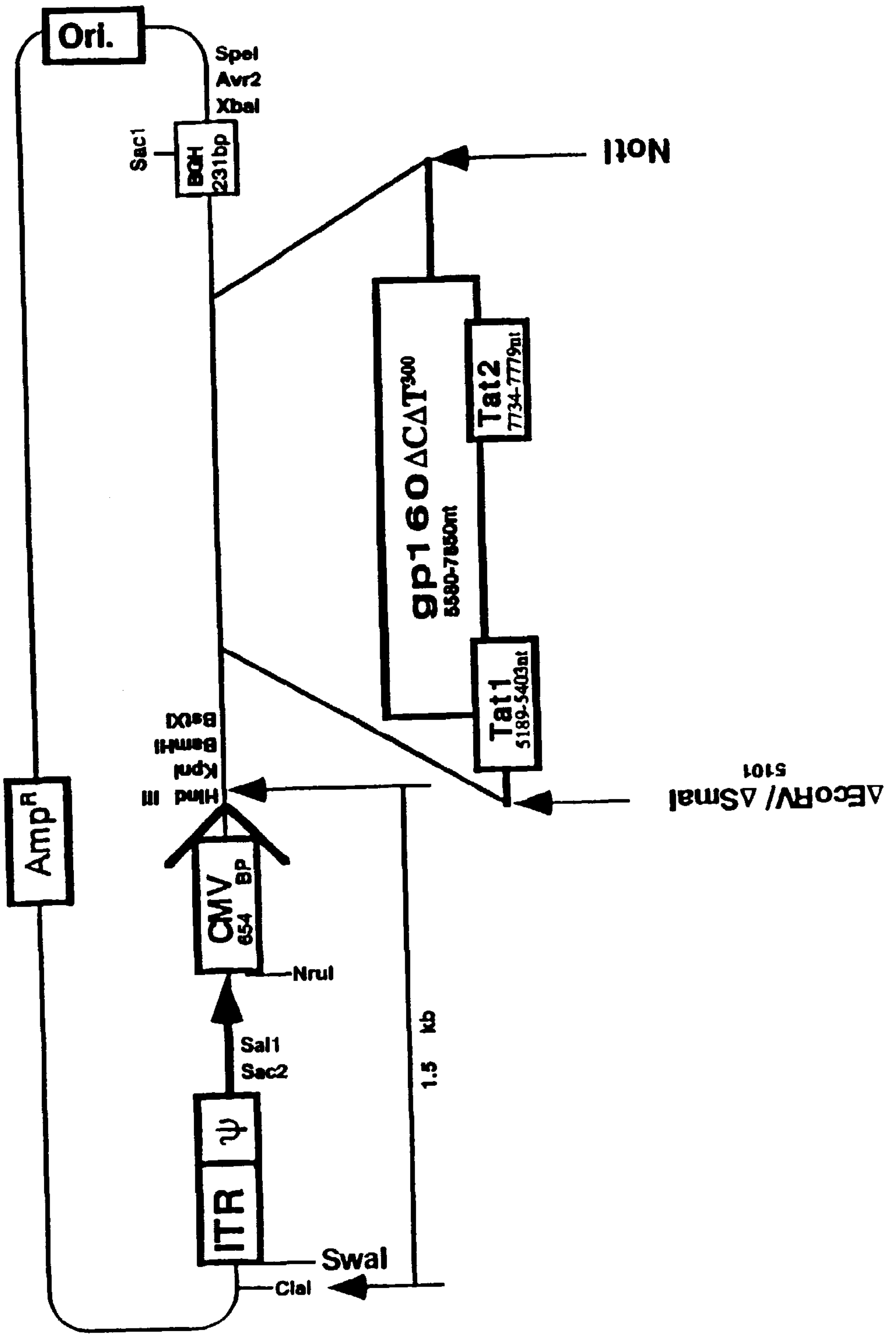
FIG. 22 illustrates a shuttle vector pLAd-$E'''\Delta C\Delta T^{300}$.T.

Yet another adenoviral vector, Ad-E$^m$ΔCΔT$^{300}$.T/G.IL2, was constructed to carry coding sequences for multiple HIV antigens from HIV-1 strain BH10. The sequence from HIV-1 strain BH10 that encodes full length Env/gp160 (nucleotide position 5580-8150) was modified by deleting the sequence encoding the cleavage site and a 300 nt sequence encoding the cytosolic domain, but still including sequence for full length Tat (T). DNA sequence of this insert [SEQ ID NO: 23] is shown in FIG. 46, and was inserted into the left end (E1 region) of the adenoviral genome using a shuttle vector, resulting in a shuttle vector pLAd-E$^m$ΔCΔT$^{300}$.T (FIG. 22).

Both pLAd-E$^m$ΔCΔT$^{300}$.T and pRAd-ORF6-G.IL2 (FIG. 19B) were linearized using appropriate restriction enzymes and ligated to the backbone of the adenovirus (FIG. 4B), resulting in the recombinant adenoviral vector Ad-E$^m$ΔCΔT$^{300}$.T/G.IL2.

8) Ad-E$^m$ΔC/E$^m$ΔC

Figure 23A:
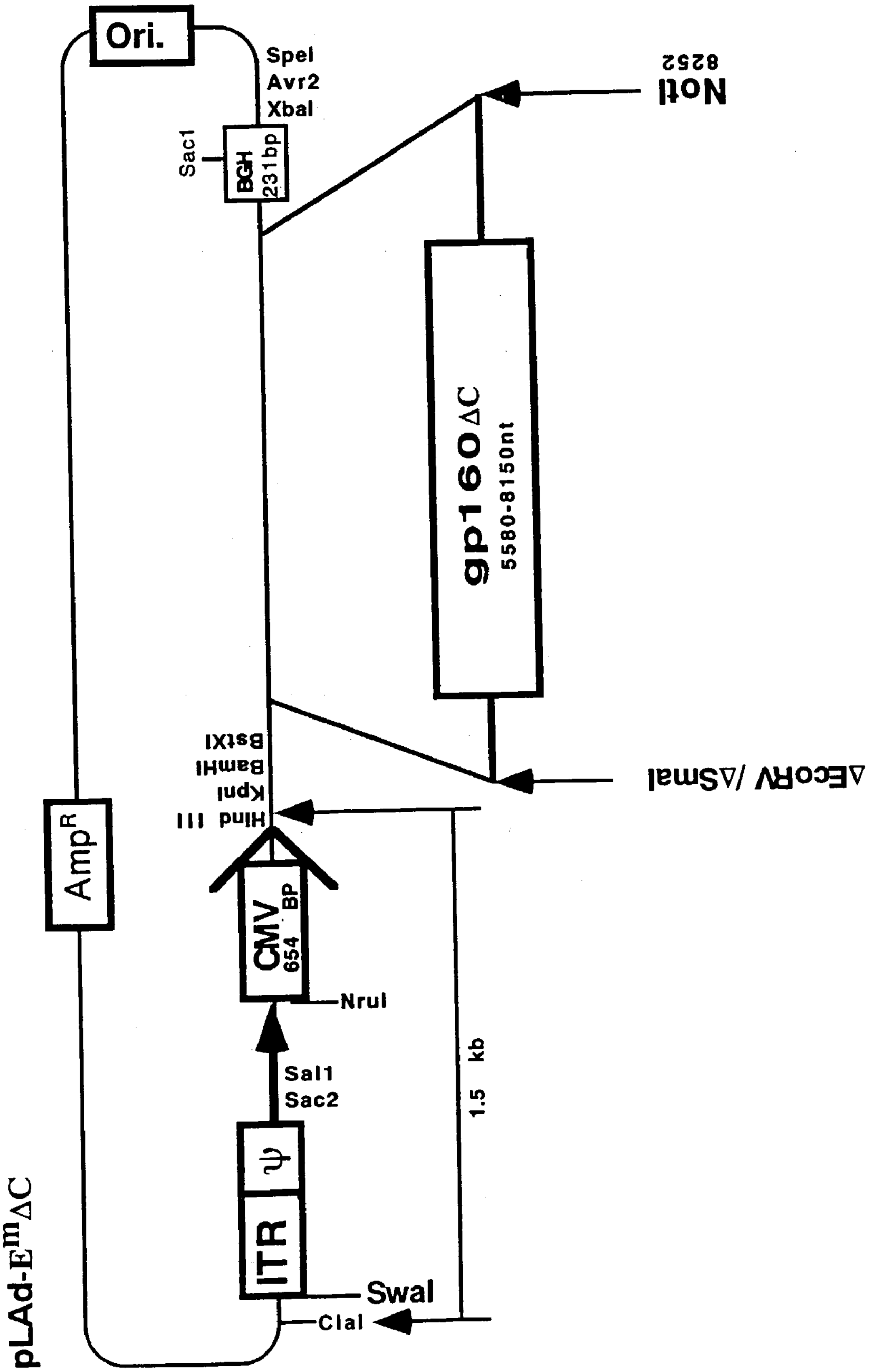
FIG. 23A illustrates a shuttle vector pLAd-$E'''\Delta C$.

Yet another adenoviral vector, Ad-E$^m$ΔC/E$^m$ΔC, was constructed to carry coding sequences for two copies of a modified Env from HIV-1 strain BH10. The sequence from HIV-1 strain BH10 that encodes full length Env/gp160 (nucleotide position 5580-8150, preceding Kozak sequence) was modified by deleting the sequence encoding the cleavage site. DNA sequence of the modified Env [SEQ ID NO: 24] is shown in FIG. 47, and was inserted into the left end (E1 region) of the adenoviral genome using a shuttle vector, resulting in a shuttle vector pLAd-E$^m$ΔC (FIG. 23A).

Figure 23B:
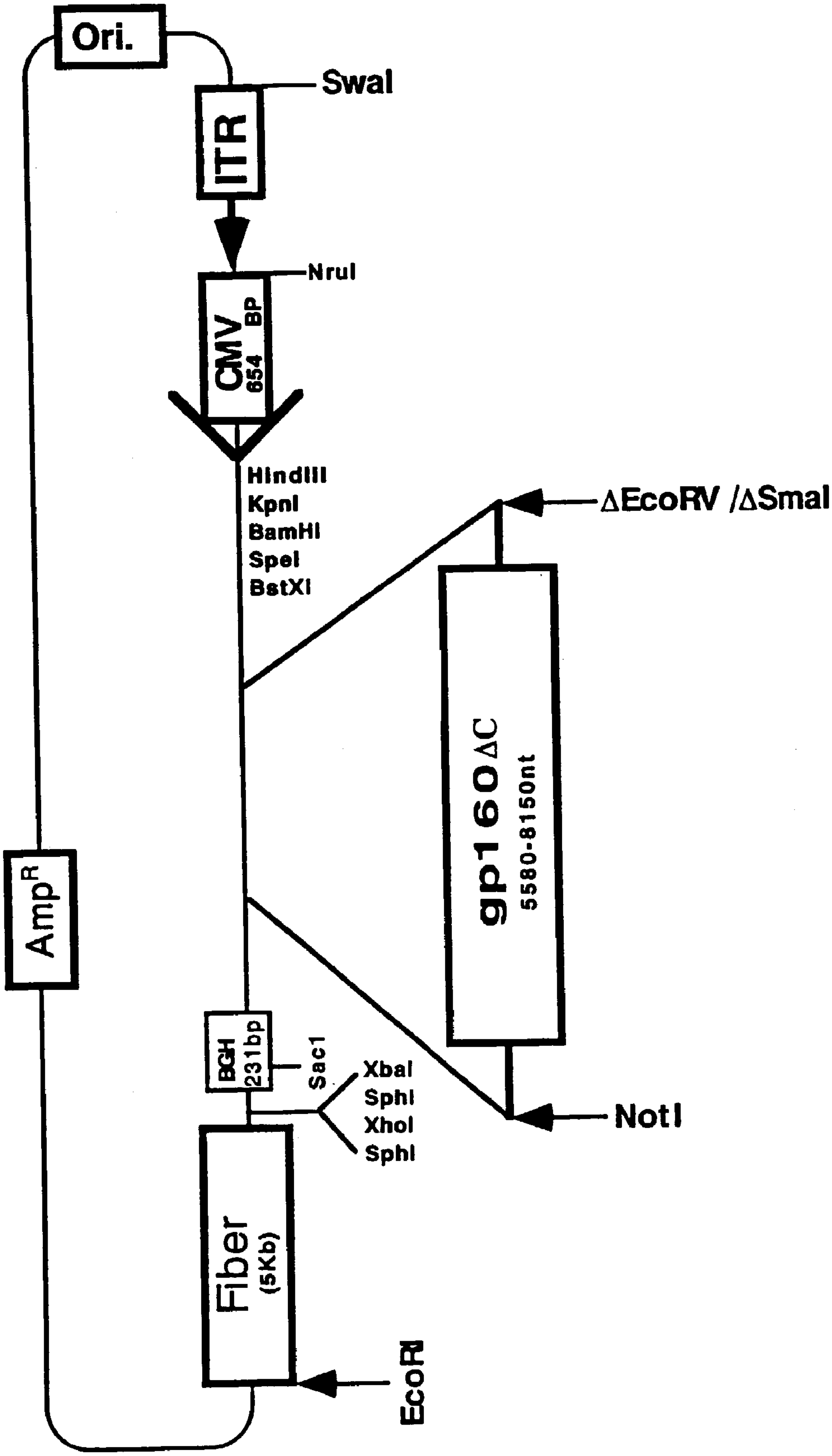
FIG. 23B illustrates a shuttle vector pRAd-ORF6-$E'''\Delta C$.

The DNA sequence encoding the modified Env (E$^m$ΔC) [SEQ ID NO: 24] was also inserted into E4 region of the adenoviral genome using a shuttle vector, resulting in shuttle vector pRAd-ORF6-E$^m$ΔC (FIG. 23B).

Both pLAd-E$^m$ΔC and pRAd-ORF6-E$^m$ΔC were linearized using appropriate restriction enzymes and ligated to the backbone of the adenovirus (FIG. 4B), resulting in the recombinant adenoviral vector Ad-E$^m$ΔC/E$^m$ΔC.

9) Ad-E$_m$.V3$^m$/G.IL-2

Yet another adenoviral vector, Ad-E$^m$.V3$^m$/G.IL-2, was constructed to carry coding sequences for modified HIV-1 Env having multi-clade V3 loops and Gag, and IL-2. Sequences encoding V3 loop from clade B, A, C, D, E, F, and G within Group M of HIV-1 are shown in FIG. 48. As shown in FIG. 48, for clade B (HIV-1 strain BH10) DNA sequence encoding V3 loop, nt 885-992 [SEQ ID NO: 25], was chosen. In this particular embodiment, for clade A (HIV-1 strain 192UG037WHO.01083hED) DNA sequence encoding V3 loop, nt 888-992 [SEQ ID NO: 26], was chosen. For clade C (HIV-1 strain 192BR025WHO.01093hED) DNA sequence encoding V3 loop, nt 876-980 [SEQ ID NO: 27], was chosen. For clade D (HIV-1 strain 192UG024.2) DNA sequence encoding V3 loop, nt 888-989 [SEQ ID NO: 28], was chosen. For clade E (HIV-1 strain 193TH976.17) DNA sequence encoding V3 loop, nt 894-998 [SEQ ID NO: 29], was chosen. For clade F (HIV-1 strain 193BR020.17) DNA sequence encoding V3 loop, nt 888-992 [SEQ ID NO: 30], was chosen. For clade G (HIV-1 strain 192RU131.9) DNA sequence encoding V3 loop, nt 885-989 [SEQ ID NO: 31], was chosen.

The DNA sequences encoding V3 loops from HIV clade A, C, D, E, F, and G were ligated by PCR to form a single fragment containing multiclade V3 loops. Primers for cloning these V3 loops from their cognate HIV clades are listed in FIG. 57. Since V3 loop of HIV clade B is already contained in the backbone of HIV-1 gp120, the cloned V3 loops from clade A, C, D, E, F, and G were inserted after V3 loop of clade B.

FIG. 24 illustrate a process for generating the ligated multiclade V3 loops by PCR and subsequent cloning into a construct encoding a modified gp120 of clade B. As illustrated in FIG. 24, each of the gene fragments encoding the envelope V3 loop region from clade A, C, D, E, F, and G was individually amplified by PCR using a set of forward and reverse primers listed in FIG. 57. Parameters for the PCR cycles are the following:

| | |
|---|---|
| denature: | 94° C. for 1 min; |
| annealing: | 50 to 60° C. for 30 sec; and |
| extension: | 72° C. for 1 min; |
| for 20 cycles. | |

The PCR product encoding V3 loop of one clade was ligated with another using PCR. For example, the PCR products encoding V3 loops of clade A and C were mixed together, ligated and amplified by PCR using the primers 1 and 4 as shown in FIG. 24, procuding an A/C fragment. Similarly, a PCR product encoding the ligated V3 loops of clade D and E was generated using primers 5 and 8, producing a D/E fragment; and clade F and G using primers 9 and 12 (FIG. 24), producing a F/G fragment.

Still referring to FIG. 24, the A/C and D/E fragments were ligated by PCR using primers 1 and 8 and cloned into a vector at EcoRI and BamHI sites. The F/G fragment was restriction digested with BamH1 and XbaI and fused with the sequence A/C/D/E to generate the multi-clade sequence ACDEFG (V3m).

To generate two repeats of the multi-clade ACDEFG sequence, the final PCR product encoding the multi-clade ACDEFG sequence was restriction digested with AvaI (at primer 1 and 12) and re-ligated head-to-tail, yielding the two repeat multiclade sequence 2×V3$^{m}$. The DNA sequence encoding $V_3$m or 2×V3m was then inserted after the sequence encoding V3 loop of clade B in a construct encoding gp120 which was modified as follows.

Figure 25:
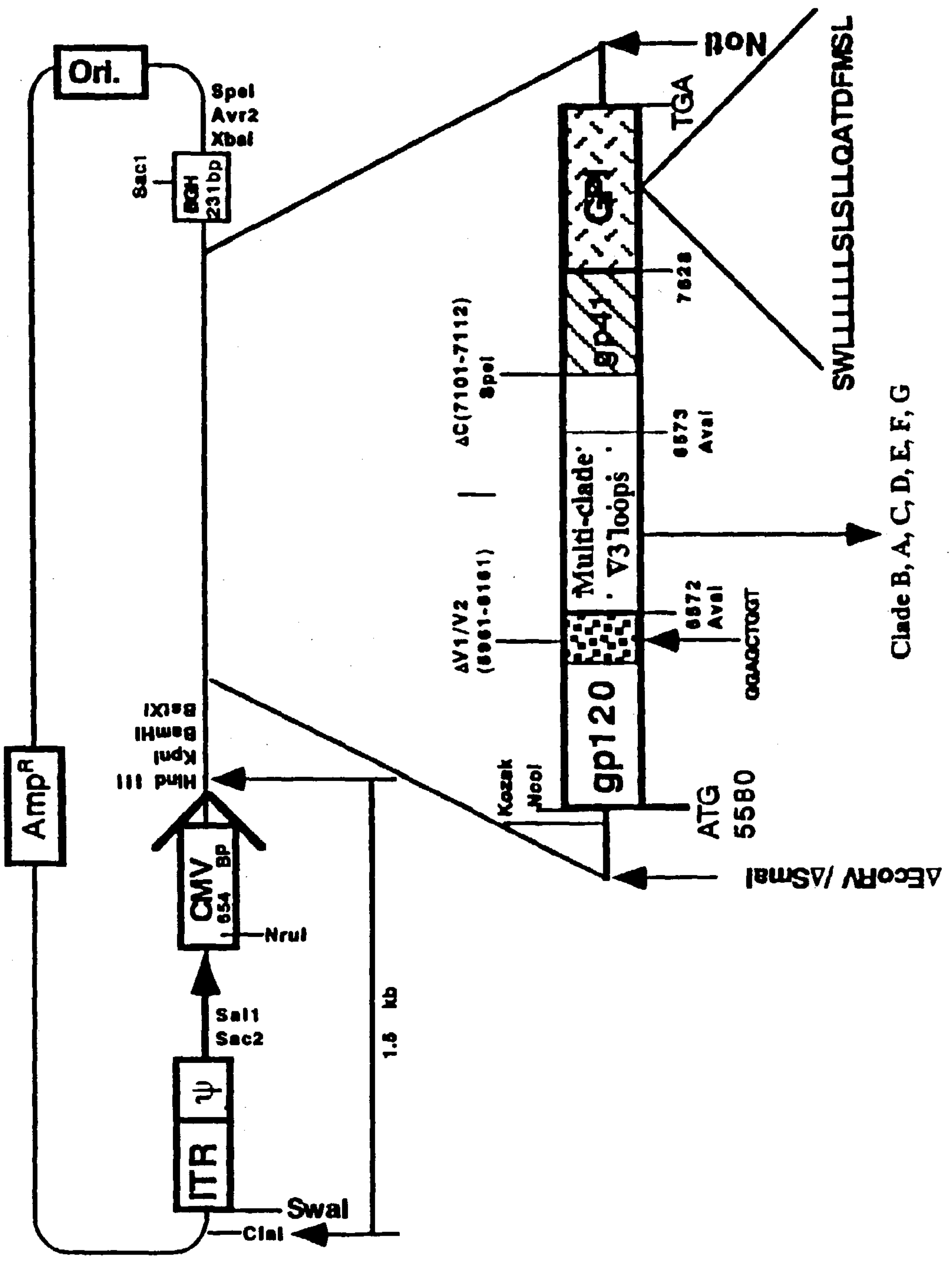
FIG. 25 illustrates a shuttle vector pLAd-$E'''$.V3.

DNA sequence encoding Env (nt 5580-8150) from HIV strain BH10 (clade B) was modified by a) deleting the sequence encoding the cleavage site (nt 7101-7112); b) deleting V1 and V2 loops (nt 5961-6161) and inserting nucleotide sequence GGA GCT GGT [SEQ ID NO: 12] that encodes amino acid sequence GAG [SEQ ID NO: 13]; c) inserting the multi-clade V3 loop (V3$^{m}$) sequence at position nt 6572; and d) replacing gp41 transmembrane domain sequence with a GPI anchor sequence encoding glycophosphatidyl inositol, SWLLLLLLSLSLLQATDFMSL [SEQ ID NO: 9]. DNA sequence encoding this modified Env [SEQ ID NO: 32] (the amino acid sequence of which is SEQ ID NO: 33, FIG. 49B) is shown in FIG. 49A, and was inserted into the left end (E1 region) of the adenoviral genome using a shuttle vector, resulting in a shuttle vector pLAd-E$^{m}$.V3$^{m}$ (FIG. 25).

Both pLAd-E$^{m}$.V3$^{m}$ and pRAd-ORF6-G.IL2 (FIG. 19B) were linearized using appropriate restriction enzymes and ligated to the backbone of the adenovirus (FIG. 4B), resulting in the recombinant adenoviral vector Ad-E$^{m}$.V3$^{m}$/G.IL2.

10) Shuttle Vector pLAd-E$^{m}$.2×V3$^{m}$

Figure 26:
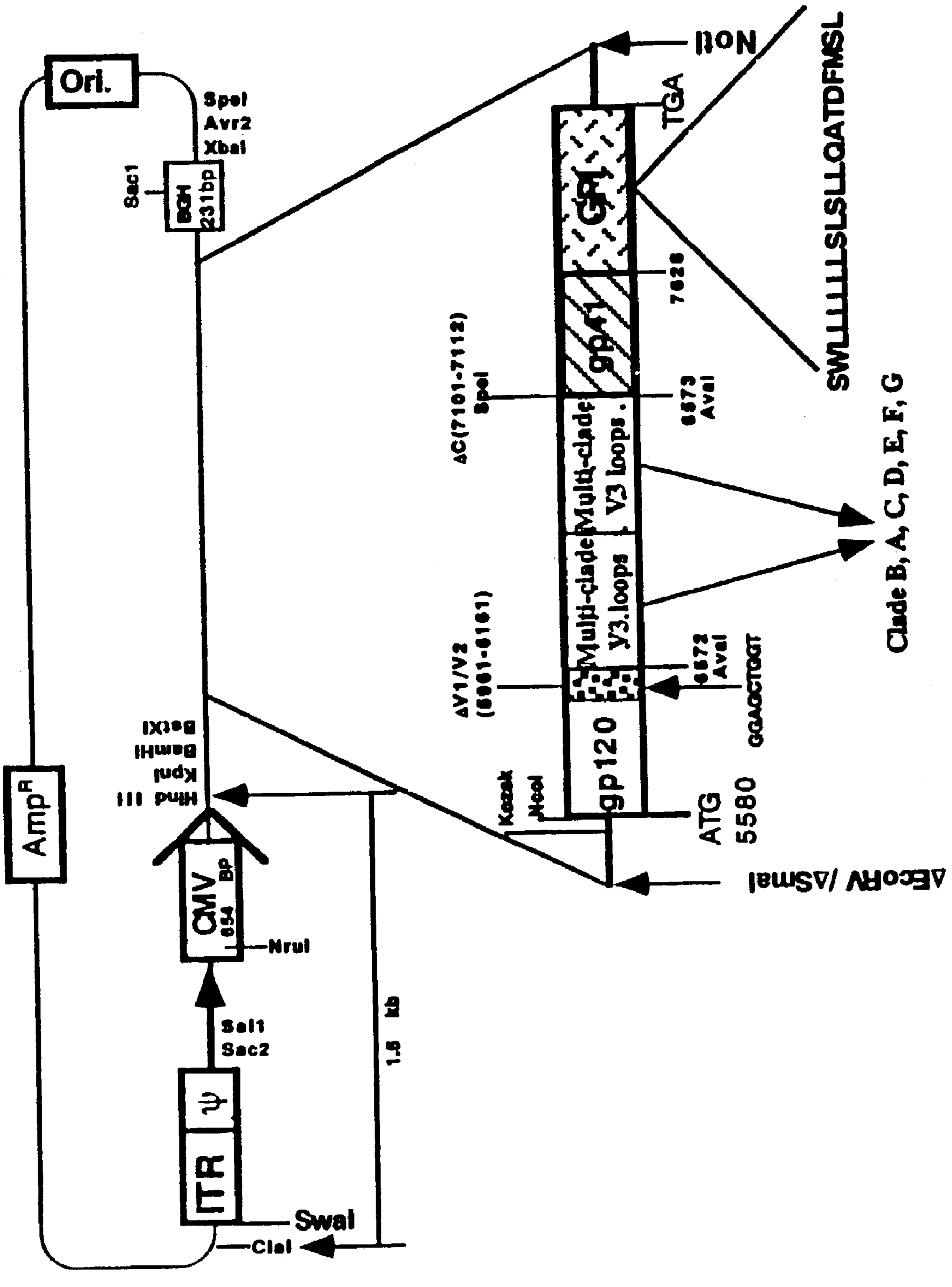
FIG. 26 illustrates a shuttle vector pLAd-$E'''$.2×V3.

To increase the expression level of the multi-clade V3 loops, the sequnece encoding two repeats of V3$^{m}$ sequence (2×V3$^{m}$, constructed above) was inserted into the sequence encoding the modified Env described in section 9) above. The resulting shuttle vector is designated pLAd-E$^{m}$.2×V3$^{m}$ and is shown in FIG. 26.

11) Shuffle Vectors Encoding p17 and/or p24

In nature the Pr55 Gag protein can be processed into four different proteins, p17MA, p24CA, p7NC, and p6. The p17MA protein remains associated with the inner side of the lipid envelope, and plays an important role in anchoring of envelope to the viral particle. The p24CA protein of all retroviruses contains a major homology region (MHR) that is required for efficient viral replication and particle production. Elispot data obtained implicates that p17MA (or p17) and p24CA (or p24) may have contributed significantly the specific CTL response in the Pr55 gag protein in peptide mapping experiments. According to the present invention, these HIV structural proteins are expressed by the recombinant virus to elicit specific CTL response to HIV infection. Further, these structure proteins can be modified to include a signal peptide (e.g., the HIV gp120 signal peptide encoded by SEQ ID NO: 74: atgagagtgaaggagaaatatcagcacttgtggagatgggggtggagatgg-ggcaccatgctccttgggatgttgatgatctgtagtgct) sequence which facilitates the secretion of these intracellular proteins by the infected cells. Moreover, by adding a membrane anchoring domain (e.g, the HIV gp41 transmembrane domain encoded by SEQ ID NO: 75: ttattcataatgatagtaggaggcttggtaggtttaaga-atagtttttgctgtactttctgtagtgaatagagttaggcagggatattcaccattatcg-tttcagacccacctcccaatcccgaggggga) to the secreted form of the HIV protein, such a modified HIV structural protein is rendered membrane bound, which better presents the HIV antigen to the body's immune system. These modifications may confer a much stronger immunogenicity to the mutant antigen than the native antigen which are trapped intracellularly.

Adenoviral shuttle vectors were constructed to encode the processed Gag proteins, p17, p24, and p17/24, each in three different forms: natural form, secreted form and membrane bound form.

Figure 27A:
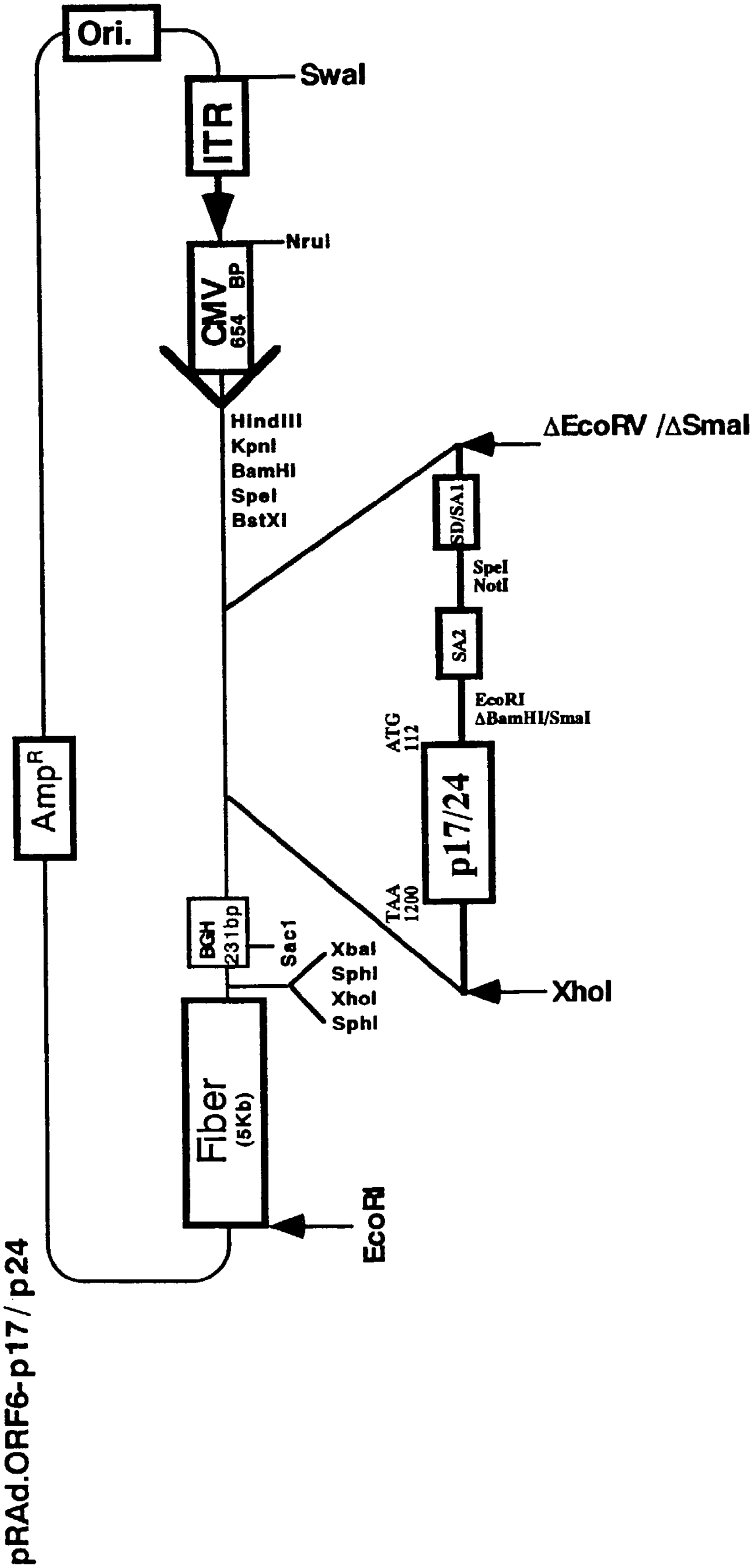
FIG. 27A illustrates a shuttle vector pRAd-ORF6-p17/p24.
Figure 27B:
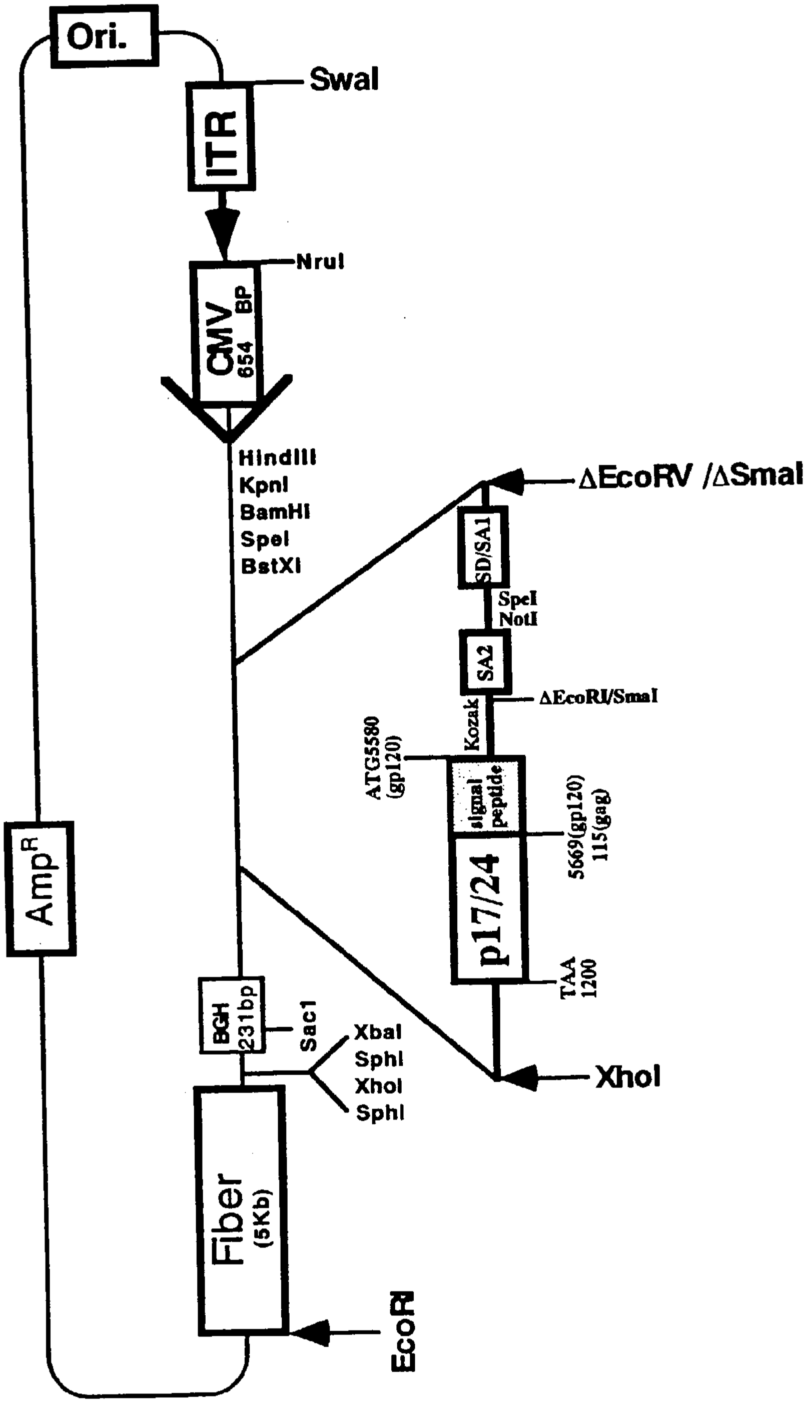
FIG. 27B illustrates a shuttle vector pRAd-ORF6-p17/p24 sec.
Figure 27C:
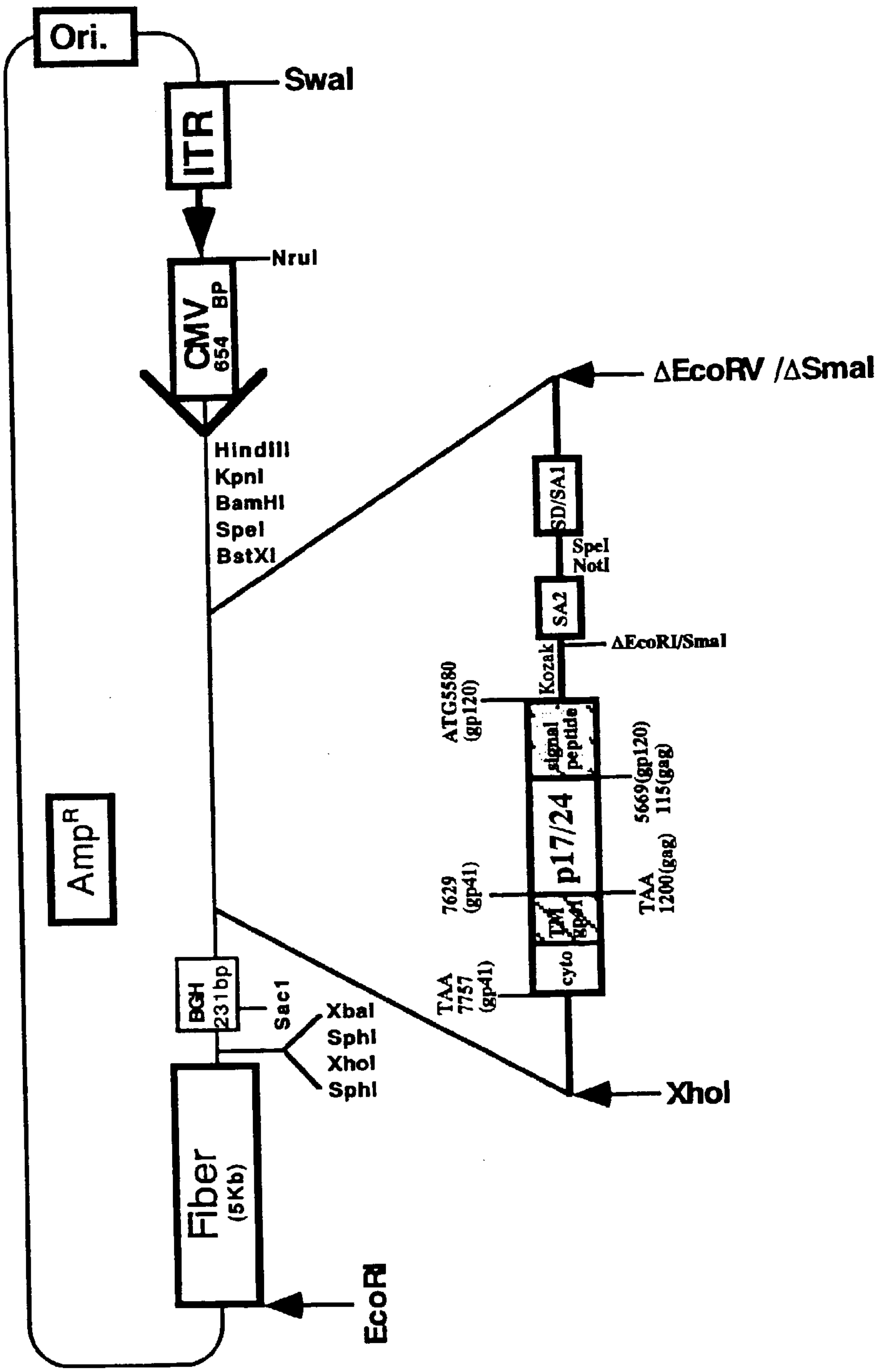
FIG. 27C illustrates a shuttle vector pRAd-ORF6-p17/p24 MB.

DNA sequences of p17/p24 in the three forms [SEQ ID NOs: 34-36] are shown in FIG. 50A (corresponding amino acid sequences [SEQ ID NOs: 37-39], FIG. 50B) and were each inserted into E4 region of the adenoviral genome using a shuttle vector, resulting in shuttle vector pRAd-ORF6-p17/24 (natural form, FIG. 27A), pRAd-ORF6-p17/24 sec (secreted form, FIG. 27B), and pRAd-ORF6-p17/24 MB (membrane-bound form, FIG. 27C), respectively.

Figure 28A:
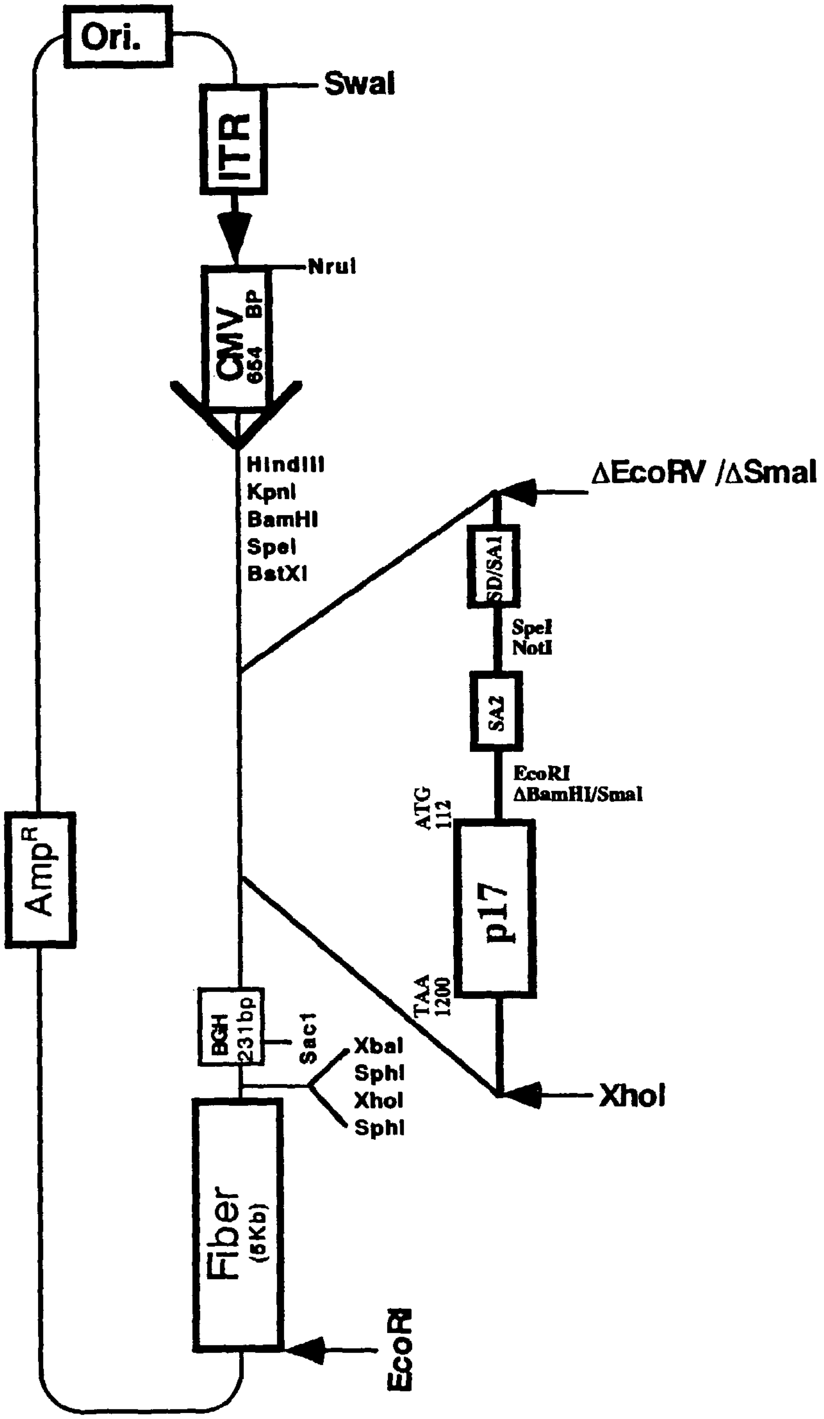
FIG. 28A illustrates a shuttle vector pRAd-ORF6-p17.
Figure 28B:
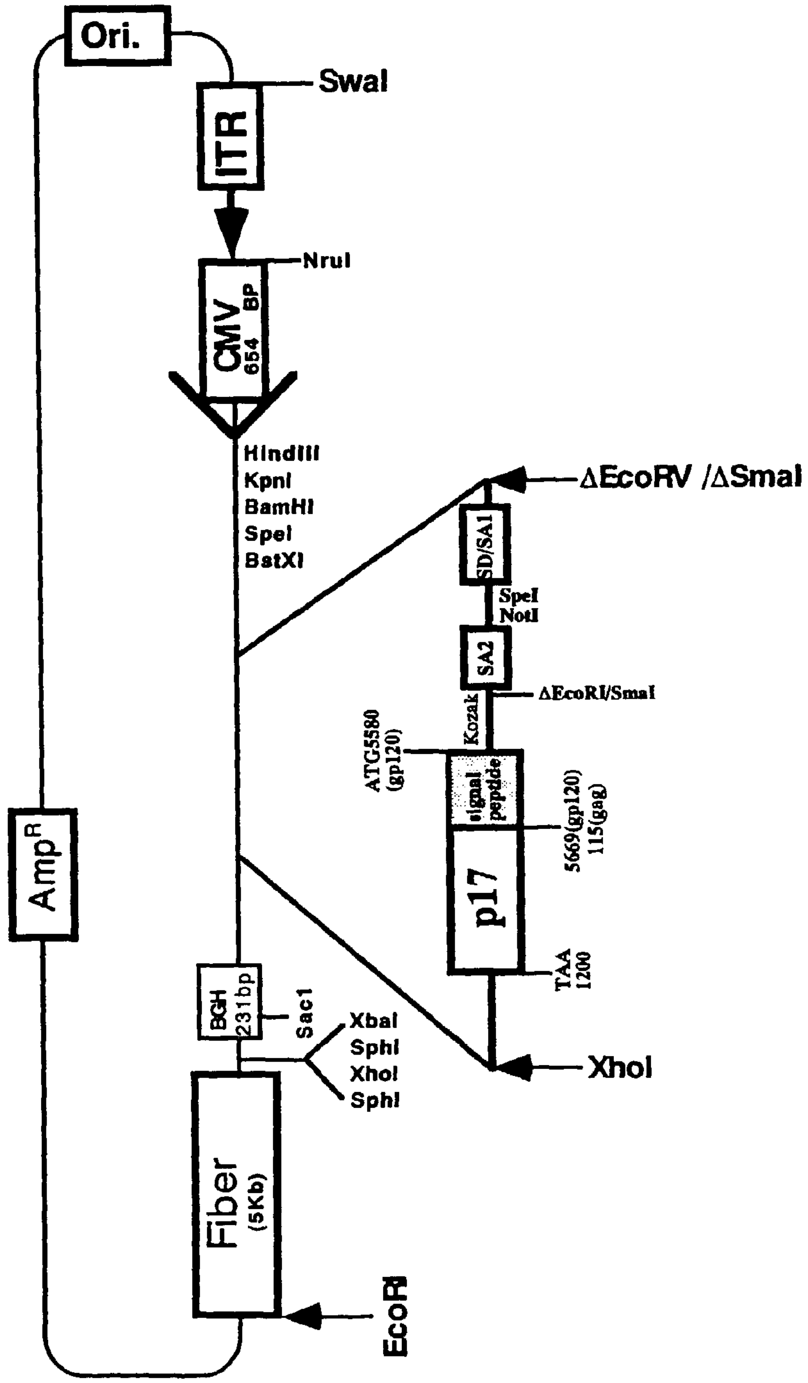
FIG. 28B illustrates a shuttle vector pRAd-ORF6-p17 sec.
Figure 28C:
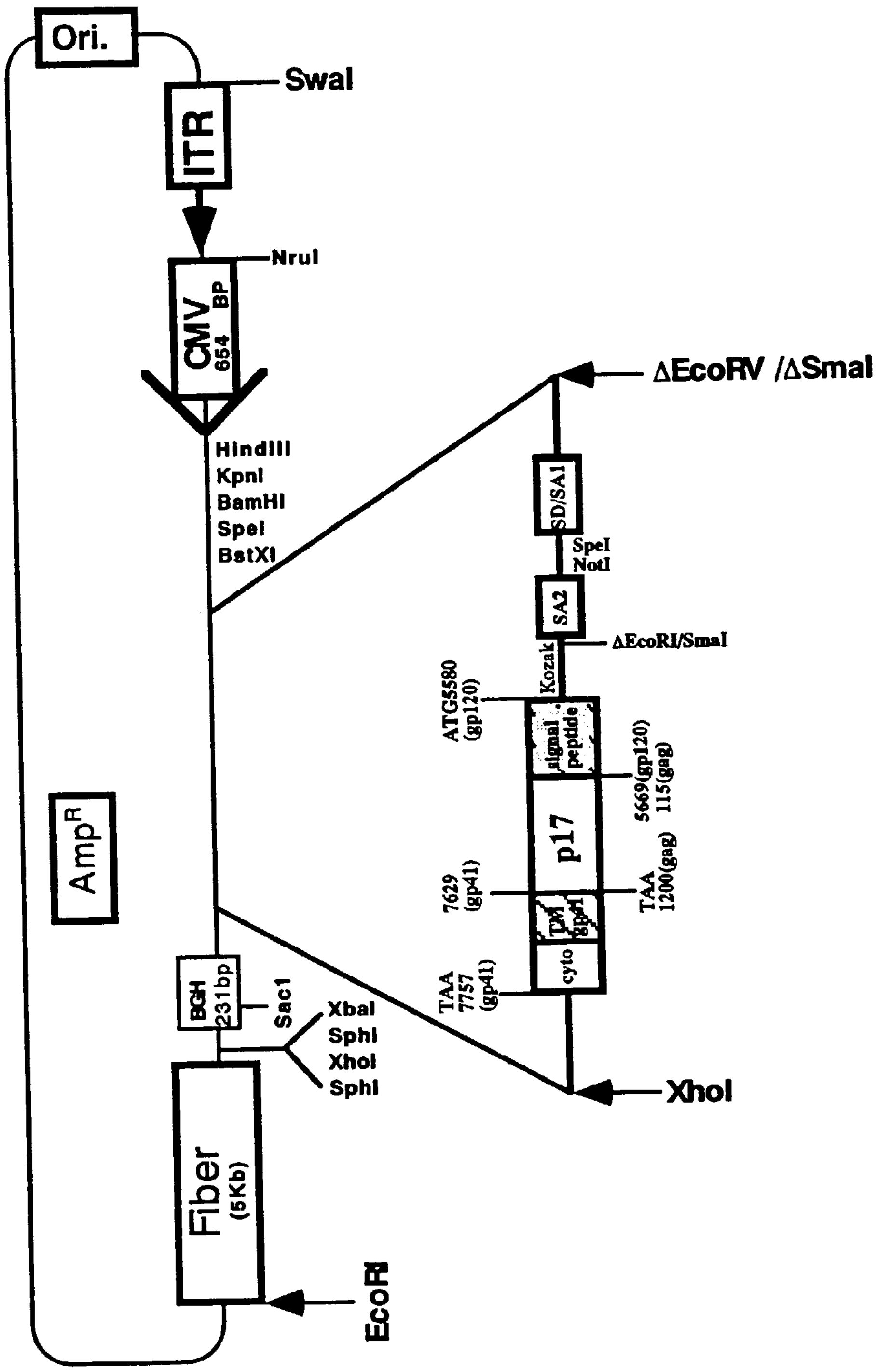
FIG. 28C illustrates a shuttle vector pRAd-ORF6-p17 MB.

DNA sequences of p17 in the three forms [SEQ ID NOs: 40-42] are shown in FIG. 51A (corresponding amino acid sequences [SEQ ID NOs: 43-45], FIG. 51B) and were each inserted into E4 region of the adenoviral genome using a shuttle vector, resulting in shuttle vector pRAd-ORF6-p17 (natural form, FIG. 28A), pRAd-ORF6-p17 sec (secreted form, FIG. 28B), and pRAd-ORF6-p17 MB (membrane-bound form, FIG. 28C), respectively.

Figure 29A:
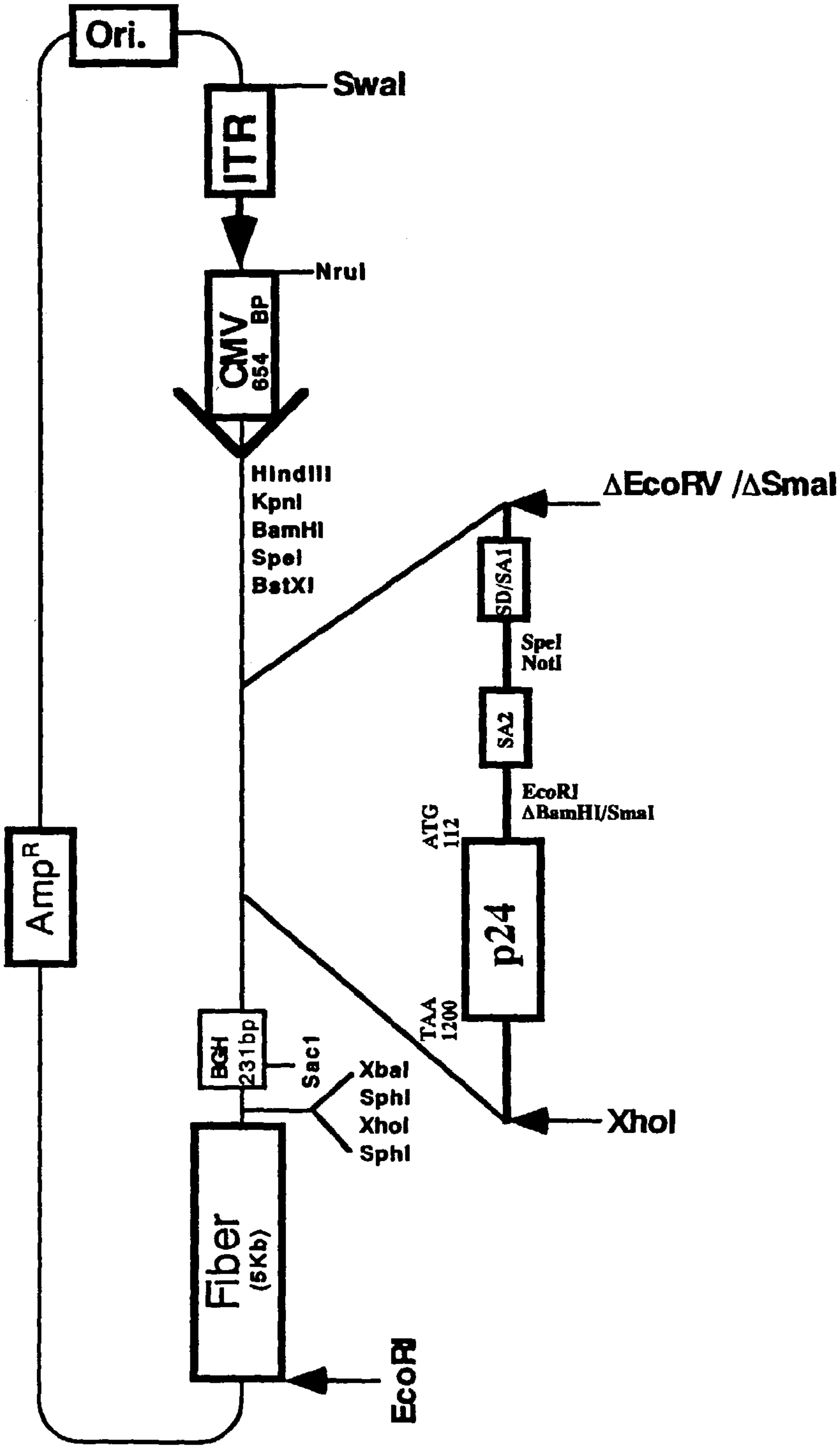
FIG. 29A illustrates a shuttle vector pRAd-ORF6-p24.
Figure 29B:
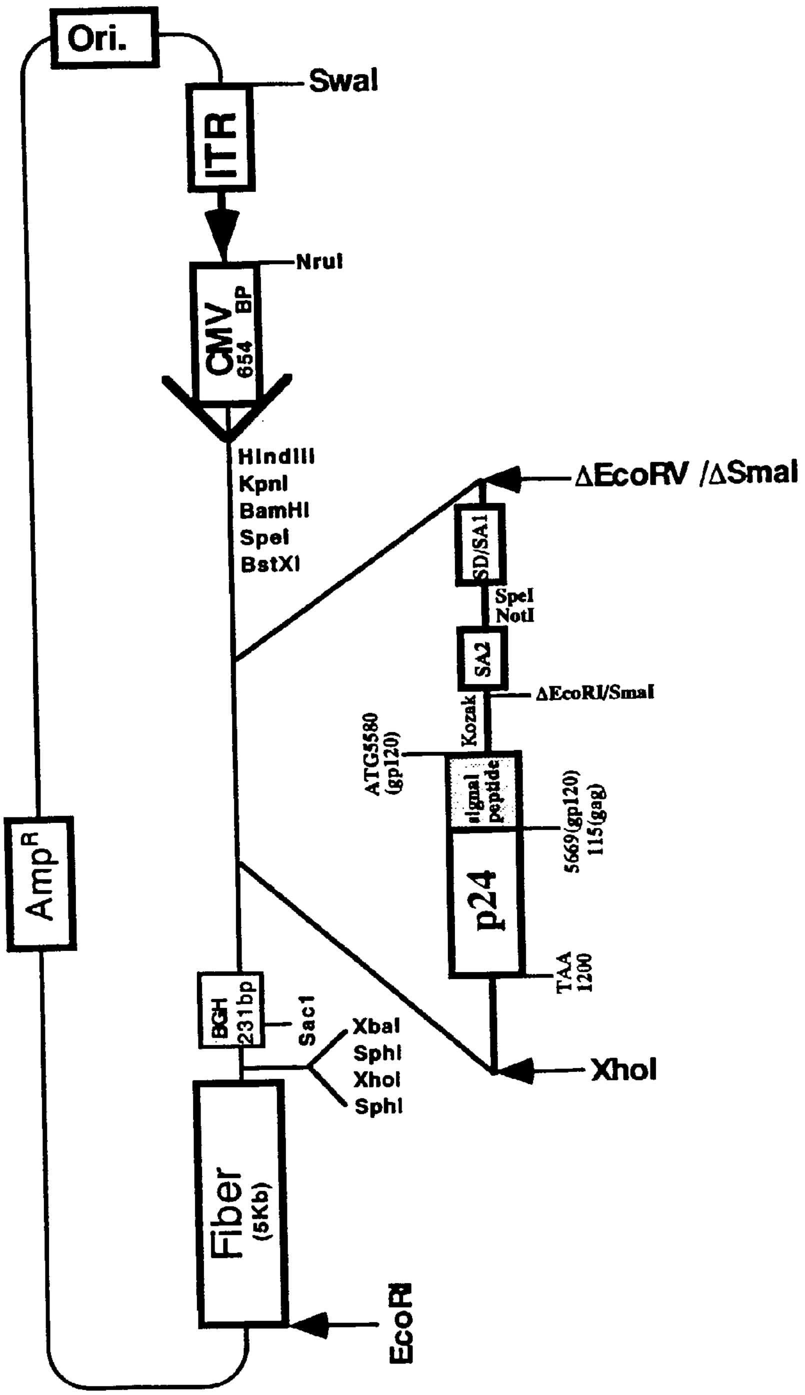
FIG. 29B illustrates a shuttle vector pRAd-ORF6-p24 sec.
Figure 29C:
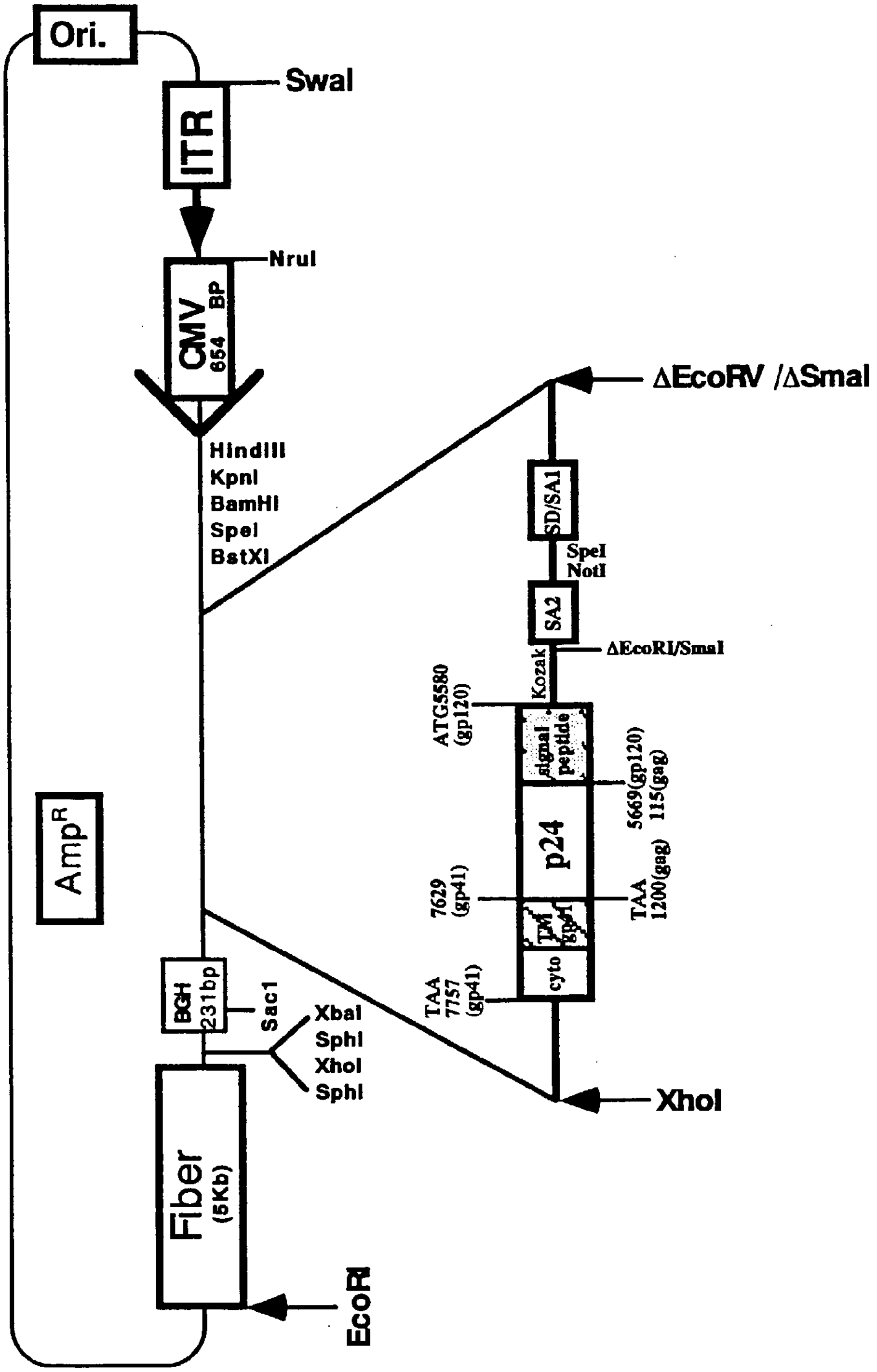
FIG. 29C illustrates a shuttle vector pRAd-ORF6-p24 MB.

DNA sequences of p24 in the three forms [SEQ ID NOs: 46-48] are shown in FIG. 52A (corresponding amino acid sequences [SEQ ID NOs: 49-51], FIG. 52B) and were each inserted into E4 region of the adenoviral genome using a shuttle vector, resulting in shuttle vector pRAd-ORF6-p24 (natural form, FIG. 29A), pRAd-ORF6-p24 sec (secreted form, FIG. 29B), and pRAd-ORF6-p24 MB (membrane-bound form, FIG. 29C), respectively.

The pLAd- and pRAd-shuttle vectors constructed above can be combined in a combinatorial way to generate a wide variety of recombinant adenoviral vectors. The following are just a few examples of such recombinant adenoviral vectors.

12) Ad-E$^{m}$.2×V3$^{m}$/p17/24 MB

Figure 30A:
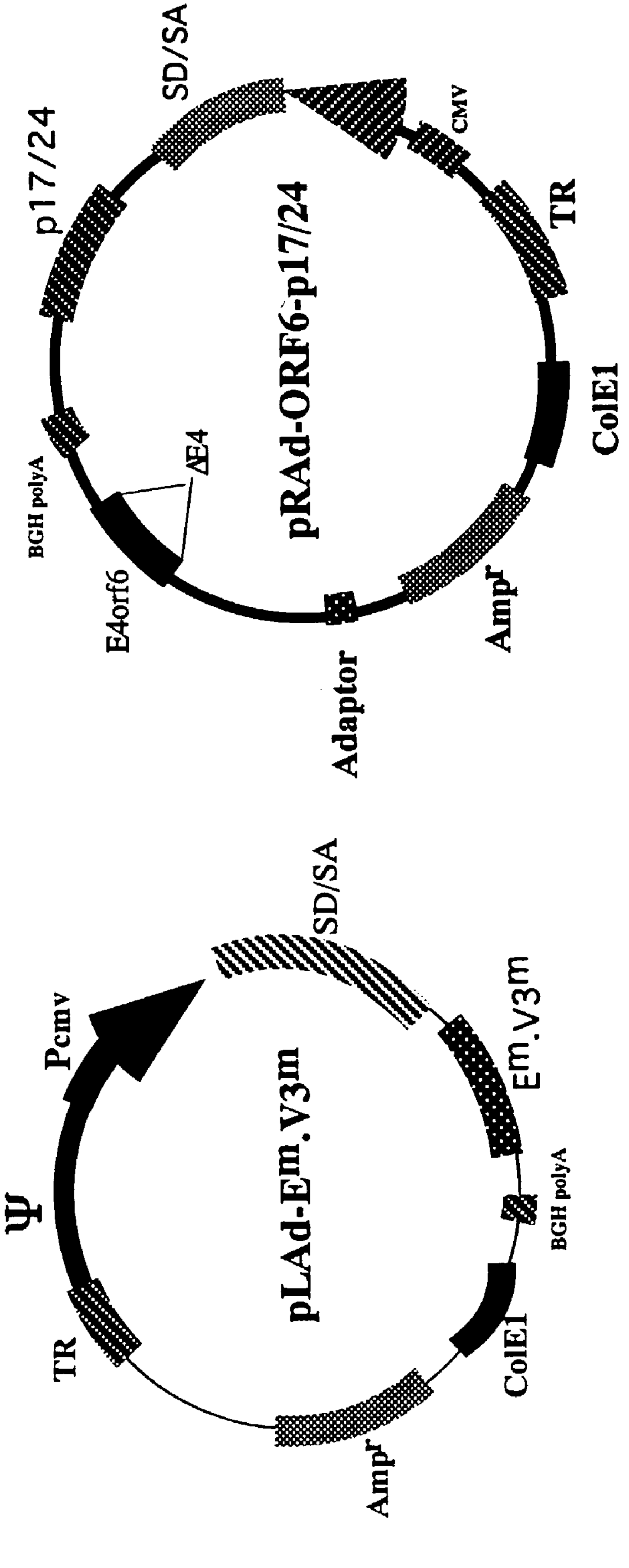
FIGS. 30A-B illustrate a process of construction of Ad-$E'''$.2×$V3'''$/p17/p24 MB.
Figure 30B:
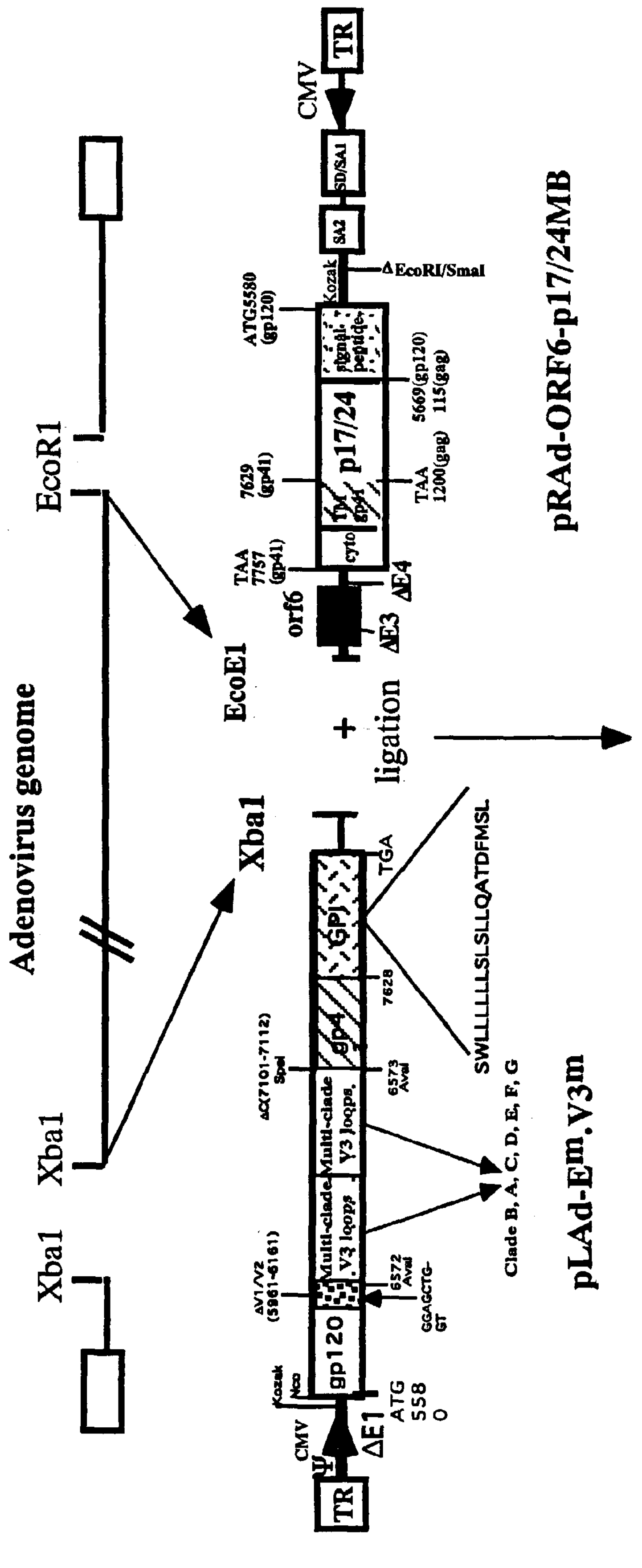

FIGS. 30A-B illustrate the construction of a recombinant adenoviral vector encoding modified Env containing two copies of multi-clade V3 loops and p17/p24 in membrane-bound form. As illustrated in FIGS. 30A-B, pLAd-E$^{m0.2}$×V3$^{m}$ (details of the vector shown in FIG. 26) and pRAd-ORF6-p17/24 MB (details of the vector shown in FIG. 27C) were linearized using EcoR1 and Xba1 restriction enzymes and ligated to the backbone of the adenovirus, resulting in the recombinant adenoviral vector Ad-E$^{m}$.2×V3$^{m}$/p17/24 MB.

13) Ad-E$^{m}$.2×V3$^{m}$/p17 MB

Figure 31A:
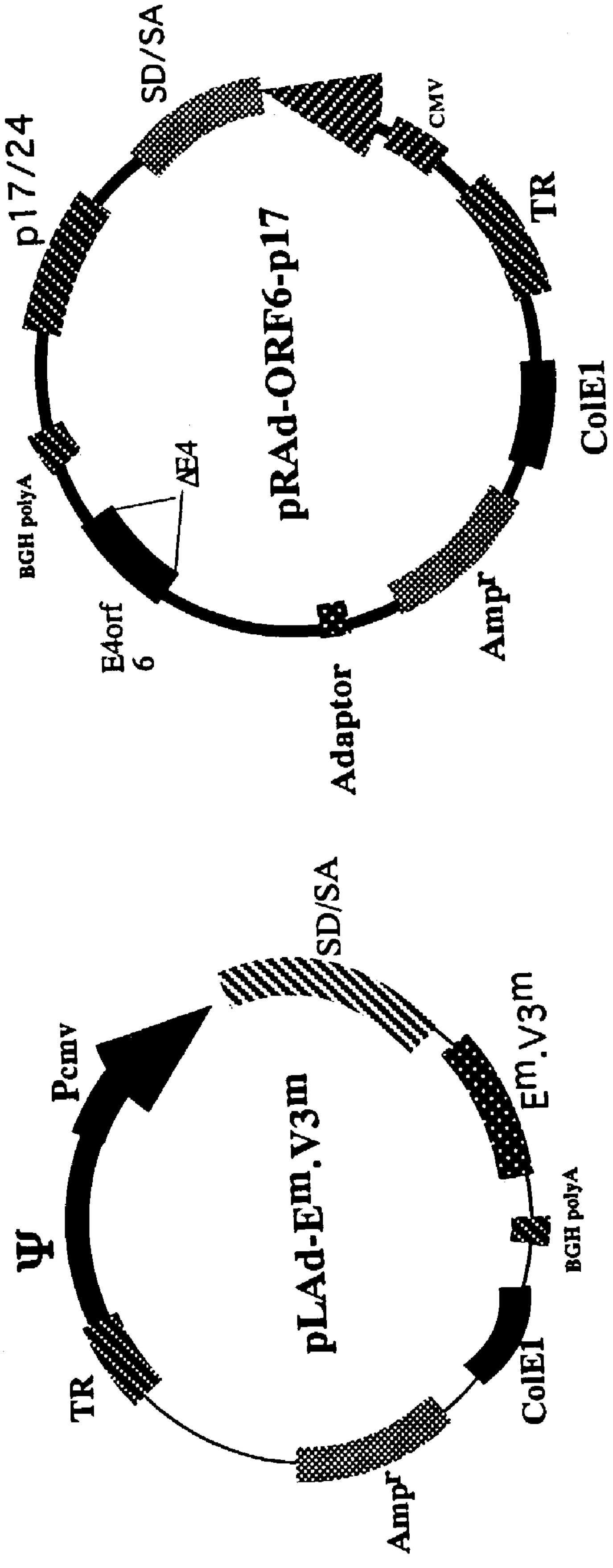
FIGS. 31A-B illustrate a process of construction of Ad-$E'''$.2×$V3'''$/p17 MB.
Figure 31B:
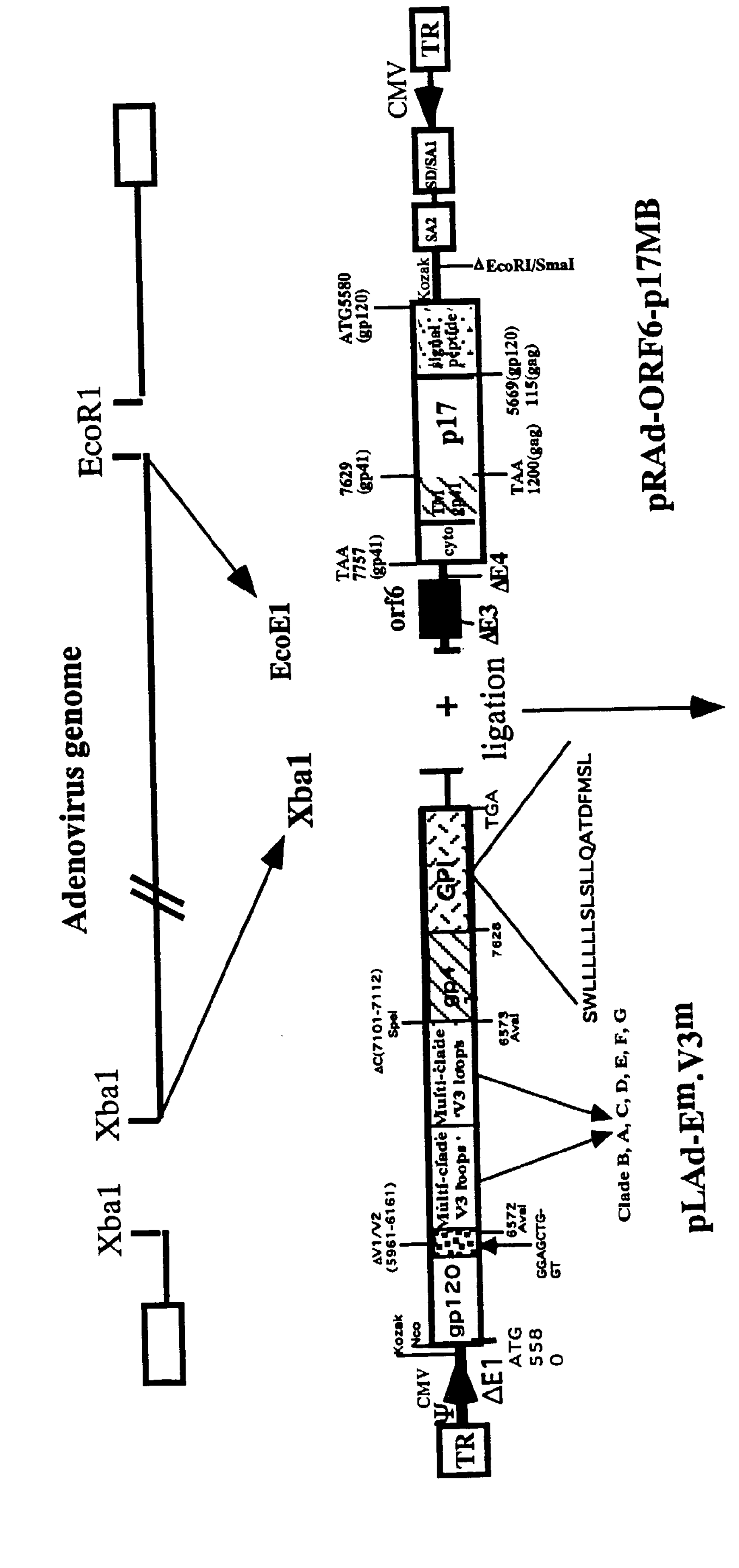

FIGS. 31A-B illustrate the construction of a recombinant adenoviral vector encoding modified Env containing two copies of multi-clade V3 loops and p17 in membrane-bound form. As illustrated in FIGS. 31A-B, pLAd-E$^{m}$.2×V3$^{m}$ (details of the vector shown in FIG. 26) and pRAd-ORF6-p17 MB (details of the vector shown in FIG. 28C) were linearized using EcoR1 and Xba1 restriction enzymes and ligated to the backbone of the adenovirus, resulting in the recombinant adenoviral vector Ad-E$^{m}$.2×V3$^{m}$/p17 MB.

14) Ad-E$_{m}$.2×V3$^{m}$/p24 MB

Figure 32A:
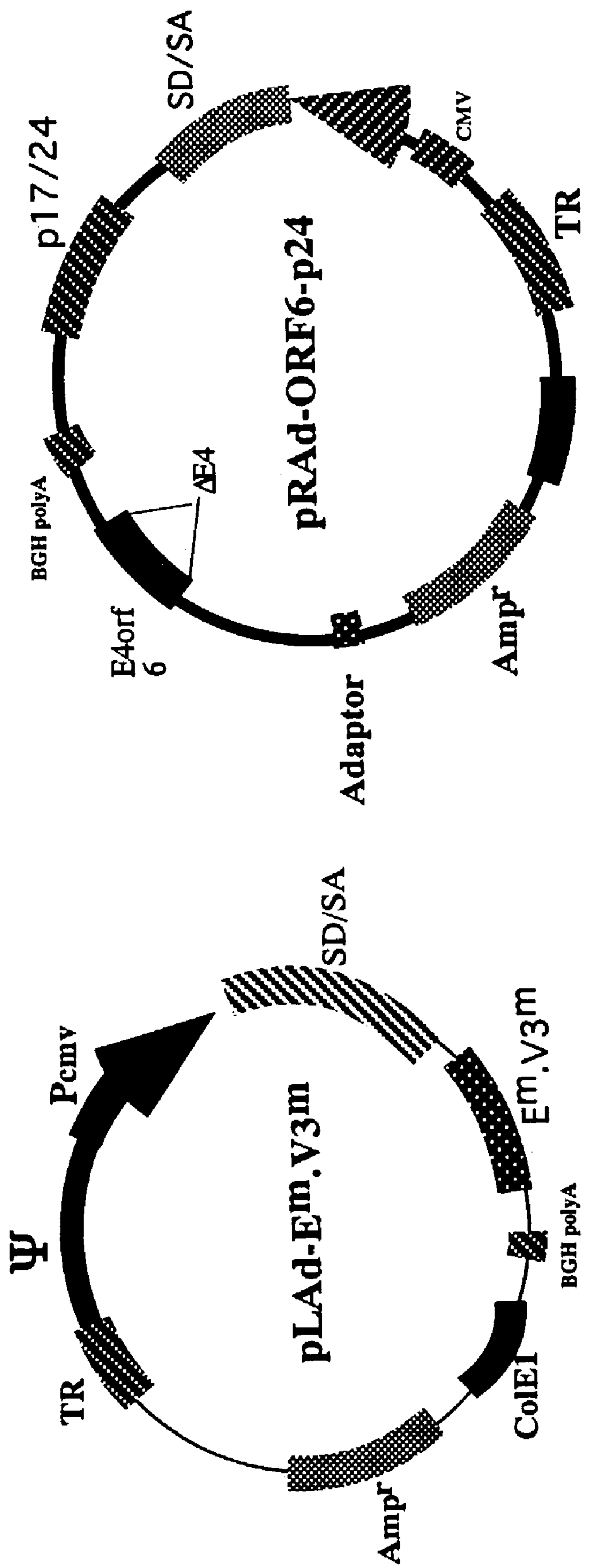
FIGS. 32A-B illustrate a process of construction of Ad-$E'''$.2×$V3'''$/p24 MB.
Figure 32B:
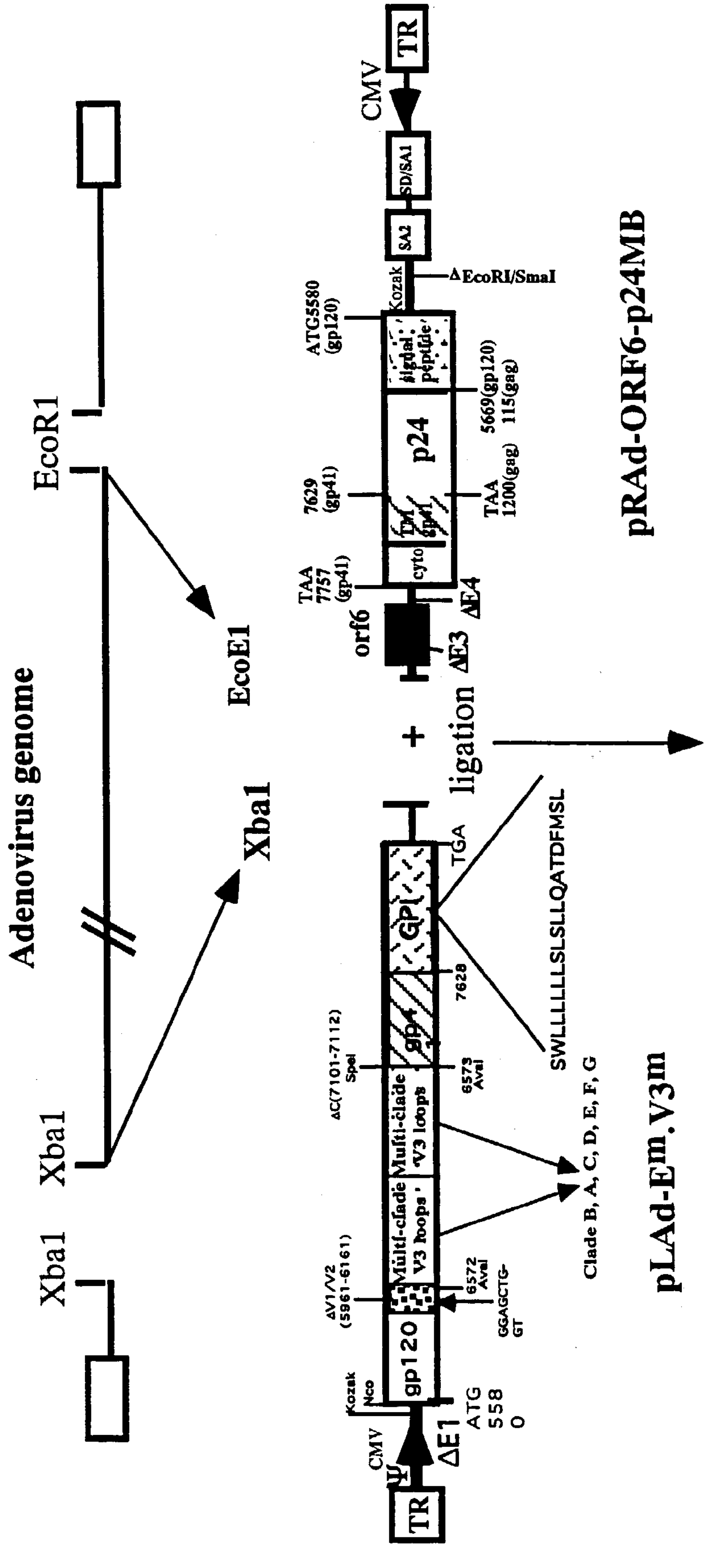

FIGS. 32A-B illustrate the construction of a recombinant adenoviral vector encoding modified Env containing two copies of multi-clade V3 loops and p24 in membrane-bound form. As illustrated in FIGS. 32A-B, pLAd-E$^{m}$.2×V3$^{m}$ (details of the vector shown in FIG. 26) and pRAd-ORF6-p24 MB (details of the vector shown in FIG. 29C) were linearized using EcoR1 and Xba1 restriction enzymes and ligated to the backbone of the adenovirus, resulting in the recombinant adenoviral vector Ad-E$^{m}$.2×V3$^{m}$/p24 MB.

15) Ad-E$^{m}$ΔCΔT$^{300}$.2×V3$^{m}$.T./p17/24 sec

Figure 33:
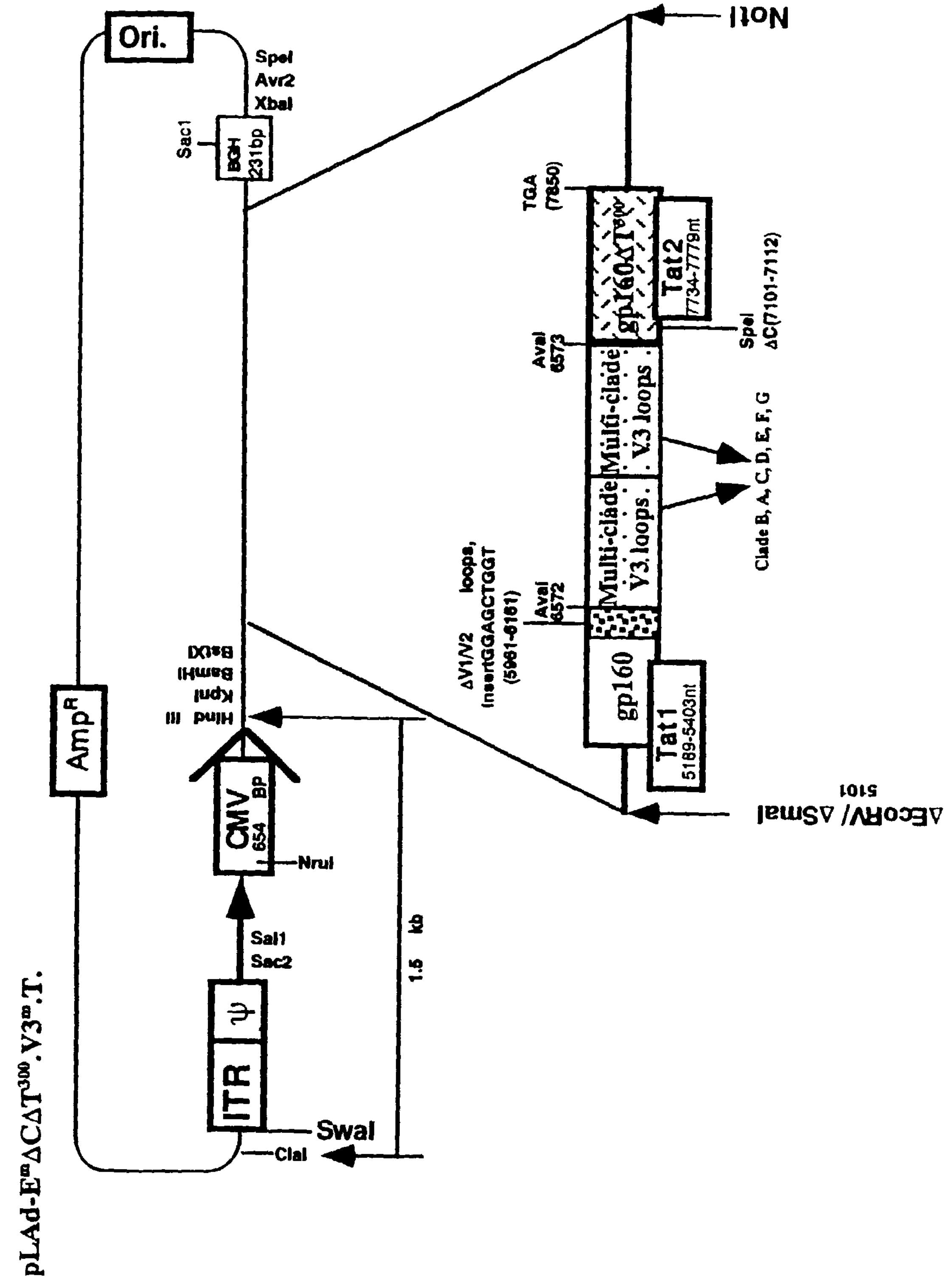
FIG. 33 illustrates a shuttle vector pLAd-$E'''\Delta C\Delta T^{300}$.2×$V3'''$.T.

DNA sequence encoding Env (including Tat1 (nt 5189-5403) and Tat2 (7734-7779)) from HIV strain BH10 was modified by a) deleting the sequence encoding the cleavage site (nt 7101-7112); b) deleting V1 and V2 loops (nt 5961-6161) and inserting nucleotide sequence GGA GCT GGT [SEQ ID NO: 12] that encodes amino acid sequence GAG [SEQ ID NO: 13]; c) inserting two copies of the multi-clade V3 loop (2×V3$^{m}$) sequence at position nt 6572; and d) deleting the cytosolic domain of 100 amino acids in length (encoded by nucleotide at position 7850-8150). DNA sequence encoding this modified Env [SEQ ID NO: 52] (the amino acid sequence of which is SEQ ID NO: 53, FIG. 53B) is shown in FIG. 53A, and was inserted into the left end (E1 region) of the adenoviral genome using a shuttle vector, resulting in a shuttle vector pLAd-E$^{m}$ΔCΔT$^{300}$.2×V3$^{m}$.T (FIG. 33).

Both pLAd-E$^{m}$ΔCΔT$^{300}$.2×V3$^{m}$.T and pRAd-ORF6-p17/24 sec (FIG. 27B) were linearized using appropriate restriction enzymes and ligated to the backbone of the adenovirus (FIG. 4B), resulting in the recombinant adenoviral vector Ad-E$^{m}$ΔCΔT$^{300}$.2×V3$^{m}$.T./p17/24 sec.

16) Ad-E$^{m}$ΔCΔT$^{300}$.2×V3$^{m}$.T./p17/24 MB

Both pLAd-E$^{m}$ΔCΔT$^{300}$.2×V3$^{m}$.T (FIG. 33) and pRAd-ORF6-p17/24 MB (FIG. 27C) were linearized using appropriate restriction enzymes and ligated to the backbone of the adenovirus (FIG. 4B), resulting in the recombinant adenoviral vector Ad-E$^{m}$ΔCΔT$^{300}$.2×V3$^{m}$.T./p17/24 MB.

17) Ad-E$^{m}$ΔCΔT$^{99}$.2×V3$^{m}$.T.R/p17/24 sec

Figure 34:
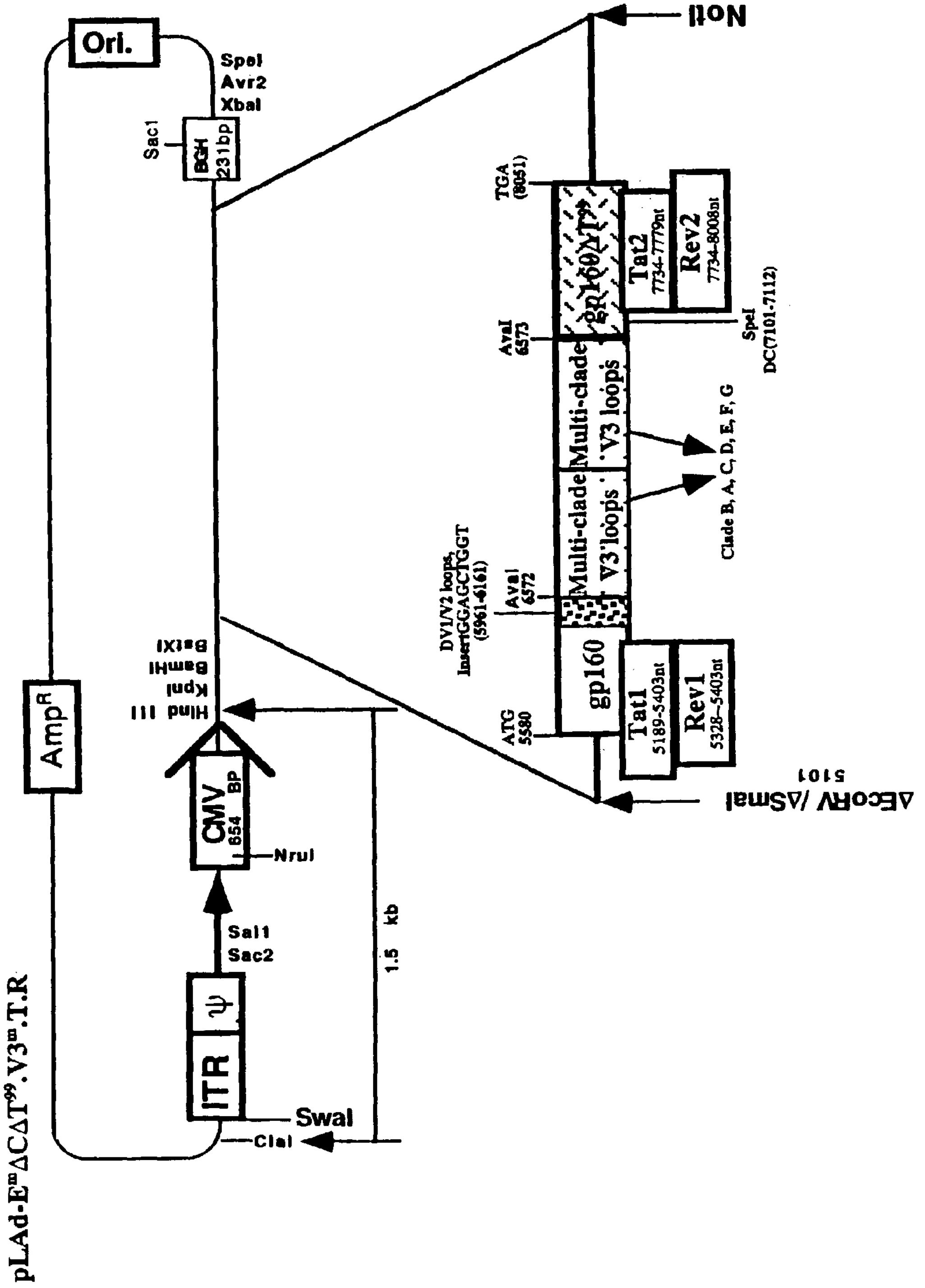
FIG. 34 illustrates a shuttle vector pLAd-$E'''\Delta C\Delta T^{99}$.2×$V3'''$.T.R.

DNA sequence encoding Env (including Tat1 (nt 5189-5403), Rev1 (nt 5328-5403), Tat2 (7734-7779) and Rev2 (7734-8008)) from HIV strain BH10 was modified by a) deleting the sequence encoding the cleavage site (nt 7101-7112); b) deleting V1 and V2 loops (nt 5961-6161) and inserting nucleotide sequence GGA GCT GGT [SEQ ID NO: 12] that encodes amino acid sequence GAG [SEQ ID NO: 13]; c) inserting two copies of the multi-clade V3 loop (2×V3$^{m}$) sequence at position nt 6572; and d) deleting the cytosolic domain of 33 amino acids in length (nt 8687-8785). DNA sequence encoding this modified Env [SEQ ID NO: 54] (the amino acid sequence of which is SEQ ID NO: 55, FIG. 54B) is shown in FIG. 54A, and was inserted into the left end (E1 region) of the adenoviral genome using a shuttle vector, resulting in a shuttle vector pLAd-E$^{m}$ΔCΔT$^{300}$.2×V3$^{m}$.T.R (FIG. 34).

Both pLAd-E$^{m}$ΔCΔT$^{300}$.2×V3$^{m}$.T.R and pRAd-ORF6-p17/24 sec (FIG. 27B) were linearized using appropriate restriction enzymes and ligated to the backbone of the adenovirus (FIG. 4B), resulting in the recombinant adenoviral vector Ad-E$^{m}$ΔCΔT$^{99}$.2×V3$^{m}$.T.R/p17/24 sec.

18) Ad-E$^{m}$ΔCΔT$^{99}$.2×V3$^{m}$.T.R17/24 MB

Both pLAd-E$^{m}$ΔCΔT$^{99}$.2×V3m.T.R (FIG. 34) and pRAd-ORF6-p17/24 MB (FIG. 27C) were linearized using appropriate restriction enzymes and ligated to the backbone of the adenovirus (FIG. 4B), resulting in the recombinant adenoviral vector Ad-E$^{m}$ΔCΔT$^{99}$.2×V3$^{m}$.T.R/p17/24 MB.

19) Ad-E$^{m}$ΔCΔT$^{300}$.2×V3$^{m}$.T/G.PI

Figure 35:
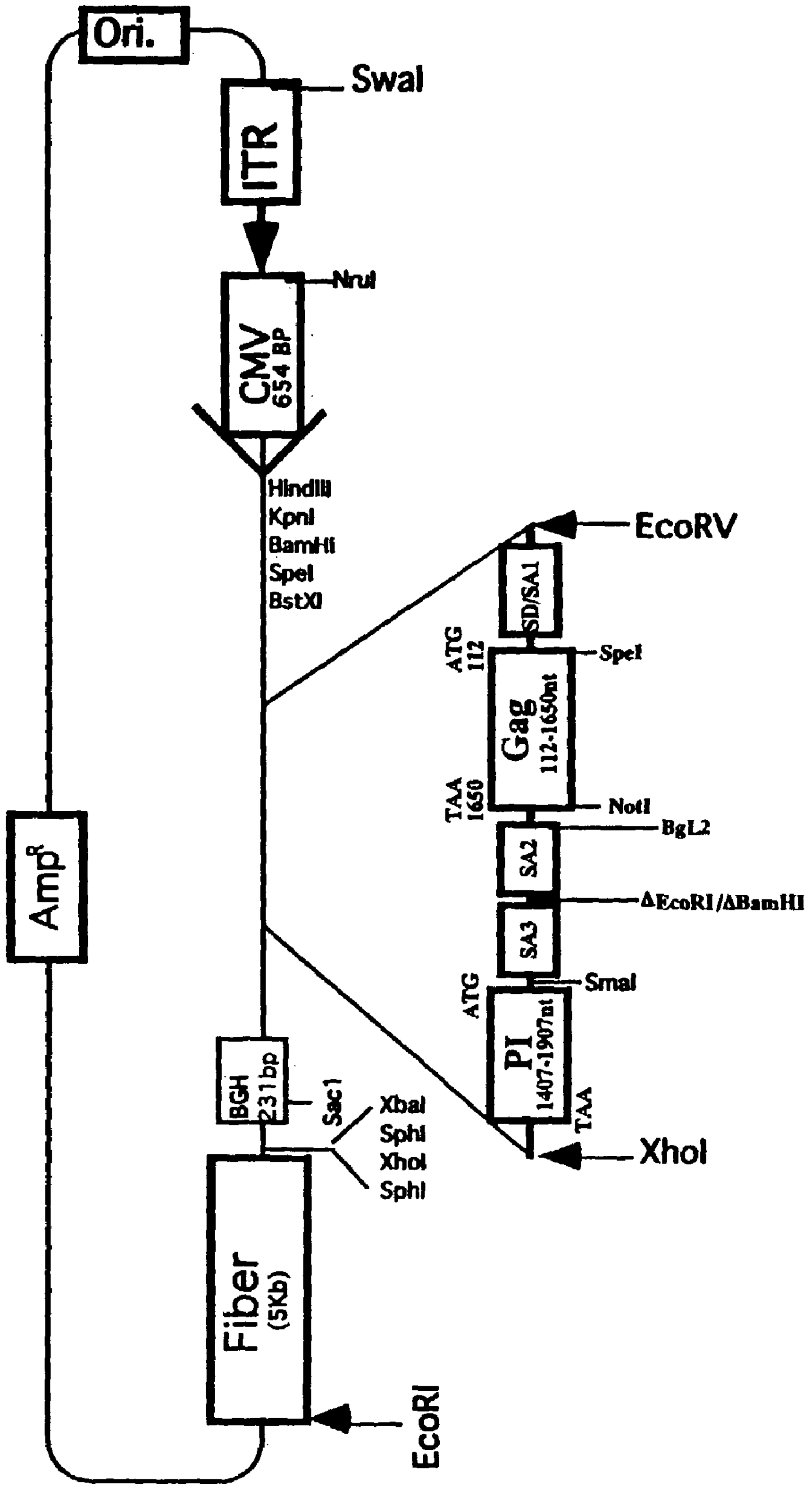
FIG. 35 illustrates a shuttle vector pRAd-ORF6-G.PI.

Peptide mapping and Elispot data indicate that specific regions of the Gag protein may play significant roles in eliciting CTL response in animals immunized with the adenoviral vectors of the present invention. To facilitate efficient expression of p17MA and p24CA by the adenoviral vector, DNA sequence encoding the protease (PI, DNA SEQ ID NO: 56, FIG. 55A; amino acid SEQ ID NO: 57, FIG. 55B) from the pol region of HIV strain BH10 was inserted into a region downstream from the sequence encoding Gag in a shuttle vector pRAd-ORF6-G.PI (FIG. 35). As illustrated in FIG. 35, Gag and PI are expressed separately from a CMV promoter via a retroviral splicing donor (SD) and acceptor (SA) mechanism at two splicing acceptor sites, $SA_1$ and $SA_2$/$SA_3$.

Both pLAd-E$^{m}$ΔCΔT$^{300}$.2×V3$^{m}$.T (FIG. 33) and pRAd-ORF6/G.PI (FIG. 35) were linearized using appropriate restriction enzymes and ligated to the backbone of the adenovirus (FIG. 4B), resulting in the recombinant adenoviral vector Ad-E$^{m}$ΔCΔT$_{300}$.2×V3$^{m}$.T/G.PI.

20) Ad-E$^{m}$ΔCΔT$^{300}$. 2×V3$^{m}$.TIG-PI

Figure 36:
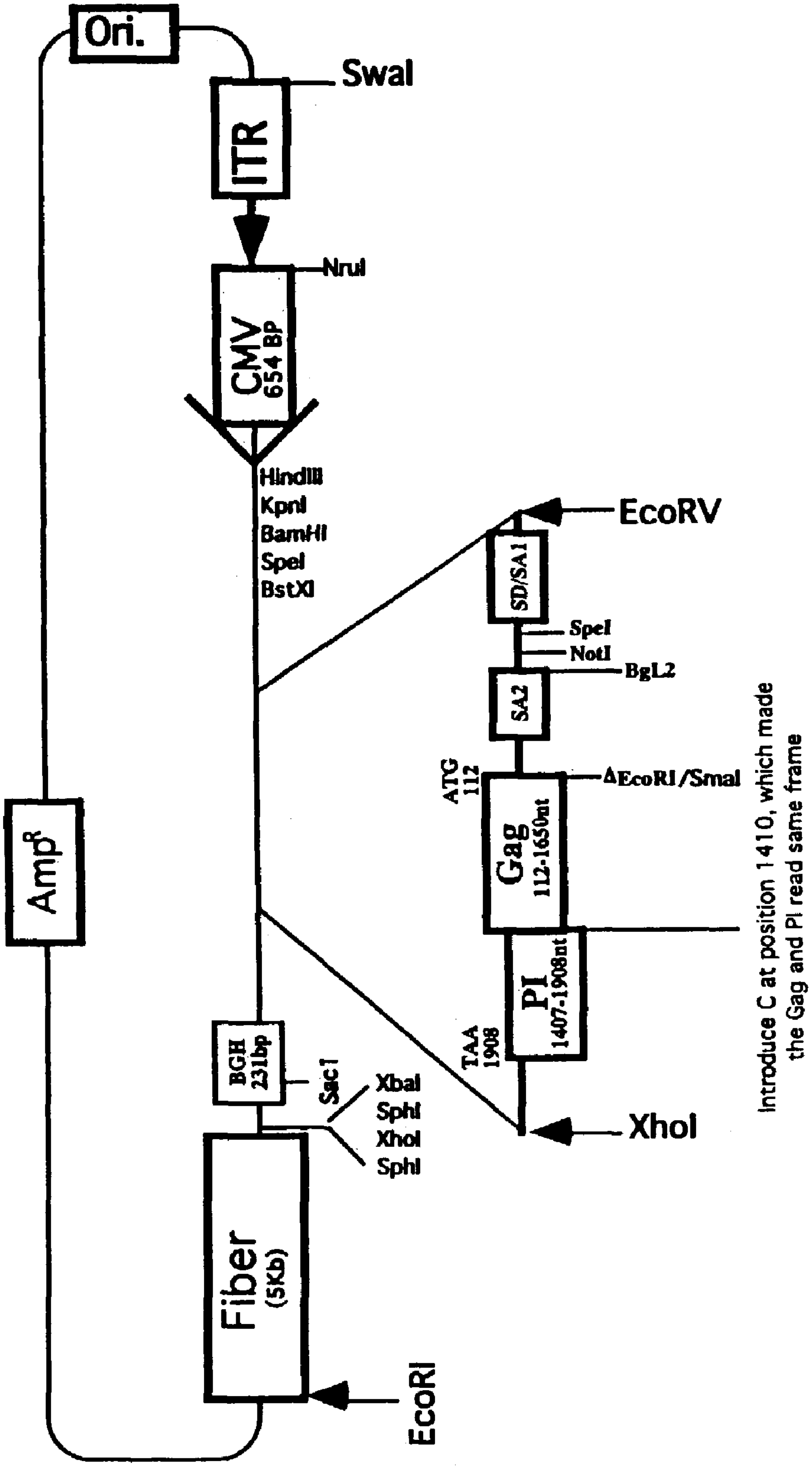
FIG. 36 illustrates a shuttle vector pRAd-ORF6-G-PI.

Alternatively, the HIV protease PI was expressed as a fusion protein with Gag by inserting a C residue at position nt1410 to allow pol to be read within the same reading frame of gag. DNA [SEQ ID NO: 58] and amino acid [SEQ ID NO: 59] sequences of the Gag-PI fusion protein are shown in FIGS. 56A and 56B, respectively. As illustrated in FIG. 36, Gag and PI are expressed from the same CMV promoter within the same reading frame. The resulting shuttle vector is designated as pRAd-ORF6/G-PI.

Both pLAd-E$^{m}$ΔCΔT$^{300}$.2×V3$^{m}$.T (FIG. 33) and pRAd-ORF6/G-PI (FIG. 36) were linearized using appropriate restriction enzymes and ligated to the backbone of the adenovirus (FIG. 4B), resulting in the recombinant adenoviral vector Ad-$E^m\Delta C\Delta T^{300}$.2×$V3^m$.T/G-PI.

21) pRAd-ORF6-Gag/PI-RT

Figure 58:
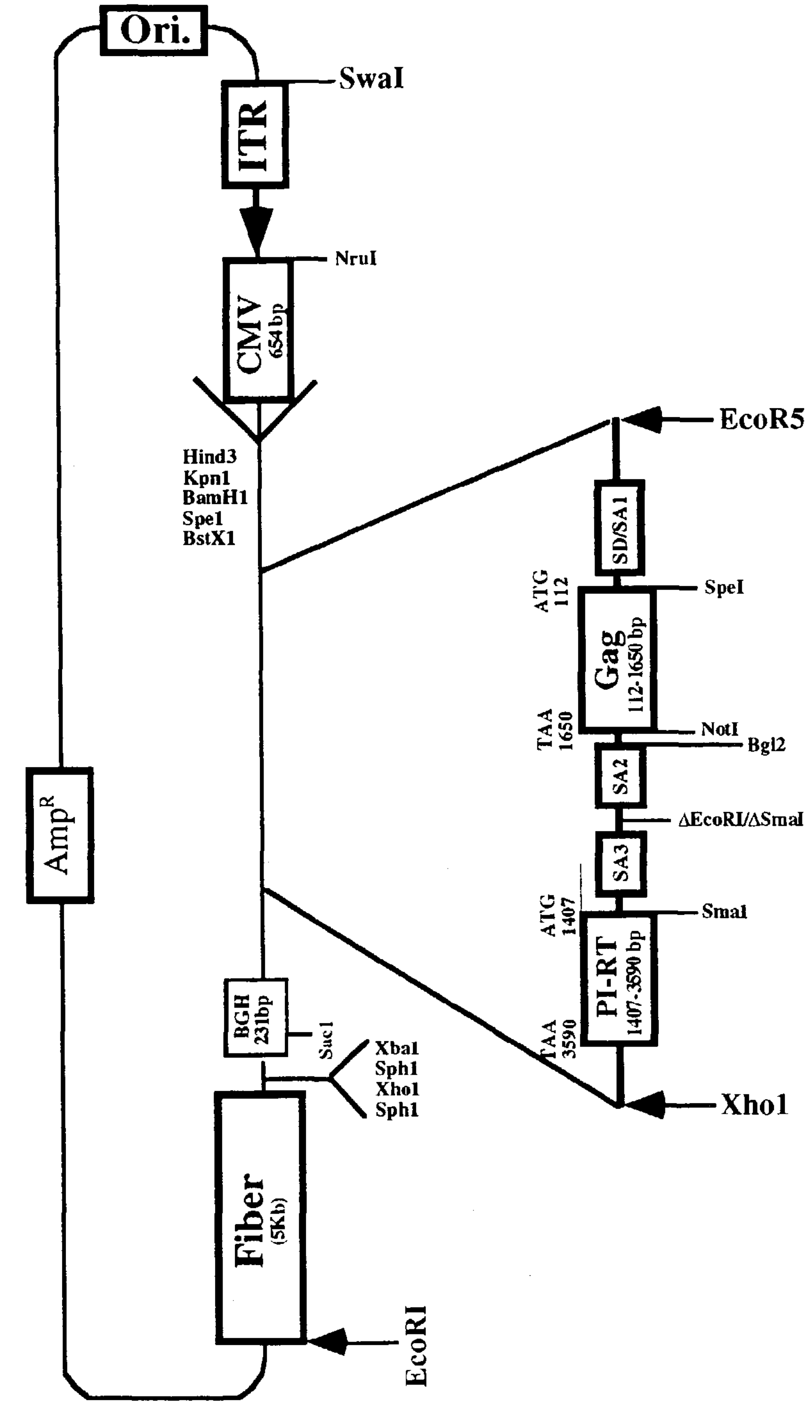
FIG. 58 illustrates a shuttle vector pRAd-ORF6-Gag/PI-RT.

DNA sequence encoding the protease (PI) and reverse transcriptase (RT) from the pol region of HIV strain BH10 was inserted into a region downstream from the sequence encoding Gag in a shuttle vector pRAd-ORF6-Gag/PI-RT (FIG. 58). As illustrated in FIG. 58, Gag and PI-RT are expressed separately from a CMV promoter via a retroviral splicing donor (SD) and acceptor (SA) mechanism at two splicing acceptor sites, $SA_1$ and $SA_2/SA_3$.

The right shuttle vector pRAd-ORF6-Gag/PI-RT can be combined with any of the left shuttle vector (pLAd) described above to generate a recombinant adenoviral vector.

22) pRAd-ORF6-Gag-PI-RT

Figure 59:
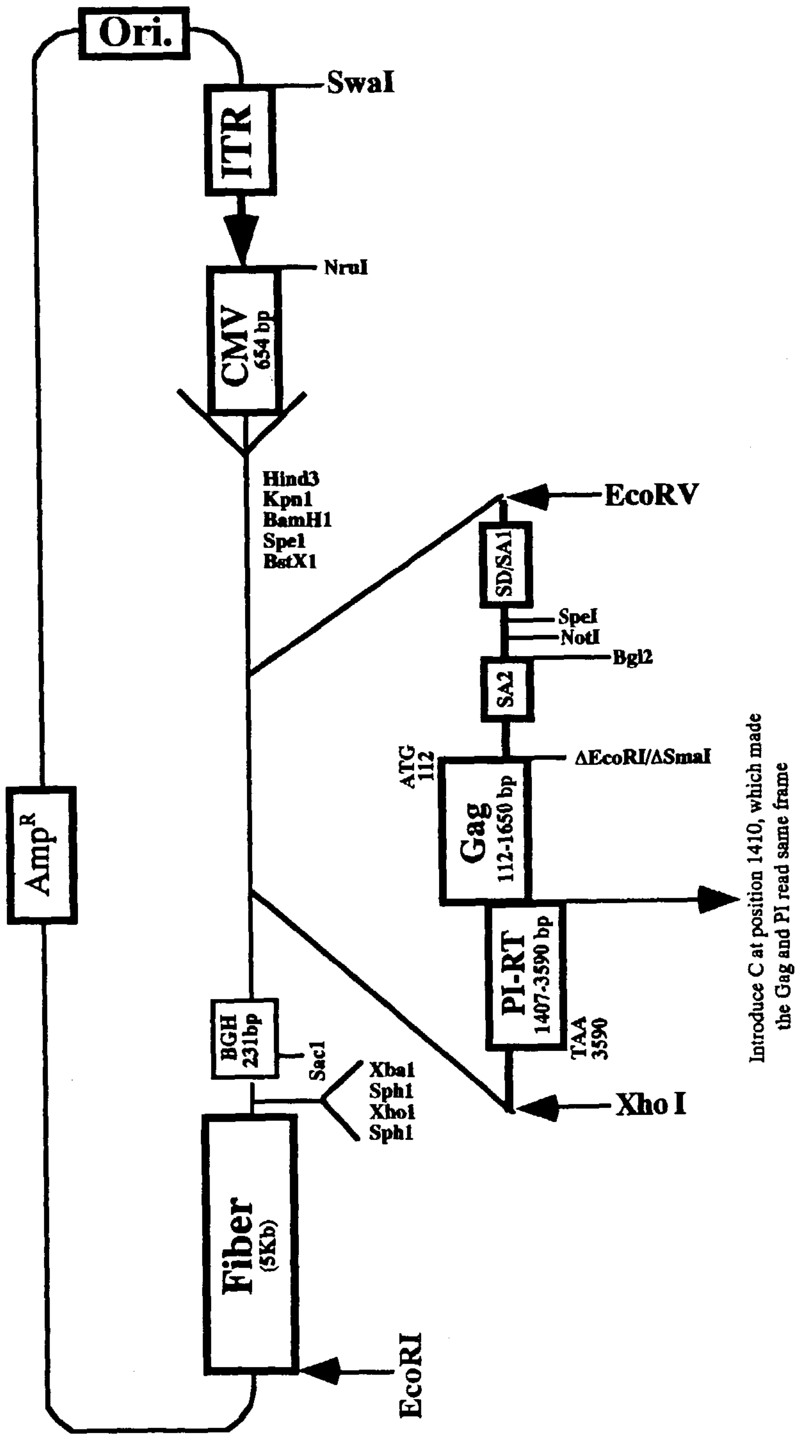
FIG. 59 illustrates a shuttle vector pRAd-ORF6-Gag-PI-RT.

Alternatively, PI-RT was expressed as a fusion protein with Gag by inserting a C residue at position nt1410 to allow pol to be read within the same reading frame of gag. As illustrated in FIG. 59, Gag and PI-RT are expressed from the same CMV promoter within the same reading frame. The resulting shuttle vector is designated as pRAd-ORF6-Gag-PI-RT.

The right shuttle vector pRAd-ORF6-Gag-PI-RT can be combined with any of the left shuttle vector (pLAd) described above to generate a recombinant adenoviral vector.

23) pRAd-ORF6-Gag/Pol

Figure 60:
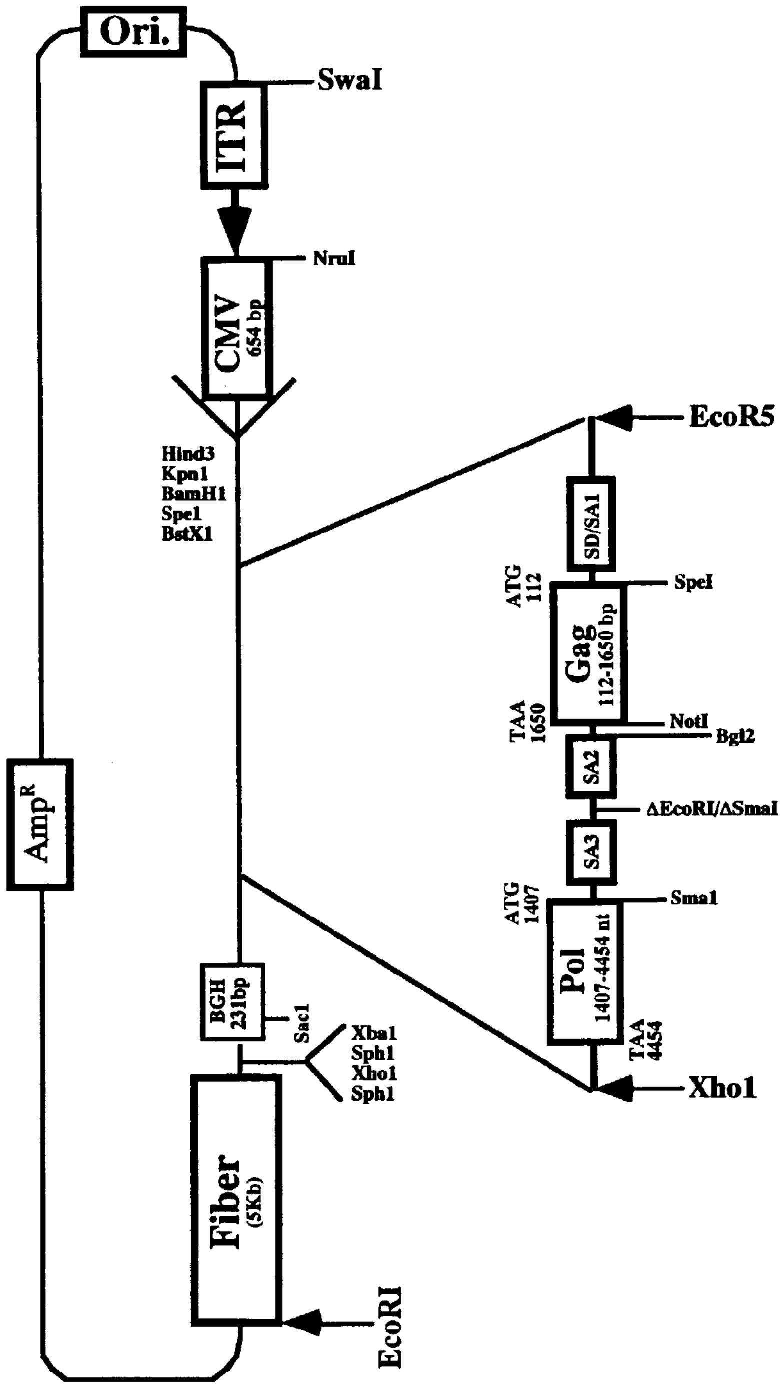
FIG. 60 illustrates a shuttle vectorpRAd-ORF6-Gag/Pol.

DNA sequence encoding the HIV enzymes PI, RT and IN from the pol region of HIV strain BH10 was inserted into a region downstream from the sequence encoding Gag in a shuttle vector pRAd-ORF6-Gag/Pol (FIG. 60). As illustrated in FIG. 60, Gag and Pol are expressed separately from a CMV promoter via a retroviral splicing donor (SD) and acceptor (SA) mechanism at two splicing acceptor sites, $SA_1$ and $SA_2/SA_3$.

The right shuttle vector pRAd-ORF6-Gag/Pol can be combined with any of the left shuttle vector (pLAd) described above to generate a recombinant adenoviral vector.

24) pRAd-ORF6-Gag-Pol

Figure 61:
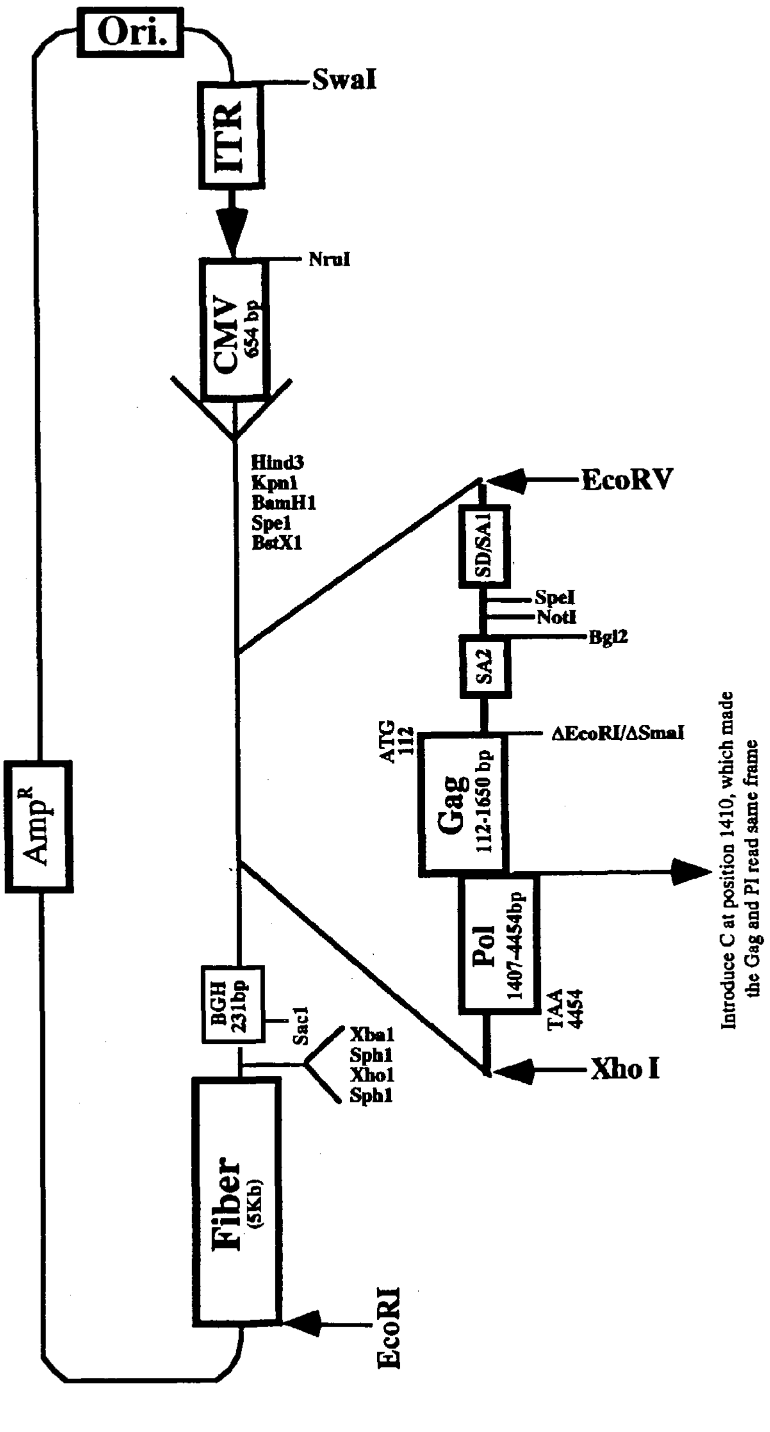
FIG. 61 illustrates a shuttle vectorpRAd-ORF6-Gag-Pol.

Alternatively, Pol was expressed as a fusion protein with Gag by inserting a C residue at position nt1410 to allow pol to be read within the same reading frame of gag. As illustrated in FIG. 61, Gag and Pol are expressed from the same CMV promoter within the same reading frame. The resulting shuttle vector is designated as pRAd-ORF6-Gag-Pol.

The right shuttle vector pRAd-ORF6-Gag-Pol can be combined with any of the left shuttle vector (pLAd) described above to generate a recombinant adenoviral vector.

B. Immune Responses of Animals to the Adenoviral Vaccine Against HIV Antigens

Experimental mice were inoculated with the adoviral vaccine constructed above, Ad.tat.env.IL2 (also designated as "Ad-E.T.R/IL2" as described above, section A, subsection 1)), to elicit immune response to the HIV antigens expressed by this vector. Immunogenicity of the adenoviral vector was determined by measuring titers of antibody against HIV tat and env.

Figure 6:
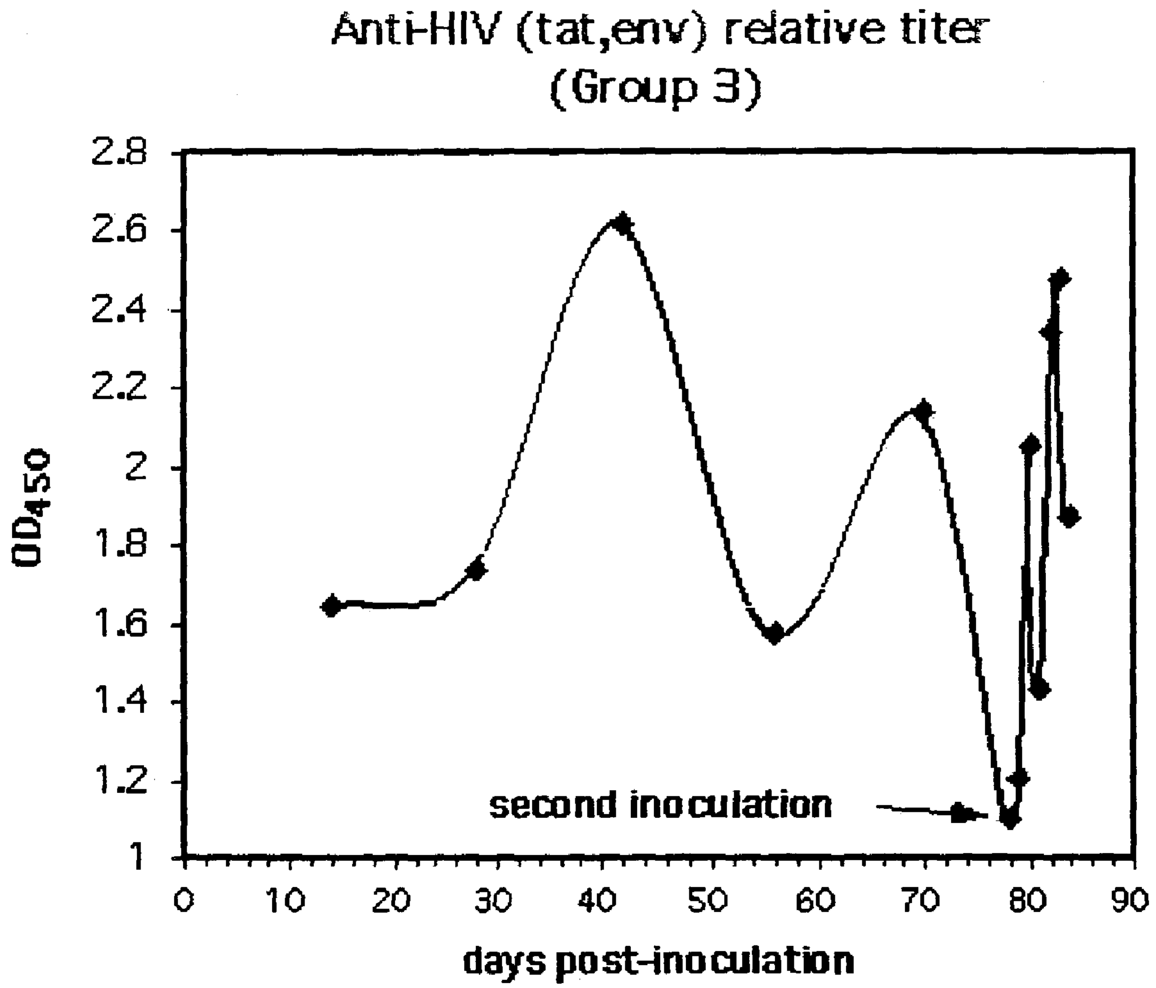
FIG. 6 shows relative titers of antibody against HIV antigens in a group of mice.
Figure 7:
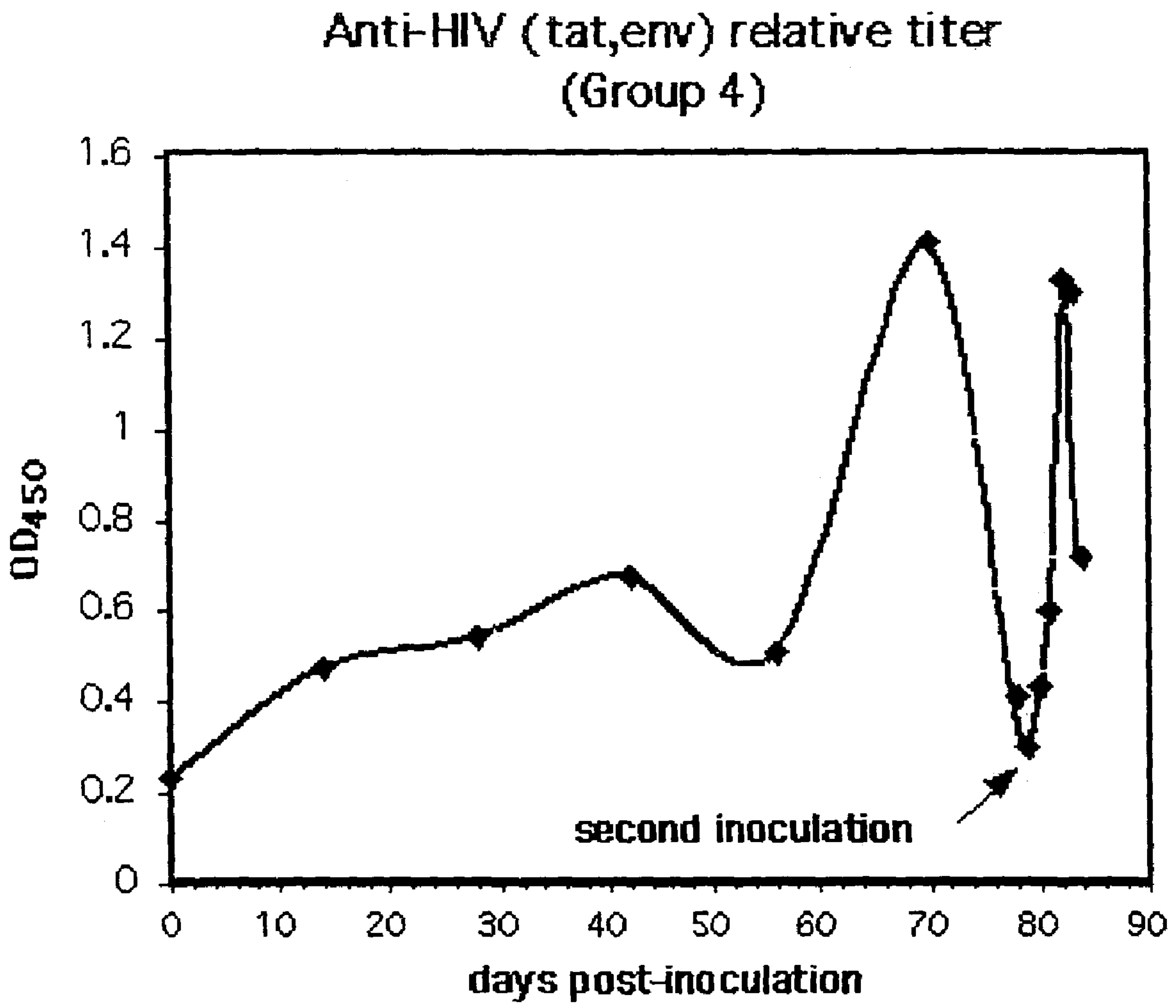
FIG. 7 shows relative titers of antibody against HIV antigens in another group of mice.

FIGS. 6 and 7 show the immunogenicity of Ad.tat.env.IL2 against the HIV Env protein in two groups of mice, respectively. These groups of C57BL/6 mice (supplied by Charles River Laboratories. Wilmington, Mass.) were injected intramuscularly with $10^7$ pfu Ad.tat.env.IL2 on different dates as indicated in the figures. Blood (about 150-500 μl for each animal) was collected from four animals every two weeks following inoculation and serum was prepared. At 77 days post-inoculation, these mice were re-challenged with an additional $10^7$ pfu of Ad.tat.env.IL2. Blood was collected from three animals every day following secondary challenge. Titers of antibody elicited against HIV tat and env were determined by ELISA against Ad.tat.env.IL2-infected HeLa cell lysates.

Briefly, lysates of the HeLa cells infected with Ad.tat.env.IL2 were prepared as follows. HeLa cells were infected with Ad.tat.env.IL2 at a multiplicity of infection (MOI) of 20. Fourty-eight hours post infection, HeLa cells were harvested and resuspended in a buffer that contained 1% TritonX-100. A post-nuclear supernatant was obtained by centrifuging the lysates at 15,000×g for 5 min. The lysates were diluted to 10 μg/ml for coating wells of ELISA plates. Standard ELISA assays were performed to measure OD450 of the sera and relative titers of antibody against HIV tat and env proteins were calculated by normalizing against the mean of the CD450 of mouse pre-immunization sera.

As shown in FIG. 6, the three mice in this group had strong immune responses to the HIV antigens expressed by the adenoviral vector Ad.tat.env.IL2, with the highest titer of antibody against HIV antigens reached in about 42 days post inoculation. The second inoculation with Ad.tat.env.IL2 boosted the immune reponse again and very high titers were achieved within about 5 days of the second inoculation.

As shown in FIG. 7, the three mice in this group also had strong immune responses to the HIV antigens expressed by the adenoviral vector Ad.tat.env.IL2, with the highest titer of antibody against HIV antigens reached in about 70 days post inoculation. The second inoculation with Ad.tat.env.IL2 boosted the immune reponse again and very high titers were achieved within about 5 days of the second inoculation.

FIGS. 12A-B show the antibody production elicited by the recombinant adenoviral vectors Ad.3C.env.gag (also designated as "Ad-3C/$E^m\Delta C\Delta T^{300}$-G" as described above, section A, subsection 2)) in mice. C57BL/6 mice were injected intramuscularly with $10^7$ pfu Ad.3C.env.gag. At 77 days post-inoculation, these mice were re-challenged with an additional $10^7$ pfu Ad.3C.env.gag. Relative antibody titers of these mice were determined by ELISA against purified recombinant Gag (obtained from the NIH AIDS Research and Reference Reagent Program, Bethesda, Md.) at week 10 post-immunization (or prime) (FIG. 12A) and week 14 post-prime/week 3 post-boost (FIG. 12B). As shown in FIGS. 12A and 12B, the mice inoculated with Ad.3C.env.gag had strong immune responses to the HIV antigen Gag.

Figure 13:
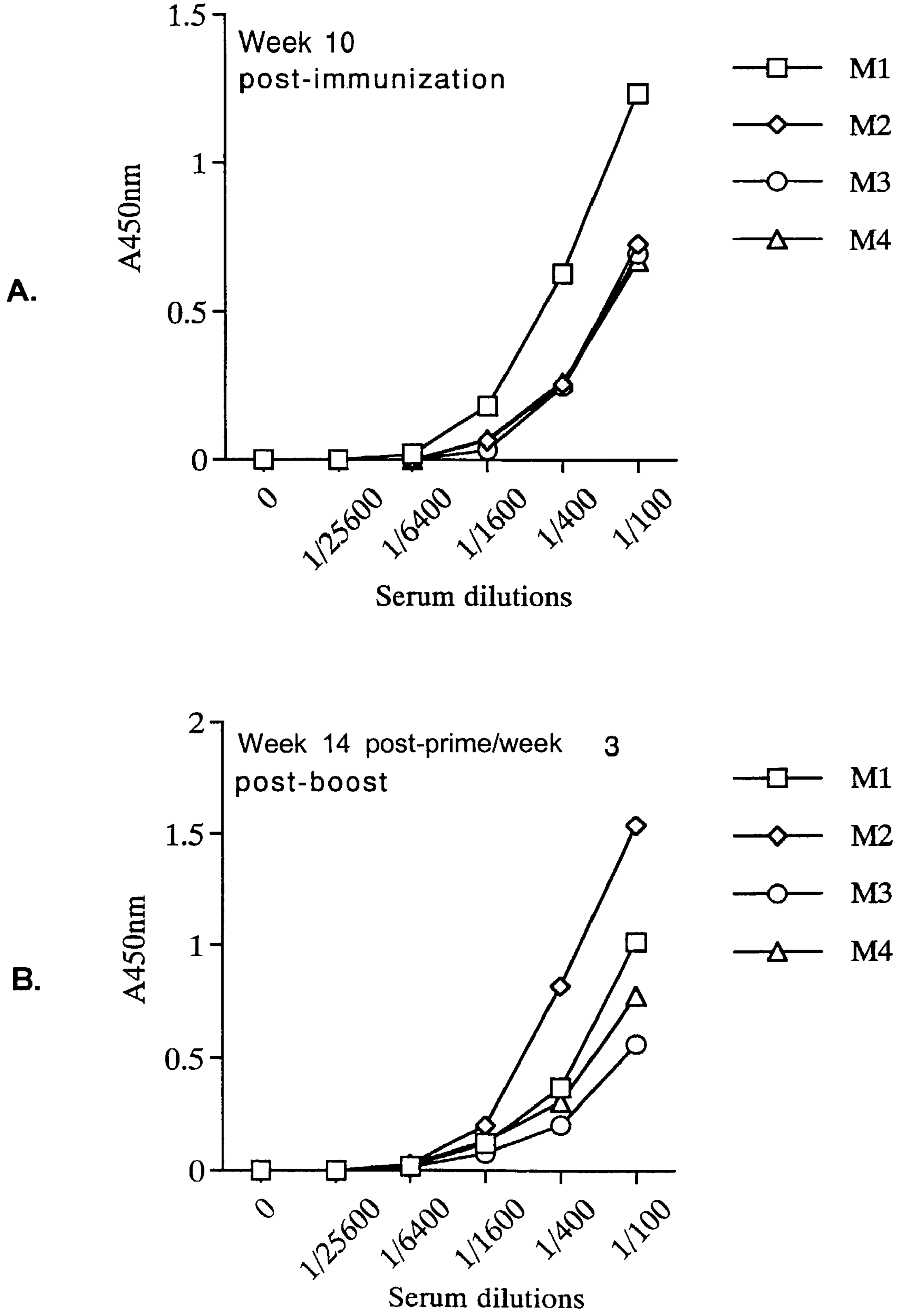
FIG. 13A shows relative titers of antibody against HIV Gag in mice in week 10 post-immunization with Ad-3C/$E'''$Δ-CΔ$T^{99}$-G.
FIG. 13B shows relative titers of antibody against HIV Gag in mice in week 14 post-immunization/week 3 post-boost with Ad-3C/$E'''$ΔCΔ$T^{99}$-G.

FIGS. 13A-B show the antibody production elicited by the recombinant adenoviral vectors Ad.3C.env.rev.gag (also designated as "Ad-3C/$E^m\Delta C\Delta T^{99}$.T.R-G" as described above in section A, subsection 3)) in mice. C57BL/6 mice were injected intramuscularly with $10^7$ pfu Ad.3C.env.rev.gag. At 77 days post-inoculation, these mice were re-challenged with an additional $10^7$ pfu Ad.3C.env.rev.gag. Relative antibody titers of these mice were determined by ELISA against recombinant purified Gag at week 10 post-immunization (or prime) (FIG. 13A) and week 14 post-prime/week 3 post-boost (FIG. 13B). As shown in FIGS. 13A and 13B, the mice inoculated with Ad.3C.env.rev.gag had strong immune responses to the HIV antigen Gag.

C. Activation of Cytotoxic T Lymphocytes (CTL) by Immunization with the Adenoviral Vaccines Against HIV Antigens Activation of cytotoxic T lymphocytes (CTL) by immunization with the adenoviral vaccine against HIV antigens was measured by using two independent assays: an IFNγ assay and a granzyme A assay. The IFNγ and granzyme assays were designed to detect antigen-specific activation of T-cells. IFNγ is secreted by activated CTL and $T_H1$ helper T cells which function specifically in the cellular immune pathway. Granzyme A is also secreted by activated CTL. The basic approach is to incubate splenocytes with target cells that express antigens of interest and look for secretion of IFNγ or granzyme A into the medium.

1) IFNγ Assay

This assay is a modification of the standard $^{51}$Cr-release lytic assay (Current Protocols in Immunology, Coligan et al., eds.) except that the target cells are not radiolabeled prior to incubation with the splenocytes. Detailed procedures for this assay are described in Di Fabio et al. (1994) "Quantitation of human influenza virus-specific cytotoxic T lymphocytes: correlation of cytotoxicity and increased numbers of IFN-gamma-(or IFNγ-) producing CD8+ T cells" Int. Immunol. 6:11-9. Briefly, about $1\times10^5$ splenocytes were incubated with $10^5$ target cells (e.g., infected with appropriate viruses carrying the target antigens) in a total volume of 100 μl. Cells were incubated for 4 h at 37° C. IFNγ was measured by ELISA from 25 μl medium.

Activation of CTL in mice inoculated with the adenoviral vaccine against HIV antigens was determined by using the IFNγ assay described above. Briefly, twelve C57BL/6 mice were injected intramuscularly with $10^7$ pfu Ad.tat.env.IL2. Spleens were harvested from 4 inoculated mice at the time points indicated in FIGS. 8A-C. Splenocytes were activated by incubation with B16-F1 cells (a melanoma cell line from C57BL/6, ATCC No: CRL-6323) that had been infected with Ad.tat.env.IL2. At day seven after stimulation, activated splenocytes were mixed with B16-F1 cells infected with the indicated viruses. IFNγ secretion into the medium was determined by ELISA (R&D Systems, Minneapolis, Minn.).

Figure 8A:
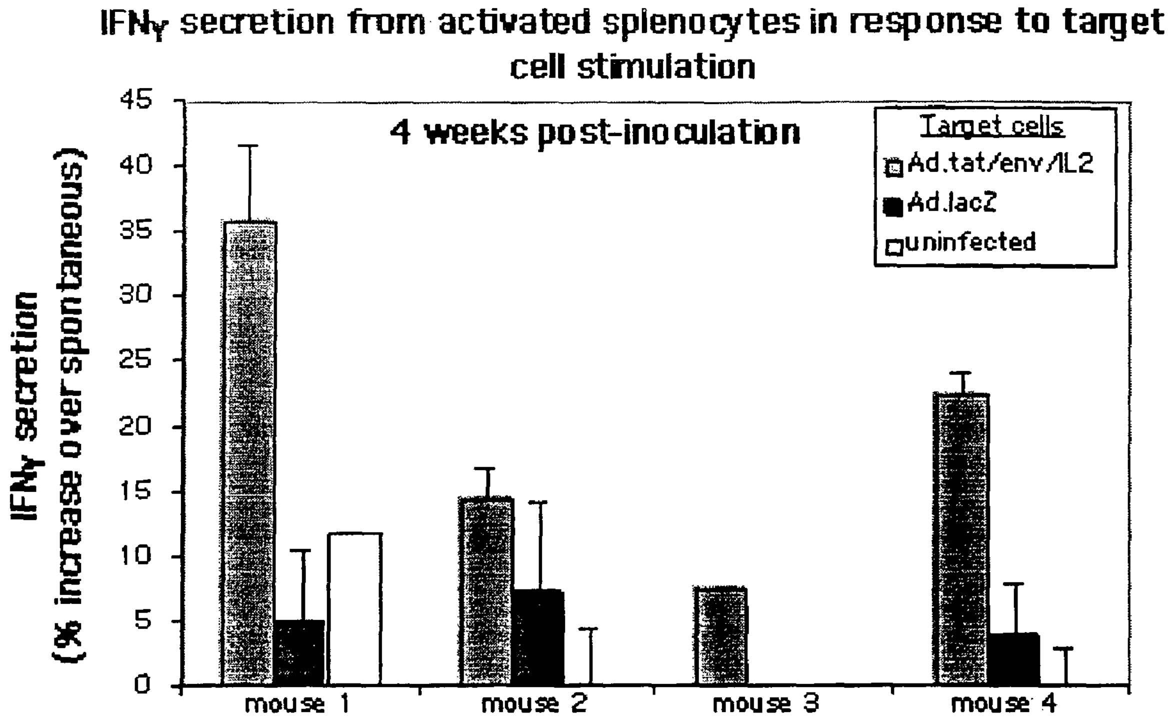
FIGS. 8A-C show INF-γ secretion from activated splenocytes harvested from mice inoculated with adenoviral vectors in response to target cell stimulation.
Figure 8B:
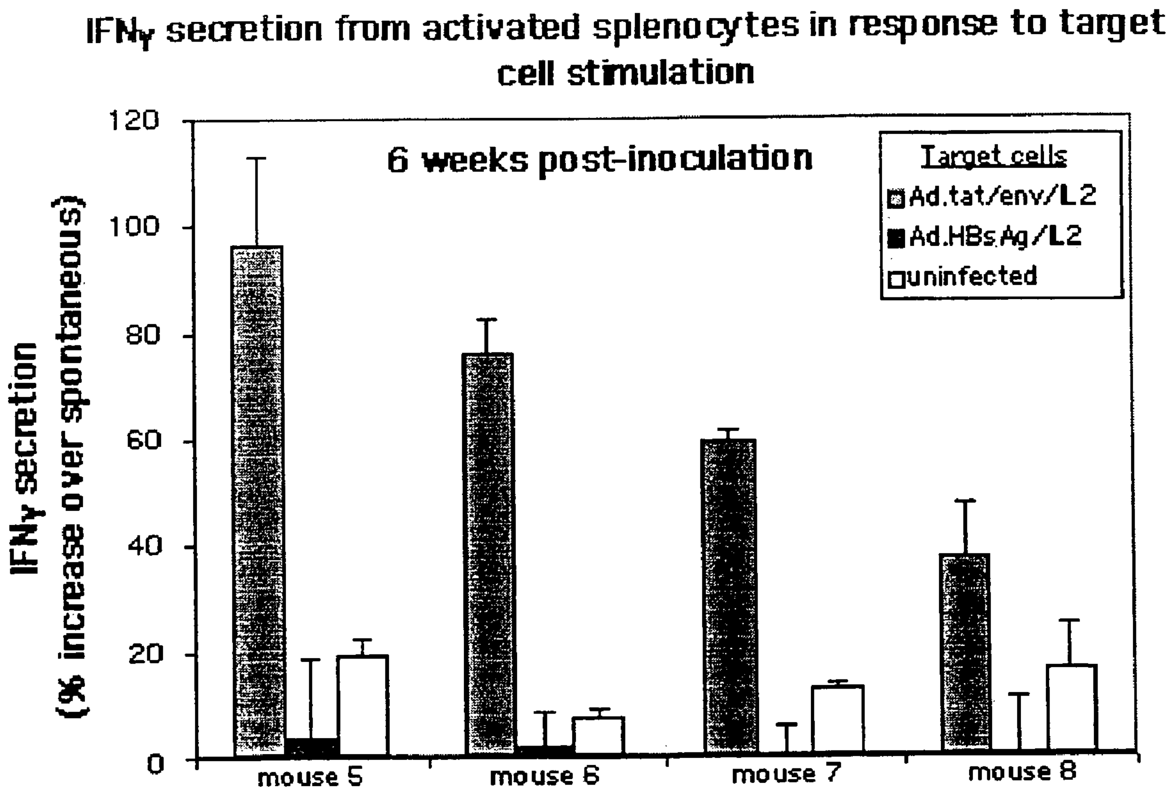
Figure 8C:
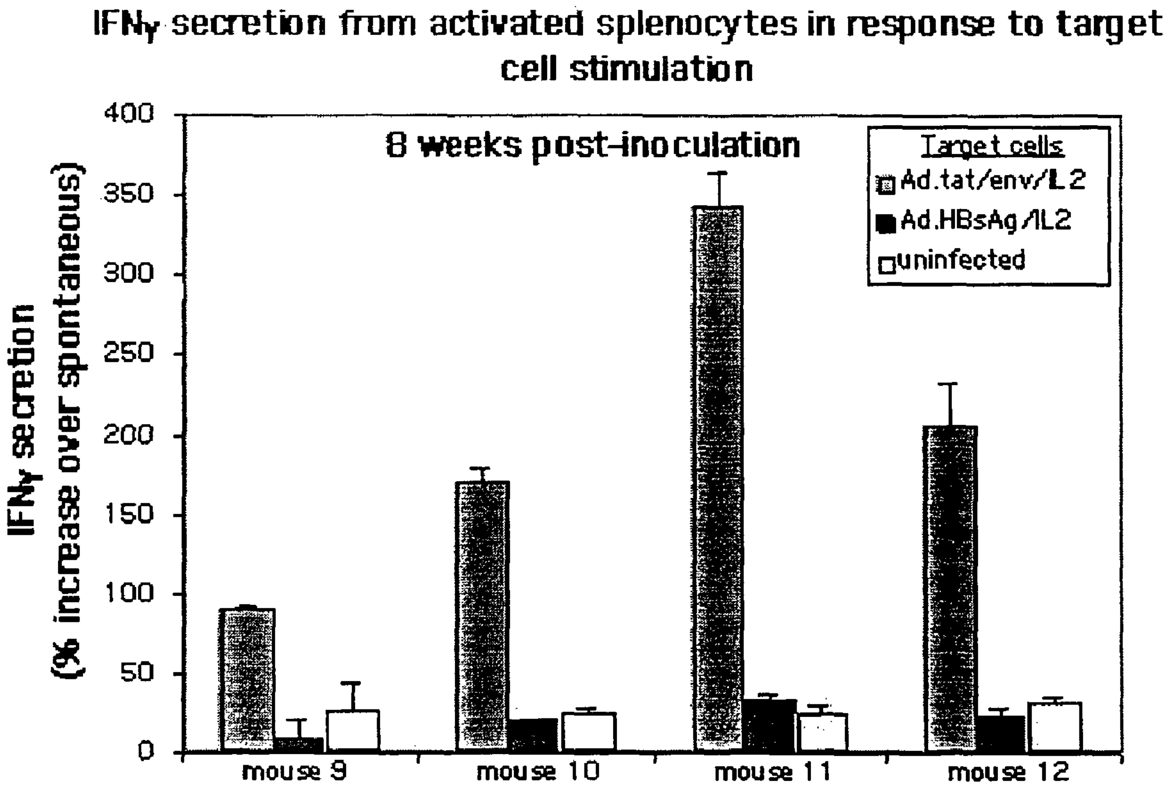

FIGS. 8A-C show percent increases in the amount of IFNγ secreted into the medium over the period of time ranging from 4-8 weeks post inoculation. As shown in FIG. 8A, secretion of IFNγ increased significantly in splenocytes of the four mice harvested 4 weeks post inoculation with Ad.tat.env.IL2. In contrast, little increase in IFNγ secretion occurred when the splenocytes were incubated with B16-F1 cells infected with an adenoviral vector expressing non-specifc protein β-Gal (Ad.lacZ) or uninfected B16-F1 cells.

Secrection of IFNγ increased more in the splenocytes of mice harvested 6 weeks post inoculation as shown in FIG. 8B. Noticeably, there was near 100% increase in secrection of IFNγ in splenocytes of mouse 5 (FIG. 8B).

Secrection of IFNγ increased more dramatically in the splenocytes of mice harvested 8 weeks post inoculation as shown in FIG. 8C. There was more than 300% increase in secrection of IFNγ in splenocytes of mouse 11 (FIG. 8C).

These results demonstrate that strong humoral immune responses against HIV, such as induction of high titer antibody and activation of CTL specifically targeting HIV antigens, have been achieved by inoculating animals with the adenoviral vaccine expressing both HIV viral antigens and an immuno-stimulator such as IL-2. The immune responses resemble those during a recovering of viral infection diseases. These results tend to show that the genetic vaccines of the present invention that mimics natural viral infection hold great promises as efficacious vaccines for humans against HIV.

2) Granzyme A Assay

Granzyme A assay was performed using a protocol modified from the one described in Deitz et al. (2000) "MHC I-dependent antigen presentation is inhibited by poliovirus protein 3A" Proc. Natl. Acad. Sci. 97:13790-13795. The granzyme A assay described in Deitz et al. was a modification of a protocol described in: Kane et al. (1989) "Cytolytic T-lymphocyte response to isolated class I H-2 proteins and influenza peptides" Nature (London) 340:157-159.

Granzyme A Assays were performed following similar procedures as for IFNγ assays with the following exceptions. Granzyme A secretion into the medium was determined by an enzymatic assay. Units of granzyme A were determined by calculating the slope of activity during the linear phase of the reaction. One unit of granzyme A was defined as the amount of enzyme required to convert the substrate to 1 $OD_{405}$ in one hour.

Briefly, about $1\times10^5$ activated splenocytes and about $1\times10^5$ target cells were incubated together as for the IFNγ assays. Granzyme A activity was determined by combining 20 μl medium with 180 μl reaction mixture (0.2 mM BLT (N-α-benzyloxycarbonyl-L-lysinethiobenzyl ester, Sigma, St. Louis, Mo.), 0.22 mM DTNB (5,5'-dithio-bis(2-nitrobenzoicacid, Sigma, St. Louis, Mo.)) in 96-well plates and incubating at room temperature. Absorbance at 405 nm was monitored over a period of several hours. Slopes of enzyme activity were determined for the linear phase of the reaction and converted to units of enzyme.

Figure 9:
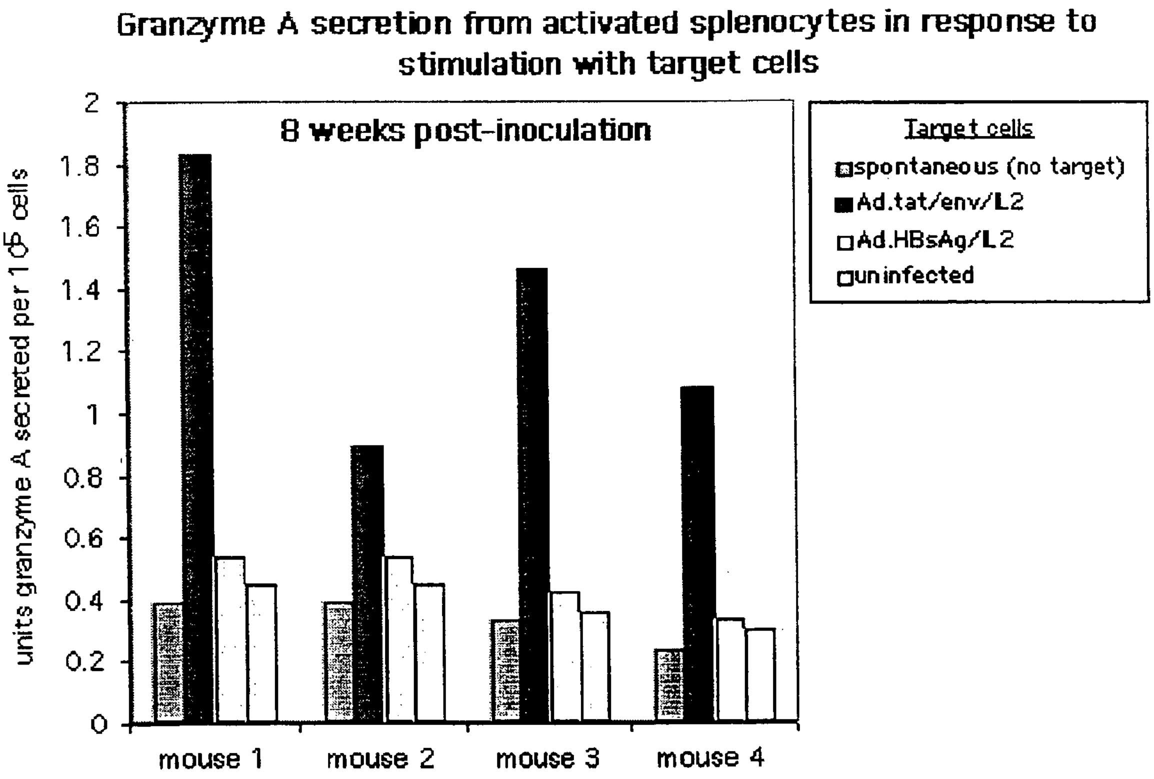
FIG. 9 shows granzyme A secretion from activated splenocytes harvested from mice inoculated with adenoviral vectors in response to target cell stimulation.

FIG. 9 shows increases in the amount of granzyme A secreted into the medium for splenocytes of mice harvested 8 weeks post inoculation. As shown in FIG. 9, secretion of granzyme A increased significantly in splenocytes of the four mice harvested 8 weeks post inoculation with Ad.tat.env.IL2. In contrast, much less granzyme A secretion occurred when the splenocytes were incubated with B16-F1 cells infected with an adenoviral vector expressing non-specifc protein β-Gal (Ad.lacZ), an adenoviral vector expressing both hepatitis B surface antigen and IL-2 (Ad.HBsAg/IL2) or uninfected B16-F1 cells. Similarly, there is little spontaneous granzyme A secrection in these splenocytes not incubated with the target cells.

FIG. 14A shows the results of the granzyme A assays for series 1 mice at various time points indicated, including week 4, 6, 8 post-immunization and week 12/1, 13/2, 14/3 (prime/boost) post-secondary inoculation with Ad.3C.env.gag.

FIG. 14B shows the results of the granzyme A assays for series 2 mice at various time points indicated, including week 2, 4, 6, 8 post-immunization with Ad.3C.env.gag.

These results, obtained by using the granzyme A assay independent from the IFNγ assay, again demonstrate that strong activation of CTL specifically targeting HIV antigens was induced by inoculating mice with the adenoviral vaccine expressing both HIV viral antigens and an immuno-stimulator such as IL-2. These results also support the belief that the genetic vaccines provided by the present invention hold great promises as efficacious vaccines for humans against HIV.

3) ELISPOT Assay

ELISPOT assays were performed to determine CTL activation in mice inoculated with the recombinant adenoviral vectors, Ad.3C.env.gag and Ad.3C.env.gag.rev. C57BL/6 mice were inoculated with $10^7$ pfu Ad.3C.env.gag or Ad.3C.env.gag.rev. Mice were sacrificed at two-week intervals and splenocytes were prepared (see Current Protocols in Immunology, Coligan et al. eds.). At week 11, mice were inoculated with a second dose of 107 pfu of Ad.3C.env.gag or Ad.3C.env.gag.rev. $2\times10^5$ splenocytes were incubated with $4\times10^4$ MC57G cells (ATCC #CRL-2295) that had been infected with vaccinia viruses expressing either Env, Gag, or Rev, in 96-well, mouse IFNγ, ELISPOT plates (R&D Systems, Minneapolis, Minn.) for 30 h. Non-specific activation was monitored following the addition of 4 μg/ml PHA (Sigma, St. Louis, Mo.) instead of antigen-expressing cells.

IFNγ spots were visualized as per the kit instructions and counted. Wild type and recombinant vaccinia viruses were obtained from the NIH AIDS Research and Reference Reagent Program, Bethesda, Md.

FIG. 15A shows the ELISPOT results for the four mice in serie1 at week 13/2 post-prime/boost with Ad.3C.env.gag. FIG. 15B shows the ELISPOT results for the four mice in serie1 at week 13/2 post-prime/boost with Ad.3C.env.rev.gag. These results indicate that immunization of mice with the genetic vaccines of the present invention induced strong activation of CTL against HIV Gag.

3. Genetic Vaccine Against Hepatitis B Virus

Embodiments of the genetic vaccine against hepatitis B virus and methods of their construction are described in detail as follows.

1) Construction of Replication-Defective Adenoviral Vaccines Against Hepatitis B Virus Two adenoviral vectors, Ad.HBsAg.IL2 and Ad.HBc Ag.IL2, were constructed to carry the coding sequences for a hepatitis B surface antigen (HBsAg) and a HBV core antigen (HBcAg), respectively. In the same vector, DNA sequence encoding interleukin-2 (IL-2) was also included and expressed by a promoter different from that for expressing the viral antigen. This design is believed to be able to ensure high level expression of both the viral antigens and the immunostimulator IL-2 and to enhance immunogenicity of the adenoviral vaccine. As shown by experimental data presented in the next section, both of these two adenoviral vectors are capable of eliciting strong and long-lasting immune responses in animals against hepatitis B antigens.

These two adenoviral vectors, Ad.HBsAg.IL2 and Ad.HBcAg.IL2, were constructed using strategies similar to those for constructing the adenoviral vaccines against Ebola virus as described in detail above.

a) Ad.HBsAg.IL2

Briefly, full length HBsAg (with a silent mutation caused by deletion of Xba I site) was inserted into the left end (E1 region) of the adenoviral genome using a shuttle vector pLAd (FIG. 4A, left side), resulting in a shuttle vector pLAd-CMV-HBsAg.

The sequence encoding IL-2 (with a silent mutation caused by deletion of Xba I site) was inserted into E4 region of the adenoviral genome using the shuttle vector pRAd (FIG. 4A, right side), resulting in a shuttle vector pRAd-CMV-IL2.

Both pLAd-CMV-HBsAg and pRAd-CMV-IL2 were linearized using appropriate restriction enzymes such as Xba I and EcoRI and ligated to the backbone of the adenovirus (FIG. 4B), resulting in the recombinant adenoviral vector designated Ad.HBsAg.IL2.

a) Ad.HBcAg.IL2

Briefly, sequences encoding full length HBsAg (with a silent mutation caused by deletion of Xba I site) and full length HBcAg were inserted into the left end (E1 region) of the adenoviral genome using a shuttle vector pLAd (FIG. 4A, left side). HBsAg and HBcAg are expressed separately from another CMV promoter via a retroviral splicing donor (SD) and acceptor (SA) mechanism at two splicing acceptor sites, $SA_1$ and $SA_2$. The shuttle vector produced is designated pLAd-CMV-SD/$SA_1$-HBsAg-$SA_2$-HbcAg.

Sequences encoding multiple immuno-stimulators, including IL-2 (with a silent mutation caused by deletion of Xba I site), INF-γ, and GMCSF, were inserted into E4 region of the adenoviral genome using the shuttle vector pRAd (FIG. 4A, right side). These three immuno-stimulators are expressed separately from another CMV promoter via a retroviral splicing donor (SD) and acceptor (SA) mechanism at three splicing acceptor sites, $SA_1$, $SA_2$, and $SA_3$. The shuttle vector produced is designated pRAd-CMV-SD/$SA_1$-IL2-$SA_2$-INFγ-$SA_3$-GMCSF.

Both pLAd-CMV-SD/SA,-HBsAg-$SA_2$-HbcAg and pRAd-CMV-SD/$SA_1$-IL2-$SA_2$-INFγ-$SA_3$-GMCSF were linearized using appropriate restriction enzymes such as Xba I and EcoRI and ligated to the backbone of the adenovirus (FIG. 4B), resulting in the recombinant adenoviral vector designated Ad.HBcAg.IL2.

2) Immune Responses of Animals to the Adenoviral Vaccines Against HBV Antigens

Experimental mice were inoculated with the adoviral vaccine constructed above, Ad.HBsAg.IL2 and Ad.HBcAg.IL2, to elicit immune response to the hepatitis B surface antigen and core antigen expressed by these two vectors, respectively. Immunogenicity of these adenoviral vectors was determined by measuring titers of antibodies against HBsAg and HbcAg, respectively.

a) HBV Surface Antigen (HBsAg) Antibody Titers

Figure 10A:
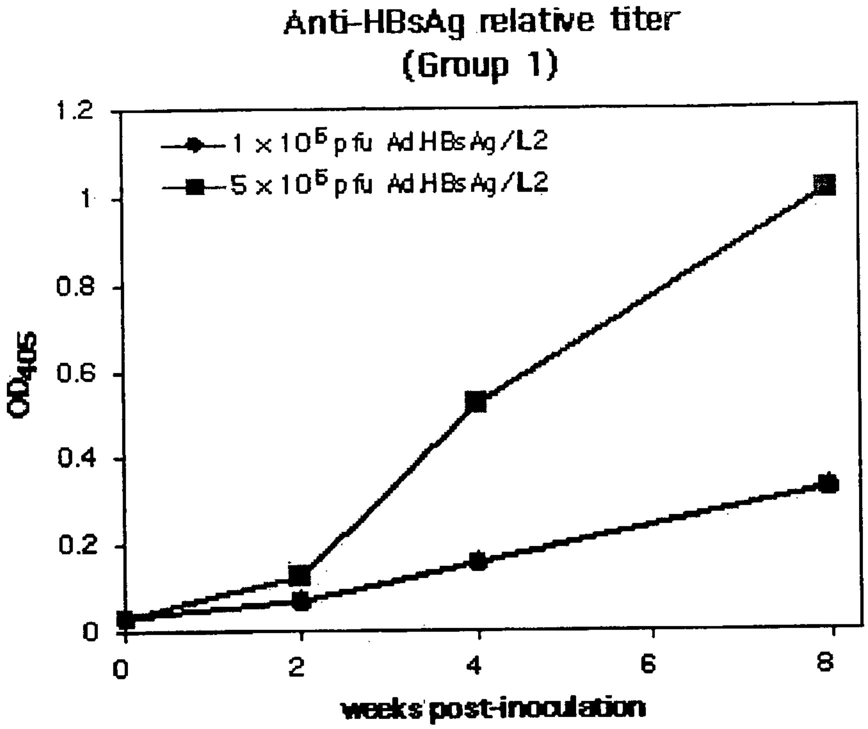
FIG. 10A shows relative titers of antibody against HBV surface antigen in a group of mice.
Figure 10B:
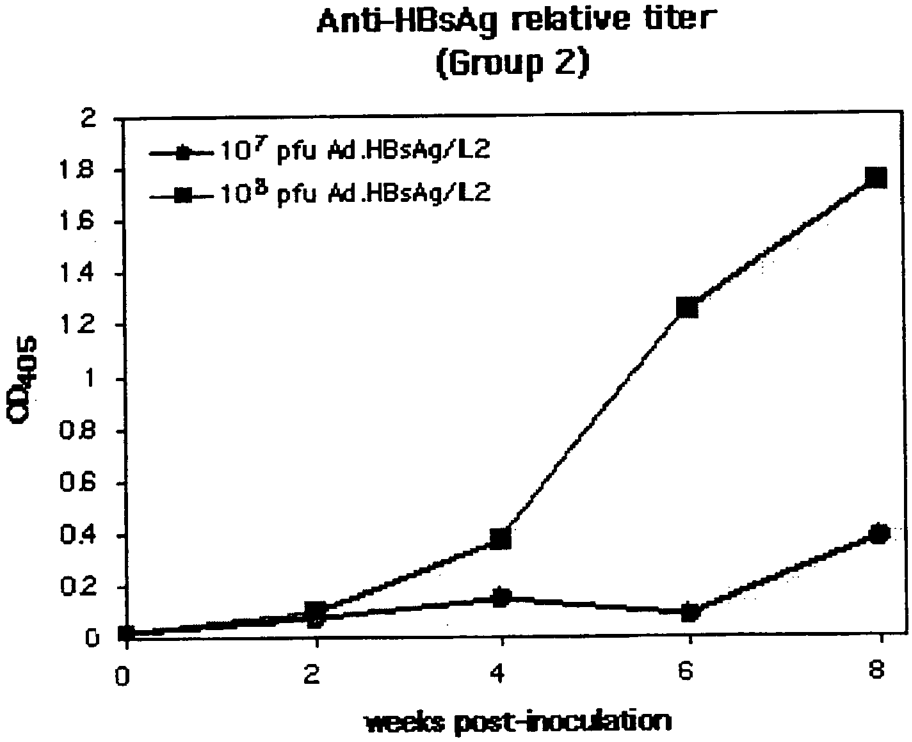
FIG. 10B shows relative titers of antibody against HBV surface antigen in another group of mice.

CD-1 mice (Charles River Laboratories, Wilmington, Mass.) were injected intramuscularly with several different concentrations of Ad.HBsAg.IL2: $10^0$, $1\times10^6$, $1\times10^7$, $1\times10^8$, $5\times10^5$, $5\times10^6$, and $5\times10^7$ pfu virus. FIG. 10A shows the relative Anti-HBsAg antibody titers measured for sera harvested from mice inoculated with $1\times10^5$ and $5\times10^5$ pfu. Serum in each measurement was diluted 1:500. FIG. 10B shows the relative Anti-HbsAg antibody titers measured for sera harvested from mice inoculated with $1\times10^7$ and $1\times10^8$ pfu. Serum in each measurement was diluted 1:1500.

To measure the relative titers of the Anti-HbsAg antibody elicited by Ad.HBsAg.IL2, blood (about 150-500 μl) from each animal was collected from immunized mice every two weeks and serum was prepared. Blood was incubated at room temperature for 2-3 h to allow for clotting. The blood was then chilled overnight at 4° C. to shrink the clot. Unclotted liquid was transferred to a clean tube and centrifuged at 2000×g for 5 min. The supernatant was transferred to another clean tube. Sodium azide ($NaN_3$) was added to 0.05% as a preservative. Small aliquots were kept at 4° C. for short-term storage. Long-term storage was at −80° C.

Relative anti-HBsAg titers were determined by ELISA against recombinant HBsAg purified from yeast (from Aldevron, LLC, Fargo, N.D.). As shown in FIG. 10A, the mice in group 1 had increasingly strong immune responses to HBsAg expressed by the adenoviral vector, Ad.HBsAg.IL2, within 8 weeks post inoculation. This vector with a titer as low as $5\times10^5$ pfu was sufficient to elicit high levels of antibody specifically against HBsAg.

FIG. 10B shows the immunogenicity of Ad.HBsAg.IL2 with higher titers. As shown in FIG. 10B, immunogenicity of Ad.HBsAg.IL2 increased dramatically as the titer of the adenoviral vector was increased from $1\times10^7$ pfu to $1\times10^8$ pfu.

These results demonstrate that the adenoviral vector expressing both hepatitis B surface antigen and IL-2 can induce strong immune response specifically targeting the viral antigen in mice inoculated with this vector. These results also support the belief that the genetic vaccines provided by the present invention hold great promises as efficacious vaccines for humans against hepatitis B virus.

b) HBV core antigen (HBcAg) antibody titers Groups of C57BL/6 mice (Charles River Laboratories, Wilmington, Mass.) were injected intramuscularly with $1\times10^7$ pfu Ad.HBcAg.IL2 on different dates. Blood was collected from four animals every two weeks following inoculation and serum was prepared. At 91 days (Group 3, FIG. 11A) or 84 days (Group 4, FIG. 11B) post-inoculation, mice were re-challenged with an additional $1\times10^7$ pfu virus. Blood was collected from three animals every day following secondary challenge. Antibody titer was determined by ELISA against recombinant HBcAg purified from *E. coli* (from Chemicon International, Inc., Temecula, Calif.).

Figure 11A:
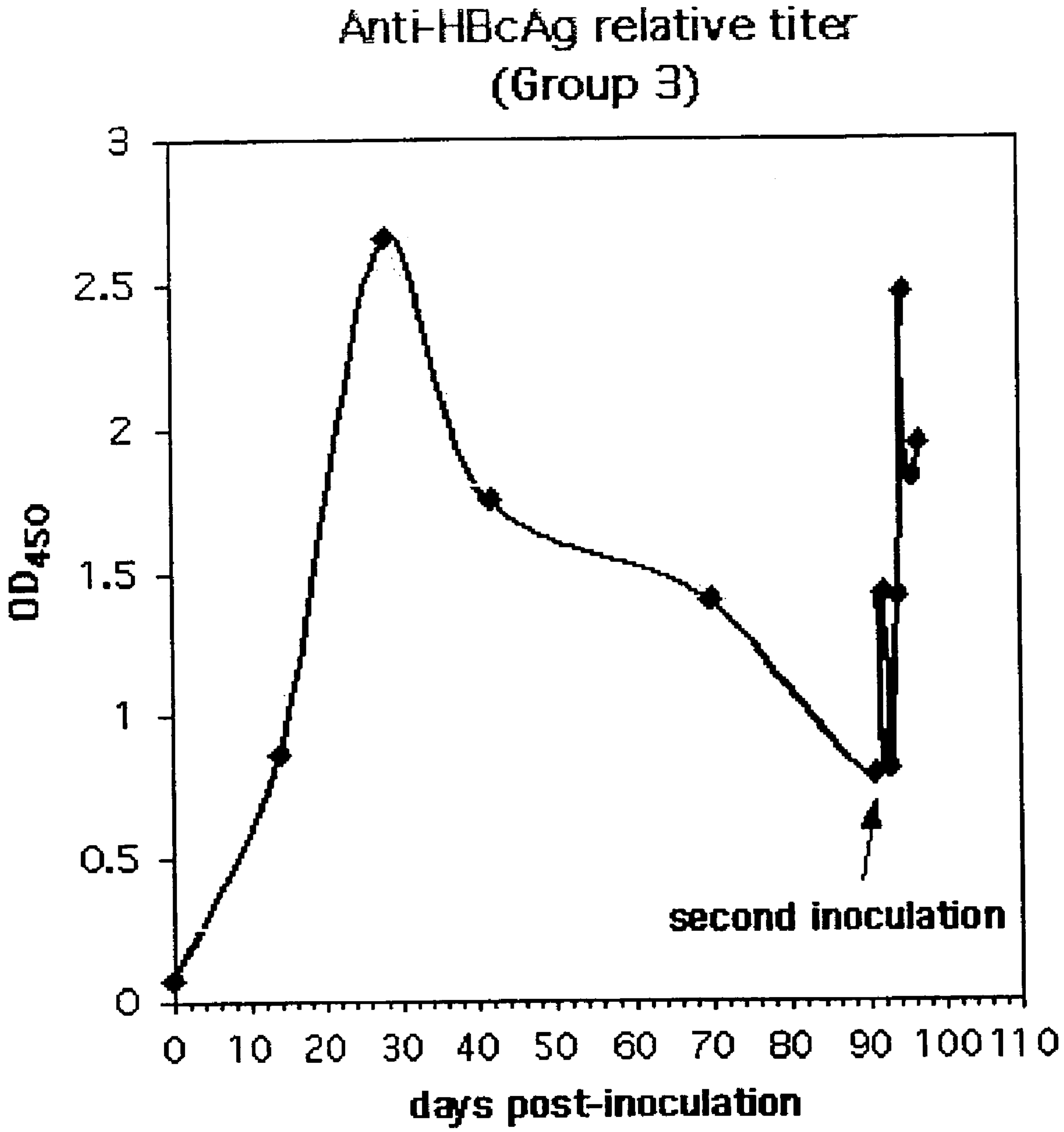
FIG. 11A shows relative titers of antibody against HBV core antigen in a group of mice.

As shown in FIG. 11A, mice in group 3 had strong immune response to the hepatitis core antigen HBcAg expressed by the adenoviral vector Ad.HBcAg.IL2, with the highest titer of antibody against HBcAg reached in about 28 days post inoculation. The second inoculation with Ad.HBcAg.IL2 boosted the immune reponse again and very high titers were achieved within about 3 days of the second inoculation.

Figure 11B:
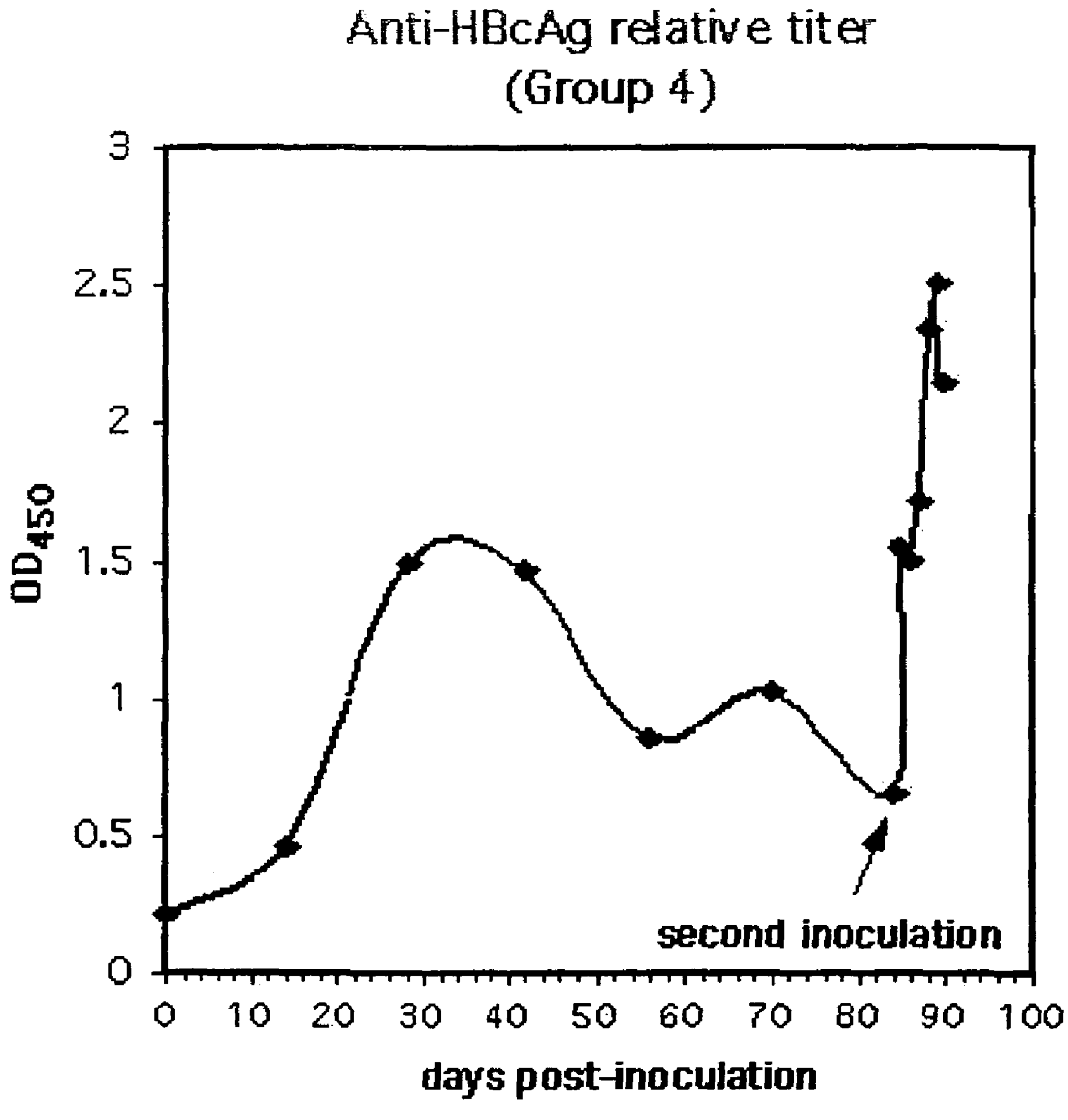
FIG. 11B shows relative titers of antibody against HBV core antigen in another group of mice.

As shown in FIG. 11B, mice in group 4 also had strong immune response to the hepatitis core antigen HBcAg expressed by the adenoviral vector Ad.HBcAg.IL2, with the high titer of antibody against HBcAg reached in about 34 days post inoculation. The second inoculation with Ad.HBcAg.IL2 boosted the immune reponse again and very high titers were achieved within about 3 days of the second inoculation.

These results demonstrate that the adenoviral vector expressing both hepatitis B core antigen and IL-2 can also induce strong immune response specifically targeting the viral antigen in mice inoculated with this vector. These results once again support the belief that the genetic vaccines provided by the present invention hold great promises as efficacious vaccines for humans against hepatitis B virus.

---

What is claimed is:

1. A method for producing an immune response of a host to infection of a first and a second pathogenic virus, comprising:

administering to the host a first recombinant adenovirus comprising a first antigen sequence heterologous to native adenovirus and encoding a first viral antigen from the first pathogenic virus, expression of the first viral antigen by the first recombinant adenovirus eliciting an immune response directed against the first viral antigen in a host upon infection of the host by the first recombinant adenovirus;

administering to the host a second recombinant adenovirus comprising a second antigen sequence heterologous to native adenovirus and encoding a second viral antigen from the second pathogenic virus, expression of the second viral antigen by the second recombinant adenovirus eliciting an immune response directed against the second viral antigen in a host upon infection of the host by the second recombinant adenovirus, wherein adenoviral backbones of the first and the second recombinant adenoviruses are of the same serotype selected from the group consisting of adenovirus serotype 1-51, wherein either an entire or a part of the fiber region comprising either one of knob, shaft, penton base domain of the fiber region or a combination thereof, of the second recombinant adenovirus is of a serotype that is different from the serotype of fiber region of the first recombinant adenovirus and wherein the first or second recombinant adenovirus further comprises an immuno-stimulator sequence that is heterologous to native adenovirus and encodes an immuno-stimulator such that the immune response elicited by the first and second recombinant adenovirus generates an antibody directed against the first viral antigen, the second viral antigen or a combination thereof wherein the first and the second pathogenic viral antigen are inserted into E1, E3 or E4 region of the first and the second adenovirus vectors, and wherein the immune-stimulatory sequence is inserted into E4, E3 or E1 region of the first and the second adenovirus vectors, in which region does not contain the first and/or the second pathogenic virus antigen;

isolating the antibody generated after said administration of the first and the second recombinant adenovirus; and administering the antibody to the host or to another host, thereby producing the immune response of the host to infection of the first and the second pathogenic virus.

2. The method of claim 1, wherein administering to the host the first or second recombinant adenovirus is performed intramuscularly, intratracheally, subcutaneously, intranasally, intradermally, rectally, orally or parentally.

3. The method of claim 1, wherein the first viral antigen encoded by the first recombinant adenovirus is the same as the second viral antigen encoded by the second recombinant adenovirus.

4. The method of claim 1, wherein the second recombinant adenovirus is administered to the host at least one week post the administration of the first recombinant adenovirus.

5. The method of claim 1, wherein the first or second recombinant adenovirus is replication-incompetent.

6. The method of claim 1, wherein the first and the second pathogenic viruses are the same.

7. The method of claim 1, wherein the first and the second pathogenic viruses are of the same type but of different subtype or clade.

8. The method of claim 1, wherein the first and the second pathogenic viruses are different types of the same virus.

9. The method of claim 1, wherein the first or second pathogenic virus is a human immunodeficiency virus.

10. The method of claim 9, wherein the first or second viral antigen is an HIV surface, core/capsid, regulatory, enzyme or accessory protein.

11. The method of claim 9, wherein the first or second viral antigen is selected from the group consisting of HIV gp120, gp41, Gag, p17, p24, p2, p7, p1, p6, Tat, Rev, PR, RT, IN, Vif, Vpr, Vpx, Vpu and Nef.

12. The method of claim 1, further comprising:

harvesting serum from the host after the administration of the first and second recombinant adenovirus.

13. The method of claim 12, wherein the host is a human or a non-human primate.

14. The method of claim 12, further comprising:

storing the serum for at least 12 hour; and then administering the serum to the host or another host.

15. The method of claim 14, wherein the other host is a human or a non-human primate.

16. The method of claim 1, wherein the host or the other host is a human or a non-human primate.

17. The method of claim 1, wherein the first or second viral antigen is a full-length antigenic viral protein or a portion of the antigenic viral protein that contains the predominant antigen, neutralizing antigen or epitope of the first or second pathogenic antigen.

18. The method of claim 1, wherein the first or second viral antigen is a modified antigen that is mutated from a glycoprotein of the first or second pathogenic virus such that the first or second viral antigen is rendered non-functional as a viral component but retains its antigenicity.

* * * * *